US011015207B2

(12) United States Patent
Jin

(10) Patent No.: US 11,015,207 B2
(45) Date of Patent: May 25, 2021

(54) RNAS FROM PATHOGENS INHIBIT PLANT IMMUNITY

(71) Applicant: The Regents of the University of California, Oakland, CA (US)

(72) Inventor: Hailing Jin, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/140,179

(22) Filed: Sep. 24, 2018

(65) Prior Publication Data

US 2019/0078116 A1 Mar. 14, 2019

Related U.S. Application Data

(62) Division of application No. 14/505,378, filed on Oct. 2, 2014, now Pat. No. 10,119,148.

(60) Provisional application No. 61/886,004, filed on Oct. 2, 2013.

(51) Int. Cl.
*C12N 15/82* (2006.01)

(52) U.S. Cl.
CPC ................................ *C12N 15/8282* (2013.01)

(58) Field of Classification Search
CPC ................................................. C12N 15/8282
USPC ......................................................... 800/279
See application file for complete search history.

(56) References Cited

U.S. PATENT DOCUMENTS

| | | | |
|---|---|---|---|
| 6,653,535 | B1 | 11/2003 | Tarczynski |
| 7,834,243 | B2 | 11/2010 | Schweizer |
| 10,119,148 | B2 | 11/2018 | Jin |
| 2003/0221211 | A1 | 11/2003 | Rottmann |
| 2004/0029283 | A1 | 2/2004 | Fillatti |

FOREIGN PATENT DOCUMENTS

| | | |
|---|---|---|
| EP | 1 888 754 | 5/2011 |
| WO | 2013/025670 A1 | 2/2013 |

OTHER PUBLICATIONS

Yan et al. The Plant Cell 24:415-427 (Year: 2012).*
Ashida H. et al., "Shigella deploy multiple countermeasures against host innate immune responses" *Curr. Opin. Microbiol.* 14, 16-23 (2011).
Bozkurt T.O. et al., "Oomycetes, effectors, and all that jazz" *Curr. Opin. Plant Biol.* 15, 483-492 (2012).
Dean et al., "The top 10 fungal pathogens in molecular plant pathology," Mol Plant Pathol (2012) 13(4):414-430.
Ellendorff U. et al., "RNA silencing is required for Arabidopsis defence against Verticillium wilt disease" *J. Exp. Bot.* 60, 591 (2009).
Gan et al., "Bacterially expressed dsRNA protects maize against SCMV infection," Plant Cell Reports 29(11):1261-1268 (2010).
Govindarajulu et al., "Host-induced gene silencing inhibits the biotrophic pathogen causing downy mildew of lettuce," Plant Biotechnology Journal (2015) 13(7):875-883.
Hilbi H. et al., "Secretive Bacterial Pathogens and the Secretory Pathway" *Traffic* 13, 1187 (2012).
Jiang N, Yan Y, Janbon G, Pan J, Zhu X."Identification and functional demonstration of miRNAs in the fungus Cryptococcus neoformans" *PLoS One.* 2012; 7:e52734.
Katiyar-Agarwal S, Jin H., "Role of small RNAs in host-microbe interactions" *Annu Rev Phytopathol.* 2010; 48:225-226.
Lee HC et al. "Diverse pathways generate microRNA-like RNAs and Dicer-independent small interfering RNAs in fungi" *Mol Cell.* 2010; 38:803-814.
Lu et al., "RNA silencing in plants by the expression of siRNA duplexes," Nucleic Acids Res. 32(21):e171 (2004).
Mi S.J. et al., "Sorting of Small RNAs into Arabidopsis Argonaute Complexes Is Directed by the 50 Terminal Nucleotide" *Cell* 133, 116 (2008).
Montgomery T.A. et al., "Specificity of ARGONAUTE7-miR390 Interaction and Dual Functionality in TAS3 Trans-Acting siRNA Formation" *Cell* 133, 128 (2008).
Nowara et al., "HIGS: Host-Induced Gene Silencing in the Obligate Biotrophic Fungal Pathogen Blumeria graminis," Plant Cell (2010) 22(9):3130-3141.
Nunes CC et al. "Diverse and tissue-enriched small RNAs in the plant pathogenic fungus, Magnaporthe oryzae" *MBC Genomics.* 2011; 12:288.
Nunes et al., "Host-induced gene silencing: a tool for understanding fungal host interaction and for developing novel disease control strategies," Mol Plant Pathol (2012) 13(5):519-529.
Qutob D, Patrick Chapman B, Gijzen M., "Transgenerational gene silencing causes gain of virulence in a plant pathogen" *Nature Comm.* 2013; 4:1349.
Rafiqi M. et al., "Challenges and progress towards understanding the role of effectors in plant—fungal interactions" *Curr. Opin. Plant Biol.* 15, 477-482 (2012).
Raman V et al. "Physiological stressors and invasive plant infections alter the small RNA transcriptome of the rice blast fungus, Magnaporthe oryzae" *MBC Genomics.* 2011; 14:326.
Ruiz-Ferrer V, Voinnet O. "Roles of plant small RNAs in biotic stress responses" *Annu Rev Plant Biol.* 2009, 60:485-510.
Tang et al., "Construction of short tandem target mimic (STTM) to block the functions of plant and animal microRNAs" *Methods* 58:118-125 (2012).

(Continued)

*Primary Examiner* — Li Zheng
(74) *Attorney, Agent, or Firm* — Kilpatrick Townsend & Stockton LLP

(57) ABSTRACT

Provided are pathogen-resistant plants comprising a heterologous expression cassette, the expression cassette comprising a promoter operably linked to a polynucleotide that is complementary to, or mediates destruction, of a plant immunity suppressing sRNA of a pathogen, wherein the plant is less susceptible to the pathogen compared to a control plant lacking the expression cassette. Methods of making and cultivating pathogen-resistant plants are also provided.

19 Claims, 15 Drawing Sheets

Specification includes a Sequence Listing.

(56) References Cited

OTHER PUBLICATIONS

Tang et al., "Short Tandem Target Mimic: A Long Journey to the Engineered Molecular Landmine for Selective Destruction/ Blockage of MicroRNAs in Plants and Animals", Journal of Genetics and Genomics, vol. 40, No. 6, Jun. 20, 2013, pp. 291-296.
Wessner B, Gryadunov-Masutti L, Tschan H, Bachl N, Roth E. "Is there a role for microRNAs in exercise immunology? A synopsis of current literature and future developments" *Exerc Immunol Rev.* 2010;16:22-29.
Yan et al., "Effective Small RNA Destruction by the Expression of a Short Tandem Target Mimic in Arabidopsis" *Plant Cell* 24:415-427 (2012).
Zhang X et al. "Arabidopsis Argonaute 2 regulates innate immunity via miRNA393(*)-mediated silencing of a Golgi-localized SNARE gene, MEMB12" *Mol Cell.* 2011; 42:356-366.
Zhou J et al., "Identification of microRNA-like RNAs in a plant pathogenic fungus Sclerotinia sclerotiorum by high-throughput sequencing" *Mol Gen Genet.* 2012;287-282.

* cited by examiner

FIG. 8A
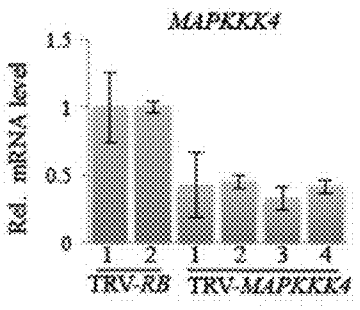
FIG. 8B
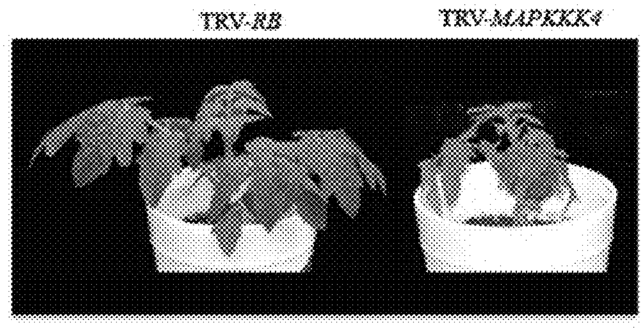
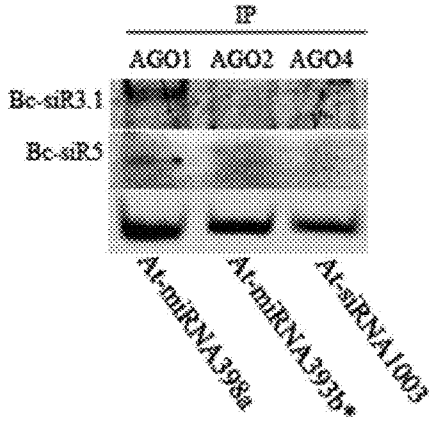
FIG. 9

| Library | Total reads | Total reads *B. cinerea* | % *B. cinerea* reads |
|---|---|---|---|
| *Arabidopsis*, 0 hpi (*B. cinerea*) | 71,793,267 | 68,811 | 0.14 |
| *Arabidopsis*, 24 hpi (*B. cinerea*) | 101,220,872 | 609,204 | 0.65 |
| *Arabidopsis*, 48 hpi (*B. cinerea*) | 59,594,013 | 296,764 | 0.53 |
| *Arabidopsis*, 72 hpi (*B. cinerea*) | 41,478,258 | 338,325 | 0.82 |
| *S. lycopersicum* leaf, 0 hpi (*B. cinerea*) | 2,630,614 | 623 | 0.02 |
| *S. lycopersicum* leaf, 24 hpi (*B. cinerea*) | 1,586,314 | 6,315 | 0.28 |
| *S. lycopersicum* leaf, 72 hpi (*B. cinerea*) | 1,580,667 | 5,918 | 0.37 |
| *S. lycopersicum* fruit, 0 hpi (*B. cinerea*) | 6,334,100 | 1,381 | 0.02 |
| *S. lycopersicum* fruit, 24 hpi (*B. cinerea*) | 6,021,895 | 14,908 | 0.25 |
| *S. lycopersicum* fruit, 72 hpi (*B. cinerea*) | 3,617,356 | 458,590 | 12.68 |
| *B. cinerea*, *in vitro* culture, conidiospores | 787,441 | 787,441 | 100.0 |
| *B. cinerea*, *in vitro* culture, mycelia | 1,716,701 | 1,716,701 | 100.0 |
| *B. cinerea*, *in vitro* culture, total biomass | 18,086,243 | 18,086,243 | 100.0 |

*FIG. 15*

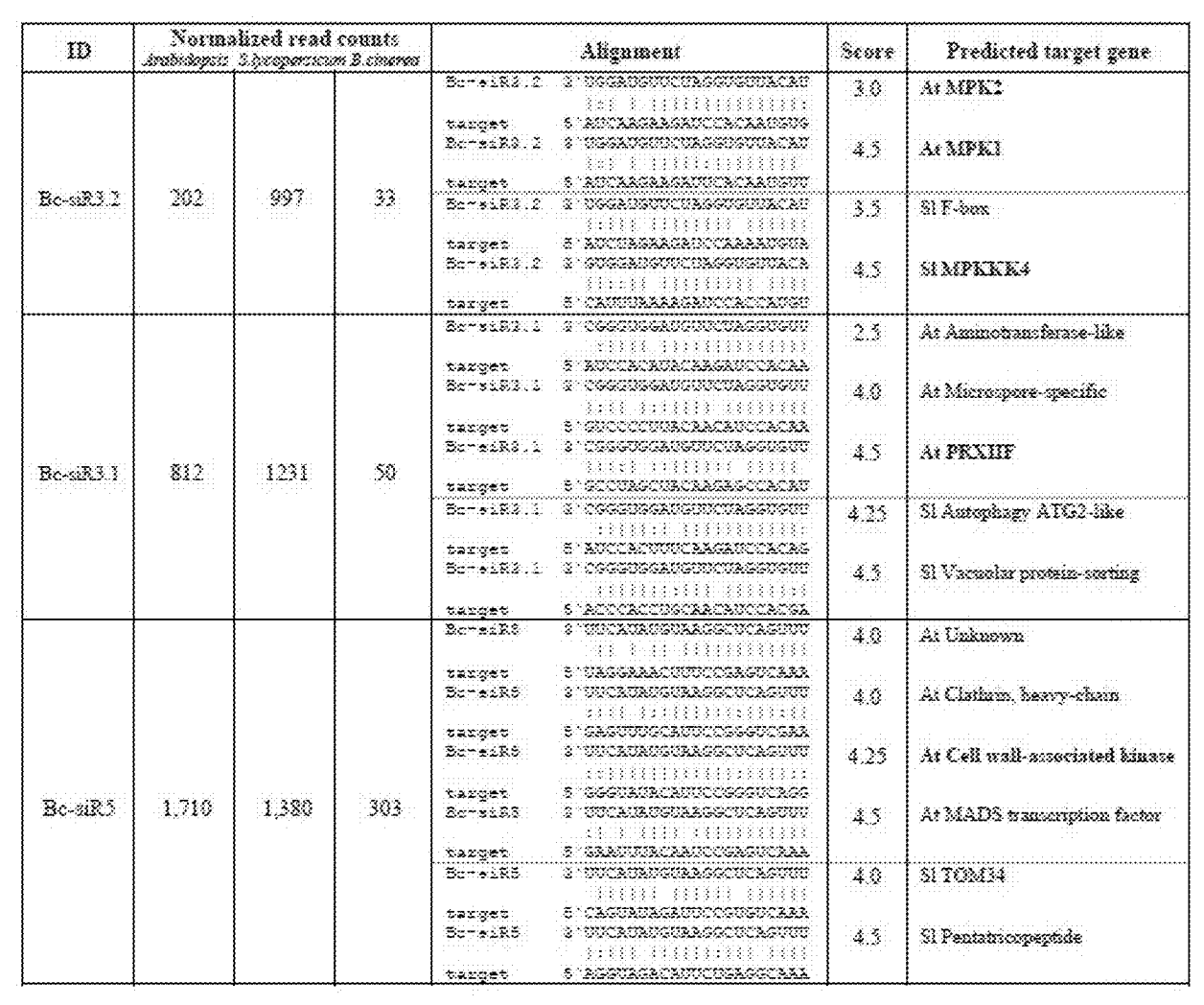

| ID | Normalized read counts *Arabidopsis* | *S.lycopersicum* | *B.cinerea* | Alignment | Score | Predicted target gene |
|---|---|---|---|---|---|---|
| Bc-siR3.2 | 202 | 997 | 33 | Bc-siR3.2 3' UGGAUGUUCUAGGUGUUACAU<br>target 5' AUCAAGAAGAUCCACAAUGUG | 3.0 | At MPK2 |
| | | | | Bc-siR3.2 3' UGGAUGUUCUAGGUGUUACAU<br>target 5' AUCAAGAAGAUUCACAAUGUU | 4.5 | At MPK1 |
| | | | | Bc-siR3.2 3' UGGAUGUUCUAGGUGUUACAU<br>target 5' AUCUAGAAAGAUCCAAAAUGUA | 3.5 | Sl F-box |
| | | | | Bc-siR3.2 3' GUGGAUGUUCUAGGUGUUACA<br>target 5' CAUUUAAAAGAUCCACCAUGU | 4.5 | Sl MPKKK4 |
| Bc-siR3.1 | 812 | 1231 | 50 | Bc-siR3.1 3' CGGGUGGAUGUUCUAGGUGUU<br>target 5' AUCCACAUACAAGAUCCACAA | 2.5 | At Aminotransferase-like |
| | | | | Bc-siR3.1 3' CGGGUGGAUGUUCUAGGUGUU<br>target 5' GUCCCCUUACAACAUCCACAA | 4.0 | At Microspore-specific |
| | | | | Bc-siR3.1 3' CGGGUGGAUGUUCUAGGUGUU<br>target 5' GCCUAGCUACAAGAGCCACAU | 4.5 | At PKXIIF |
| | | | | Bc-siR3.1 3' CGGGUGGAUGUUCUAGGUGUU<br>target 5' AUCCACUUUCAAGAUCCACAG | 4.25 | Sl Autophagy ATG2-like |
| | | | | Bc-siR3.1 3' CGGGUGGAUGUUCUAGGUGUU<br>target 5' ACCCACCUGCAACAUCCACGA | 4.5 | Sl Vacuolar protein-sorting |
| Bc-siR5 | 1,710 | 1,380 | 303 | Bc-siR5 3' UUCAUAUGUAAGGCUCAGUUU<br>target 5' UAGGAAACUUUCCGAGUCAAA | 4.0 | At Unknown |
| | | | | Bc-siR5 3' UUCAUAUGUAAGGCUCAGUUU<br>target 5' GAGUUUGCAUUCCGGGUCGAA | 4.0 | At Clathrin, heavy-chain |
| | | | | Bc-siR5 3' UUCAUAUGUAAGGCUCAGUUU<br>target 5' GGGUAUACAUUCCGGGUCAGG | 4.25 | At Cell wall-associated kinase |
| | | | | Bc-siR5 3' UUCAUAUGUAAGGCUCAGUUU<br>target 5' GAAUUUACAAUCCGAGUCAAA | 4.5 | At MADS transcription factor |
| | | | | Bc-siR5 3' UUCAUAUGUAAGGCUCAGUUU<br>target 5' CAGUAUAGAUUCCGUGUCAAA | 4.0 | Sl TOM34 |
| | | | | Bc-siR5 3' UUCAUAUGUAAGGCUCAGUUU<br>target 5' AGGUAGACAUUCUGAGGCAAA | 4.5 | Sl Pentatricopeptide |

FIG. 16

RNAS FROM PATHOGENS INHIBIT PLANT IMMUNITY

CROSS-REFERENCE TO RELATED APPLICATIONS

The present application is a divisional of U.S. application Ser. No. 14/505,378, filed Oct. 2, 2014, which claims priority to U.S. Provisional Application No. 61/886,004, filed Oct. 2, 2013, the entire content of each of which is incorporated by reference herein for all purposes.

STATEMENT AS TO RIGHTS TO INVENTIONS MADE UNDER FEDERALLY SPONSORED RESEARCH AND DEVELOPMENT

This invention was made with Government support under Grant No. MCB-0642843, IOS-1257576 awarded by the National Science Foundation, a NIH grant (R01 GM093008). The government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing named "081906-1099170-214920US_SEQ.txt", created on Sep. 24, 2018, 224,616 bytes, machine format IBM-PC, MS-Windows operating system, is hereby incorporated by reference in its entirety for all purposes.

BACKGROUND OF THE INVENTION

*Botrytis cinerea* is a fungal pathogen that infects almost all vegetable and fruit crops and annually causes $10-100 billion losses worldwide. With its broad host range, *B. cinerea* is a useful model for studying the pathogenicity of aggressive fungal pathogens. Many pathogens of plants and animals deliver effectors into host cells to suppress host immunity (H. Ashida et al., *Curr. Opin. Microbiol.* 14, 16 (2011); M. Rafiqi et al., *Curr. Opin. Plant Biol.* 15, 477 (2012); T. O. Bozkurt et al., *Curr. Opin. Plant Biol.* 15, 483 (2012); H. Hilbi, et al., *Traffic* 13, 1187 (2012)).

sRNAs induce gene silencing by binding to Argonaute (AGO) proteins and directing the RNA-induced silencing complex (RISC) to genes with complementary sequences. sRNAs from both plant and animal hosts have been recognized as regulators in host-microbial interaction (5-8). Although sRNAs are also present in various fungi and oomycetes, including many pathogens (9-14), it has not been clear whether they regulate host-pathogen interaction.

BRIEF SUMMARY OF THE INVENTION

The present application provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide that is complementary to, or mediates destruction, of a plant immunity suppressing sRNA of a pathogen, wherein the plant is less susceptible to the pathogen compared to a control plant lacking the expression cassette.

In some embodiments, the polynucleotide encodes a short tandem target mimic (STTM) of the sRNA. In some embodiments, the STTM is engineered from primers (a forward primer and a reverse primer) listed in Table 2. In some embodiments, the polynucleotide encodes an antisense nucleic acid that is complementary to the sRNA.

The present application also provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide that is an sRNA-resistant target that encodes a protein that functions in plant immunity, wherein the promoter is heterologous to the polynucleotide. In some embodiments, a plant into which the expression cassette has been introduced has enhanced pathogen resistance compared to a control plant lacking the expression cassette.

In some embodiments, the polynucleotide is substantially (e.g., at least 60, 70, 75, 80, 85, 90, or 95%) identical to any of SEQ ID NOS:4-13. In some embodiments, the polynucleotide is an sRNA-resistant target encoding mitogen activated protein kinase 1 (MPK1), mitogen activated protein kinase 2 (MPK2), peroxiredoxin (PRXIIF), cell-wall associated kinase (WAK), or tomato mitogen activated protein kinase kinase kinase 4 (MAPKKK4). In some embodiments, the polynucleotide is an sRNA-resistant target of a gene listed in FIG. 1, Table 1, or Table 3. In some embodiments, the polynucleotide is resistant to gene silencing by an sRNA listed in Table 1. In some embodiments, the polynucleotide is resistant to gene silencing by Bc-siR3.1, Bc-siR3.2, or Bc-siR5.

In some embodiments, the sRNA comprises a sequence listed in Table 1. In some embodiments, the sRNA comprises the sequence of Bc-siR3.1, Bc-siR3.2, or Bc-siR5.

In some embodiments, the pathogen is *Botrytis*. In some embodiments, the pathogen is *Botrytis cinera*.

In some embodiments, the promoter is an inducible promoter. In some embodiments, the promoter is pathogen inducible. In some embodiments, the promoter is induced upon infection by *Botrytis*. In some embodiments, the promoter is substantially (e.g., at least 60, 70, 75, 80, 85, 90, or 95%) identical to *Arabidopsis* BIK1 (SEQ ID NO:1), *Arabidopsis* PDF1.2 (SEQ ID NO:2), or tomato TPK1b (SEQ ID NO:3). In some embodiments, the promoter is stress-inducible. In some embodiments, the promoter is tissue-specific. In some embodiments, the promoter is specifically expressed in the epidermis. In some embodiments, the promoter is substantially (e.g., at least 60, 70, 75, 80, 85, 90, or 95%) identical to *Arabidopsis* ML1 (SEQ ID NO:14) or tomato ML1 (SEQ ID NO:15).

In another aspect, the present invention provides for expression cassettes comprising: a promoter operably linked to a polynucleotide that is complementary to, or mediates destruction, of a plant immunity suppressing sRNA of a pathogen, wherein the plant is less susceptible to the pathogen compared to a control plant lacking the expression cassette; or comprising a promoter operably linked a polynucleotide that is an sRNA-resistant target that encodes a protein that functions in plant immunity, wherein the promoter is heterologous to the polynucleotide. Isolated nucleic acids comprising said expression cassettes are also provided.

In still another aspect, the present invention provides for expression vectors comprising an expression cassette as described herein.

In another aspect, methods of making a pathogen-resistant plant are provided. In some embodiments, the method comprises:

introducing the nucleic acid comprising an expression cassette as described herein into a plurality of plants; and selecting a plant comprising the expression cassette In yet another aspect, methods of cultivating a plurality of pathogen-resistant plants are provided.

*Arabidopsis* and *S. lycopersicum* libraries, indicating that those Bc-siRNAs were induced during infection. Similarly, Bc-SIR5 showed induction upon infection.

Figure 6A:
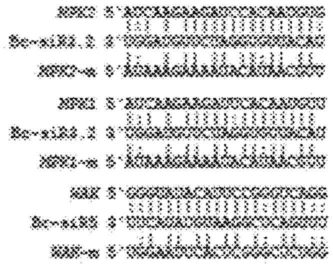
Figure 6B:
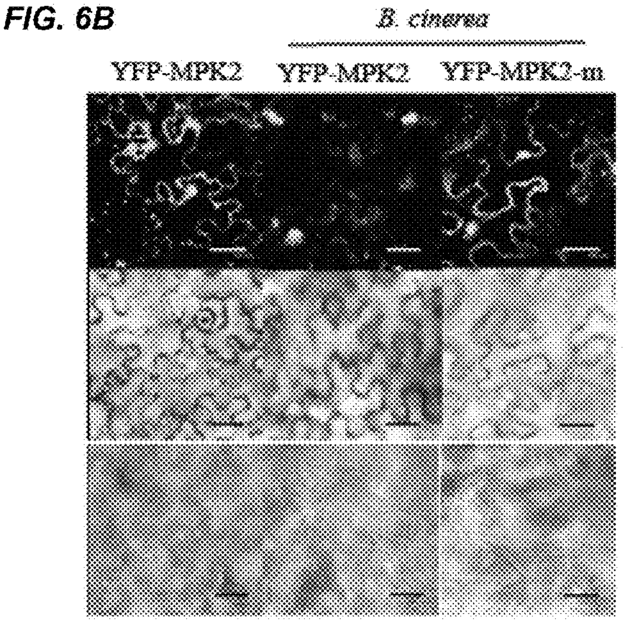
Figure 6C:
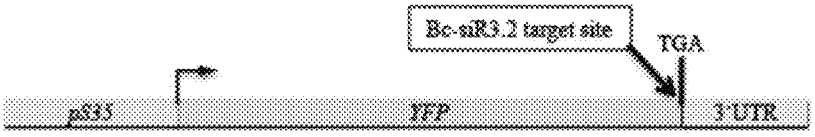

FIGS. 6A-6C. (A) Target site and target site mutated versions of Bc-siRNA *Arabidopsis* target genes that were used in this study (SEQ ID NOS:16, 17-19, 17 and 20-23, respectively). (B) *B. cinerea* mycelium coincided with target gene suppression of YFP-MPK2 (center), but not YFP-MPK2-m (right) in *N. benthamiana* at 24 hpi; YFP-MPK2 without fungal infection was used as a control (left). Upper panel: YFP; bottom panel: YFP/bright field overlay; scale bar: 50 μm. (C) A schematic diagram of the YFP sensor carrying a Bc-siR3.2 target site.

Figure 7A:
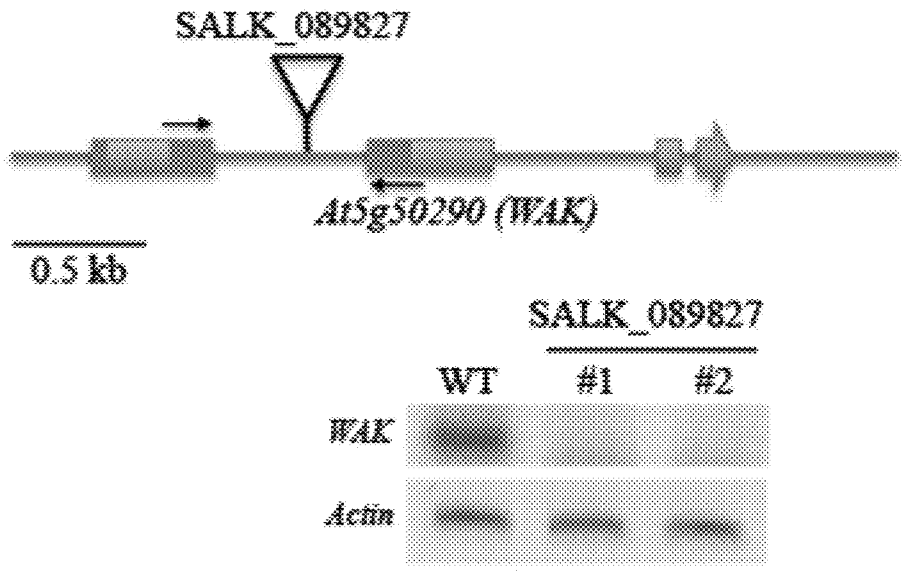
Figure 7B:
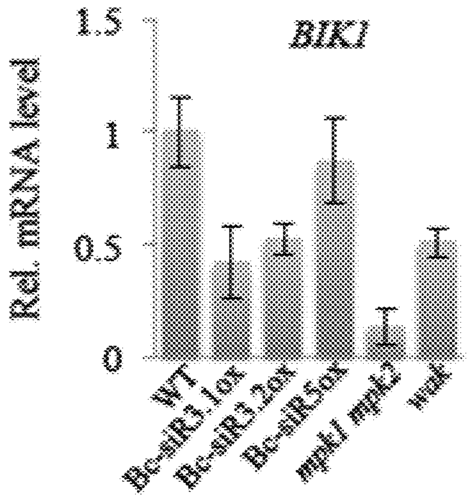

FIGS. 7A-7B. Isolation and characterization of Bc-siRNA target mutants and Bc-siRNAox lines. (A) Isolation of a loss-of function mutant line for WAK gene (At5g50290). Expression of WAK was completely knocked out in the T-DNA insertion line shown by RT-PCR. (B) Induction of BIK1 expression in response to *B. cinerea* infection was reduced in Bc-siR3.1ox and Bc-iR3.2ox lines, mpk1 mpk2, and wak mutant lines. Relative transcript levels of BIK1 were measured by real time RT-PCR. Error bars indicate standard deviation (SD) of three technical replicates. Similar results were obtained from two biological repeats.

FIGS. 8A-8B. *S. lycopersicum* MAPKKK4 gene knock-down by TRV-induced gene silencing. (A) Expression of MAPKKK in *S. lycopersicum* TRV-MAPKKK4 silenced plants was measured by qRT-PCR using actin as an internal control. Error bars indicate SD of three technical replicates. Similar results were obtained from three biological repeats. (B) TRV-MAPKKK4 silenced plants exhibited a dwarf phenotype as compared with control plants (TRV-RB).

FIG. 9. Bc-siR3.1 and Bc-siR5 were specifically loaded into *Arabidopsis* AGO1 during infection, but not into AGO2 or AGO4, as revealed by AGO-IP followed by RT-PCR. Endogenous plant sRNAs were used as internal controls for IP: At-miR398a for AGO1, At-miR393b* for AGO2, and At-siR1003 for AGO4.

Figure 10:
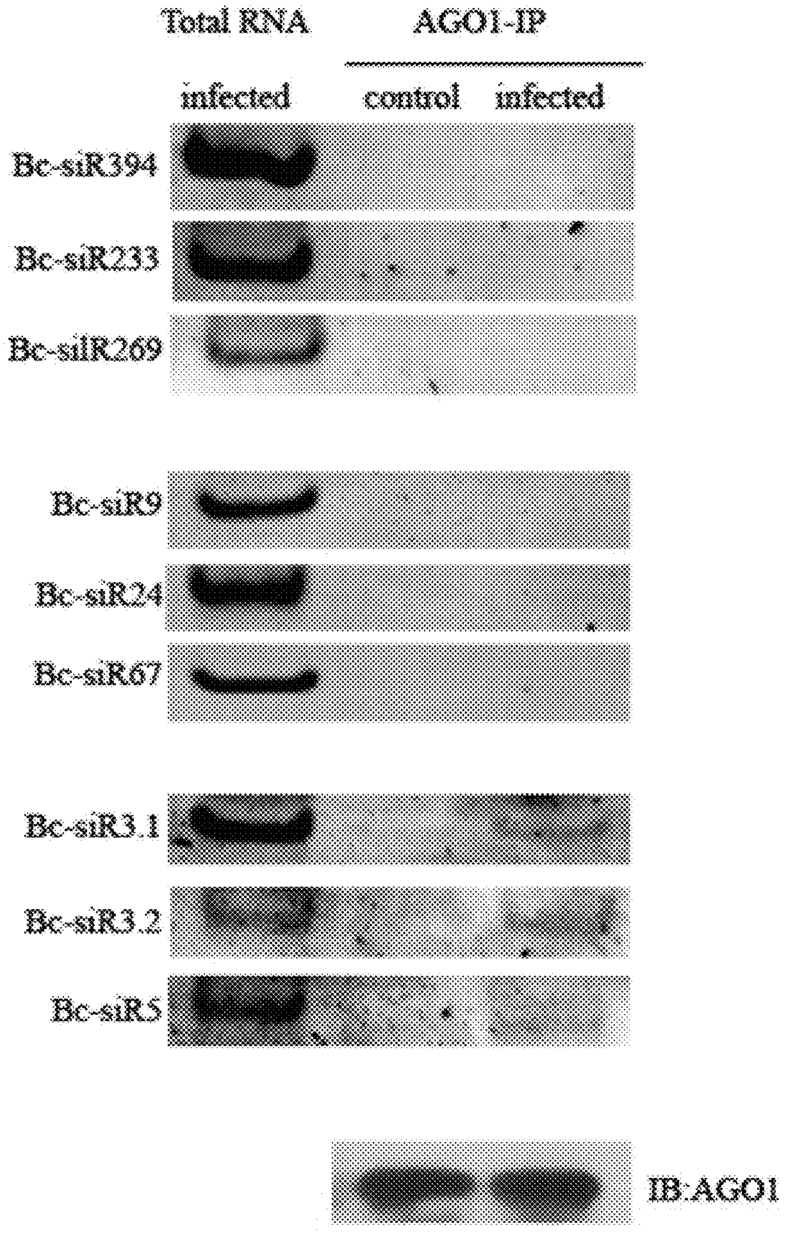

FIG. 10. The sRNAs that have no predicted plant targets (Bc-siR394, Bc-siR233, Bc-siR269) or have predicted targets that were not down-regulated (Bc-siR9, Bc-siR24, Bc-siR67) by *B. cinerea* infection are not present in the AGO-associated fractions.

Figure 11A:
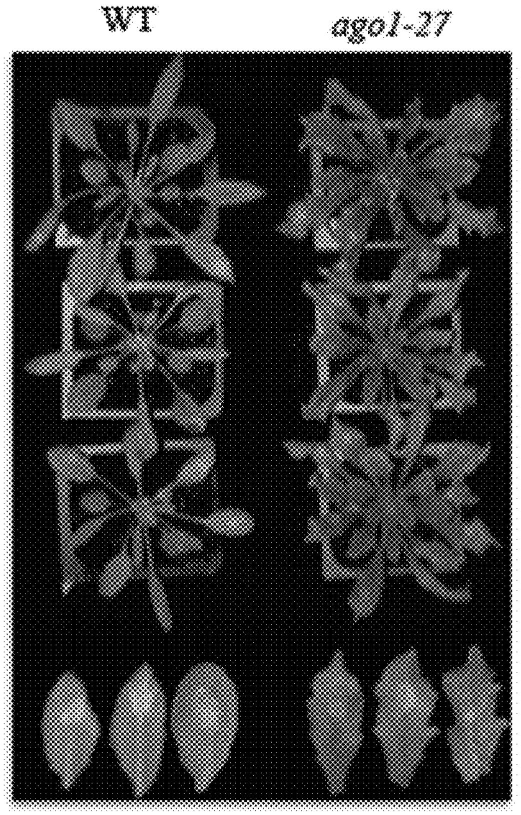
Figure 11B:
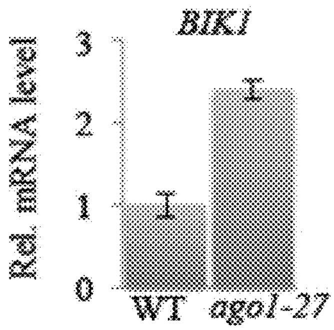

FIGS. 11A-11B. *Arabidopsis* ago1-27 is more resistant to *B. cinerea* infection than wild-type. (A) ago1-27 displayed reduced disease phenotype upon *B. cinerea* infection. (B) Induction of BIK1 in response to *B. cinerea* infection was increased in ago1-27.

Figure 12:
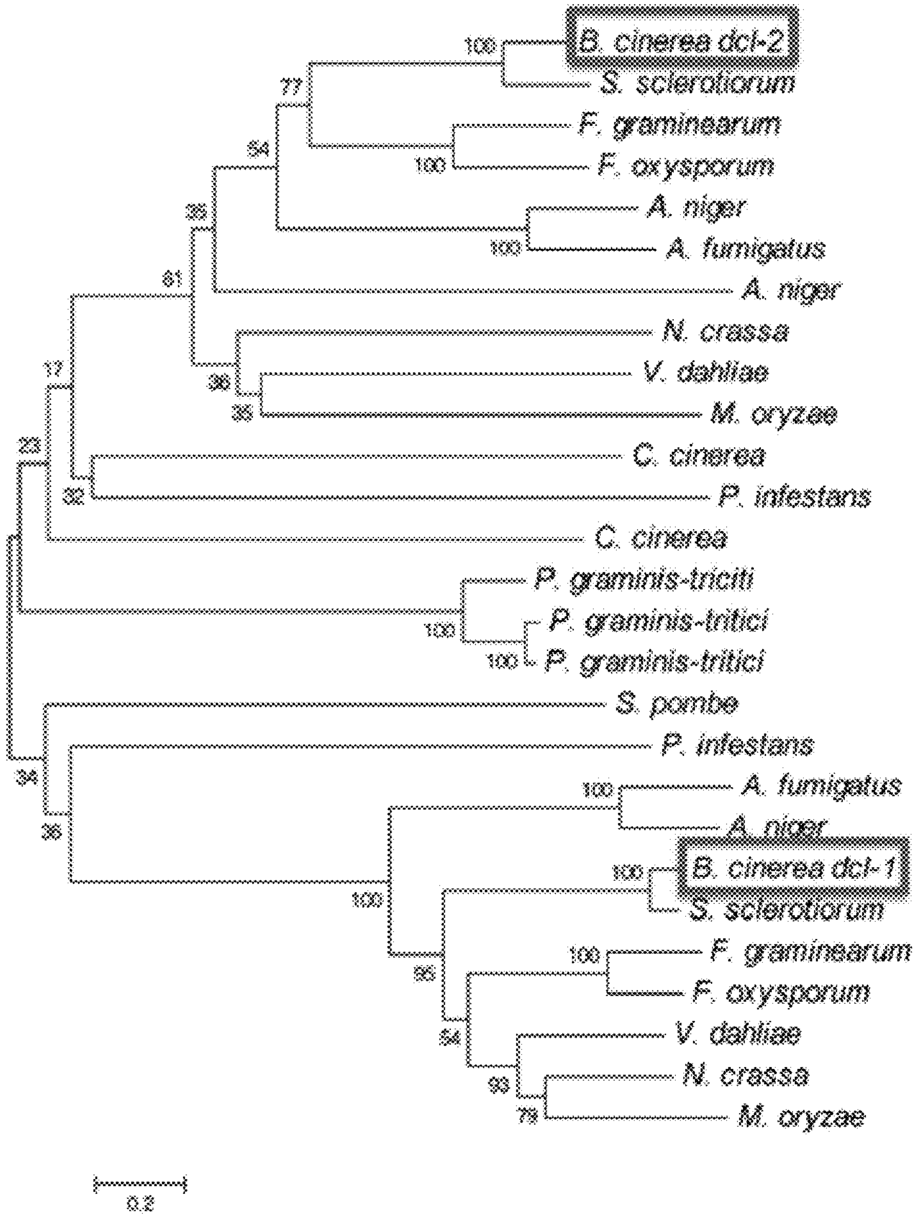

FIG. 12. The phylogenetic tree of DCL proteins in pathogenic fungi. *Schizosaccharomyces pombe* and *Neurospora crassa* were used as references. An oomycete pathogen *Phytophthora infestans* was also included.

FIGS. 13A-13D. Generation of *B. cinerea* dcl1, dcl2 single mutants and the dcl1 dcl2 double mutant by homologous recombination. (A) Schematic diagram of Bc-DCL1 and Bc-DCL2 knockout strategy by homologous recombination. Black arrows indicate primers used for genotyping. (B) The dcl1, dcl2, and dcl1 dcl2 knockout strains were confirmed by RT-PCR. (C) *B. cinerea* dcl1, dcl2, and dcl1 dcl2 mutant strains showed gradual growth retardation and delayed development of conidiospores: upper panel shows radial growth after 3 days, bottom panel shows condition at 21 days. (D) Two Bc-sRNAs, Bc-microRNA-like RNA2 (Bc-milR2) and Bc-siR1498, were identified as Dicer-independent and were expressed in dcl1 dcl2.

Figure 14A:
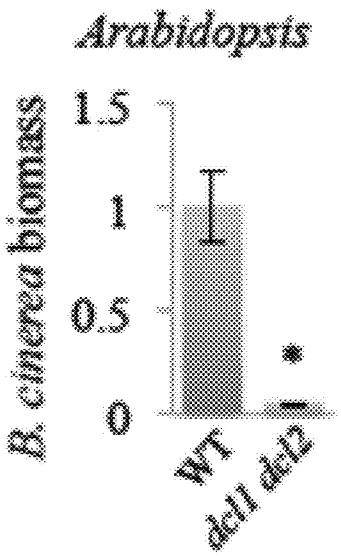
Figure 14B:
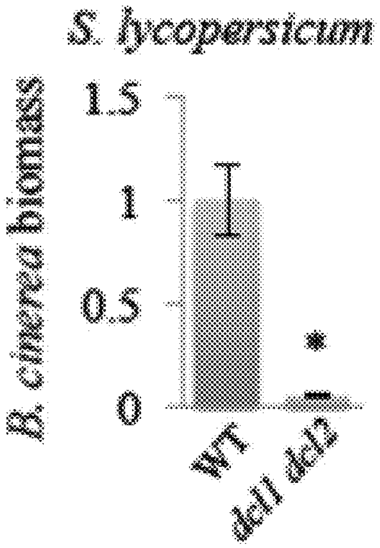

FIGS. 14A-14B. The biomass of the *B. cinerea* dcl1 dcl2 mutant strain was strongly reduced as compared with the wild-type strain during infection of both *Arabidopsis* (A) and *S. lycopersicum* (B), as quantified by qPCR at 72 hpi and 48 hpi, respectively.

FIG. 15. Statistical analysis of the sRNA libraries from cultured *B. cinerea, B. cinerea*-infected *Arabidopsis*, and *B. cinerea*-infected *S. lycopersicum.*

FIG. 16. The predicted host targets of sRNAs Bc-siR3.1, Bc-siR3.2, and Bc-siR5 (SEQ ID NOS:24, 25, 24, 26, 24, 27-31, 30, 32, 30, 33, 30, 34, 30, 35-37, 36, 38, 36, 39, 36, 40, 36, 41, 36 and 42, respectively). Normalized read counts are given in reads per million *B. cinerea* sRNAs. Reads were summed from individual sRNA libraries for each category: cultured *B. cinerea, B. cinerea*-infected *Arabidopsis, B. cinerea*-infected *S. lycopersicum*. Target gene alignment was scored as described in Materials and Methods.

DEFINITIONS

The term "pathogen-resistant" or "pathogen resistance" refers to an increase in the ability of a plant to prevent or resist pathogen infection or pathogen-induced symptoms. Pathogen resistance can be increased resistance relative to a particular pathogen species or genus (e.g., *Botrytis*), increased resistance to multiple pathogens, or increased resistance to all pathogens (e.g., systemic acquired resistance).

"Pathogens" include, but are not limited to, viruses, bacteria, nematodes, fungi or insects (see, e.g., Agrios, *Plant Pathology* (Academic Press, San Diego, Calif. (1988)). In some embodiments, the pathogen is a fungal pathogen. In some embodiments, the pathogen is *Botrytis.*

The term "plant immunity suppressing sRNA" refers to an sRNA that induces gene silencing in a plant of one or more genes that function or are predicted to function in plant immunity. For example, in some embodiments a plant immunity suppressing sRNA is an sRNA that induces gene silencing of a mitogen-activated protein kinase (e.g., MPK1, MPK2, or MAPKKK4), an oxidative stress-related gene (e.g., periredoxin (PRXIIF), or a cell wall-associated kinase (WAK). Exemplary plant immunity suppressing sRNAs are listed, for example, in FIG. 16 and Table 1.

The term "sRNA" refers to "small RNA," a short non-coding RNA sequence. In some embodiments, an sRNA sequence comprises less than about 250 nucleotides (e.g., less than 250 nucleotides, less than 200 nucleotides, less than 150 nucleotides, less than 100 nucleotides, or less than 50 nucleotides). In some embodiments, an sRNA sequence comprises about 50-250 nucleotides, about 15-250 nucleotides, about 20-200 nucleotides, about 50-200 nucleotides, about 20-100 nucleotides, about 20-50 nucleotides, or about 20-30 nucleotides. In some embodiments, a sRNA sequence induces gene silencing, e.g., in a host plant. For example, in some embodiments a sRNA sequence induces gene silencing by directing a host's (e.g., host plant's) RNA-induced silencing complex (RISC) to genes with complementary sequences ("target genes").

The term "sRNA-resistant target," as used with reference to a polynucleotide sequence, refers to a polynucleotide sequence having a synonymous mutation relative to a sRNA target gene, wherein the polynucleotide sequence of the sRNA-resistant target comprises one or more nucleotide mutations relative to the polynucleotide sequence of the sRNA target gene that decreases the ability of the sRNA (e.g., a pathogen sRNA) to induce gene silencing of the sRNA-resistant target gene and wherein the amino acid sequence (e.g., protein sequence) that is encoded by the polynucleotide sequence of the sRNA-resistant target is identical to the amino acid sequence that is encoded by the polynucleotide sequence of the sRNA target gene. In some embodiments, the polynucleotide sequence of the sRNA-resistant target comprises 1, 2, 3, 4, 5, 6, 7, 8, 9, 10 or more nucleotide mutations relative to the polynucleotide sequence of the sRNA target gene.

The term "nucleic acid" or "polynucleotide" refers to a single or double-stranded polymer of deoxyribonucleotide or ribonucleotide bases read from the 5' to the 3' end. Nucleic acids may also include modified nucleotides that permit correct read through by a polymerase and do not significantly alter expression of a polypeptide encoded by that nucleic acid.

The phrase "nucleic acid encoding" or "polynucleotide encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

Two nucleic acid sequences or polypeptides are said to be "identical" if the sequence of nucleotides or amino acid residues, respectively, in the two sequences is the same when aligned for maximum correspondence as described below. "Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. When percentage of sequence identity is used in reference to proteins or peptides, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity" or "substantially identical," as used in the context of polynucleotide or polypeptide sequences, refers to a sequence that has at least 60% sequence identity to a reference sequence. Alternatively, percent identity can be any integer from 60% to 100%. Exemplary embodiments include at least: 60%, 65%, 70%, 75%, 80%, 85%, 90%, 91%, 92%, 93%, 94%, 95%, 96%, 97%, 98%, or 99%, as compared to a reference sequence using the programs described herein; preferably BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

The term "complementary to" is used herein to mean that a polynucleotide sequence is complementary to all or a portion of a reference polynucleotide sequence. In some embodiments, a polynucleotide sequence is complementary to at least 15, at least 20, at least 25, at least 30, at least 40, at least 50, at least 75, at least 100, at least 125, at least 150, at least 175, at least 200, or more contiguous nucleotides of a reference polynucleotide sequence. In some embodiments, a polynucleotide sequence is "substantially complementary" to a reference polynucleotide sequence if at least 70%, at least 75%, at least 80%, at least 85%, at least 90%, or at least 95% of the polynucleotide sequence is complementary to the reference polynucleotide sequence.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

DETAILED DESCRIPTION OF THE INVENTION

I. Introduction

As described in the Examples section below, it has been surprisingly discovered that small RNAs (sRNAs) from a plant pathogen can suppress genes involved in plant immunity. Without being bound to a particular theory, it is believed that the pathogen sRNAs suppress immunity in a host plant by using the host plant's own gene silencing mechanisms to suppress genes that function in plant immunity.

Thus, one aspect of the present invention relates to enhancing a plant's pathogen resistance by blocking, attenuating, or targeting for destruction the pathogen sRNAs. In some embodiments, a pathogen sRNA is blocked, attenuated, or targeted for destruction using a complementary polynucleotide sequence (e.g., an antisense nucleic acid sequence that is complementary or substantially complementary to the sRNA) or using a short tandem target mimic (STTM) targeting the sRNA. In some embodiments, the complementary polynucleotide sequence or STTM that targets the pathogen sRNA is expressed in a plant (e.g., in an expression cassette operably linked to a promoter), wherein the plant is less susceptible to the pathogen as compared to a control plant in which complementary polynucleotide sequence or STTM is not expressed.

In another aspect, the present invention relates to enhancing a plant's pathogen resistance by expressing sRNA-resistant target genes involved in plant immunity in plants to overcome the effect of the pathogen sRNAs. In some embodiments, the sRNA-resistant target genes are expressed under the control of a promoter (e.g., a pathogen-inducible promoter, a stress-inducible promoter, or a tissue-specific promoter).

II. Pathogen sRNAs and Attenuation of Pathogen sRNAs

In one aspect, methods of blocking or attenuating plant immunity-suppressing sRNAs of pathogens are provided. In some embodiments, the method comprises expressing in a plant a polynucleotide that is complementary or substantially complementary to the pathogen sRNA or that mediates destruction of the pathogen sRNA. In some embodiments, the polynucleotide encodes a short tandem target mimic (STTM) targeting the sRNA. In some embodiments, the polynucleotide encodes an antisense nucleic acid that is complementary or substantially complementary to the sRNA. In some embodiments, the method comprises expressing in the plant the polynucleotide that is complementary or substantially complementary to the pathogen sRNA or that mediates destruction of the pathogen sRNA under the control of a promoter, e.g., a constitutively active promoter, an inducible promoter, or tissue-specific promoter (e.g., a stress inducible promoter, a pathogen inducible promoter, or an epidermis-specific promoter).

In another aspect, plants having blocked or attenuated function of pathogen sRNAs are provided. In some embodiments, the plant comprises a heterologous expression cassette, the expression cassette comprising a promoter operably linked to a polynucleotide that is complementary or substantially complementary to the pathogen sRNA or that mediates destruction of the pathogen sRNA, wherein the plant is less susceptible to the pathogen relative to a control plant lacking the expression cassette. In some embodiments, the expression cassette comprises a polynucleotide that encodes a short tandem target mimic (STTM) targeting the sRNA. In some embodiments, the expression cassette comprises a polynucleotide that encodes an antisense nucleic acid that is complementary or substantially complementary to the sRNA. In some embodiments, the expression cassette comprises a promoter that is an inducible promoter (e.g., stress inducible or pathogen inducible). In some embodiments, the expression cassette comprises a promoter that is a constitutively active promoter. In some embodiments, the promoter is tissue-specific (e.g., epidermis-specific).

In yet another aspect, expression cassettes comprising a promoter operably linked to a polynucleotide that is complementary to, or mediates destruction, of a plant immunity suppressing sRNA of a pathogen, wherein the promoter is heterologous to the polynucleotide, or isolated nucleic acids comprising said expression cassettes, are provided. In some embodiments, the expression cassette comprises a polynucleotide that encodes a short tandem target mimic (STTM) targeting the sRNA. In some embodiments, the expression cassette comprises a polynucleotide that encodes an antisense nucleic acid that is complementary or substantially complementary to the sRNA. In some embodiments, the expression cassette comprises a promoter that is an inducible promoter (e.g., stress inducible or pathogen inducible). In some embodiments, the expression cassette comprises a promoter that is a constitutively active promoter. In some embodiments, the promoter is tissue-specific (e.g., epidermis-specific). In some embodiments, a plant in which the expression cassette is introduced is less susceptible to the pathogen compared to a control plant lacking the expression cassette.

Pathogen sRNAs

In some embodiments, the plant immunity suppressing sRNA is from a viral, bacterial, fungal, nematode, or insect pathogen. In some embodiments, the sRNA is from a fungal pathogen. Examples of plant fungal pathogens include, but are not limited to, *Botyritis, Magnaporthe, Sclerotinia, Puccinia, Fusarium, Mycosphaerella, Blumeria, Colletotrichum, Ustilago*, and *Melampsora*. See, e.g., Dean et al., *Mol Plant Pathol* 13:804 (2012). In some embodiments, the pathogen is *Botyritis*. In some embodiments, the pathogen is *Botyritis cinera*.

In some embodiments, the pathogen sRNA comprises a sequence of about 15-250 nucleotides, about 15-150 nucleotides, about 15-100 nucleotides, about 15-50 nucleotides, about 20-50 nucleotides, about 15-30, or about 20-30 nucleotides. In some embodiments, the pathogen sRNA comprises a sequence of about 15, 16, 17, 18, 19, 20, 21, 22, 23, 24, 25, 26, 27, 28, 29, or 30 nucleotides.

In some embodiments, the pathogen sRNA comprises a sequence of about 15-250 nucleotides that specifically targets (e.g., induces gene silencing of) a gene encoding a protein that functions or is predicted to function in plant immunity. In some embodiments, the pathogen sRNA comprises a sequence of about 15-250 nucleotides that specifically targets a gene that encodes mitogen activated protein kinase 1 (MPK1), mitogen activated protein kinase 2 (MPK2), peroxiredoxin (PRXIIF), cell-wall associated kinase (WAK), or mitogen activated protein kinase kinase kinase 4 (MAPKKK4). In some embodiments, the pathogen sRNA comprises a sequence of about 15-250 nucleotides that specifically targets any of SEQ ID NOs:4-13 or a portion thereof.

In some embodiments, the pathogen sRNA comprises a sequence listed in FIG. 16 (e.g., Bc-siR3.2, Bc-siR3.1, or Bc-siR5) or Table 1 (e.g., Bc-siR1, Bc-siR1010, Bc-siR3.1, Bc-siR3.2, Bc-siR1008, Bc-siR5, Bc-siR9, Bc-siR10, Bc-siR18, Bc-siR15, Bc-siR17, Bc-siR22, Bc-siR24, Bc-siR25, Bc-siR1015, Bc-siR20, Bc-siR1021, Bc-siR1002, Bc-siR28, Bc-siR31, Bc-siR29, Bc-siR41, Bc-siR35, Bc-siR57, Bc-siR43, Bc-siR40, Bc-siR38, Bc-siR46, Bc-siR48, Bc-siR1007, Bc-siR56, Bc-siR49, Bc-siR58, Bc-siR63, Bc-siR1005, Bc-siR60, Bc-siR61, Bc-siR62, Bc-siR65, Bc-siR67, Bc-siR68, Bc-siR73, Bc-siR81, Bc-siR82, Bc-siR86, Bc-siR91, Bc-siR92, Bc-siR95, Bc-siR1017, Bc-siR97, Bc-siR99, Bc-siR1013, Bc-siR102, Bc-siR1011, Bc-siR109, Bc-siR1018, Bc-siR114, Bc-siR1020, Bc-siR1016, Bc-siR1003, Bc-siR124, Bc-siR127, Bc-siR128, Bc-siR130, Bc-siR1004, Bc-siR144, Bc-siR137, Bc-siR140, Bc-siR141, Bc-siR156, Bc-siR161, Bc-siR163, or Bc-siR1001). In some embodiments, the pathogen sRNA comprises the sequence of Bc-siR3.1 (TTGTGGATCTTGTAGGTGGGC; SEQ ID NO:43), Bc-siR3.2 (TACATTGTGGATCTTGTAGGT; SEQ ID NO:44), or Bc-siR5 (TTTGACTCGGAATGTATACTT; SEQ ID NO:45).

Polynucleotides Targeting Pathogen sRNAs

In some embodiments, the function of a pathogen sRNA as described herein in a plant is blocked, attenuated, or reduced by expressing in the plant a polynucleotide that is complementary or substantially complementary to the sRNA or that mediates the destruction of the sRNA. As used herein, the term "mediates destruction of an sRNA" refers to inducing or promoting the degradation of a small RNA (e.g., by a small RNA degrading nuclease). In some embodiments, the polynucleotide encodes a short tandem target mimic (STTM) that targets the sRNA. In some embodiments, the polynucleotide encodes an antisense nucleic acid that is complementary or substantially complementary to the sRNA.

Short Tandem Target Mimics

In some embodiments, a short tandem target mimic (STTM) construct is used to block or attenuate function or activity of the pathogen sRNA. STTMs are composed of two short polynucleotide sequences mimicking small RNA target sites (e.g., one or more pathogen sRNA sites as described herein), separated by a linker of an empirically determined optimal size. STTMs trigger efficient degradation of targeted sRNAs by small RNA degrading nucleases. See Yan et al., *Plant Cell* 24:415-427 (2012).

Typically, the STTM is designed to have two noncleavable sRNA binding sites separated by a spacer. The two noncleavable sRNA binding sites can be either identical (to target one specific sRNA) or slightly different to target two slightly different sRNAs. The optimal length of the spacer is typically from about 48 to 88 nucleotides, although shorter or longer spacer sequences can be used. The sequences of the spacer should be relatively AT rich and able to form a stable stem. Methods of designing and testing STTM constructs are described, e.g., in Yan et al., *Plant Cell* 24:415-427 (2012), and in Tang et al., *Methods* 58:118-125 (2012), incorporated by reference herein.

In some embodiments, the polynucleotide comprises an STTM construct that targets an sRNA sequence listed in FIG. 16 (e.g., Bc-siR3.2, Bc-siR3.1, or Bc-siR5) or Table 1 (e.g., Bc-siR1, Bc-siR1010, Bc-siR3.1, Bc-siR3.2, Bc-siR1008, Bc-siR5, Bc-siR9, Bc-siR10, Bc-siR18, Bc-siR15, Bc-siR17, Bc-siR22, Bc-siR24, Bc-siR25, Bc-siR1015, Bc-siR20, Bc-siR1021, Bc-siR1002, Bc-siR28, Bc-siR31, Bc-siR29, Bc-siR41, Bc-siR35, Bc-siR57, Bc-siR43, Bc-siR40, Bc-siR38, Bc-siR46, Bc-siR48, Bc-siR1007, Bc-siR56, Bc-siR49, Bc-siR58, Bc-siR63, Bc-siR1005, Bc-siR60, Bc-siR61, Bc-siR62, Bc-siR65, Bc-siR67, Bc-siR68, Bc-siR73, Bc-siR81, Bc-siR82, Bc-siR86, Bc-siR91, Bc-siR92, Bc-siR95, Bc-siR1017, Bc-siR97, Bc-siR99, Bc-siR1013, Bc-siR102, Bc-siR1011, Bc-siR109, Bc-siR1018, Bc-siR114, Bc-siR1020, Bc-siR1016, Bc-siR1003, Bc-siR124, Bc-siR127, Bc-siR128, Bc-siR130, Bc-siR1004, Bc-siR144, Bc-siR137, Bc-siR140, Bc-siR141, Bc-siR156, Bc-siR161, Bc-siR163, or Bc-siR1001).

In some embodiments, the polynucleotide comprises an STTM construct that is generated using a pair of primers (a forward primer and a reverse primer) listed in Table 2. The STTM primers (e.g., the primers listed in Table 2) are used to amplify and clone into an expression vector a STTM construct having a sequence that targets an sRNA of interest (e.g., an sRNA listed in FIG. 16 or Table 1, e.g., any of Bc-siR1, Bc-siR1010, Bc-siR3.1, Bc-siR3.2, Bc-siR1008, Bc-siR5, Bc-siR9, Bc-siR10, Bc-siR18, Bc-siR15, Bc-siR17, Bc-siR22, Bc-siR24, Bc-siR25, Bc-siR1015, Bc-siR20, Bc-siR1021, Bc-siR1002, Bc-siR28, Bc-siR31, Bc-siR29, Bc-siR41, Bc-siR35, Bc-siR57, Bc-siR43, Bc-siR40, Bc-siR38, Bc-siR46, Bc-siR48, Bc-siR1007, Bc-siR56, Bc-siR49, Bc-siR58, Bc-siR63, Bc-siR1005, Bc-siR60, Bc-siR61, Bc-siR62, Bc-siR65, Bc-siR67, Bc-siR68, Bc-siR73, Bc-siR81, Bc-siR82, Bc-siR86, Bc-siR91, Bc-siR92, Bc-siR95, Bc-siR1017, Bc-siR97, Bc-siR99, Bc-siR1013, Bc-siR102, Bc-siR1011, Bc-siR109, Bc-siR1018, Bc-siR114, Bc-siR1020, Bc-siR1016, Bc-siR1003, Bc-siR124, Bc-siR127, Bc-siR128, Bc-siR130, Bc-siR1004, Bc-siR144, Bc-siR137, Bc-siR140, Bc-siR141, Bc-siR156, Bc-siR161, Bc-siR163, or Bc-siR1001). In some embodiments, the STTM construct is expressed under the control of a promoter as described in Section IV below, e.g., a constitutively active promoter, an inducible promoter, or a tissue-specific promoter.

Antisense Technology

In some embodiments, antisense technology is used to block or attenuate function or activity of the pathogen sRNA. The antisense nucleic acid sequence that is transformed into plants is substantially identical to the pathogen sRNA sequence to be blocked. In some embodiments, the antisense polynucleotide sequence is complementary to the pathogen sRNA sequence to be blocked. However, the sequence does not have to be perfectly identical to inhibit expression. Thus, in some embodiments, an antisense polynucleotide sequence that is substantially complementary (e.g., at least 70%, at least 75%, at least 80%, at least 85%, at least 90%, or at least 95% complementary) to the pathogen sRNA sequence to be blocked can be used (e.g., in an expression cassette under the control of a heterologous promoter, which is then transformed into plants such that the antisense nucleic acid is produced). In some embodiments, the antisense polynucleotide is expressed under the control of a promoter as described in Section IV below, e.g., a constitutively active promoter, an inducible promoter, or a tissue-specific promoter.

In some embodiments, the polynucleotide encodes an antisense nucleic acid sequence that is complementary or substantially (e.g., at least 70%, at least 75%, at least 80%, at least 85%, at least 90%, or at least 95%) complementary to an sRNA sequence listed in FIG. 16 (e.g., an antisense nucleic acid sequence that is complementary or substantially complementary to Bc-siR3.2, Bc-siR3.1, or Bc-siR5) or Table 1 (e.g., an antisense nucleic acid sequence that is complementary or substantially complementary to Bc-siR1, Bc-siR1010, Bc-siR3.1, Bc-siR3.2, Bc-siR1008, Bc-siR5, Bc-siR9, Bc-siR10, Bc-siR18, Bc-siR15, Bc-siR17, Bc-siR22, Bc-siR24, Bc-siR25, Bc-siR1015, Bc-siR20, Bc-siR1021, Bc-siR1002, Bc-siR28, Bc-siR31, Bc-siR29, Bc-siR41, Bc-siR35, Bc-siR57, Bc-siR43, Bc-siR40, Bc-siR38, Bc-siR46, Bc-siR48, Bc-siR1007, Bc-siR56, Bc-siR49, Bc-siR58, Bc-siR63, Bc-siR1005, Bc-siR60, Bc-siR61, Bc-siR62, Bc-siR65, Bc-siR67, Bc-siR68, Bc-siR73, Bc-siR81, Bc-siR82, Bc-siR86, Bc-siR91, Bc-siR92, Bc-siR95, Bc-siR1017, Bc-siR97, Bc-siR99, Bc-siR1013, Bc-siR102, Bc-siR1011, Bc-siR109, Bc-siR1018, Bc-siR114, Bc-siR1020, Bc-siR1016, Bc-siR1003, Bc-siR124, Bc-siR127, Bc-siR128, Bc-siR130, Bc-siR1004, Bc-siR144, Bc-siR137, Bc-siR140, Bc-siR141, Bc-siR156, Bc-siR161, Bc-siR163, or Bc-siR1001).

Other methods of using oligonucleotide or polynucleotide constructs for blocking the function of small RNAs as described herein can also be used, such as target mimicry (see, e.g., Franco-Zorrilla et al., *Nat Genet.* 39:1033-1037 (2007)) and "sponges" (see, e.g., Ebert et al., *Nat. Methods* 4:721-726 (2007)).

III. Expression of sRNA-Resistant Targets

In another aspect, methods of making plants that are resistant to one or more pathogen sRNAs are provided. In some embodiments, the method comprises:

introducing into a plant a heterologous expression cassette comprising a promoter operably linked to a polynucleotide that is an sRNA-resistant target that encodes a protein that functions in plant immunity, wherein the promoter is heterologous to the polynucleotide; and selecting a plant comprising the expression cassette.

In another aspect, expression cassettes comprising a promoter operably linked to a polynucleotide encoding a sRNA-resistant target, isolated nucleic acids comprising said expression cassettes, or plants comprising said expression cassettes, are provided. In some embodiments, a plant into which the expression cassette has been introduced has enhanced pathogen resistance relative to a control plant lacking the expression cassette. In some embodiments, a plant into which the expression cassette has been introduced has enhanced resistance to a fungal pathogen (e.g., *Botrytis*, e.g., *B. cinera*) relative to a control plant lacking the expression cassette.

In some embodiments, the promoter is heterologous to the polynucleotide. In some embodiments, the polynucleotide encoding the sRNA-resistant target is operably linked to an inducible promoter. In some embodiments, the promoter is pathogen inducible (e.g., a *Botrytis* inducible promoter). In some embodiments, the promoter is stress inducible (e.g., an abiotic stress inducible promoter). In some embodiments, the promoter is tissue-specific (e.g., epidermis-specific).

sRNA-Resistant Targets

In some embodiments, the polynucleotide is an sRNA-resistant target that encodes a protein that functions or is predicted to function in plant immunity. As used herein, an sRNA-resistant target is a polynucleotide sequence having a synonymous mutation of a sequence that is targeted by a pathogen sRNA. As used herein, the term "synonymous mutation" refers to a change, relative to a reference sequence, in a DNA sequence that encodes for a protein or peptide (e.g., at 1, 2, 3, 4, 5, 6, 7, 8, 9, 10, or more nucleotides relative to the reference sequence), wherein the change does not alter the amino acid that is encoded. For example, in some embodiments, pathogen sRNAs target plant immunity genes such as mitogen-activated protein kinases (including but not limited to, mitogen-activated protein kinase 1 (MPK1) or mitogen-activated protein kinase 2 (MPK2)); accordingly, in some embodiments an sRNA-resistant target comprises a synonymous mutation of a plant gene that encodes a mitogen-activated protein kinase (e.g., a synonymous mutation of MPK1 or MPK2).

In some embodiments, a polynucleotide sequence is an sRNA-resistant target if the polynucleotide sequence if the amino acid encoded by the polynucleotide sequence is produced at a detectable level. In some embodiments, a polynucleotide sequence is an sRNA-resistant target if the polynucleotide sequence if the amount of amino acid produced by a plant expressing the polynucleotide sequence in the presence of a pathogen sRNA is decreased by no more than 50%, 40%, 30%, 20%, 10%, 5%, or less relative to the amount of amino acid produced by a control plant expressing the polynucleotide sequence in the absence of the pathogen sRNA. Whether a polynucleotide is an sRNA-resistant target can be tested, for example, using a coexpression assay in *Nicotiana benthamiana* in which the sRNA is coexpressed with a polynucleotide sequence (e.g., a target gene or a synonymous mutation of the target gene) and the level of gene silencing induced by sRNA is measured. See, e.g., Example 1.

In some embodiments, the polynucleotide encodes a protein that functions or is predicted to function in plant immunity. In some embodiments, the polynucleotide comprises an sRNA-resistant target gene or predicted target gene listed in FIG. 16, Table 1, or Table 3. In some embodiments, the polynucleotide comprises a synonymous mutation of an sRNA target gene that encodes mitogen activated protein kinase 1 (MPK1), mitogen activated protein kinase 2 (MPK2), peroxiredoxin (PRXIIF), cell-wall associated kinase (WAK), or mitogen activated protein kinase kinase kinase 4 (MAPKKK4). In some embodiments, the polynucleotide comprises a synonymous mutation of an sRNA target gene in tomato selected from Solyc08g081210.2.1, Solyc03g061650.1.1, Solyc01g108160.2.1, Solyc09g014790.2.1, Solyc03g112190.2.1, or Solyc07g066530.2.1. In some embodiments, the polynucleotide comprises a synonymous mutation of an sRNA target gene in *Vitis* selected from VIT_10s0092g00240, VIT_12s0028g01140, VIT_06s0009g01890, VIT_10s0116g00190, VIT_05s0020g01790, VIT_01s0011g01000, VIT_05s0077g01510.

In some embodiments, the polynucleotide is substantially identical (e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13. In some embodiments, the polynucleotide is a homolog of any of SEQ ID NOS:4-13 (e.g., a homolog found in a species of Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malta, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, or *Zea*).

In some embodiments, the polynucleotide is substantially identical (e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to any of SEQ ID NOS:4-13, comprises 1, 2, 3, 4, 5, 6, 7, 8, 9, 10 or more nucleotide mutations relative to SEQ ID NOS:4-13, and encodes an identical protein as SEQ ID NOS:4-13. Non-limiting examples of nucleotide mutations (synonymous mutations) that can be made in the sequences of SEQ ID NOS:4-13 are described below in Example 3, as shown in the alignments of sRNA sequences to wild-type target gene sequences and mutated target gene sequences.

In some embodiments, the sRNA-resistant target gene comprises a polynucleotide sequence that is resistant to gene silencing by an sRNA listed in FIG. 16 or Table 1. In some embodiments, the sRNA-resistant target comprises a polynucleotide sequence that is resistant to gene silencing by Bc-siR3.1 (TTGTGGATCTTGTAGGTGGGC; SEQ ID NO:43), Bc-siR3.2 (TACATTGTGGATCTTGTAGGT; SEQ ID NO:44), or Bc-siR5 (TTTGACTCGGAATGTATACTT; SEQ ID NO:45).

IV. Polynucleotides and Recombinant Expression Vectors

The isolation of polynucleotides of the invention may be accomplished by a number of techniques. For instance, oligonucleotide probes based on the sequences disclosed here can be used to identify the desired polynucleotide in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. Alternatively, cDNA libraries from plants or plant parts (e.g., flowers) may be constructed.

The cDNA or genomic library can then be screened using a probe based upon a sequence disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Polynucleotides can also be synthesized by well-known techniques as described in the technical literature. See, e.g., Carruthers et al., Cold Spring Harbor Symp. *Quant. Biol.* 47:411-418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Once a polynucleotide sequence that is complementary to the pathogen sRNA or that mediates destruction of the pathogen sRNA, or a polynucleotide that is a sRNA-resistant target, is obtained, it can be used to prepare an expression cassette for expression in a plant. In some embodiments, expression of the polynucleotide is directed by a heterologous promoter.

Any of a number of means well known in the art can be used to drive expression of the polynucleotide sequence of interest in plants. Any organ can be targeted, such as shoot vegetative organs/structures (e.g. leaves, stems and tubers), epidermis, roots, flowers and floral organs/structures (e.g. bracts, sepals, petals, stamens, carpels, anthers and ovules), seed (including embryo, endosperm, and seed coat) and fruit. Alternatively, expression can be conditioned to only occur under certain conditions (e.g., using an inducible promoter).

For example, a plant promoter fragment may be employed to direct expression of the polynucleotide sequence of interest in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide sequence of interest in a specific tissue (tissue-specific promoters) or may be otherwise under more precise environmental control (inducible promoters). Examples of tissue-specific promoters under developmental control include promoters that initiate transcription only in certain tissues, such as the epidermis, leaves, or guard cells (including but not limited to those described in WO/2005/085449; U.S. Pat. Nos. 6,653,535; 7,834,243; EP Patent No. 1 888 754; Li et al., *Sci China C Life Sci.* 2005 April; 48(2):181-6; Husebye, et al., *Plant Physiol*, April 2002, Vol. 128, pp. 1180-1188; Plesch, et al., *Gene*, Volume 249, Number 1, 16 May 2000, pp. 83-89(7), and Sessions et al., *Plant J*, October 1999, Vol. 20, pp. 259-263, each of which is incorporated by reference). Examples of environmental conditions that may affect transcription by inducible promoters include the presence of a pathogen, anaerobic conditions, elevated temperature, or the presence of light.

In some embodiments, the promoter is an inducible promoter. In some embodiments, the promoter is stress inducible (e.g., inducible by abiotic stress). In some embodiments, the promoter is pathogen inducible. In some embodiments, the promoter is induced upon infection by *Botrytis*. Non-limiting examples of pathogen inducible promoters include *Botrytis*-Induced Kinase 1 (BIK1) and the plant defensing gene PDF1.2. See, e.g., Penninckx et al., *Plant Cell* 10:2103-2113 (1998); see also Veronese et al., *Plant Cell* 18:257-273 (2006). In some embodiments, the promoter is *A. thaliana* BIK1 (SEQ ID NO:1) or is substantially identical to *A. thaliana* BIK1 (SEQ ID NO:1). In some embodiments, the promoter is *A. thaliana* PDF1.2 (SEQ ID NO:2) or is substantially identical to *A. thaliana* PDF1.2 (SEQ ID NO:2). In some embodiments, the promoter is TPK1b (SEQ ID NO:3) or is substantially identical to TPK1b (SEQ ID NO:3).

In some embodiments, the promoter is a tissue-specific promoter. In some embodiments, the promoter is specifically expressed in the epidermis. Non-limiting examples of epidermis-specific promoters include Meristem Layer 1 (ML1). See, e.g., Takada et al., *Development* 140:1919-1923 (2013). In some embodiments, the promoter is substantially (e.g., at least 60, 70, 75, 80, 85, 90, or 95%) identical to *Arabidopsis* ML1 (SEQ ID NO:14) or tomato ML1 (SEQ ID NO:15).

In some embodiments, a polyadenylation region at the 3'-end of the coding region can be included. The polyadenylation region can be derived from a NH3 gene, from a variety of other plant genes, or from T-DNA.

The vector comprising the sequences will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

V. Production of Transgenic Plants

As detailed herein, embodiments of the present invention provide for transgenic plants comprising recombinant expression cassettes for expressing a polynucleotide sequence as described herein (e.g., a polynucleotide sequence that is complementary to the pathogen sRNA or that mediates destruction of the pathogen sRNA, or a polynucleotide encoding a sRNA-resistant target). In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

In some embodiments, the transgenic plants comprising recombinant expression cassettes for expressing a polynucleotide sequence as described herein have increased or enhanced pathogen resistance compared to a plant lacking the recombinant expression cassette, wherein the transgenic plants comprising recombinant expression cassettes for expressing the polynucleotide sequence have about the same growth as a plant lacking the recombinant expression cassette. Methods for determining increased pathogen resistance are described, e.g., in Section VI below.

A recombinant expression vector as described herein may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of the polynucleotide sequence of interest is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced pathogen resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer enhanced pathogen resistance on essentially any plant. Thus, the invention has use over a broad range of plants, including species from the genera Asparagus, *Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and *Zea*. In some embodiments, the plant is a tomato plant. In some embodiments, the plant is a vining plant, e.g., a species from the genus *Vitis*. In some embodiments, the plant is an ornamental plant. In some embodiments, the plant is a vegetable- or fruit-producing plant. In some embodiments, the plant is a monocot. In some embodiments, the plant is a dicot.

VI. Selecting for Plants with Enhanced Pathogen Resistance

Plants with enhanced pathogen resistance can be selected in many ways. One of ordinary skill in the art will recognize that the following methods are but a few of the possibilities. One method of selecting plants with enhanced pathogen resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). One of skill in the art will recognize that resistance responses of plants vary depending on many factors, including what pathogen, compound, or plant is used. Generally, enhanced resistance is measured by the reduction or elimination of disease symptoms (e.g., reduction in the number or size of lesions or reduction in the amount of fungal biomass on the plant or a part of the plant) when compared to a control plant. In some cases, however, enhanced resistance can also be measured by the production of the hypersensitive response (HR) of the plant (see, e.g., Staskawicz et al. (1995) *Science* 268(5211): 661-7). Plants with enhanced pathogen resistance can produce an enhanced hypersensitive response relative to control plants.

Enhanced pathogen resistance can also be determined by measuring the increased expression of a gene operably linked a defense related promoter. Measurement of such expression can be measured by quantifying the accumulation of RNA or subsequent protein product (e.g., using northern or western blot techniques, respectively (see, e.g., Sambrook et al. and Ausubel et al.).

VII. Examples

The following examples are offered to illustrate, but not limit the claimed invention.

Example 1: Fungal Small RNAs Suppress Plant Immunity by Hijacking Host RNA Interference Pathways

*Botrytis cinerea* is a fungal pathogen that infects almost all vegetable and fruit crops and annually causes $10-100 billion losses worldwide. With its broad host range, *B. cinerea* is a useful model for studying the pathogenicity of aggressive fungal pathogens. Many pathogens of plants and animals deliver effectors into host cells to suppress host immunity (H. Ashida et al., *Curr. Opin. Microbiol.* 14, 16 (2011); M. Rafiqi et al., *Curr. Opin. Plant Biol.* 15, 477 (2012); T. O. Bozkurt et al., *Curr. Opin. Plant Biol.* 15, 483 (2012); H. Hilbi, et al., *Traffic* 13, 1187 (2012)). All the pathogen effectors studied so far are proteins. Here we find that small RNA (sRNA) molecules derived from *B. cinerea* can act as effectors to suppress host immunity.

sRNAs induce gene silencing by binding to Argonaute (AGO) proteins and directing the RNA-induced silencing complex (RISC) to genes with complementary sequences. sRNAs from both plant and animal hosts have been recognized as regulators in host-microbial interaction (5-8).

Although sRNAs are also present in various fungi and oomycetes, including many pathogens (9-14), it has not been clear whether they regulate host-pathogen interaction.

To explore the role of *B. cinerea* sRNAs in pathogenicity, we profiled sRNA libraries prepared from *B. cinerea* (strain B05.10)-infected *Arabidopsis thaliana* Col-0 leaves collected at 0, 24, 48, and 72 h post inoculation (hpi) and from *B. cinerea*-infected *Solanum lycopersicum* (tomato) leaves and fruits at 0, 24, and 72 hpi. sRNA libraries prepared from *B. cinerea* mycelia, conidiospores and total biomass after 10 days of culture were used as controls. By using 100 normalized reads per million *B. cinerea* sRNA reads as a cutoff, we identified a total of 832 sRNAs that were present in both *B. cinerea*-infected *Arabidopsis* and *S. lycopersicum* libraries and had more reads in these two libraries than in the cultured *B. cinerea* libraries, with sequences exactly matching the *B. cinerea* B05.10 genome (15) but not *Arabidopsis* or *S. lycopersicum* genomes or cDNA (see, FIGS. 15 and 16 and Table 1). The closest sequence matches in *Arabidopsis* or *S. lycopersicum* contained a minimum of 2 mismatches. Among them, 27 had predicted microRNA-like precursor structures. A similar number of microRNA-like sRNAs was found in *Sclerotinia sclerotiorum* (9). We found that 73 Bc-sRNAs could target host genes in both *Arabidopsis* and *S. lycopersicum* under stringent target prediction criteria (FIG. 15). Among them, 52 were derived from 6 retrotransposon long terminal repeats (LTR) loci in the *B. cinerea* genome, 13 were from intergenic regions of 10 loci, and 8 were mapped to 5 protein coding genes.

Figure 5:
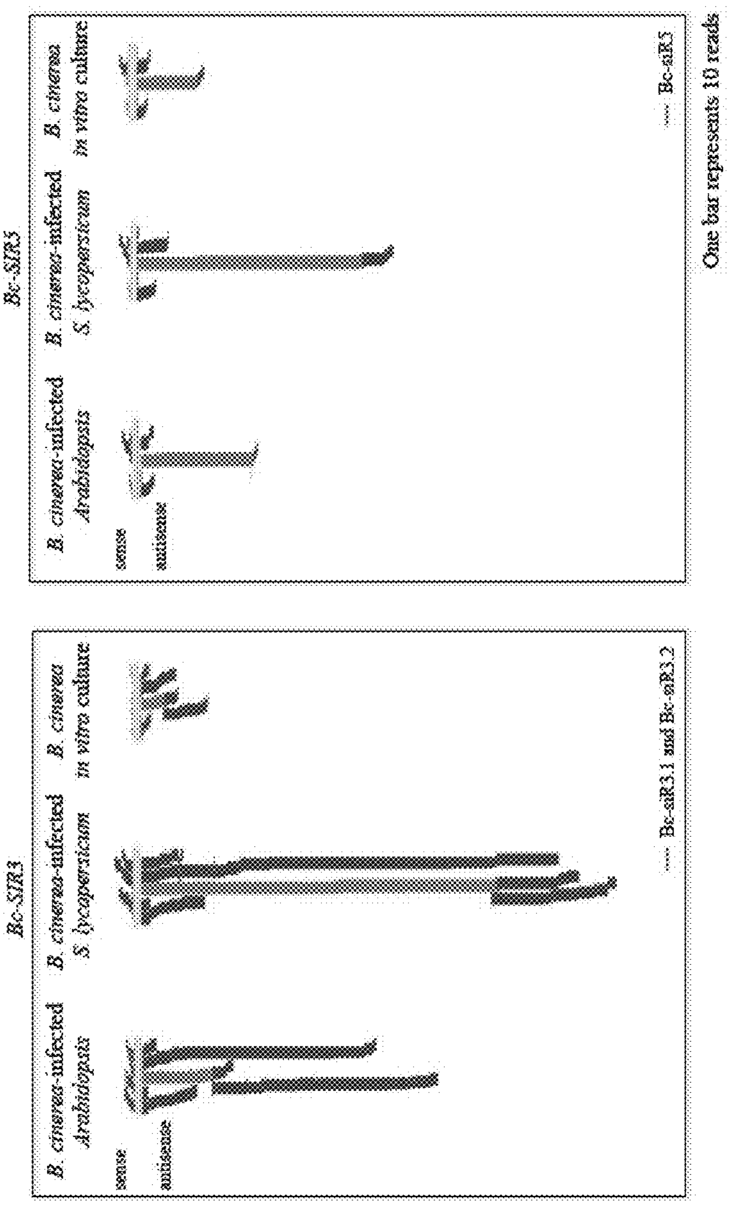
FIG. 5. Genomic map and read distribution of Bc-SIR3 and Bc-SIR5 loci. The genomic regions of 60 nt up- and downstream of the Bc-sRNA of interest were included. Sequence reads of Bc-siR3 and Bc-siR5 in *B. cinerea*-infected *Arabidopsis* (0, 24, 48, 72 hpi), *B. cinerea*-infected *S. lycopersicum* (leaf/fruit 0, 24, 72 hpi), or in vitro culture *B. cinerea* sRNA libraries (conidiospores, mycelia, total biomass) (see, FIG. 15) are shown in three individual panels. Bc-siR3 and Bc-siR5 reads are in red. In vitro culture *B. cinerea* sRNA libraries did not show a clear peak for Bc-siR3.1 or Bc-siR3.2 compared to *B. cinerea*-infected

Some of the predicted plant targets, such as MAPKs, are likely to function in plant immunity. To test whether Bc-sRNAs could indeed suppress host genes during infection, three Bc-sRNAs (Bc-siR3.1, Bc-siR3.2, and Bc-siR5) were selected for further characterization (FIG. 16). These Bc-sRNAs were among the most abundant sRNAs that were 21 nt in length and had potential targets likely to be involved in plant immunity in both *Arabidopsis* and *S. lycopersicum*. These sRNAs were also enriched after infection (FIGS. 1A-1B, FIG. 5, and FIG. 16), and were the major sRNA products from their encoding loci, LTR retrotransposons (FIG. 5). Bc-siR3.1 and Bc-siR3.2 were derived from the same locus with a four-nucleotide shift in sequence.

Figures 1A, 1B, 1C, 1D, 1E, 1F, 1G:
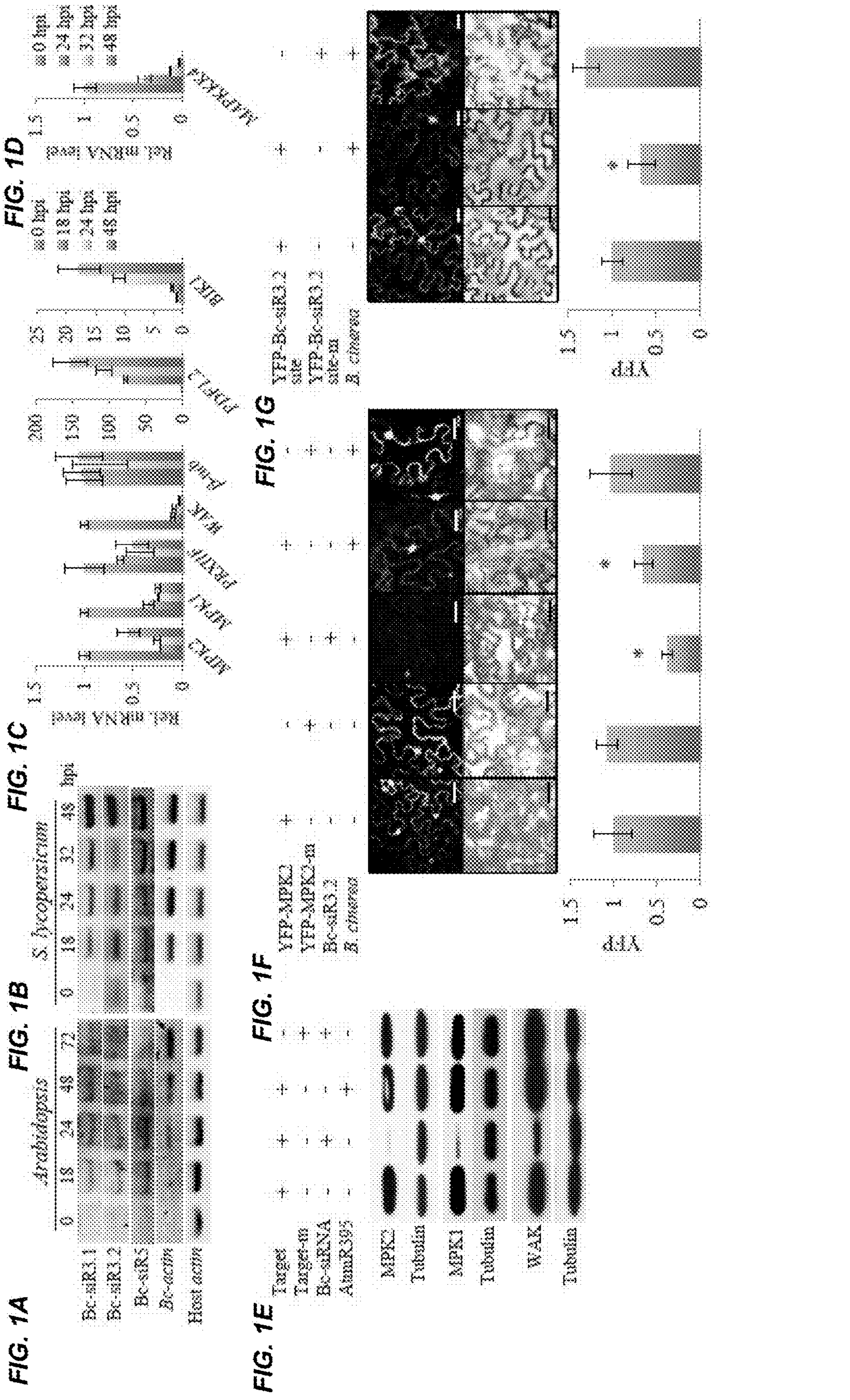
FIGS. 1A-1G. Bc-sRNAs silence host target genes in both *Arabidopsis* and *S. lycopersicum* during *B. cinerea* infection. (A) Bc-siR3.1, Bc-siR3.2, and Bc-siR5 were expressed during infection of *Arabidopsis* as detected at 18, 24, 48, and 72 hpi and, (B) *S. lycopersicum* leaves at 18, 24, 32, 48 hpi by RT-PCR. Actin genes of *B. cinerea*, and *Arabidopsis* and *S. lycopersicum* were used as internal controls. Similar results were obtained from three biological replicates. (C) The *Arabidopsis* targets of Bc-siRNAs were suppressed at 24, 32, and 48 hpi of *B. cinerea* infection. PDF1.2, BIK1 and β-tubulin were used as controls. (D) The *S. lycopersicum* target gene MAPKKK4 was suppressed upon *B. cinerea* infection. Expression (C and D) was measured by quantitative RT (qRT)-PCR using actin as an internal control. Error bars indicate standard deviation of three technical replicates. Similar results were seen in three biological replicates. (E) Co-expression of Bc-siR3.2 or Bc-siR5 with their host targets (HA-tagged) in *N. benthamiana* revealed target silencing by Western blot analysis. Co-expression of AtmiR395 or target site-mutated versions of target genes was used as controls. (F) Expression of YFP-MPK2 or its synonymously mutated version (YFP-MPK2-m) after infection of *B. cinerea* was observed by confocal microscopy. Co-expression of YFP-MPK2 and Bc-siR3.2 was used as a control. (G) Expression of the YFP sensors carrying a Bc-siR3.2 target site of MPK2 or a Bc-siR3.2 target site-m was analyzed after infection of *B. cinerea*. Samples were examined at 24 hpi. Upper panel: YFP; bottom panel: YFP/bright field overlay; scale bars (F, G), 37.5 μm. Error bars indicate standard deviation of 20 images (F, G). The asterisk indicates significant difference (two-tail t-test; $p<0.01$). Similar results were obtained in three biological replicates in E-G.

To determine whether Bc-sRNAs could trigger silencing of host genes, we examined the transcript levels of the predicted target genes after *B. cinerea* infection. The following *Arabidopsis* genes were targeted in the coding regions and were suppressed after *B. cinerea* infection: mitogen activated protein kinase 2 (MPK2) and MPK1, which are targeted by Bc-siR3.2; an oxidative stress-related gene peroxiredoxin (PRXIIF), which is targeted by Bc-siR3.1; and a putative cell wall-associated kinase gene (WAK), which is targeted by Bc-siR5 (FIG. 1C). In contrast, the plant defense marker genes PDF1.2 and BIK1 (P. Veronese et al., *Plant Cell* 18, 257 (2006)), which do not contain the Bc-sRNA target sites, were highly induced upon *B. cinerea* infection (FIG. 1C). We conclude that suppression of some but not all genes is a result of sequence-specific sRNA interaction and not due to cell death within infected lesions. Bc-siR3.2, which silences *Arabidopsis* MPK1 and MPK2, was enriched also in *S. lycopersicum* leaves upon *B. cinerea* infection and was predicted to target another member of the MAPK signaling cascade in *S. lycopersicum*, MAPKKK4 (FIG. 1B, FIG. 16). Expression of MAPKKK4 was indeed suppressed upon *B. cinerea* infection (FIG. 1D).

To confirm that the suppression of the targets was indeed triggered by Bc-sRNAs, we performed co-expression assays in *Nicotiana benthamiana*. Expression of HA-epitope tagged MPK2, MPK1, and WAK was reduced when they were co-expressed with the corresponding Bc-sRNAs but not when co-expressed with *Arabidopsis* miR395 that shared no sequence similarity (FIG. 1E). The silencing was abolished, however, when the target genes carried a synonymously mutated version of the relevant Bc-sRNA target sites (FIG. 6A, FIG. 1E). We also observed suppression of YFP-tagged target MPK2 by *B. cinerea* infection at 24 hpi (FIG. 1F and FIG. 6B); when the Bc-siR3.2 target site of MPK2 was mutated, infection by *B. cinerea* failed to suppress its expression (FIG. 1F). Thus, Bc-siR3.2 delivered from *B. cinerea* is sufficient for inducing silencing of wild type MPK2 but cannot silence target site-mutated MPK2. Similarly, of the YFP-sensors with wild type or mutated Bc-siR3.2 target sites (FIG. 6C), only the wild type sensor was suppressed after *B. cinerea* infection (FIG. 1G).

Figures 2A, 2B, 2C, 2D, 2E, 2F:
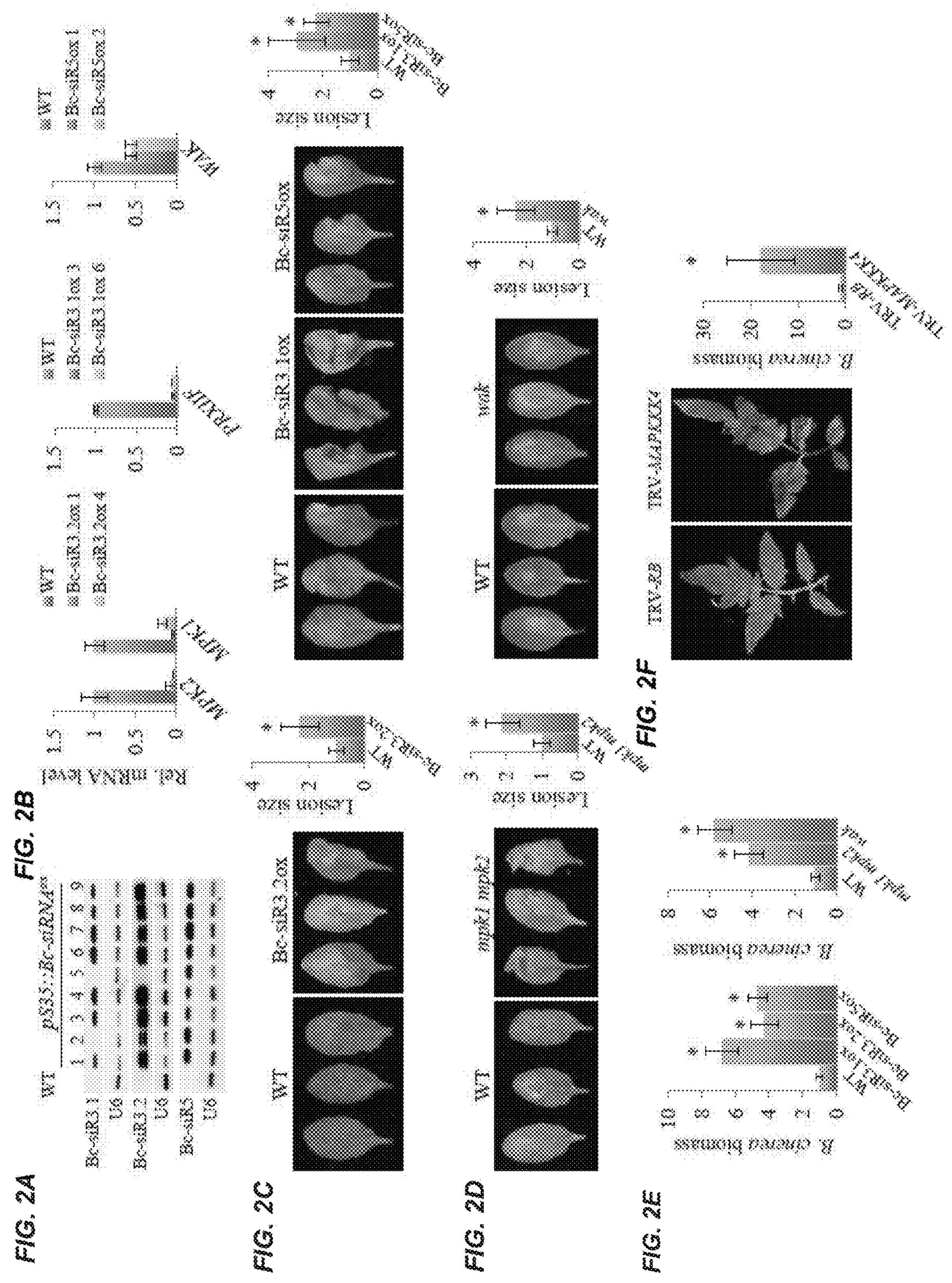
FIGS. 2A-2F. Bc-sRNAs trigger silencing of host targets that are involved in host immunity. (A) Expression of Bc-siR3.1, BcsiR3.2, or Bc-siR5 in transgenic *Arabidopsis* ectopically expressing Bc-siRNAs under the Cauliflower Mosaic Virus promoter 35S (Bc-sRNAox) was examined by Northern blot analysis. Highly expressed lines were selected for the following experiments. (B) Bc-sRNAox lines showed constitutive silencing of respective Bc-siRNA target genes measured by qRT-PCR. Two independent lines for each Bc-sRNAs were examined. Similar results were observed in two generations of the selected transgenic lines. (C) Bc-sRNAox plants exhibited enhanced disease susceptibility to *B. cinerea* compared to the wild type. (D) Loss-of-function mutants of Bc-siR3.2 and Bc-siR5 targets mpk1 mpk2 and wak displayed enhanced disease susceptibility. In all pathogen assays (C and D), lesion sizes were measured at 96 hpi. Error bars indicate the standard deviation of 20 leaves. (E) Biomass of *B. cinerea* was measured by qPCR at 96 hpi. Error bars indicate standard deviation of three technical replicates. For C, D and E, similar results were obtained from three biological repeats. (F) Virus-induced gene silencing (VIGS) of MAPKKK4 exhibited enhanced disease susceptibility to *B. cinerea* in *S. lycopersicum* (examined at 72 hpi) compared to control plants (TRV-RB). RB is a late-blight resistance gene that is not present in tomato. We chose to use a TRV vector with a fragment from a foreign gene as a control to eliminate the potential side effect of viral disease symptoms caused by TRV empty vector. Spray inoculation was used because silencing sectors are not uniform within the VIGS plants. Three sets of experiments with each of 6-10 plants for each construct were performed, and similar results were obtained. The asterisk indicates significant difference (two-tail t-test, $p<0.01$) in C-F.

To test the effect of Bc-sRNAs on host plant immunity, we generated transgenic *Arabidopsis* plants that ectopically expressed Bc-siR3.1, Bc-siR3.2, or Bc-siR5 using a plant artificial miRNA vector (FIG. 2A) (17). These Bc-sRNA expression (Bc-sRNAox) lines showed normal morphology and development without pathogen challenge when compared to the wild type plants, and expression of the target genes was suppressed (FIG. 2B). With pathogen challenge, all of the Bc-sRNAox lines displayed enhanced susceptibility to *B. cinerea* (FIG. 2C, 2E). The results indicate that these Bc-sRNAs play a positive role in *B. cinerea* pathogenicity.

Enhanced disease susceptibility of the Bc-sRNAox lines suggests that the target genes of these Bc-sRNAs are likely to be involved in host immunity against *B. cinerea*. Plants with mutated target genes showed normal morphology and development without pathogen challenge. The *Arabidopsis* targets of Bc-siR3.2, MPK1 and MPK2, are homologs that share 87% amino acid identity. These genes are functionally redundant and are co-activated in response to various stress factors (18). The mpk1 mpk2 double mutant exhibited enhanced susceptibility to *B. cinerea* (FIG. 2D, 2E). A T-DNA knockout mutant of the Bc-siR5 target WAK (SALK_089827) (FIG. 7A) also displayed enhanced susceptibility to *B. cinerea* (FIG. 2D, 2E). Consistent with this, Bc-siRNAox lines as well as mpk1 mpk2 and wak showed lower induction of the defense marker gene BIK1 (FIG. 7B). These results suggest that the MPK1, MPK2, and WAK genes, all of which are targeted by Bc-sRNAs, participate in the plant's immune response to *B. cinerea*. To determine whether MAPKKK4 is involved in *S. lycopersicum* defense response against *B. cinerea*, we applied the virus-induced gene silencing (VIGS) approach to knock down MAPKKK4 in *S. lycopersicum* using tobacco rattle virus (TRV) (FIG. 8A) (19). VIGS of TRV-MAPKKK4 caused a dwarf phenotype (FIG. 8B). The MAPKKK4-silenced plants showed enhanced disease susceptibility in response to *B. cinerea* and contained >15 times more fungal biomass than the control plants (FIG. 2F). We conclude that Bc-sRNAs silence plant genes to suppress host immunity during early infection.

These fungal sRNAs hijack the plant's own gene silencing mechanism. 63 of the 73 Bc-sRNAs that had predicted *Arabidopsis* and *S. lycopersicum* targets were 20-22 nucleotides in length with a 5' terminal U (see Table 1). This sRNA structure is favored for binding to AGO1 in *Arabidopsis* (S. J. Mi et al., *Cell* 133, 116 (2008); T. A. Montgomery et al., *Cell* 133, 128 (2008)). In order to determine whether Bc-sRNAs act through *Arabidopsis* AGO1, we immunoprecipitated AGO1 from *B. cinerea*-infected *Arabidopsis* collected at 24, 32 and 48 hpi and analyzed the AGO1-associated sRNAs. Bc-siR3.1, Bc-siR3.2 and Bc-siR5 were clearly detected in the AGO1-associated fraction pulled down from the infected plant samples but hardly in the control (FIG. 3A) or in the AGO2- and AGO4-associated sRNA fractions (FIG. 9). The sRNAs that had no predicted plant targets or had predicted targets that were not down-regulated by *B. cinerea* infection were not found in the AGO1-associated fractions (FIG. 10).

Figures 3A, 3B, 3C, 3D:
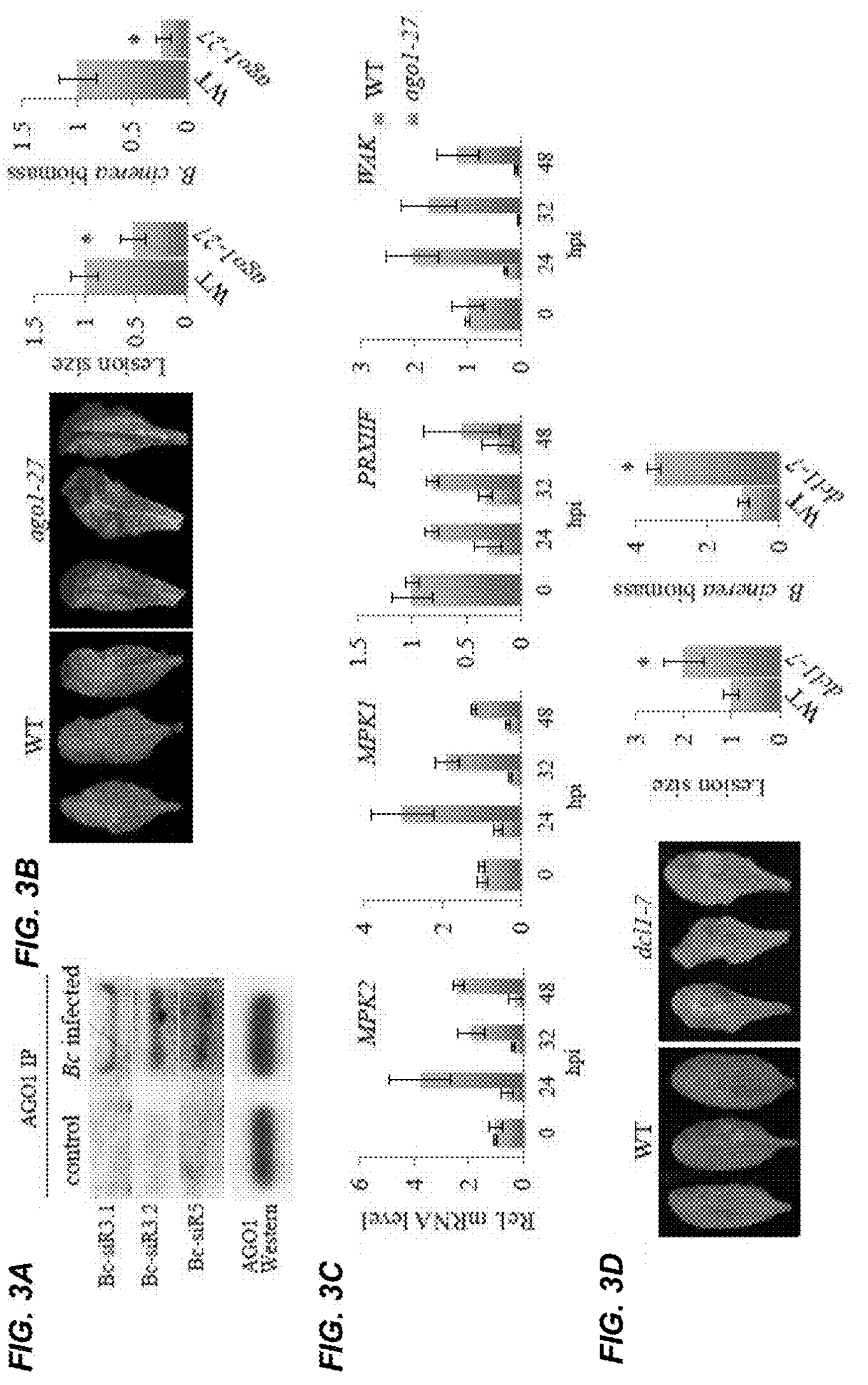
FIGS. 3A-3D. Bc-sRNAs hijack *Arabidopsis* AGO1 to suppress host immunity genes. (A) Loading of Bc-siR3.1, Bc-siR3.2 and Bc-siR5 into *Arabidopsis* AGO1 during infection was detected by AGO1-IP followed by RT-PCR. AGO1 from *B. cinerea*-infected leaves harvested at 24, 32 and 48 hpi was pulled down by AGO1 peptide antibody, and RNA was extracted from the AGO1-IP fraction. As a control, non-infected leaves mixed with *B. cinerea* mycelium (at least twice as much as that in *B. cinerea*-infected leaves at 48 hpi) were used to rule out any binding between AGO1 and Bc-sRNAs during the experimental procedures. Similar results were obtained from at least three biological repeats. (B) *Arabidopsis* ago1-27 exhibited reduced disease susceptibility to *B. cinerea* compared to the wild type. Lesion size of at least 20 leaves and fungal biomass were measured at 96 hpi. (C) Silencing of MPK2, MPK1, PRXIIF, and WAK during *B. cinerea* infection was abolished in ago1-27. (D) *Arabidopsis* dcl1-7 exhibited enhanced disease susceptibility to *B. cinerea* compared to the wild type. Similar results were obtained from three biological repeats (B-D). The asterisk indicates significant difference (two-tail t-test, $p<0.01$) in B, D.

If AGO1 plays an essential role in Bc-sRNA-mediated host gene silencing, we would expect to see reduced disease susceptibility in the ago1 mutant since these Bc-sRNAs could no longer suppress host immunity genes. For plants carrying the ago1-27 mutant allele (J. B. Morel et al., *Plant Cell* 14, 629 (2002)) and were inoculated with *B. cinerea*, the disease level was significantly less than on the wild type (FIG. 3B and FIG. 11A). Consistent with this, BIK1 induction was increased compared to wild type (FIG. 11B). Furthermore, the expression of Bc-siR3.2 targets MPK2 and MPK1, Bc-siR3.1 target PRXIIF, and Bc-siR5 target WAK in ago1-27 was not suppressed compared to wild type infected plants after *B. cinerea* infection (FIG. 3C). On the contrary, *Arabidopsis* miRNA biogenesis mutant dicer-like (dcl) 1-7 that shows similar morphological defects to ago1-27 exhibited an enhanced disease level to *B. cinerea* (FIG. 3D). These results suggest that the increased resistance phenotype we observed in ago1-27 is not caused by any reduced vigor or pleiotropic phenotype, but due to the function of the Bc-siRNAs, and that *Arabidopsis* DCL1 is not required for the function of Bc-siRNAs. Thus, *B. cinerea* Bc-sRNAs evidently hijacked host RNAi machinery by loading into AGO1; the complex in turn suppressed host immunity genes.

Figures 4A, 4B, 4C, 4D, 4E, 4F, 4G:
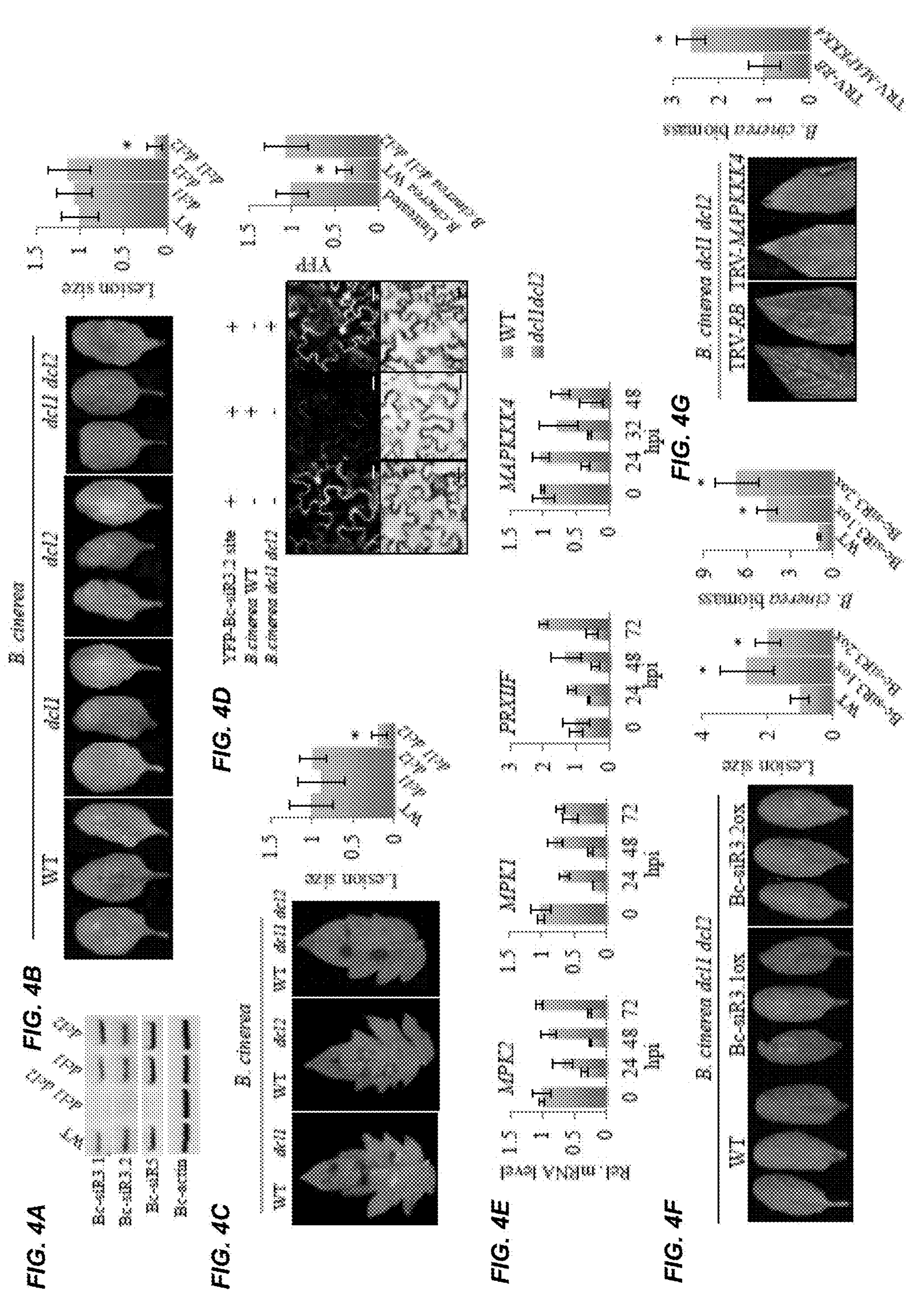
FIGS. 4A-4G. *B. cinerea* dcl1 dcl2 double mutant is compromised in virulence. (A) *B. cinerea* dcl1 dcl2 double mutant, but not dcl1 or dcl2 single mutants were impaired in generating Bc-siR3.1, Bc-siR3.2, and Bc-siR5 as revealed by RT-PCR. *B. cinerea* dcl1 dcl2 double mutant, but not dcl1 or dcl2 single mutants, produced much weaker disease symptoms than the wild type in *Arabidopsis* (B) and *S. lycopersicum* (C), as demonstrated by the lesion size measured of 20 leaves at 96 hpi and 48 hpi, respectively. Similar results were obtained from three biological repeats. (D) Expression of the sensor YFP-Bc-siR3.2 target site was silenced by wild type *B. cinerea* upon infection, but not by the dcl1 dcl2 mutant at 24 hpi (scale bar: 75 μm). Error bars indicate standard deviation of 20 images. Experiments were repeated two times with similar results. (E) *B. cinerea* dcl1 dcl2 mutant was compromised in suppression of MPK2, MPK1, PRXIIF in *Arabidopsis*, and MAPKKK4 in *S. lycopersicum*. Similar results were seen in two biological repeats. (F) *Arabidopsis* Bc-siR3.1ox and Bc-siR3.2ox lines were more susceptible to *B. cinerea* dcl1 dcl2 strain than Col-0 wild type. (G) Enhanced disease phenotype of dcl1 dcl2 infection was also observed on three TRV-MAPKKK4 silenced *S. lycopersicum* plants. Experiments in F and G were repeated three times with similar results. *B. cinerea* biomass was quantified at 96 hpi. The asterisk (in B, C, D, F, G) indicates significant difference (two-tail t-test; $p<0.01$).
Figure 13A:
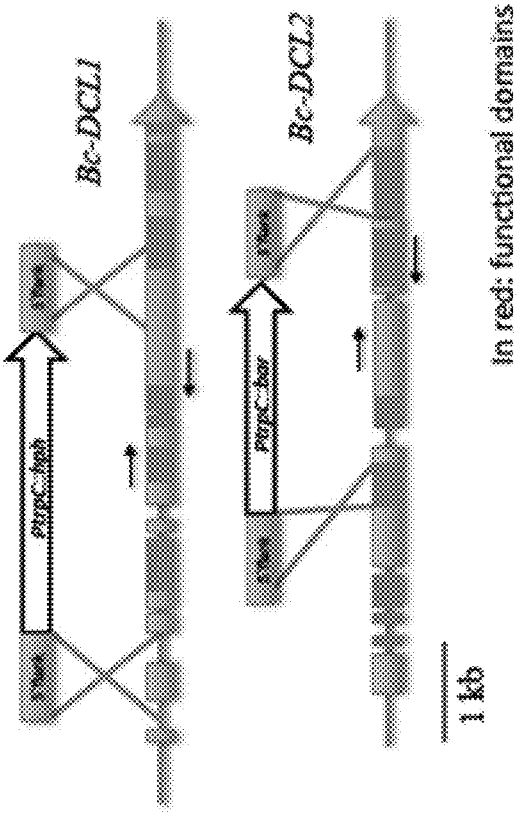
Figure 13B:
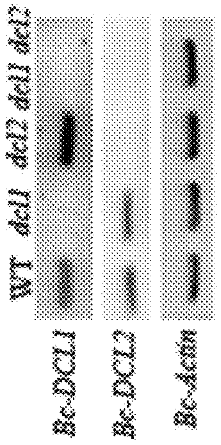
Figure 13C:
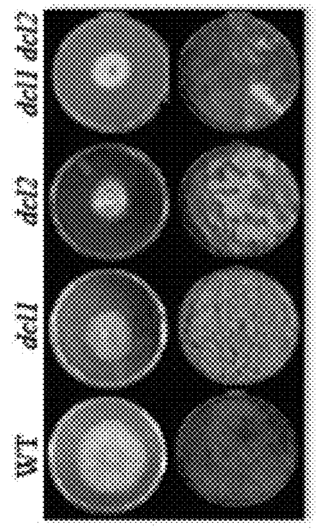
Figure 13D:
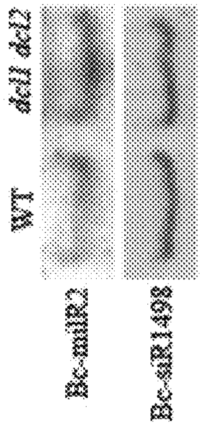

To delete the siR3 and siR5 loci from the *B. cinerea* genome by homologous recombination would be an ideal way to confirm their function; however, it is not feasible because siR3 is from a LTR with 3 copies and siR5 is from a LTR with 13 copies. To better understand the function and biogenesis of the Bc-sRNAs, we chose to knock out the *B. cinerea DCL genes, which encode the core sRNA processing enzymes. B. cinerea* strain B05.10 possesses two Dicer-like genes (Bc-DCL1 and Bc-DCL2) (FIG. 12). We generated dcl1 and dcl2 single and dcl1 dcl2 double knockout mutant strains through homologous recombination (FIG. 13A-13B). We found that dcl1 and dcl2 single mutants showed reduced growth and delayed sporulation (FIG. 13C). The dcl1 dcl2 double mutant displayed a more obvious phenotype than each of the single mutants, suggesting partial functional redundancy between DCL1 and DCL2 in *B. cinerea*. Bc-siR3.1, Bc-siR3.2, and Bc-siR5 could not be detected in the dcl1 dcl2 double mutant (FIG. 4A), indicating that they were DCL-dependent, while two other Bc-siRNAs, Bc-milR2 and Bc-siR1498, could still be detected in dcl1 dcl2 double mutant (FIG. 13D). Fungi have diverse sRNA biogenesis pathways, and not all sRNAs are DCL-dependent (H. C. Lee et al., *Mol. Cell* 38, 803 (2010)). The dcl1 dcl2 double mutant caused significantly smaller lesions than the wild type or dcl1 and dcl2 single mutants on both *Arabidopsis* and *S. lycopersicum* leaves (FIG. 4B-4C), in consistence with the significantly reduced fungal biomass at 72 hpi in *Arabidopsis* and 48 hpi in *S. lycopersicum* (FIG. 14), which indicates that the virulence of the dcl1 dcl2 mutant was greatly reduced. These results further support the conclusion that Bc-siRNAs, particularly Bc-siR3.1, Bc-siR3.2 and Bc-siR5 that depend on DCL function, contribute to the pathogenicity of *B. cinerea*. Mutation of dcl1 or dcl2 in *B. cinerea* caused delayed growth and sporulation (FIG. 13C) but had no effect on pathogenicity (FIG. 4B-4C). Furthermore, expression of the YFP sensor carrying the Bc-siR3.2 target site in *N. benthamiana* was silenced when infected with wild type *B. cinerea*. The suppression was abolished when inoculated with the dcl1 dcl2 strain (FIG. 4D), indicating that the dcl1 dcl2 double mutant was unable to generate Bc-siR3.2 to suppress the target. We also confirmed the inability of dcl1 dcl2 to suppress Bc-siR3.1 and Bc-siR3.2 target genes MPK2, MPK1, and PRXIIF in *Arabidopsis* and MAPKKK4 in tomato upon infection (FIG. 4E). Consistent with this, the dcl1 dcl2 virulence was partially restored when infected on *Arabidopsis* Bc-siR3.1ox and Bc-siR3.2ox plants as well as in tomato TRV-MAPKKK4 silenced plants (FIG. 4F-4G).

Animal and plant pathogens have evolved virulence or effector proteins to counteract host immune responses. Various protein effectors have been predicted or discovered in fungal or oomycete pathogens from whole-genome sequencing and secretome analysis (M. Rafiqi et al., *Curr. Opin. Plant Biol.* 15, 477 (2012); T. O. Bozkurt et al., *Curr. Opin. Plant Biol.* 15, 483 (2012)), although delivery mechanisms are still under active investigation (D. Kale et al., *Cell* 142, 284 (2010); S. Wawra et al., *Curr. Opin. Microbiol.* 15, 685 (2012); M. Rafiqi et al., *Plant Cell* 22, 2017 (2010); S. Schornack et al., *Proc. Natl. Acad. Sci. USA* 107, 17421 (2010); S. Wawra et al., *Proc. Natl. Acad. Sci. USA* 109, 2096 (2012)). Here, we show that sRNAs as well can act as effectors through a mechanism that silences host genes in order to debilitate plant immunity and achieve infection. The sRNAs from *B. cinerea* hijack the plant RNAi machinery by binding to AGO proteins which in turn direct host gene silencing. Another fungal plant pathogen, *Verticllium* (*V.*) *dahliae*, also depends on AGO1 function for its pathogenicity (U. Ellendorff, et al., *J. Exp. Bot.* 60, 591 (2009)). The implications of these findings suggest an extra mechanism underlying pathogenesis promoted by sophisticated pathogens with the capability to generate and deliver small regulatory RNAs into hosts to suppress host immunity.

Material and Methods

Generation of dcl1, dcl2 Single and Double Mutants of *B. cinerea*

By using homologous recombination and the *Agrobacterium tumefaciens*-mediated transformation system adapted from Utermark and Karlovsky (U. Utermark, P. Karlovsky, *Protocol Exchange*, published online 20 Mar. 2008 (10.1038/nprot.2008.83)), we generated dcl1, dcl2 and dcl1 dcl2 deletion mutants in *B. cinerea* strain B05.10. Transformants were selected with 70 ppm hygromycin or 100 ppm $NH^4$-glufosinate.

Plant Materials and Protocols

Plant materials used in this study are: *Arabidopsis thaliana* ecotype Col-0, *Solanum lycopersicum* (tomato) cultivar Moneymaker, and *Nicotiana benthamiana, Arabidopsis* knockout mutants mpk1 mpk2 (SALK_063847×SALK_019507) (D. Ortiz-Masia et al., *FEBS Lett.* 581, 1834-1840 (2007)) and wak (SALK_089827).

The Gateway pEarley vectors (with YFP & HA tags) were used for expression of Bc-sRNA target genes (K. W. Earley et al., *Plant J.* 45, 616-629 (2006)). Bc-sRNAs were cloned into the miRNA319a backbone vector (R. Schwab et al., *Plant Cell* 18, 1121-1133 (2006)) and transferred into the Gateway vector pEarley100 (without tag) for expression.

Transient co-expression assays in *N. benthamiana* were performed as described in (X. Zhang et al., *Mol. Cell* 42, 356-366 (2011)).

Virus-induced gene silencing (VIGS) was performed by cloning a 294-bp MPKKK4 gene fragment into the TRV2 vector (Y. L. Liu et al., *Plant J.* 31, 777-786 (2002)).

Pathogen Assay

Four-week-old plants were inoculated by applying a single 20 μl droplet per leaf or by spray-inoculating the entire plant, using $2\times10^5$ spores/ml for *Arabidopsis* and $1\times10^4$ spores/ml for *S. lycopersicum* and *N. benthamiana*. Disease was assessed by measuring lesion size (ImageJ software) and/or by quantifying *B. cinerea* biomass using quantitative PCR with *B. cinerea*-specific ITS primers (FIG. 8).

Confocal Microscopy

YFP-tagged protein expression in *N. benthamiana* was quantified using the confocal microscopy system Leica SP2. Z-series images (10 images in a distance of 0.7 μM) were merged to gain average signal intensity. Merged images were exported as TIFF files and YFP quantity was measured using the ImageJ software.

AGO Immunoprecipitation (IP)

*Arabidopsis* AGO IP (X. Zhang et al., *Mol. Cell* 42, 356-366 (2011)) was conducted with 5 g fresh leaves collected at 24, 32 and 48 h after spray inoculation with *B. cinerea*. Uninfected leaves mixed with at least double amount of *B. cinerea* biomass as in 48 hpi samples were used as a control. AGO1 was purified with a peptide-specific antibody. AGO2 and AGO4 IPs were conducted using native promoter-driven transgenic epitope HA-tagged and c-MYC-tagged lines, respectively and commercial HA and c-MYC antibodies.

sRNA RT-PCR

RNA was extracted from *B. cinerea*-infected plant tissue or the AGO pull-down fraction using the Trizol method. Purified RNA was treated with DNase I and then used in RT-PCR (E. Varkonyi-Gasic et al., *Plant Methods* 3, 12 (2007)) to detect Bc-sRNAs. 35-40 cycles were used for detecting Bc-sRNAs, 22-28 cycles were used for detecting actin genes from *Arabidopsis, S. lycopersicum* and *B. cinerea*. Primers used for reverse transcription and amplification of Bc-siRNAs are listed in Table 2.

sRNA Cloning and Illumina HiSeq Data Analysis sRNAs (18-28 nucleotides) were isolated by 15% PAGE and libraries were constructed using the miRCat cloning system and deep sequencing was performed on an Illumina HiSeq 2000. The sequence datasets of sRNA libraries from *B. cinerea* (GSE45320), *B. cinerea*-infected *Arabidopsis* (GSE45323) and *B. cinerea*-infected *S. lycopersicum* (GSE45321) are available at the NCBI database. The sRNA sequencing reads were preprocessed with the procedure of quality control and adapter trimming by using fastx-toolkit (http://hannonlab.cshl.edu/fastx_toolkit/index.html). Following adapter trimming, sequences were mapped to *B. cinerea* B05.10, *Arabidopsis* (TAIR10), or *S. lycopersicum* (ITAG_SL2.40) genomes and only the reads that matched perfectly to each genome were used for further analysis. The read number for each distinct sRNA was normalized to the total *B. cinerea* mapped reads in *B. cinerea*-infected *A. thaliana* and *S. lycopersicum* libraries. The ratio of total *B. cinerea* mapped reads of *A. thaliana* and *S. lycopersicum* libraries is 2.5:1, so we divide the normalized siRNA read number of *S. lycopersicum* by 2.5.

The sRNAs we selected have satisfied the following conditions: 1) it must be present in both *B. cinerea*-infected *A. thaliana* and *S. lycopersicum* libraries; 2) its normalized read number was larger than 100 in *A. thaliana* or *S. lycopersicum* libraries; 3) its normalized reads must be higher than that in cultured *B. cinerea* libraries and 4) it has predicted targets in both *A. thaliana* and *S. lycopersicum.*

Target gene prediction for Bc-sRNA was performed using TAPIR1.1 (E. Bonnet et al., *Bioinformatics* 26, 1566-1568 (2010)) with more stringent requirement than described in (E. Bonnet et al., *Bioinformatics* 26, 1566-1568 (2010)). No gap or bulge within the alignment between the sRNA and the target was allowed, and the 10th nucleotide of the sRNA must perfectly match its target. At most one mismatch or two wobbles was allowed from position 2 to 12. A maximum of two continuous mismatches was allowed and a score of 4.5 was used as a cutoff. If a sRNA has predicted targets in both *A. thaliana* and *S. lycopersicum*, it was selected. The sRNAs were grouped if their 5' end position and 3' end position were within 3 nucleotides on the genomic loci. We presented the selected sRNAs with targets in both *A. thaliana* and *S. lycopersicum* in Table 1.

TABLE 1

<table>
<tr><td colspan="10">Bc-sRNAs that have predicted targets in both Arabidopsis and S. lycopersicum.</td></tr>
<tr><td>Bc-siRNA ID, locus, and siRNA sequence</td><td colspan="3">Normalized read counts</td><td colspan="2">Target gene alignment</td><td>SEQ ID</td><td></td><td>Target gene</td><td>Putative function of</td></tr>
<tr><td>(5'-3')</td><td>A</td><td>S</td><td>B</td><td colspan="2">and aligned score</td><td>NO:</td><td>AS*</td><td>ID/target site</td><td>target gene</td></tr>
<tr><td>siR1<br>SIR1 LTR<br>transposon<br>TCGAAG<br>CAAGAG<br>TAGAATT<br>CTG (SEQ<br>ID NO: 46)</td><td>147.4</td><td>3015.92</td><td>36.4</td><td>Bc-siRNA<br><br>Target</td><td>3'GTCTTAAGATGAGAACGAAGCT 5'<br>| ||||| | |||||:||||:<br>5'CTGAATTATCCTCTTGTTTCGG 3'</td><td>46<br><br>47</td><td>4.5</td><td>AT5G06290.1<br>686~708(CDS)</td><td>2-cysteine<br>peroxiredoxin B</td></tr>
<tr><td></td><td></td><td></td><td></td><td>Bc-siRNA<br><br>Target</td><td>3'GTCTTAAGATGAGAACGAAGCT 5'<br>|:|||||| :|||||||||:|:<br>5'CGGAATTCCGCTCTTGCTTTGG 3'</td><td>46<br><br>48</td><td>4.25</td><td>Solyc01g068070.2.1<br>1754~1776(cDNA)</td><td>Wd-repeat<br>protein<br>(AHRD V1 *-*-<br>C1FDE0_9CHLO);<br>contains<br>Interpro<br>domain(s)<br>IPR017986<br>WD40 repeat,<br>region</td></tr>
<tr><td>siR1010<br>SIR1010<br>Intergenic<br>region<br>TCGGGG<br>GAATTTT<br>TGATTGC<br>T (SEQ ID<br>NO: 49)</td><td>2484.9</td><td>1644.16</td><td>2403.2</td><td>Bc-siRNA<br><br>Target</td><td>3'TCGTTAGTTTTTAAGGGGGCT 5'<br>:|:|||| |||:|||||:||:<br>5'GGTAATCTAAAGTTCCCTCGG 3'</td><td>49<br><br>50</td><td>4.5</td><td>AT1G69330.1<br>566~587(CDS)</td><td>RING/U-box<br>superfamily<br>protein</td></tr>
<tr><td></td><td></td><td></td><td></td><td>Bc-siRNA<br><br>Target</td><td>3'TCGTTAGTTTTTAAGGGGGCT 5'<br>|| |:| |||||||:||:|||<br>5'AGAAGTGAAAAATTTCCTCGA 3'</td><td>49<br><br>51</td><td>4.5</td><td>Solyc07g018350.2.1<br>581~602(cDNA)</td><td>DNA<br>mismatch<br>repair protein<br>muts (AHRD<br>V1 *-*-<br>Q16P35_AEDAE);<br>contains<br>Interpro<br>domain(s)<br>IPR015536<br>DNA<br>mismatch</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>repair protein MutS-homolog MSH6</td></tr>
<tr><td>siR3.1 SIR2 LTR transposon TTGTGGA TCTTGTA GGTGGG C (SEQ ID NO: 52)</td><td>812.1</td><td>1231.08</td><td>49.9</td><td>Bc-siRNA<br><br>Target</td><td>3'CGGGTGGATGTTCTAGGTGTT 5'<br>:|||| |||||||||||||<br>5'ATCCACATACAAGATCCACAA 3'</td><td>52<br><br>53</td><td>3.25</td><td>AT1G50760.1<br>86~107(CDS)</td><td>Aminotransferase-like, plant mobile domain family protein</td></tr>
<tr><td></td><td></td><td></td><td></td><td>Bc-siRNA<br><br>Target</td><td>3'CGGGTGGATGTTCTAGGTGTT 5'<br>|||:| ||||||| |||||<br>5'GCCTAGCTACAAGAGCCACAT 3'</td><td>52<br><br>54</td><td>4.5</td><td>AT3G06050.1<br>333~354(CDS)</td><td>peroxiredoxin IIF</td></tr>
<tr><td></td><td></td><td></td><td></td><td>Bc-siRNA<br><br>Target</td><td>3'CGGGTGGATGTTCTAGGTGTT 5'<br>|:|| |:||||| ||||||||<br>5'GTCCCCTTACAACATCCACAA 3'</td><td>52<br><br>55</td><td>4</td><td>AT5G46795.1<br>401~422(CDS)</td><td>microspore-specific promoter 2</td></tr>
<tr><td></td><td></td><td></td><td></td><td>Bc-siRNA<br><br>Target</td><td>3'CGGGTGGATGTTCTAGGTGTT 5'<br>:||||:| |||||||||||:<br>5'ATCCACTTTCAAGATCCACAG 3'</td><td>52<br><br>56</td><td>4.25</td><td>Solyc01g108160.2.1<br>3210~3231(cDNA)</td><td>Autophagy-related protein 2 (AHRD V1 *-*- C1GCV2_PARBD); contains Interpro domain(s) IPR015412 ATG2, C-terminal</td></tr>
<tr><td></td><td></td><td></td><td></td><td>Bc-siRNA<br><br>Target</td><td>3'CGGGTGGATGTTCTAGGTGTT 5'<br>|||||||:||| ||||||:|<br>5'ACCCACCTGCAACATCCACGA 3'</td><td>52<br><br>57</td><td>4.5</td><td>Solyc09g014790.2.1<br>1194~1215(cDNA)</td><td>Class E vacuolar protein-sorting machinery protein hse1 (AHRD V1 *--- HSE1_EMENI); contains Interpro domain(s) IPR018205 VHS subgroup</td></tr>
</table>

TABLE 1-continued

<table>
<tr><th colspan="11">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>siR3.2<br>SIR2 LTR<br>transposon<br>TACATTG<br>TGGATCT<br>TGTAGGT<br>(SEQ ID<br>NO: 58)</td><td>202.1</td><td>996.52</td><td>33.1</td><td>Bc-siRNA<br><br>Target</td><td>3'TGGATGTTCTAGGTGTTACAT 5'<br>|:| | |||||:||||||||<br>5'ATCAAGAAGATTCACAATGTT 3'</td><td>58<br><br>59</td><td>4.5</td><td>AT1G10210.1<br>291~312(CDS)</td><td>mitogen-<br>activated<br>protein kinase 1</td></tr>
<tr><td></td><td></td><td></td><td></td><td>Bc-siRNA<br><br>Target</td><td>3'TGGATGTTCTAGGTGTTACAT 5'<br>|:| | ||||||||||||||:<br>5'ATCAAGAAGATCCACAATGTG 3'</td><td>58<br><br>60</td><td>3</td><td>AT1G59580.1<br>353~374(CDS)</td><td>mitogen-<br>activated<br>protein kinase<br>homolog 2</td></tr>
<tr><td></td><td></td><td></td><td></td><td>Bc-siRNA<br><br>Target</td><td>3'TGGATGTTCTAGGTGTTACAT 5'<br>|:||:||||:||:|:||||||<br>5'ATCTGCAAGGTCTATAATGTA 3'</td><td>58<br><br>61</td><td>4</td><td>AT3G16830.1<br>585~606(CDS)</td><td>TOPLESS-<br>related 2</td></tr>
<tr><td></td><td></td><td></td><td></td><td>Bc-siRNA<br><br>Target</td><td>3'TGGATGTTCTAGGTGTTACAT 5'<br>||:|:||||:||||||| ||:<br>5'ACTTGCAAGGTCCACAAGGTG 3'</td><td>58<br><br>62</td><td>4.5</td><td>AT4G28300.1<br>1444~1465(CDS)</td><td>Protein of<br>unknown<br>function<br>(DUF1421)</td></tr>
<tr><td></td><td></td><td></td><td></td><td>Bc-siRNA<br><br>Target</td><td>3'TGGATGTTCTAGGTGTTACAT 5'<br>|:||| |||||||| ||||||<br>5'ATCTAGAAGATCCAAAATGTA 3'</td><td>58<br><br>63</td><td>3.5</td><td>Solyc03g061650.1.1<br>907~928(cDNA)</td><td>F-box/LRR-<br>repeat protein<br>At3g26922<br>(AHRD V1 *-*-<br>FBL47_ARATH);<br>contains<br>Interpro<br>domain(s)<br>IPR006566<br>FBD-like</td></tr>
<tr><td></td><td></td><td></td><td></td><td>Bc-siRNA<br><br>Target</td><td>3'TGGATGTTCTAGGTGTTACAT 5'<br>| | ||||||| ||||||||:<br>5'AGCCACAAGATGCACAATGTG 3'</td><td>58<br><br>64</td><td>4.5</td><td>Solyc09g091030.2.1<br>1510~1531(cDNA)</td><td>Beta-amylase<br>(AHRD V1<br>****<br>E0AE02_SOLLC);<br>contains<br>Interpro<br>domain(s)<br>IPR013781<br>Glycoside<br>hydrolase,<br>subgroup,</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'-GUGGAUGUUCUAGGUGUUACA 5'<br>||::|| ||||||||| ||||<br>5'CAUUUAAAAGAUCCACCAUGU 3'</td><td>65<br><br>66</td><td>4.5</td><td>Solyc08g081210.2.1<br>1936~1956(cDNA)</td><td>catalytic core MPKKK4</td></tr>
<tr><td>siR1008 SIR6 CDS (spurious gene) TGTGATG ATGATCA GTTTATG C (SEQ ID NO: 67)</td><td>4255.7</td><td>635.28</td><td>299.8</td><td>Bc-siRNA<br><br>Target</td><td>3'CGTATTTGACTAGTAGTAGTGT 5'<br>|| ||||| ||||||||||:|<br>5'TCAGAAACTAATCATCATCATA 3'</td><td>67<br><br>68</td><td>4</td><td>AT1G04650.1<br>2418~2440(CDS)</td><td>unknown protein, hypothetical protein</td></tr>
<tr><td></td><td></td><td></td><td></td><td>Bc-siRNA<br><br>Target</td><td>3'CGTATTTGACTAGTAGTAGTGT 5'<br>|||||||| |||||:||||:|<br>5'TCATAAACTAATCATTATCATA 3'</td><td>67<br><br>69</td><td>4</td><td>AT4G39180.2<br>1911~1933(3'UTR)</td><td>Sec14p-like phosphatidylinositol transfer family protein</td></tr>
<tr><td></td><td></td><td></td><td></td><td>Bc-siRNA<br><br>Target</td><td>3'CGTATTTGACTAGTAGTAGTGT 5'<br>||| |:||| ||||||||||<br>5'GCAGAGACTCATCATCATCACC 3'</td><td>67<br><br>70</td><td>3.5</td><td>AT5G36940.1<br>221~243(CDS)</td><td>cationic amino acid transporter 3</td></tr>
<tr><td></td><td></td><td></td><td></td><td>Bc-siRNA<br><br>Target</td><td>3'CGTATTTGACTAGTAGTAGTGT 5'<br>||||| :||||||||||| |||<br>5'GCATATGCTGATCATCATAACA 3'</td><td>67<br><br>71</td><td>4.25</td><td>Solyc05g012030.1.1<br>603~625(cDNA)</td><td>At1g69160/F4N2_9 (AHRD V1 ***-Q93Z37_ARATH)</td></tr>
<tr><td></td><td></td><td></td><td></td><td>Bc-siRNA<br><br>Target</td><td>3'CGTATTTGACTAGTAGTAGTGT 5'<br>||| ||:| ||||||||| |||<br>5'GCAAAAGCAGATCATCATGACA 3'</td><td>67<br><br>72</td><td>4.5</td><td>Solyc06g076130.2.1<br>1605~1627(cDNA)</td><td>Unknown Protein (AHRD V1)</td></tr>
<tr><td>siR5 SIR3 LTR transposon TTTGACT CGGAAT GTATACT T (SEQ ID NO: 73)</td><td>1710</td><td>1380</td><td>302.6</td><td>Bc-siRNA<br><br>Target</td><td>3'TTCATATGTAAGGCTCAGTTT 5'<br>:| | |||| ||||||||||<br>5'GAATTTACAATCCGAGTCAAA 3'</td><td>73<br><br>74</td><td>4.5</td><td>AT3G05860.1<br>655~676(CDS)</td><td>MADS-box transcription factor family protein</td></tr>
<tr><td></td><td></td><td></td><td></td><td>Bc-siRNA<br><br>Target</td><td>3'TTCATATGTAAGGCTCAGTTT 5'<br>|| | || |||||||||||<br>5'TAGGAAACTTTCCGAGTCAAA 3'</td><td>73<br><br>75</td><td>4</td><td>AT3G07730.1<br>491~512(CDS)</td><td>unknown protein, hypothetical protein, uncharacterized protein</td></tr>
</table>

TABLE 1-continued

Bc-sRNAs that have predicted targets in both *Arabidopsis* and *S. lycopersicum*.

<table>
<tr><th rowspan="2">Bc-siRNA ID, locus, and siRNA sequence (5'-3')</th><th colspan="3">Normalized read counts</th><th colspan="2" rowspan="2">Target gene alignment and aligned score</th><th rowspan="2">SEQ ID NO:</th><th rowspan="2">AS*</th><th rowspan="2">Target gene ID/target site</th><th rowspan="2">Putative function of target gene</th></tr>
<tr><th>A</th><th>S</th><th>B</th></tr>
<tr><td></td><td></td><td></td><td></td><td>Bc-siRNA</td><td>3'TTCATATGTAAGGCTCAGTTT 5'</td><td>73</td><td>4</td><td>AT3G08530.1<br>3491~3512(CDS)</td><td>Clathrin, heavy chain</td></tr>
<tr><td></td><td></td><td></td><td></td><td></td><td>:||| |:|||||||:|||:||</td><td></td><td></td><td></td><td></td></tr>
<tr><td></td><td></td><td></td><td></td><td>Target</td><td>5'GAGTTTGCATTCCGGGTCGAA 3'</td><td>76</td><td></td><td></td><td></td></tr>
<tr><td></td><td></td><td></td><td></td><td>Bc-siRNA</td><td>3'TTCATATGTAAGGCTCAGTTT 5'</td><td>73</td><td>4.5</td><td>Solyc03g112190.2.1<br>1764~1785(cDNA)</td><td>Pentatricopeptide repeat-containing protein (AHRD V1 ***- D7LRK9_ARALY); contains Interpro domain(s) IPR002885 Pentatricopeptide repeat</td></tr>
<tr><td></td><td></td><td></td><td></td><td></td><td>|:||| ||||||:||| ||||</td><td></td><td></td><td></td><td></td></tr>
<tr><td></td><td></td><td></td><td></td><td>Target</td><td>5'AGGTAGACATTCTGAGGCAAA 3'</td><td>77</td><td></td><td></td><td></td></tr>
<tr><td></td><td></td><td></td><td></td><td>Bc-siRNA</td><td>3'TTCATATGTAAGGCTCAGTTT 5'</td><td>73</td><td>4</td><td>Solyc07g066530.2.1<br>910~931(cDNA)</td><td>Mitochondrial import receptor subunit TOM34 (AHRD V1 *--- B5X380_SALSA); contains Interpro domain(s) IPR011990 Tetratricopeptide-like helical</td></tr>
<tr><td></td><td></td><td></td><td></td><td></td><td>|||||| |||||| ||||||</td><td></td><td></td><td></td><td></td></tr>
<tr><td></td><td></td><td></td><td></td><td>Target</td><td>5'CAGTATAGATTCCGTGTCAAA 3'</td><td>78</td><td></td><td></td><td></td></tr>
<tr><td></td><td></td><td></td><td></td><td>Bc-siRNA</td><td>3'-UUCAUAUGUAAGGCUCAGUUU 5'</td><td>79</td><td>4.25</td><td>AT5G50290<br>495~515(CDS)</td><td>wall associated kinase</td></tr>
<tr><td></td><td></td><td></td><td></td><td></td><td>::||||||||||||:||||::</td><td></td><td></td><td></td><td></td></tr>
<tr><td></td><td></td><td></td><td></td><td>Target</td><td>5'GGGUAUACAUUCCGGGUCAGG 3'</td><td>80</td><td></td><td></td><td></td></tr>
<tr><td>siR9 SIR6 CDS (spurious gene) TTTTATG ATGAGC ATTTTTA GA (SEQ ID NO: 81)</td><td>3847.8</td><td>120.16</td><td>231.7</td><td>Bc-siRNA</td><td>3'AGATTTTTACGAGTAGTATTTT 5'</td><td>81</td><td>4.5</td><td>AT1G73880.1<br>146~168(CDS)</td><td>UDP-glucosyl transferase 89B1</td></tr>
<tr><td></td><td></td><td></td><td></td><td></td><td>|||:||| ||||||:||:|||</td><td></td><td></td><td></td><td></td></tr>
<tr><td></td><td></td><td></td><td></td><td>Target</td><td>5'ACTAGAAAAGCTCATTATGAAA 3'</td><td>82</td><td></td><td></td><td></td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence</th><th colspan="3">Normalized read counts</th><th colspan="2">Target gene alignment</th><th>SEQ ID</th><th></th><th>Target gene</th><th>Putative function of</th></tr>
<tr><th>(5'-3')</th><th>A</th><th>S</th><th>B</th><th colspan="2">and aligned score</th><th>NO:</th><th>AS*</th><th>ID/target site</th><th>target gene</th></tr>
<tr><td></td><td></td><td></td><td></td><td>Bc-siRNA<br><br>Target</td><td>3'AGATTTTTACGAGTAGTATTTT 5'<br>|:||:|||| |||| |||||||<br>5'TTTAGAAATTCTCAGCATAAAA 3'</td><td>81<br><br>83</td><td>4</td><td>Solyc04g005540.2.1<br>1920~1942(cDNA)</td><td>Cc-nbs-lrr, resistance protein</td></tr>
<tr><td></td><td></td><td></td><td></td><td>Bc-siRNA<br><br>Target</td><td>3 'AGATTTTTACGAGTAGTATTTT 5'<br>||| :||| |:||||||||||<br>5'TCTTGAAACGTTCATCATAAAA 3'</td><td>81<br><br>84</td><td>4.25</td><td>Solyc05g007170.2.1<br>7265~7287(cDNA)</td><td>Cc-nbs-lrr, resistance protein with an R1 specific domain</td></tr>
<tr><td></td><td></td><td></td><td></td><td>Bc-siRNA<br><br>Target</td><td>3'AGATTTTTACGAGTAGTATTTT 5'<br>|:|:| ||||||:||:||||||<br>5'TTTGATAATGCTTATTATAAAA 3'</td><td>81<br><br>85</td><td>4</td><td>Solyc07g017880.2.1<br>780~802(cDNA)</td><td>Peroxidase (AHRD V1 **** D4NYQ9_9ROSI); contains Interpro domain(s) IPR002016 Haem peroxidase, plant/fungal/bacterial</td></tr>
<tr><td></td><td></td><td></td><td></td><td>Bc-siRNA<br><br>Target</td><td>3'AGATTTTTACGAGTAGTATTTT 5'<br>||:||||||:||||||:|||<br>5'GCTGAAAATGTTCATCATGAAA 3'</td><td>81<br><br>86</td><td>3.5</td><td>Solyc10g050580.1.1<br>306~328(cDNA)</td><td>Protein binding protein (AHRD V1 ***- D7M3B0_ARALY)</td></tr>
<tr><td></td><td></td><td></td><td></td><td>Bc-siRNA<br><br>Target</td><td>3'AGATTTTTACGAGTAGTATTTT 5'<br>|||:||:| ||||| ||||||:<br>5'TCTGAAGAAGCTCAACATAAAG 3'</td><td>81<br><br>87</td><td>4.5</td><td>Solyc11g013490.1.1<br>561~583(cDNA)</td><td>Beta-1,3-galactosyltransferase 6 (AHRD V1 ***- B6UBH3_MAIZE); contains Interpro domain(s) IPR002659 Glycosyl transferase, family 31</td></tr>
<tr><td>siR10 SIR2 LTR transposon TTTTCTA GGTTGTA GGGTGCT (SEQ ID NO: 88)</td><td>2234.2</td><td>689.6</td><td>56.5</td><td>Bc-siRNA<br><br>Target</td><td>3'TCGTGGGATGTTGGATCTTTT 5'<br>||:| :||:||:|||||||||<br>5'AGTAATCTGCAGCCTAGAAAA 3'</td><td>88<br><br>89</td><td>4.25</td><td>AT1G63860.1<br>1124~1145(CDS)</td><td>Disease resistance protein (TIR-NBS-LRR class) family</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'TCGTGGGATGTTGGATCTTTT 5'<br>|| |::| ||||||||||||:<br>5'AGAATTCGACAACCTAGAAAG 3'</td><td>88<br><br>90</td><td>4</td><td>AT5G09260.1 511~532(CDS)</td><td>vacuolar protein sorting-associated protein 20.2</td></tr>
<tr><td></td><td></td><td></td><td></td><td>Bc-siRNA<br><br>Target</td><td>3'TCGTGGGATGTTGGATCTTTT 5'<br>||| |:| ||||||:|||||<br>5'TGCAACTTTCAACCTGGAAAA 3'</td><td>88<br><br>91</td><td>4.5</td><td>Solyc04g050970.2.1 19~40(cDNA)</td><td>Receptor protein kinase-like protein (AHRD V1 **** Q9LRY1_ARATH); contains Interpro domain(s) IPR002290 Serine/threonine protein kinase</td></tr>
<tr><td></td><td></td><td></td><td></td><td>Bc-siRNA<br><br>Target</td><td>3'TCGTGGGATGTTGGATCTTTT 5'<br>||||: |||||||:||||:||<br>5'AGCATACTACAACTTAGAGAA 3'</td><td>88<br><br>92</td><td>4.25</td><td>Solyc05g014650.2.1 541~562(cDNA)</td><td>Iojap-like protein (AHRD V1 *-*- B5ZUF1_RHILW); contains Interpro domain(s) IPR004394 Iojap-related protein</td></tr>
<tr><td>siR18 SIR1 LTR transposon TAGCCA AAACAG AGTCGAT CA (SEQ ID NO: 93)</td><td>155.7</td><td>1260.68</td><td>16.2</td><td>Bc-siRNA<br><br>Target</td><td>3'ACTAGCTGAGACAAAACCGAT 5'<br>|  ||| ||||||||||||:<br>5'TATTCGTCTCTGTTTTGGCTG 3'</td><td>93<br><br>94</td><td>4.5</td><td>AT2G01110.1 511~532(CDS)</td><td>Sec-independent periplasmic protein translocase</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence</th><th colspan="3">Normalized read counts</th><th></th><th>Target gene alignment</th><th>SEQ ID</th><th></th><th>Target gene</th><th>Putative function of</th></tr>
<tr><th>(5'-3')</th><th>A</th><th>S</th><th>B</th><th></th><th>and aligned score</th><th>NO:</th><th>AS*</th><th>ID/target site</th><th>target gene</th></tr>
<tr><td></td><td></td><td></td><td></td><td>Bc-siRNA<br><br>Target</td><td>3'ACTAGCTGAGACAAAACCGAT 5'<br>|| |:|||||||| |||:||<br>5'TGTTTGACTCTGTTGTGGTTA 3'</td><td>93<br><br>95</td><td>4.5</td><td>AT2G31980.1<br>490~511(CDS)</td><td>PHYTOCYSTATIN 2</td></tr>
<tr><td></td><td></td><td></td><td></td><td>Bc-siRNA<br><br>Target</td><td>3'ACTAGCTGAGACAAAACCGAT 5'<br>||:|||| |:|| |||||||<br>5'TGGTCGAGTTTGGTTTGGCTA 3'</td><td>93<br><br>96</td><td>4.5</td><td>AT3G26300.1<br>1345~1366(CDS)</td><td>cytochrome P450, family 71, subfamily B, polypeptide 34</td></tr>
<tr><td></td><td></td><td></td><td></td><td>Bc-siRNA<br><br>Target</td><td>3'ACTAGCTGAGACAAAACCGAT 5'<br>||||:| |||||| |||||<br>5'TGATTGCCTCTGTTATGGCTT 3'</td><td>93<br><br>97</td><td>4.5</td><td>AT3G47440.1<br>366~387(CDS)</td><td>tonoplast intrinsic protein 5; 1</td></tr>
<tr><td></td><td></td><td></td><td></td><td>Bc-siRNA<br><br>Target</td><td>3'ACTAGCTGAGACAAAACCGAT 5'<br>| | |:||||||||||:||<br>5'GGTTAGGCTCTGTTTTGGTTA 3'</td><td>93<br><br>98</td><td>4.5</td><td>AT4G37160.1<br>52~73(CDS)</td><td>SKU5 similar 15</td></tr>
<tr><td></td><td></td><td></td><td></td><td>Bc-siRNA<br><br>Target</td><td>3'ACTAGCTGAGACAAAACCGAT 5'<br>||| | |||||||||| |||<br>5'TGAGCAACTCTGTTTTGTCTA 3'</td><td>93<br><br>99</td><td>4</td><td>Solyc02g071770.2.1<br>1000~1021(cDNA)</td><td>DUF1264 domain protein (AHRD V1 **-- A1CBM4_ASPCL); contains Interpro domain(s) IPR010686 Protein of unknown function DUF1264</td></tr>
<tr><td></td><td></td><td></td><td></td><td>Bc-siRNA<br><br>Target</td><td>3'ACTAGCTGAGACAAAACCGAT 5'<br>||||:||:|||||||| ||<br>5'TGATTGATTCTGTTTTGCCTT 3'</td><td>93<br><br>100</td><td>4</td><td>Solyc03g059420.2.1<br>2896~2917(cDNA)</td><td>Sister chromatid cohesion 2 (AHRD V1 **-- D7M7D7_ARALY); contains Interpro domain(s) IPR016024 Armadillo-type fold</td></tr>
<tr><td></td><td></td><td></td><td></td><td>Bc-siRNA<br><br>Target</td><td>3'ACTAGCTGAGACAAAACCGAT 5'<br>|||| | ||||||||||:|:<br>5'TGATAGTCTCTGTTTTGGTTG 3'</td><td>93<br><br>101</td><td>3.5</td><td>Solyc07g017240.1.1<br>1~22(cDNA)</td><td>Unknown Protein (AHRD V1)</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>siR15<br>SIR3 LTR<br>transposon<br>TGTGTTG<br>AACCTTG<br>TTGTTTG<br>A (SEQ ID<br>NO: 102)</td><td>936.7</td><td>926.6</td><td>155</td><td>Bc-siRNA<br><br>Target</td><td>3'AGTTTGTTGTTCCAAGTTGTGT 5'<br>|:||| || ||||||| |||||<br>5'TTAAAAAAAAAGGTTCCACACA 3'</td><td>102<br><br>103</td><td>4.5</td><td>AT2G23080.1<br>1250~1272(3'UTR)</td><td>Protein kinase superfamily protein</td></tr>
<tr><td></td><td></td><td></td><td></td><td>Bc-siRNA<br><br>Target</td><td>3'AGTTTGTTGTTCCAAGTTGTGT 5'<br>|||| ||||||| ||||||||<br>5'CCAAAGAACAAGGCTCAACACA 3'</td><td>102<br><br>104</td><td>4</td><td>AT3G46920.1<br>3478~3500(CDS)</td><td>Protein kinase superfamily protein with octicosapeptide/Phox/Bem1p domain</td></tr>
<tr><td></td><td></td><td></td><td></td><td>Bc-siRNA<br><br>Target</td><td>3'AGTTTGTTGTTCCAAGTTGTGT 5'<br>||:|| |||||||| |||||||<br>5'TCGAAAAACAAGGTGCAACACA 3'</td><td>102<br><br>105</td><td>3.5</td><td>AT5G48860.1<br>291~313(CDS)</td><td>unknown protein, hypothetical protein, uncharacterized protein</td></tr>
<tr><td></td><td></td><td></td><td></td><td>Bc-siRNA<br><br>Target</td><td>3'AGTTTGTTGTTCCAAGTTGTGT 5'<br>| :|||||||||||||:||:|<br>5'TGGAACAACAAGGTTCAGCATA 3'</td><td>102<br><br>106</td><td>4.25</td><td>Solyc01g088020.2.1<br>786~808(cDNA)</td><td>Protein transport protein sec31 (AHRD V1 **-- C8V1I6_EMENI); contains Interpro domain(s) IPR017986 WD40 repeat, region</td></tr>
<tr><td>siR17<br>SIR6 CDS<br>(spurious<br>gene)<br>TAAAAT<br>GATGAA<br>TGGCACT<br>GG (SEQ<br>ID<br>NO: 107)</td><td>1682.7</td><td>589.2</td><td>245.8</td><td>Bc-siRNA<br><br>Target</td><td>3'GGTCACGGTAAGTAGTAAAAT 5'<br>||||| |||||:|:|||||:<br>5'ACAGTGACATTCGTTATTTTG 3'</td><td>107<br><br>108</td><td>4.5</td><td>AT1G56190.1<br>1738~1759(3'UTR)</td><td>Phosphoglycerate kinase family protein</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence<br>(5'-3')</th><th colspan="3">Normalized read counts</th><th colspan="2">Target gene alignment<br>and aligned score</th><th>SEQ ID<br>NO:</th><th>AS*</th><th>Target gene<br>ID/target site</th><th>Putative function of<br>target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'GGTCACGGTAAGTAGTAAAAT 5'<br>:|||| |||||:||||||| |<br>5'TCAGTTCCATTTATCATTTCA 3'</td><td>107<br><br>109</td><td>4.5</td><td>AT1G72740.1<br>661~682(CDS)</td><td>Homeodomain-like/winged-helix DNA-binding family protein</td></tr>
<tr><td></td><td></td><td></td><td></td><td>Bc-siRNA<br><br>Target</td><td>3'GGTCACGGTAAGTAGTAAAAT 5'<br>| |||||||||||||||:<br>5'ACCATGCCATTCATCATTTTG 3'</td><td>107<br><br>110</td><td>4.5</td><td>Solyc05g005950.2.1<br>262~283(cDNA)</td><td>Solute carrier family 15 member 4 (AHRD V1 **-- S15A4_XENLA); contains Interpro domain(s) IPR000109 TGF-beta receptor, type I/II extracellular region</td></tr>
<tr><td></td><td></td><td></td><td></td><td>Bc-siRNA<br><br>Target</td><td>3'GGTCACGGTAAGTAGTAAAAT 5'<br>| |||||||||||||||:<br>5'ACCATGCCATTCATCATTTTG 3'</td><td>107<br><br>111</td><td>4.5</td><td>Solyc05g005960.2.1<br>69~90(cDNA)</td><td>Peptide transporter 1 (AHRD V1 **-* Q7XAC3_VICFA); contains Interpro domain(s) IPR000109 TGF-beta receptor, type I/II extracellular region</td></tr>
<tr><td></td><td></td><td></td><td></td><td>Bc-siRNA<br><br>Target</td><td>3'GGTCACGGTAAGTAGTAAAAT 5'<br>|:| ||:||||| ||||||||<br>5'CTACTGTCATTCTTCATTTTA 3'</td><td>107<br><br>112</td><td>4</td><td>Solyc08g075450.2.1<br>222~243(cDNA)</td><td>Nodulin-like protein (AHRD V1 ***- Q9FHJ9_ARATH); contains Interpro domain(s) IPR000620 Protein of</td></tr>
</table>

TABLE 1-continued

<table>
<tr><th colspan="9">Bc-sRNAs that have predicted targets in both *Arabidopsis* and *S. lycopersicum*.</th></tr>
<tr><th>Bc-siRNA ID, locus, and siRNA sequence</th><th colspan="3">Normalized read counts</th><th>Target gene alignment</th><th>SEQ ID</th><th></th><th>Target gene</th><th>Putative function of</th></tr>
<tr><th>(5'-3')</th><th>A</th><th>S</th><th>B</th><th>and aligned score</th><th>NO:</th><th>AS*</th><th>ID/target site</th><th>target gene</th></tr>
<tr><td></td><td></td><td></td><td></td><td></td><td></td><td></td><td></td><td>unknown function DUF6, transmembrane</td></tr>
<tr><td></td><td></td><td></td><td></td><td>Bc-siRNA 3'GGTCACGGTAAGTAGTAAAAT 5'<br>|:| ||:||||| ||||||||<br>Target 5'CTACTGTCATTCTTCATTTTA 3'</td><td>107<br><br>113</td><td>4</td><td>Solyc08g075460.2.1 424~445(cDNA)</td><td>Nodulin-like protein (AHRD V1 ***- Q9FHJ9_ARATH); contains Interpro domain(s) IPR000620 Protein of unknown function DUF6, transmembrane</td></tr>
<tr><td>siR22 SIR3 LTR transposon TAACGTG GTCAAG GGTGTA GT (SEQ ID NO: 114)</td><td>370</td><td>995.72</td><td>63.3</td><td>Bc-siRNA 3'TGATGTGGGAACTGGTGCAAT 5'<br>: | ||||:||||||||||:<br>Target 5'GATTCACCTTTGACCACGTTG 3'</td><td>114<br><br>115</td><td>4.25</td><td>AT3G17360.1 625~646(CDS)</td><td>phragmoplast orienting kinesin 1</td></tr>
<tr><td></td><td></td><td></td><td></td><td>Bc-siRNA 3'TGATGTGGGAACTGGTGCAAT 5'<br>| ||:|:|||| ||||||:<br>Target 5'ACAACGCTCTTGTCCACGTTG 3'</td><td>114<br><br>116</td><td>4.5</td><td>AT5G66510.1 438~459(CDS)</td><td>gamma carbonic anhydrase 3</td></tr>
<tr><td></td><td></td><td></td><td></td><td>Bc-siRNA 3'TGATGTGGGAACTGGTGCAAT 5'<br>||||| |||||| |||||||:<br>Target 5'ACTACTCCCTTGCCCACGTTG 3'</td><td>114<br><br>117</td><td>3.5</td><td>Solyc01g005240.2.1 1912~1933(cDNA)</td><td>Aspartokinase (AHRD V1 ***- B9RGY9_RICCO); contains Interpro domain(s) IPR001341 Aspartate kinase region</td></tr>
<tr><td>siR24 SIR3 LTR</td><td>1210.2</td><td>651.72</td><td>429.9</td><td>Bc-siRNA 3'CAGTTTGTCTCTCCTGGTTAGT 5'<br>|||::| |||||||||||||</td><td>118</td><td>3.5</td><td>AT5G04990.1 1226~1248(CDS)</td><td>SAD1/UNC-84 domain</td></tr>
</table>

TABLE 1-continued

<table>
<tr><th colspan="11">Bc-sRNAs that have predicted targets in both Arabidopsis and S. lycopersicum.</th></tr>
<tr><th>Bc-siRNA ID, locus, and siRNA sequence</th><th colspan="3">Normalized read counts</th><th colspan="2">Target gene alignment</th><th>SEQ ID</th><th></th><th>Target gene</th><th>Putative function of</th></tr>
<tr><th>(5'-3')</th><th>A</th><th>S</th><th>B</th><th colspan="2">and aligned score</th><th>NO:</th><th>AS*</th><th>ID/target site</th><th>target gene</th></tr>
<tr><td>transposon TGATTGG TCCTCTC TGTTTGA C (SEQ ID NO: 118)</td><td></td><td></td><td></td><td>Target</td><td>5'ATCAGGCTGAGAGGACCAATCA 3'</td><td>119</td><td></td><td></td><td>protein 1</td></tr>
<tr><td></td><td></td><td></td><td></td><td>Bc-siRNA<br><br>Target</td><td>3'CAGTTTGTCTCTCCTGGTTAGT 5'<br>|||||||| |||||:||||| |<br>5'GTCAAACAAAGAGGGCCAATAA 3'</td><td>118<br><br>120</td><td>4</td><td>Solyc02g069090.2.1<br>2009~2031(cDNA)</td><td>Cathepsin B (AHRD V1 ***-Q1HER6_NICBE); contains Interpro domain(s) IPR015643 Peptidase C1A, cathepsin B</td></tr>
<tr><td></td><td></td><td></td><td></td><td>Bc-siRNA<br><br>Target</td><td>3'CAGTTTGTCTCTCCTGGTTAGT 5'<br>|||:| | ||||||:||||||<br>5'TTCAGAAATAGAGGATCAATCA 3'</td><td>118<br><br>121</td><td>4.5</td><td>Solyc03g007390.2.1<br>2085~2107(cDNA)</td><td>Pentatricopeptide repeat-containing protein (AHRD V1 ***-D7ML46_ARALY); contains Interpro domain(s) IPR002885 Pentatricopeptide repeat</td></tr>
<tr><td></td><td></td><td></td><td></td><td>Bc-siRNA<br><br>Target</td><td>3'CAGTTTGTCTCTCCTGGTTAGT 5'<br>|| |:||||||||||| |:|||<br>5'GTGAGACAGAGAGGACAAGTCA 3'</td><td>118<br><br>122</td><td>4.5</td><td>Solyc03g097450.2.1<br>1351~1373(cDNA)</td><td>SWI/SNF complex subunit SMARCC1 (AHRD V1 *---SMRC1_HUMAN); contains Interpro domain(s) IPR007526 SWIRM</td></tr>
<tr><td></td><td></td><td></td><td></td><td>Bc-siRNA<br><br>Target</td><td>3'CAGTTTGTCTCTCCTGGTTAGT 5'<br>|| | |:|||||||:||||||<br>5'ATCTACCGGAGAGGATCAATCA 3'</td><td>118<br><br>123</td><td>4.5</td><td>Solyc09g089970.1.1<br>287~309(cDNA)</td><td>Unknown Protein (AHRD V1)</td></tr>
</table>

TABLE 1-continued

<table>
<tr><th colspan="10">Bc-sRNAs that have predicted targets in both *Arabidopsis* and *S. lycopersicum*.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>siR25<br>SIR2 LTR<br>transposon<br>TAGTGA<br>ATCAAAT<br>TTTGGTT<br>TT (SEQ<br>ID<br>NO: 124)</td><td>2747.8</td><td>15.64</td><td>20.8</td><td>Bc-siRNA<br><br>Target</td><td>3'TTTTGGTTTTAAACTAAGTGAT 5'<br>:|:|:||: ||||||||||||||<br>5'GAGATCAGTATTTGATTCACTA 3'</td><td>124<br><br>125</td><td>3.75</td><td>AT5G41250.1<br>1349~1371(CDS)</td><td>Exostosin<br>family protein</td></tr>
<tr><td></td><td></td><td></td><td></td><td>Bc-siRNA<br><br>Target</td><td>3'TTTTGGTTTTAAACTAAGTGAT 5'<br>|| || ||| |||||||||||<br>5'AATACAAAACTTTGATTCACTT 3'</td><td>124<br><br>126</td><td>4</td><td>AT5G44030.1<br>3330~3352(3'UTR)</td><td>cellulose<br>synthase A4</td></tr>
<tr><td></td><td></td><td></td><td></td><td>Bc-siRNA<br><br>Target</td><td>3'TTTTGGTTTTAAACTAAGTGAT 5'<br>|||::|||||||||||:|:||<br>5'TAAATTAAAATTTGATTTATTA 3'</td><td>124<br><br>127</td><td>4.5</td><td>Solyc01g044240.2.1<br>1312~1334(cDNA)</td><td>Unknown<br>Protein<br>(AHRD V1)</td></tr>
<tr><td></td><td></td><td></td><td></td><td>Bc-siRNA<br><br>Target</td><td>3'TTTTGGTTTTAAACTAAGTGAT 5'<br>|||| |||:|||||:||||:||<br>5'AAAAACAAGATTTGGTTCATTA 3'</td><td>124<br><br>128</td><td>3.5</td><td>Solyc12g005790.1.1<br>512~534(cDNA)</td><td>Peroxidase 27<br>(AHRD V1<br>***-<br>D7LAI1_ARALY);<br>contains<br>Interpro<br>domain(s)<br>IPR002016<br>Haem<br>peroxidase,<br>plant/fungal/bacterial</td></tr>
<tr><td>siR1015<br>SIR1015<br>Intergenic<br>region<br>TTGATGG<br>TTGTCTG<br>ATCGGT<br>(SEQ ID<br>NO: 129)</td><td>1200.3</td><td>574.4</td><td>2304</td><td>Bc-siRNA<br><br>Target</td><td>3'TGGCTAGTCTGTTGGTAGTT 5'<br>|| | ||| ||||||||||<br>5'ACGGTTCACACAACCATCAA 3'</td><td>129<br><br>130</td><td>4</td><td>AT2G45030.1<br>2328~2348(3'UTR)</td><td>Translation<br>elongation<br>factor<br>EFG/EF2<br>protein</td></tr>
<tr><td></td><td></td><td></td><td></td><td>Bc-siRNA<br><br>Target</td><td>3'TGGCTAGTCTGTTGGTAGTT 5'<br>||:| |||||| ||||||:|<br>5'ACTGCTCAGACCACCATCGA 3'</td><td>129<br><br>131</td><td>4.5</td><td>AT5G02500.1<br>954~974(CDS)</td><td>heat shock<br>cognate<br>protein 70-1</td></tr>
<tr><td></td><td></td><td></td><td></td><td>Bc-siRNA<br><br>Target</td><td>3'TGGCTAGTCTGTTGGTAGTT 5'<br>|::| | |||:||||||||<br>5'ATTGCTAAGATAACCATCAA 3'</td><td>129<br><br>132</td><td>4.5</td><td>Solyc05g005180.2.1<br>437~457(cDNA)</td><td>Naphthoate<br>synthase<br>(AHRD V1<br>***-</td></tr>
</table>

TABLE 1-continued

<table>
<tr><th colspan="9">Bc-sRNAs that have predicted targets in both *Arabidopsis* and *S. lycopersicum*.</th></tr>
<tr><th>Bc-siRNA ID, locus, and siRNA sequence (5'-3')</th><th colspan="3">Normalized read counts</th><th>Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th></tr>
<tr><td></td><td></td><td></td><td></td><td></td><td></td><td></td><td></td><td>A8I2W2_CHLRE); contains Interpro domain(s) IPR010198 Naphthoate synthase</td></tr>
<tr><td></td><td></td><td></td><td></td><td>Bc-siRNA 3'TGGCTAGTCTGTTGGTAGTT 5'<br>||:| || ||||:||||:||<br>Target 5'ACTGTTCTGACAGCCATTAA 3'</td><td>129<br><br>133</td><td>4.5</td><td>Solyc06g036150.1.1<br>564~584(cDNA)</td><td>Unknown Protein (AHRD V1)</td></tr>
<tr><td></td><td></td><td></td><td></td><td>Bc-siRNA 3'TGGCTAGTCTGTTGGTAGTT 5'<br>:|| |||||||:|| |||||<br>Target 5'GCCCATCAGACGACGATCAA 3'</td><td>129<br><br>134</td><td>4.5</td><td>Solyc07g043250.1.1<br>116~136(cDNA)</td><td>Unknown Protein (AHRD V1); contains Interpro domain(s) IPR008889 VQ</td></tr>
<tr><td></td><td></td><td></td><td></td><td>Bc-siRNA 3'TGGCTAGTCTGTTGGTAGTT 5'<br>||:| || |||||||||:||<br>Target 5'ACTGTTCTGACAACCATTAA 3'</td><td>129<br><br>135</td><td>3.5</td><td>Solyc08g063100.1.1<br>438~458(cDNA)</td><td>Ulp1 protease family C-terminal catalytic domain containing protein (AHRD V1 *-*-Q60D46_SOLDE)</td></tr>
<tr><td></td><td></td><td></td><td></td><td>Bc-siRNA 3'TGGCTAGTCTGTTGGTAGTT 5'<br>||:|||::|||||||||| |<br>Target 5'ACTGATTGGACAACCATCCA 3'</td><td>129<br><br>136</td><td>4</td><td>Solyc10g006090.2.1<br>2583~2603(cDNA)</td><td>Genomic DNA chromosome 5 P1 clone MTE17 (AHRD V1 **--Q9FJ71_ARATH); contains Interpro domain(s) IPR011011 Zinc finger, FYVE/PHD-type</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th></th><th>Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'TGGCTAGTCTGTTGGTAGTT 5'<br>||:|:|::||||||||||||<br>5'ACTGGTTGGACAACCATCAC 3'</td><td>129<br><br>137</td><td>3.5</td><td>Solyc12g044780.1.1<br>816~836(cDNA)</td><td>F-box family protein (AHRD V1 *-*-D7LXD8_ARALY); contains Interpro domain(s) IPR001810 Cyclin-like F-box</td></tr>
<tr><td></td><td></td><td></td><td></td><td>Bc-siRNA<br><br>Target</td><td>3'TGGCTAGTCTGTTGGTAGTT 5'<br>||:|:|::||||||||||||<br>5'ACTGGTTGGACAACCATCAC 3'</td><td>129<br><br>138</td><td>3.5</td><td>Solyc12g044790.1.1<br>816~836(cDNA)</td><td>F-box family protein (AHRD V1 *-*-D7LXD8_ARALY); contains Interpro domain(s) IPR001810 Cyclin-like F-box</td></tr>
<tr><td>siR20 SIR2 LTR transposon TAGTGTT CTTGTTT TTCTGAT T (SEQ ID NO: 139)</td><td>1402.4</td><td>467.4</td><td>83.2</td><td>Bc-siRNA<br><br>Target</td><td>3'TTAGTCTTTTTGTTCTTGTGAT 5'<br>::| |||||:||||||||||:||<br>5'GGTGAGAAAGACAAGAACATTA 3'</td><td>139<br><br>140</td><td>4</td><td>AT3G18010.1<br>1076~1098(CDS)</td><td>WUSCHEL related homeobox 1</td></tr>
<tr><td></td><td></td><td></td><td></td><td>Bc-siRNA<br><br>Target</td><td>3'TTAGTCTTTTTGTTCTTGTGAT 5'<br>|| || ||||||||| ||||||:<br>5'AAACACAAAAACAAAAACACTG 3'</td><td>139<br><br>141</td><td>4.5</td><td>AT3G20660.1<br>43~65(5'UTR)</td><td>organic cation/carnitine transporter4</td></tr>
<tr><td></td><td></td><td></td><td></td><td>Bc-siRNA<br><br>Target</td><td>3'TTAGTCTTTTTGTTCTTGTGAT 5'<br>||| |||:||:|||||||||| |<br>5'AATAAGAGAAGCAAGAACACAA 3'</td><td>139<br><br>142</td><td>4.5</td><td>AT4G23882.1<br>549~571(CDS)</td><td>Heavy metal transport/detoxification superfamily protein</td></tr>
<tr><td></td><td></td><td></td><td></td><td>Bc-siRNA<br><br>Target</td><td>3'TTAGTCTTTTTGTTCTTGTGAT 5'<br>|:|||| ||||| ||||||||<br>5'AGTCAGCAAAACCAGAACACTC 3'</td><td>139<br><br>143</td><td>4.5</td><td>A15G17680.1<br>3220~3242(CDS)</td><td>disease resistance protein (TIR-NBS-LRR class), putative</td></tr>
<tr><td></td><td></td><td></td><td></td><td>Bc-siRNA</td><td>3'TTAGTCTTTTTGTTCTTGTGAT 5'<br>|| ||| |:||||||| |||||</td><td>139</td><td>4.5</td><td>Solyc02g076690.2.1<br>598~620(cDNA)</td><td>Cathepsin B-like cysteine</td></tr>
</table>

TABLE 1-continued

<table>
<tr><th colspan="8">Bc-sRNAs that have predicted targets in both Arabidopsis and S. lycopersicum.</th></tr>
<tr><th>Bc-siRNA ID, locus, and siRNA sequence (5'-3')</th><th>Normalized read counts<br>A S B</th><th></th><th>Target gene alignment and aligned score</th><th>SEQ ID NO:</th><th>AS*</th><th>Target gene ID/target site</th><th>Putative function of target gene</th></tr>
<tr><td></td><td></td><td>Target</td><td>5'AAACAGCAGAACAAGACCACTA 3'</td><td>144</td><td></td><td></td><td>proteinase (AHRD V1 **-* CYSP SCHMA); contains Interpro domain(s) IPR013128 Peptidase C1A, papain</td></tr>
<tr><td></td><td></td><td>Bc-siRNA<br><br>Target</td><td>3'TTAGTCTTTTTGTTCTTGTGAT 5'<br>|:|| ||||||||||:|:|||<br>5'AGTCTGAAAAACAAGGATACTT 3'</td><td>139<br><br>145</td><td>4.5</td><td>Solyc03g117110.2.1<br>462~484(cDNA)</td><td>DCN1-like protein 4 (AHRD V1 ***- B6TI85_MAIZE); contains Interpro domain(s) IPR014764 Defective in cullin neddylation</td></tr>
<tr><td></td><td></td><td>Bc-siRNA<br><br>Target</td><td>3'TTAGTCTTTTTGTTCTTGTGAT 5'<br>|:| ||||||||| ||:||||<br>5'AGTAAGAAAAACAATAATACTA 3'</td><td>139<br><br>146</td><td>4.5</td><td>Solyc03g120530.2.1<br>163~185(cDNA)</td><td>BHLH transcription factor-like protein (AHRD V1 *-** Q5ZAK6_ORYSJ); contains Interpro domain(s) IPR011598 Helix-loop-helix DNA-binding</td></tr>
<tr><td></td><td></td><td>Bc-siRNA<br><br>Target</td><td>3'TTAGTCTTTTTGTTCTTGTGAT 5'<br>|||:| ||||||||| |||||<br>5'AATTATAAAAACAAGCACACTC 3'</td><td>139<br><br>147</td><td>4.5</td><td>Solyc11g039880.1.1<br>1821~1843(cDNA)</td><td>Nucleoporin NUP188 homolog (AHRD V1 *-*- NU188_HUMAN)</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>siR1021<br>SIR1021<br>CDS<br>TACAGTG<br>ATGAAC<br>AAAACA<br>TGT (SEQ<br>ID<br>NO: 148)</td><td>2041.3</td><td>137.44</td><td>94.1</td><td>Bc-siRNA<br><br>Target</td><td>3'TGTACAAAACAAGTAGTGACAT 5'<br>|||||| || |||||||||||<br>5'ACATGTCTTATTCATCACTGTC 3'</td><td>148<br><br>149</td><td>3</td><td>AT2G40520.1<br>815~837(CDS)</td><td>Nucleotidyltransferase family protein</td></tr>
<tr><td></td><td></td><td></td><td></td><td>Bc-siRNA<br><br>Target</td><td>3'TGTACAAAACAAGTAGTGACAT 5'<br>| | ||||| |||||||||||:<br>5'AAAAGTTTTATTCATCACTGTG 3'</td><td>148<br><br>150</td><td>3.5</td><td>AT3G11530.1<br>682~704(3'UTR)</td><td>Vacuolar protein sorting 55 (VPS55) family protein</td></tr>
<tr><td></td><td></td><td></td><td></td><td>Bc-siRNA<br><br>Target</td><td>3'TGTACAAAACAAGTAGTGACAT 5'<br>||| || || |||||||:|||:<br>5'ACACGTCTTCTTCATCATTGTG 3'</td><td>148<br><br>151</td><td>4.5</td><td>Solyc05g009280.2.1<br>1339~1361(cDNA)</td><td>Fatty acid elongase 3-ketoacyl-CoA synthase (AHRD VI **** Q6DUV5_BRANA); contains Interpro domain(s) IPR012392 Very-long-chain 3-ketoacyl-CoA synthase</td></tr>
<tr><td>siR1002<br>SIR1002<br>Intergenicregion<br>ATTCTTC<br>AAATCTT<br>TGTAACA<br>CA (SEQ<br>ID<br>NO: 152)</td><td>1408.4</td><td>360.44</td><td>239.1</td><td>Bc-siRNA<br><br>Target</td><td>3'ACACAATGTTTCTAAACTTCTTA 5'<br>|||| | |||:|| |||||||||<br>5'TGTGCTCCAAGGAGTTGAAGAAT 3'</td><td>152<br><br>153</td><td>4.5</td><td>AT1G62940.1<br>111~134(CDS)</td><td>acyl-CoA synthetase 5</td></tr>
<tr><td></td><td></td><td></td><td></td><td>Bc-siRNA<br><br>Target</td><td>3'ACACAATGTTTCTAAACTTCTTA 5'<br>| ||| |:|||||| ||||||||<br>5'TCTGTAATAAAGATCTGAAGAAT 3'</td><td>152<br><br>154</td><td>4.5</td><td>AT4G30420.1<br>1039~1062(CDS)</td><td>nodulin MtN21/ EamA-like transporter family protein</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'ACACAATGTTTCTAAACTTCTTA 5'<br>| ||| |:||||||||||||||<br>5'TTTGTGATAAAGATTTGAAGAAA 3'</td><td>152<br><br>155</td><td>3.5</td><td>AT4G34380.1<br>285~308(5'UTR)</td><td>Transducin/WD40 repeat-like superfamily protein</td></tr>
<tr><td></td><td></td><td></td><td></td><td>Bc-siRNA<br><br>Target</td><td>3'ACACAATGTTTCTAAACTTCTTA 5'<br>|| ||||||||||| |||||||<br>5'TGAGTTACAAAGATCTGAAGAAA 3'</td><td>152<br><br>156</td><td>4</td><td>Solyc08g060920.2.1<br>98~121(cDNA)</td><td>Xenotropic and polytropic retrovirus receptor (AHRD V1 **-- B2GU54_XENTR); contains Interpro domain(s) IPR004331 SPX, N-terminal</td></tr>
<tr><td></td><td></td><td></td><td></td><td>Bc-siRNA<br><br>Target</td><td>3'ACACAATGTTTCTAAACTTCTTA 5'<br>||| ||:|||:|||||||:|||<br>5'TGTATTGCAAGGATTTGAGGAAA 3'</td><td>152<br><br>157</td><td>4</td><td>Solyc08g081380.2.1<br>989~1012(cDNA)</td><td>At5g63850-like protein (Fragment) (AHRD V1 *-*- Q3YI76_ARALY); contains Interpro domain(s) IPR000210 BTB/POZ-like</td></tr>
<tr><td></td><td></td><td></td><td></td><td>Bc-siRNA<br><br>Target</td><td>3'ACACAATGTTTCTAAACTTCTTA 5'<br>||| |||||:|||||||||||<br>5'TGTCATACAAGGATTTGAAGAAA 3'</td><td>152<br><br>158</td><td>4.5</td><td>Solyc12g009480.1.1<br>67~90(cDNA)</td><td>Xenotropic and polytropic retrovirus receptor (AHRD V1 **-- B2GU54_XENTR); contains Interpro domain(s) IPR004331 SPX, N-terminal</td></tr>
<tr><td>siR28<br>SIR1 LTR</td><td>415.5</td><td>727.44</td><td>29.8</td><td>Bc-siRNA</td><td>3'TTCTTCTAGTGTCAAAGTTTTT 5'<br>|:|||||||||||||||| |||</td><td>159</td><td>2.5</td><td>AT1G16760.1<br>1454~1476(CDS)</td><td>Protein kinase protein with</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence</td><td colspan="3">Normalized read counts</td><td colspan="2">Target gene alignment</td><td>SEQ ID</td><td></td><td>Target gene</td><td>Putative function of</td></tr>
<tr><td>(5'-3')</td><td>A</td><td>S</td><td>B</td><td colspan="2">and aligned score</td><td>NO:</td><td>AS*</td><td>ID/target site</td><td>target gene</td></tr>
<tr><td>transposon TTTTTGA AACTGTG ATCTTCT T (SEQ ID NO: 159)</td><td></td><td></td><td></td><td>Target</td><td>5'AGGAAGATCACAGTTTCACAAA 3'</td><td>160</td><td></td><td></td><td>adenine nucleotide alpha hydrolases-like domain</td></tr>
<tr><td></td><td></td><td></td><td></td><td>Bc-siRNA<br><br>Target</td><td>3'TTCTTCTAGTGTCAAAGTTTTT 5'<br>|:|:||||||||||||||:|||<br>5'AGGGAGATCACAGTTTCAGAAA 3'</td><td>159<br><br>161</td><td>2</td><td>AT1G78940.1<br>1425~1447(CDS)</td><td>Protein kinase protein with adenine nucleotide alpha hydrolases-like domain</td></tr>
<tr><td></td><td></td><td></td><td></td><td>Bc-siRNA<br><br>Target</td><td>3'TTCTTCTAGTGTCAAAGTTTTT 5'<br>||||||| || |||||||:|||<br>5'AAGAAGAACAAAGTTTCAGAAA 3'</td><td>159<br><br>162</td><td>4</td><td>Al2G28830.1<br>2571~2593(CDS)</td><td>PLANT U-BOX 12</td></tr>
<tr><td></td><td></td><td></td><td></td><td>Bc-siRNA<br><br>Target</td><td>3'TTCTTCTAGTGTCAAAGTTTTT 5'<br>|||||| |:|||||||:| |||<br>5'AAGAAGCTTACAGTTTTATAAA 3'</td><td>159<br><br>163</td><td>4.5</td><td>AT2G40720.1<br>2191~2213(CDS)</td><td>Tetratricopeptide repeat (TPR)-like superfamily protein</td></tr>
<tr><td></td><td></td><td></td><td></td><td>Bc-siRNA<br><br>Target</td><td>3'TTCTTCTAGTGTCAAAGTTTTT 5'<br>|:||||||| || |||||||:|<br>5'AGGAAGATCTCAATTTCAAAGA 3'</td><td>159<br><br>164</td><td>4.5</td><td>AT3G20200.1<br>1777~1799(CDS)</td><td>Protein kinase protein with adenine nucleotide alpha hydrolases-like domain</td></tr>
<tr><td></td><td></td><td></td><td></td><td>Bc-siRNA<br><br>Target</td><td>3'TTCTTCTAGTGTCAAAGTTTTT 5'<br>|:| ||:|||||||||||:|||<br>5'AGGCAGGTCACAGTTTCAGAAA 3'</td><td>159<br><br>165</td><td>3</td><td>AT4G31230.1<br>1505~1527(CDS)</td><td>Protein kinase protein with adenine nucleotide alpha hydrolases-like domain</td></tr>
<tr><td></td><td></td><td></td><td></td><td>Bc-siRNA<br><br>Target</td><td>3'TTCTTCTAGTGTCAAAGTTTTT 5'<br>||||:| || |||||||||| |<br>5'AAGAGGTTCTCAGTTTCAAATA 3'</td><td>159<br><br>166</td><td>4.5</td><td>Solyc01g080610.2.1<br>852~874(cDNA)</td><td>Unknown protein (AHRD V1); contains Interpro domain(s) IPR005508 Protein of</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>unknown function DUF313</td></tr>
<tr><td></td><td></td><td></td><td></td><td>Bc-siRNA<br><br>Target</td><td>3'TTCTTCTAGTGTCAAAGTTTTT 5'<br>||||:| || |||||||||| |<br>5'AAGAGGTTCTCAGTTTCAAATA 3'</td><td>159<br><br>167</td><td>4.5</td><td>Solyc01g080720.2.1<br>319~341(cDNA)</td><td>Pentatricopeptide repeat-containing protein (AHRD V1 ***-D7L610_ARALY); contains Interpro domain(s) IPR002885 Pentatricopeptide repeat</td></tr>
<tr><td></td><td></td><td></td><td></td><td>Bc-siRNA<br><br>Target</td><td>3'TTCTTCTAGTGTCAAAGTTTTT 5'<br>| |:| |||| |||||||||||<br>5'ACGGACATCAGAGTTTCAAAAA 3'</td><td>159<br><br>168</td><td>4.5</td><td>Solyc03g115850.2.1<br>934~956 (cDNA)</td><td>NAC domain protein IPR003441 (AHRD V1 ***-B9I557_POPTR); contains Interpro domain(s) IPR003441 No apical meristem (NAM) protein</td></tr>
<tr><td></td><td></td><td></td><td></td><td>Bc-siRNA<br><br>Target</td><td>3'TTCTTCTAGTGTCAAAGTTTTT 5'<br>|||||| |||:||||||||:||<br>5'AAGAAGTTCATAGTTTCAAGAA 3'</td><td>159<br><br>169</td><td>3</td><td>Solyc05g024450.1.1<br>196~218(cDNA)</td><td>Unknown Protein (AHRD V1)</td></tr>
<tr><td></td><td></td><td></td><td></td><td>Bc-siRNA<br><br>Target</td><td>3'TTCTTCTAGTGTCAAAGTTTTT 5'<br>|| :| ||:|||||||||||||<br>5'AATGACATTACAGTTTCAAAAA 3'</td><td>159<br><br>170</td><td>3.75</td><td>Solyc06g009200.2.1<br>664~686(cDNA)</td><td>Polygalacturonase (AHRD V1 ***-Q2M4X6_LILLO); contains Interpro domain(s) IPR000743 Glycoside hydrolase, family 28</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence</th><th colspan="3">Normalized read counts</th><th colspan="2">Target gene alignment</th><th>SEQ ID</th><th></th><th>Target gene</th><th>Putative function of</th></tr>
<tr><th>(5'-3')</th><th>A</th><th>S</th><th>B</th><th colspan="2">and aligned score</th><th>NO:</th><th>AS*</th><th>ID/target site</th><th>target gene</th></tr>
<tr><td></td><td></td><td></td><td></td><td>Bc-siRNA<br><br>Target</td><td>3'TTCTTCTAGTGTCAAAGTTTTT 5'<br>|||:| ||:|||||||||:|:|<br>5'AAGGATATTACAGTTTCAGAGA 3'</td><td>159<br><br>171</td><td>4</td><td>Solyc06g031690.2.1<br>345~367(cDNA)</td><td>Ankyrin repeat family protein (AHRD V1 ***- D7LCV0_ARALY); contains Interpro domain(s) IPR002110 Ankyrin</td></tr>
<tr><td></td><td></td><td></td><td></td><td>Bc-siRNA<br><br>Target</td><td>3'TTCTTCTAGTGTCAAAGTTTTT 5'<br>||||||||| ||||| |||||<br>5'AAGAAGATCCCAGTTACAAAAT 3'</td><td>159<br><br>172</td><td>4</td><td>Solyc07g041780.2.1<br>450~472(cDNA)</td><td>OBP3-responsive gene 4 (AHRD V1 **-- D7L9C5_ARALY)</td></tr>
<tr><td>siR31 SIR1 LTR transposon TGAGTCT TGTGGTC GTGAAT G (SEQ ID NO: 173)</td><td>117</td><td>803.16</td><td>4.7</td><td>Bc-siRNA<br><br>Target</td><td>3'GTAAGTGCTGGTGTTCTGAGT 5'<br>::||:|:||||||||| ||||<br>5'TGTTTATGACCACAAGTCTCA 3'</td><td>173<br><br>174</td><td>4.5</td><td>AT1G65550.1<br>761~782(CDS)</td><td>Xanthine/uracil permease family protein</td></tr>
<tr><td></td><td></td><td></td><td></td><td>Bc-siRNA<br><br>Target</td><td>3'GTAAGTGCTGGTGTTCTGAGT 5'<br>::||:|||| |||||||||||<br>5'TGTTTACGAACACAAGACTCA 3'</td><td>173<br><br>175</td><td>4</td><td>AT2G05970.1<br>569~590(CDS)</td><td>F-box family protein with a domain of unknown function (DUF295)</td></tr>
<tr><td></td><td></td><td></td><td></td><td>Bc-siRNA<br><br>Target</td><td>3'GTAAGTGCTGGTGTTCTGAGT 5'<br>::||:|:||||||||| ||||<br>5'TGTTTATGACCACAAGCCTCA 3'</td><td>173<br><br>176</td><td>4.5</td><td>AT5G25420.1<br>716~737(CDS)</td><td>Xanthine/uracil/ vitamin C permease</td></tr>
<tr><td></td><td></td><td></td><td></td><td>Bc-siRNA<br><br>Target</td><td>3'GTAAGTGCTGGTGTTCTGAGT 5'<br>|||:| ||||||||||:|||<br>5'AATTTAAGACCACAAGATTCA 3'</td><td>173<br><br>177</td><td>3.5</td><td>Solyc01g011090.2.1<br>3435~3456(cDNA)</td><td>Phospholipid-transporting ATPase (AHRD V1 ***- C5G6U4_AJEDR); contains Interpro domain(s)</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>IPR001757 ATPase, P-type, K/Mg/Cd/Cu/ Zn/Na/Ca/Na/ H-transporter</td></tr>
<tr><td></td><td></td><td></td><td></td><td>Bc-siRNA<br><br>Target</td><td>3'GTAAGTGCTGGTGTTCTGAGT 5'<br>|||:| ||:|||||||:|||<br>5'AATTTAAGATCACAAGATTCA 3'</td><td>173<br><br>178</td><td>4.5</td><td>Solyc01g110700.2.1 36445~36466(cDNA)</td><td>Unknown Protein (AHRD V1)</td></tr>
<tr><td></td><td></td><td></td><td></td><td>Bc-siRNA<br><br>Target</td><td>3'GTAAGTGCTGGTGTTCTGAGT 5'<br>|||:| ||:|||||||:|||<br>5'AATTTAAGATCACAAGATTCA 3'</td><td>173<br><br>179</td><td>4.5</td><td>Solyc01g111180.2.1 6734~6755(cDNA)</td><td>Unknown Protein (AHRD V1)</td></tr>
<tr><td>siR29 SIR2 LTR transposon TGTTGGA TAGTCCT TTTTGGG (SEQ ID NO: 180)</td><td>1843</td><td>87.24</td><td>28.9</td><td>Bc-siRNA<br><br>Target</td><td>3'GGGTTTTTCCTGATAGGTTGT 5'<br>||| ||:||||| ||:|||||<br>5'CCCTAAGAGGACCATTCAACA 3'</td><td>180<br><br>181</td><td>4.5</td><td>AT2G45110.1 729~750(CDS)</td><td>expansin B4</td></tr>
<tr><td></td><td></td><td></td><td></td><td>Bc-siRNA<br><br>Target</td><td>3'GGGTTTTTCCTGATAGGTTGT 5'<br>: ||||:|||||||||||||<br>5'TACAAAGAGGACTATCCAACC 3'</td><td>180<br><br>182</td><td>3.75</td><td>AT5G38990.1 1156~1177(CDS)</td><td>Malectin/receptor-like protein kinase family protein</td></tr>
<tr><td></td><td></td><td></td><td></td><td>Bc-siRNA<br><br>Target</td><td>3'GGGTTTTTCCTGATAGGTTGT 5'<br>:||||:|||||| |||||:||<br>5'TCCAAGAAGGACAATCCAGCA 3'</td><td>180<br><br>183</td><td>4</td><td>Solyc00g025660.1.1 576~597(cDNA)</td><td>Unknown Protein (AHRD V1)</td></tr>
<tr><td></td><td></td><td></td><td></td><td>Bc-siRNA<br><br>Target</td><td>3'GGGTTTTTCCTGATAGGTTGT 5'<br>:|||||:||||||:| |||||<br>5'TCCAAAGAGGACTGTGCAACA 3'</td><td>180<br><br>184</td><td>4</td><td>Solyc03g117510.2.1 745~766(cDNA)</td><td>Formamidopyrimidine-DNA glycosylase (AHRD V1 **** C5JTH8_AJEDS); contains Interpro domain(s) IPR000191 DNA glycosylase/AP lyase</td></tr>
<tr><td>siR41 SIR3 LTR</td><td>371.5</td><td>652.56</td><td>54.5</td><td>Bc-siRNA</td><td>3'AAGATGAGGGCTTTTGATAGT 5'<br>|| |:|||||:|||||||||</td><td>185</td><td>4.5</td><td>AT3G09530.1 826~847(CDS)</td><td>exocyst subunit exo70</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td>transposon TGATAGT TTTCGGG AGTAGA A (SEQ ID NO: 185)</td><td></td><td></td><td></td><td>Target</td><td>5'TTGGATTCCCGGAAACTATCA 3'</td><td>186</td><td></td><td></td><td>family protein H3</td></tr>
<tr><td></td><td></td><td></td><td></td><td>Bc-siRNA<br><br>Target</td><td>3'AAGATGAGGGCTTTTGATAGT 5'<br>| | |||:|||||||||:||<br>5'TGCCACTTCCGAAAACTGTCC 3'</td><td>185<br><br>187</td><td>4.5</td><td>AT3G19780.1<br>1248~1269(CDS)</td><td></td></tr>
<tr><td></td><td></td><td></td><td></td><td>Bc-siRNA<br><br>Target</td><td>3'AAGATGAGGGCTTTTGATAGT 5'<br>||| |||:|:|||||:||||:<br>5'TTCCACTTCTGAAAATTATCG 3'</td><td>185<br><br>188</td><td>4</td><td>Solyc05g014050.2.1<br>1422~1443(cDNA)</td><td>Inner membrane protein oxaA (AHRD V1 *-*- B9L0L4_THERP); contains Interpro domain(s) IPR001708 Membrane insertion protein, OxaA/YidC</td></tr>
<tr><td>siR35 SIR2 LTR transposon TGTACTG TGCCATG TCGCGTT (SEQ ID NO: 189)</td><td>149.7</td><td>727.44</td><td>21.2</td><td>Bc-siRNA<br><br>Target</td><td>3'TTGCGCTGTACCGTGTCATGT 5'<br>|| || |||||:||||||||<br>5'CACACGCCATGGTACAGTACA 3'</td><td>189<br><br>190</td><td>4</td><td>AT3G52810.1<br>978~999(CDS)</td><td>purple acid phosphatase 21</td></tr>
<tr><td></td><td></td><td></td><td></td><td>Bc-siRNA<br><br>Target</td><td>3'TTGCGCTGTACCGTGTCATGT 5'<br>||| | |::||||||||||||<br>5'AACACTATGTGGCACAGTACA 3'</td><td>189<br><br>191</td><td>3.5</td><td>Solyc11g017230.1.1<br>721~742(cDNA)</td><td>DNA polymerase I (AHRD V1 ***- B6U7X8_MAIZE); contains Interpro domain(s) IPR002421 5'-3' exonuclease, N-terminal</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>siR57 SIR1 LTR transposon TAGATA ATCTCTG GTTCGTT GG (SEQ ID NO: 192)</td><td>114</td><td>728.28</td><td>13.8</td><td>Bc-siRNA<br><br>Target</td><td>3'GGTTGCTTGGTCTCTAATAGAT 5'<br>:|:|||||:|:||||||||| |<br>5'TCGACGAATCGGAGATTATCGA 3'</td><td>192<br><br>193</td><td>4.5</td><td>AT3G28390.1 3253~3275(CDS)</td><td>P-glycoprotein 18</td></tr>
<tr><td></td><td></td><td></td><td></td><td>Bc-siRNA<br><br>Target</td><td>3'GGTTGCTTGGTCTCTAATAGAT 5'<br>:|:| ||| ||||||||:|||:<br>5'TCGAAGAAACAGAGATTGTCTG 3'</td><td>192<br><br>194</td><td>4.5</td><td>AT3G29575.1 350~372(CDS)</td><td>ABI five binding protein 3</td></tr>
<tr><td></td><td></td><td></td><td></td><td>Bc-siRNA<br><br>Target</td><td>3'GGTTGCTTGGTCTCTAATAGAT 5'<br>||:| |||||||||:|||||||<br>5'CCGAGGAACCAGAGGTTATCTA 3'</td><td>192<br><br>195</td><td>2.5</td><td>Solyc03g007790.2.1 2084~2106(cDNA)</td><td>Receptor-like protein kinase (AHRD V1 **** Q9FLV4_ARATH); contains Interpro domain(s) IPR002290 Serine/threonine protein kinase</td></tr>
<tr><td>siR43 SIR1 LTR transposon TGGGAG CTTTCTC TTGTTGG G (SEQ ID NO: 196)</td><td>645</td><td>501.16</td><td>122</td><td>Bc-siRNA<br><br>Target</td><td>3'GGGTTGTTCTCTTTCGAGGGT 5'<br>:|:||||||||||||||:| |<br>5'TCTAACAAGAGAAAGCTTCAA 3'</td><td>196<br><br>197</td><td>4</td><td>AT1G19050.1 592~613(CDS)</td><td>response regulator 7</td></tr>
<tr><td></td><td></td><td></td><td></td><td>Bc-siRNA<br><br>Target</td><td>3'GGGTTGTTCTCTTTCGAGGGT 5'<br>|:| ||| ||||||||:|||<br>5'ACTATCAAAAGAAAGCTTCCA 3'</td><td>196<br><br>198</td><td>4.5</td><td>AT1G26450.1 401~422(CDS)</td><td>Carbohydrate-binding X8 domain superfamily protein</td></tr>
<tr><td></td><td></td><td></td><td></td><td>Bc-siRNA<br><br>Target</td><td>3'GGGTTGTTCTCTTTCGAGGGT 5'<br>| |:|||||||||| |||||<br>5'ACAAGCAAGAGAAAGATCCCA 3'</td><td>196<br><br>199</td><td>4.5</td><td>AT1G51600.1 1398~1419(3'UTR)</td><td>ZIM-LIKE 2</td></tr>
<tr><td></td><td></td><td></td><td></td><td>Bc-siRNA<br><br>Target</td><td>3'GGGTTGTTCTCTTTCGAGGGT 5'<br>::|:|: |||||||||||||<br>5'TTCGATCAGAGAAAGCTCCCA 3'</td><td>196<br><br>200</td><td>4.25</td><td>AT1G70190.1 202~223(CDS)</td><td>Ribosomal protein L7/L12,</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>oligomerisation; Ribosomal protein L7/L12, C-terminal/adaptor protein ClpS-like</td></tr>
<tr><td></td><td></td><td></td><td></td><td>Bc-siRNA<br><br>Target</td><td>3'GGGTTGTTCTCTTTCGAGGGT 5'<br>|:|||:|: |||||||||:||<br>5'CTCAATAGAAGAAAGCTCTCA 3'</td><td>196<br><br>201</td><td>4.25</td><td>AT3G19860.1<br>979~1000(CDS)</td><td>basic helix-loop-helix (bHLH) DNA-binding superfamily protein</td></tr>
<tr><td></td><td></td><td></td><td></td><td>Bc-siRNA<br><br>Target</td><td>3'GGGTTGTTCTCTTTCGAGGGT 5'<br>| |:||| ||||||| |||||<br>5'CACGACATGAGAAAGATCCCA 3'</td><td>196<br><br>202</td><td>4.5</td><td>AT5G45030.1<br>65~86(5'UTR)</td><td>Trypsin family protein</td></tr>
<tr><td></td><td></td><td></td><td></td><td>Bc-siRNA<br><br>Target</td><td>3'GGGTTGTTCTCTTTCGAGGGT 5'<br>||::| || ||||||:|||||<br>5'CCTGAAAAAAGAAAGTTCCCA 3'</td><td>196<br><br>203</td><td>4.5</td><td>Solyc01g093970.2.1<br>809~830(cDNA)</td><td>Glycosyltransferase (AHRD V1 **--B9IC41_POPTR); contains Interpro domain(s) IPR002495 Glycosyl transferase, family 8</td></tr>
<tr><td></td><td></td><td></td><td></td><td>Bc-siRNA<br><br>Target</td><td>3'GGGTTGTTCTCTTTCGAGGGT 5'<br>||| |||:|:||:||||||||<br>5'CCCTACAGGGGAGAGCTCCCA 3'</td><td>196<br><br>204</td><td>3.5</td><td>Solyc04g039950.2.1<br>2037~2058(cDNA)</td><td>Mediator of RNA polymerase II transcription subunit 13 (AHRD V1 *-*-MED13_DICDI); contains Interpro domain(s) IPR009401 Mediator complex, subunit Med13</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td>siR40<br>SIR2 LTR<br>transposon<br>TGGAAT<br>GGGCTTG<br>TATTGGT<br>T (SEQ ID<br>NO: 205)</td><td>693.6</td><td>473.16</td><td>43</td><td>Bc-siRNA<br><br>Target</td><td>3'TTGGTTATGTTCGGGTAAGGT 5'<br>|::|||| ||| |||||||||<br>5'AGTCAATTCAATCCCATTCCA 3'</td><td>205<br><br>206</td><td>4.5</td><td>AT1G06910.1<br>756~777(CDS)</td><td>TRF-like 7</td></tr>
<tr><td></td><td></td><td></td><td></td><td>Bc-siRNA<br><br>Target</td><td>3'TTGGTTATGTTCGGGTAAGGT 5'<br>:|| |||||||||:||||||<br>5'GACATATACAAGCCTATTCCA 3'</td><td>205<br><br>207</td><td>4.5</td><td>AT1G09350.1<br>723~744(CDS)</td><td>galactinol<br>synthase 3</td></tr>
<tr><td></td><td></td><td></td><td></td><td>Bc-siRNA<br><br>Target</td><td>3'TTGGTTATGTTCGGGTAAGGT 5'<br>|| ||||:|:||||||||:||<br>5'AAGCAATGCGAGCCCATTTCA 3'</td><td>205<br><br>208</td><td>3.5</td><td>AT4G38550.1<br>604~625(CDS)</td><td>Arabidopsis<br>phospholipase-like<br>protein<br>(PEARLI 4)<br>family</td></tr>
<tr><td></td><td></td><td></td><td></td><td>Bc-siRNA<br><br>Target</td><td>3'TTGGTTATGTTCGGGTAAGGT 5'<br>|:|:||||||||| ||||:||<br>5'AGCTAATACAAGCACATTTCA 3'</td><td>205<br><br>209</td><td>4</td><td>Solyc02g037560.1.1<br>542~563(cDNA)</td><td>Ulp1 protease<br>family C-<br>terminal<br>catalytic<br>domain<br>containing<br>protein<br>(AHRD V1<br>***-<br>Q60D46_SOLDE)</td></tr>
<tr><td></td><td></td><td></td><td></td><td>Bc-siRNA<br><br>Target</td><td>3'TTGGTTATGTTCGGGTAAGGT 5'<br>:||:||||||||| ||||:||<br>5'GACTAATACAAGCACATTTCA 3'</td><td>205<br><br>210</td><td>4</td><td>Solyc08g074820.1.1<br>86~107(cDNA)</td><td>Unknown<br>Protein<br>(AHRD V1)</td></tr>
<tr><td>siR38<br>SIR2 LTR<br>transposon<br>TAATTCA<br>GGAGAC<br>GATATCG<br>T (SEQ ID<br>NO: 211)</td><td>1765.5</td><td>35.4</td><td>23.3</td><td>Bc-siRNA<br><br>Target</td><td>3'TGCTATAGCAGAGGACTTAAT 5'<br>|| || |:||||||| |||||<br>5'ACAATTTTGTCTCCTTAATTA 3'</td><td>211<br><br>212</td><td>4.5</td><td>AT3G23130.1<br>1039~1060(3'UTR)</td><td>C2H2 and<br>C2HC zinc<br>fingers<br>superfamily<br>protein</td></tr>
<tr><td></td><td></td><td></td><td></td><td>Bc-siRNA<br><br>Target</td><td>3'TGCTATAGCAGAGGACTTAAT 5'<br>:|:|||| |||||||||||:<br>5'TTGGTATCTTCTCCTGAATTG 3'</td><td>211<br><br>213</td><td>4.25</td><td>Solyc04g081500.2.1<br>836~857(cDNA)</td><td>BRCA1-A<br>complex<br>subunit BRE<br>(AHRD V1<br>***-</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>BRE_XENTR); contains Interpro domain(s) IPR010358 Brain and reproductive organ-expressed</td></tr>
<tr><td>siR46 SIR9 Intergenic region CTAACGATTGAAGGCCACCAAC (SEQ ID NO: 214)</td><td>1811.1</td><td>5.76</td><td>166.5</td><td>Bc-siRNA<br><br>Target</td><td>3'CAACCACCGGAAGTTAGCAATC 5'<br>| ||| || ||||||||||||<br>5'TTCGGTTGCGTTCAATCGTTAG 3'</td><td>214<br><br>215</td><td>4</td><td>AT5G21430.1<br>703~725(CDS)</td><td>Chaperone DnaJ-domain superfamily protein</td></tr>
<tr><td></td><td></td><td></td><td></td><td>Bc-siRNA<br><br>Target</td><td>3'CAACCACCGGAAGTTAGCAATC 5'<br>|||||||||||||||||| |:|<br>5'GTTGGTGGCCTTCAATCGCTGG 3'</td><td>214<br><br>216</td><td>3</td><td>Solyc09g007340.2.1<br>938~960(cDNA)</td><td>PWWP domain-containing protein (AHRD V1 *-*-D7L8B3_ARALY); contains Interpro domain(s) IPR000313 PWWP</td></tr>
<tr><td>siR48 SIR1 LTR transposon TGAAGTGACAGTATCGATCAA (SEQ ID NO: 217)</td><td>66.9</td><td>678.08</td><td>7.7</td><td>Bc-siRNA<br><br>Target</td><td>3'AACTAGCTATGACAGTGAAGT 5'<br>||||| ||||||||:|:|||<br>5'TTGATGGATACTGTTATTTCC 3'</td><td>217<br><br>218</td><td>4</td><td>AT2G03040.1<br>444~465(CDS)</td><td>emp24/gp25L/p24 family/GOLD family protein</td></tr>
<tr><td></td><td></td><td></td><td></td><td>Bc-siRNA</td><td>3'AACTAGCTATGACAGTGAAGT 5'<br>||||| ||||||||:|:|||</td><td>217</td><td>4</td><td>AT2G03290.1<br>444~465(CDS)</td><td>emp24/gp25L/p24</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th>Normalized read counts A</th><th>S</th><th>B</th><th colspan="2">Target gene alignment and aligned score</th><th>SEQ ID NO:</th><th>AS*</th><th>Target gene ID/target site</th><th>Putative function of target gene</th></tr>
<tr><td></td><td></td><td></td><td></td><td>Target</td><td>5'TTGATGGATACTGTTATTTCC 3'</td><td>219</td><td></td><td></td><td>family/GOLD family protein</td></tr>
<tr><td></td><td></td><td></td><td></td><td>Bc-siRNA</td><td>3'AACTAGCTATGACAGTGAAGT 5'<br>||| |||||||| ||:|||||</td><td>217</td><td>4</td><td>AT2G44430.1<br>511~532(CDS)</td><td>DNA-binding bromodomain-containing protein</td></tr>
<tr><td></td><td></td><td></td><td></td><td>Target</td><td>5'TTGTTCGATACTATCGCTTCA 3'</td><td>220</td><td></td><td></td><td></td></tr>
<tr><td></td><td></td><td></td><td></td><td>Bc-siRNA</td><td>3'AACTAGCTATGACAGTGAAGT 5'<br>|| ||:| ||||||||| |||</td><td>217</td><td>4.5</td><td>AT5G58160.1<br>1894~1915(CDS)</td><td>actin binding</td></tr>
<tr><td></td><td></td><td></td><td></td><td>Target</td><td>5'TTCATTGTTACTGTCACCTCA 3'</td><td>221</td><td></td><td></td><td></td></tr>
<tr><td></td><td></td><td></td><td></td><td>Bc-siRNA</td><td>3'AACTAGCTATGACAGTGAAGT 5'<br>||| |:|:|:||||||||||</td><td>217</td><td>3</td><td>Solyc06g068240.2.1<br>441~462(cDNA)</td><td>Pyrophosphate-energized proton pump (AHRD V1 ***-B0SRX3_LEPBP); contains Interpro domain(s) IPR004131 Inorganic H+ pyrophosphatase</td></tr>
<tr><td></td><td></td><td></td><td></td><td>Target</td><td>5'TTGCTTGGTGCTGTCACTTCA 3'</td><td>222</td><td></td><td></td><td></td></tr>
<tr><td></td><td></td><td></td><td></td><td>Bc-siRNA</td><td>3'AACTAGCTATGACAGTGAAGT 5'<br>|| || |:|:||||:||||||</td><td>217</td><td>4.5</td><td>Solyc12g099250.1.1<br>1641~1662(cDNA)</td><td>Kinase family protein (AHRD V1 ***-D7KVQ9_ARALY); contains Interpro domain(s) IPR002290 Serine/threonine protein kinase</td></tr>
<tr><td></td><td></td><td></td><td></td><td>Target</td><td>5'TTCATGGGTGCTGTTACTTCA 3'</td><td>223</td><td></td><td></td><td></td></tr>
<tr><td>siR1007<br>SIR1007</td><td>1641.7</td><td>14</td><td>0</td><td>Bc-siRNA</td><td>3'TAGGAAGGCGTCCTAGTGGATG 5'<br>:|||| || ||| |||||||||</td><td>224</td><td>4.5</td><td>AT3G09370.1<br>334~356(CDS)</td><td>myb domain protein 3r-3</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>LTR transposon GTAGGT GATCCTG CGGAAG GAT (SEQ ID NO: 224)</td><td></td><td></td><td></td><td>Target</td><td>5'GTCCTGCCACAGTATCACCTAC 3'</td><td>225</td><td></td><td></td><td></td></tr>
<tr><td></td><td></td><td></td><td></td><td>Bc-siRNA<br><br>Target</td><td>3'TAGGAAGGCGTCCTAGTGGATG 5'<br>||:||||| |||||||:|||:<br>5'ATTCTTCCACAGGATCATCTAT 3'</td><td>224<br><br>226</td><td>3</td><td>Solyc12g099450.1.1<br>514~536(cDNA)</td><td>Genomic DNA chromosome 5 TAC clone K20J1 (AHRD V1 *-*- Q9FH24_ARATH)</td></tr>
<tr><td>siR56 SIR1 LTR transposon TCGTTCA TCCTGTA GTTGCGT (SEQ ID NO: 227)</td><td>38.7</td><td>655.04</td><td>19.1</td><td>Bc-siRNA<br><br>Target</td><td>3'TGCGTTGATGTCCTACTTGCT 5'<br>|:||||||:|||||| ||||<br>5'ATGCAACTGCAGGATCAACGT 3'</td><td>227<br><br>228</td><td>4</td><td>AT5G37010.1<br>1380~1401(CDS)</td><td>unknown protein, hypothetical protein, uncharacterized protein</td></tr>
<tr><td></td><td></td><td></td><td></td><td>Bc-siRNA<br><br>Target</td><td>3'TGCGTTGATGTCCTACTTGCT 5'<br>| |||||||||||||||:| |<br>5'AAGCAACTACAGGATGAGCAA 3'</td><td>227<br><br>229</td><td>4</td><td>Solyc03g019870.2.1<br>915~936(cDNA)</td><td>Cytochrome P450</td></tr>
<tr><td>siR49 SIR2 LTR transposon TGTGGCT TATGTCT TTTGATA (SEQ ID NO: 230)</td><td>1079.5</td><td>228.76</td><td>50.6</td><td>Bc-siRNA<br><br>Target</td><td>3'ATAGTTTTCTGTATTCGGTGT 5'<br>|| |||| ||||||| ||||:<br>5'TACCAAATGACATAAACCACG 3'</td><td>230<br><br>231</td><td>4.5</td><td>AT3G45700.1<br>1535~1556(CDS)</td><td>Major facilitator superfamily protein</td></tr>
<tr><td></td><td></td><td></td><td></td><td>Bc-siRNA<br><br>Target</td><td>3'ATAGTTTTCTGTATTCGGTGT 5'<br>||:|||||:|||||||| |<br>5'AATTAAAAGGCATAAGCCAAA 3'</td><td>230<br><br>232</td><td>4.5</td><td>AT4G01410.1<br>940~961(3'UTR)</td><td>Late embryogenesis abundant (LEA) hydroxyproline-rich glycoprotein family</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th>Normalized read counts<br>A</th><th><br>S</th><th><br>B</th><th colspan="2">Target gene alignment and aligned score</th><th>SEQ ID NO:</th><th>AS*</th><th>Target gene ID/target site</th><th>Putative function of target gene</th></tr>
<tr><td></td><td></td><td></td><td></td><td>Bc-siRNA<br><br>Target</td><td>3'ATAGTTTTCTGTATTCGGTGT 5'<br>||| ||:| ||| ||||||||<br>5'TATGAAGAAACACAAGCCACA 3'</td><td>230<br><br>233</td><td>4.5</td><td>Solyc01g107100.2.1<br>82~103(cDNA)</td><td>Beta-1,4-xylosidase (AHRD V1 ***- D7LA14_ARALY)</td></tr>
<tr><td></td><td></td><td></td><td></td><td>Bc-siRNA<br><br>Target</td><td>3'ATAGTTTTCTGTATTCGGTGT 5'<br>|| :|:|:|||||||||:|||<br>5'TACTAGAGGACATAAGCTACA 3'</td><td>230<br><br>234</td><td>4.25</td><td>Solyc07g042160.2.1<br>1440~1461(cDNA)</td><td>Polygalacturonase (AHRD V1 **-- B6SZN5_MAIZE); contains Interpro domain(s) IPR012334 Pectin lyase fold</td></tr>
<tr><td>siR58 SIR1 LTR transposon TAAATTG GGATTCA TTGTCTG (SEQ ID NO: 235)</td><td>39.5</td><td>636.12</td><td>7</td><td>Bc-siRNA<br><br>Target</td><td>3'GTCTGTTACTTAGGGTTAAAT 5'<br>||||||| |||||:|||| |:<br>5'CAGACAAAGAATCTCAATATG 3'</td><td>235<br><br>236</td><td>4.5</td><td>AT4G36080.1<br>4572~4593(CDS)</td><td>phosphotransferases, alcohol group as acceptor; binding; inositol or phosphatidylinositol kinases</td></tr>
<tr><td></td><td></td><td></td><td></td><td>Bc-siRNA<br><br>Target</td><td>3'GTCTGTTACTTAGGGTTAAAT 5'<br>| ||:||||||||::||||||<br>5'CTGATAATGAATCTTAATTTA 3'</td><td>235<br><br>237</td><td>4.5</td><td>Solyc01g058540.2.1<br>1023~1044(cDNA)</td><td>WRKY transcription factor 31 (AHRD V1 *-*- C9DI20_9ROSI); contains Interpro domain(s) IPR003657 DNA-binding WRKY</td></tr>
<tr><td></td><td></td><td></td><td></td><td>Bc-siRNA<br><br>Target</td><td>3'GTCTGTTACTTAGGGTTAAAT 5'<br>:| |:|:| |||||||||||:<br>5'TATATAGTCAATCCCAATTTG 3'</td><td>235<br><br>238</td><td>4</td><td>Solyc01g109980.2.1<br>2186~2207(cDNA)</td><td>BEL1-like homeodomain protein 6 (AHRD V1 *--- BLH6_ARATH); contains Interpro</td></tr>
</table>

TABLE 1-continued

<table>
<tr><th colspan="9">Bc-sRNAs that have predicted targets in both *Arabidopsis* and *S. lycopersicum*.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>domain(s) IPR006563 POX</td></tr>
<tr><td>siR63 SIR1 LTR transposon TAATAGT TGATGA GAGAAT GT (SEQ ID NO: 239)</td><td>132.9</td><td>578.48</td><td>7.8</td><td>Bc-siRNA<br><br>Target</td><td>3'TGTAAGAGAGTAGTTGATAAT 5'<br>| ||||:|:||||||||||<br>5'TCTTTCTTTTATCAACTATTT 3'</td><td>239<br><br>240</td><td>4.5</td><td>AT5G04430.1<br>1461~1482(3'UTR)</td><td>binding to TOMV RNA 1L (long form)</td></tr>
<tr><td></td><td></td><td></td><td></td><td>Bc-siRNA<br><br>Target</td><td>3'TGTAAGAGAGTAGTTGATAAT 5'<br>| |||:|||:||:||:|||||<br>5'AGATTTTCTTATTAATTATTA 3'</td><td>239<br><br>241</td><td>4.5</td><td>AT5G48385.1<br>2124~2145(3'UTR)</td><td>FRIGIDA-like protein</td></tr>
<tr><td></td><td></td><td></td><td></td><td>Bc-siRNA<br><br>Target</td><td>3'TGTAAGAGAGTAGTTGATAAT 5'<br>:|||| | |||||||| ||||<br>5'GCATTGTATCATCAACAATTA 3'</td><td>239<br><br>242</td><td>4.5</td><td>Solyc01g096910.2.1<br>975~996(cDNA)</td><td>Vacuolar protein sorting 36 family protein (AHRD V1 ***- D7LY74_ARALY); contains Interpro domain(s) IPR007286 EAP30</td></tr>
<tr><td>siR1005 SIR1005<br><br>LTR transposon TAAAGA GTTTCTT CAATAG GA (SEQ ID NO: 243)</td><td>441.4</td><td>452.6</td><td>277.5</td><td>Bc-siRNA<br><br>Target</td><td>3'AGGATAACTTCTTTGAGAAAT 5'<br>||||| | ||||| |||||||<br>5'TCCTACTCAAGAATCTCTTTA 3'</td><td>243<br><br>244</td><td>4</td><td>AT1G20200.1<br>1224~1245(CDS)</td><td>PAM domain (PCI/PINT associated module) protein</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence<br>(5'-3')</th><th colspan="3">Normalized read counts</th><th colspan="2">Target gene alignment<br>and aligned score</th><th>SEQ ID<br>NO:</th><th><br>AS*</th><th>Target gene<br>ID/target site</th><th>Putative function of<br>target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'AGGATAACTTCTTTGAGAAAT 5'<br>||:|| ||||||:||| |||<br>5'TCTTAATGAAGAAGCTCATTA 3'</td><td>243<br><br>245</td><td>4.5</td><td>AT1G20650.1<br>1502~1523(CDS)</td><td>Protein kinase superfamily protein</td></tr>
<tr><td></td><td></td><td></td><td></td><td>Bc-siRNA<br><br>Target</td><td>3'AGGATAACTTCTTTGAGAAAT 5'<br>|||||||:||||||||||:<br>5'GGCTATTGAGGAAACTCTTTG 3'</td><td>243<br><br>246</td><td>4.5</td><td>AT1G67540.1<br>352~373(CDS)</td><td>unknown protein, hypothetical protein, uncharacterized protein</td></tr>
<tr><td></td><td></td><td></td><td></td><td>Bc-siRNA<br><br>Target</td><td>3'AGGATAACTTCTTTGAGAAAT 5'<br>|::||| |||||||||||| |<br>5'TTTTATCGAAGAAACTCTTCA 3'</td><td>243<br><br>247</td><td>4.5</td><td>AT2G23790.1<br>82~103(CDS)</td><td>Protein of unknown function (DUF607)</td></tr>
<tr><td></td><td></td><td></td><td></td><td>Bc-siRNA<br><br>Target</td><td>3'AGGATAACTTCTTTGAGAAAT 5'<br>||:|:|| |||||||| ||:<br>5'TCTTGTTCAAGAAACTCCTTG 3'</td><td>243<br><br>248</td><td>4.5</td><td>AT3G50950.1<br>2116~2137(CDS)</td><td>HOPZ-ACTIVATED RESISTANCE 1</td></tr>
<tr><td></td><td></td><td></td><td></td><td>Bc-siRNA<br><br>Target</td><td>3'AGGATAACTTCTTTGAGAAAT 5'<br>| || |||:||||||||| |<br>5'TACTCTTGGAGAAACTCTTGA 3'</td><td>243<br><br>249</td><td>4.5</td><td>AT4G14510.1<br>1862~1883(CDS)</td><td>CRM family member 3B</td></tr>
<tr><td></td><td></td><td></td><td></td><td>Bc-siRNA<br><br>Target</td><td>3'AGGATAACTTCTTTGAGAAAT 5'<br>||:| || ||||||||||| |<br>5'TCTTCTTCAAGAAACTCTTCA 3'</td><td>243<br><br>250</td><td>4.5</td><td>AT5G61290.1<br>1366~1387(CDS)</td><td>Flavin-binding monooxygenase family protein</td></tr>
<tr><td></td><td></td><td></td><td></td><td>Bc-siRNA<br><br>Target</td><td>3'AGGATAACTTCTTTGAGAAAT 5'<br>||| |||||||||||:|||:<br>5'CCCTCTTGAAGAAACTTTTTG 3'</td><td>243<br><br>251</td><td>3.5</td><td>Solyc01g091200.2.1<br>824~845(cDNA)</td><td>NAD dependent epimerase/dehydratase family protein expressed (AHRD V1 ***-Q2MJA7_ORYSJ); contains Interpro domain(s) IPR016040 NAD(P)-binding domain</td></tr>
<tr><td></td><td></td><td></td><td></td><td>Bc-siRNA<br><br>Target</td><td>3'AGGATAACTTCTTTGAGAAAT 5'<br>|:| ||||||||||||||| |<br>5'TTCAATTGAAGAAACTCTGTT 3'</td><td>243<br><br>252</td><td>4.5</td><td>Solyc04g028560.2.1<br>2604~2625(cDNA)</td><td>Zinc finger transcription factor (AHRD V1 *-** Q7K9G4_DROME); contains</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th>Normalized read counts A</th><th>Normalized read counts S</th><th>Normalized read counts B</th><th></th><th>Target gene alignment and aligned score</th><th>SEQ ID NO:</th><th>AS*</th><th>Target gene ID/target site</th><th>Putative function of target gene</th></tr>
<tr><td></td><td></td><td></td><td></td><td></td><td></td><td></td><td></td><td></td><td>Interpro domain(s) IPR013087 Zinc finger, C2H2-type/integrase, DNA-binding</td></tr>
<tr><td></td><td></td><td></td><td></td><td>Bc-siRNA<br><br>Target</td><td>3'AGGATAACTTCTTTGAGAAAT 5'<br>||| |||||||||||:|||:<br>5'CCCTCTTGAAGAAACTTTTTG 3'</td><td>243<br><br>253</td><td>3.5</td><td>Solyc05g050990.1.1 478~499(cDNA)</td><td>UDP-D-glucuronate 4-epimerase 2 (AHRD V1 **** D7M5S7_ARALY); contains Interpro domain(s) IPR016040 NAD(P)-binding domain</td></tr>
<tr><td></td><td></td><td></td><td></td><td>Bc-siRNA<br><br>Target</td><td>3'AGGATAACTTCTTTGAGAAAT 5'<br>|| ||| |:||| ||||||||<br>5'TCATATCGGAGATACTCTTTA 3'</td><td>243<br><br>254</td><td>4.5</td><td>Solyc10g005940.1.1 191~212(cDNA)</td><td>CT099 (Fragment) (AHRD V1 *--- Q4KR02_SOLCI); contains Interpro domain(s) IPR003245 Plastocyanin-like</td></tr>
<tr><td>siR60 SIR1 LTR transposon TGCAATG GAATTCG AAGACG G (SEQ ID NO: 255)</td><td>33.4</td><td>599.88</td><td>34.1</td><td>Bc-siRNA<br><br>Target</td><td>3'GGCAGAAGCTTAAGGTAACGT 5'<br>::||||||||||||:||| ||<br>5'TTGTCTTCGAATTCTATTTCA 3'</td><td>255<br><br>256</td><td>4.5</td><td>AT1G55610.1 817~838(CDS)</td><td>BRI1 like</td></tr>
<tr><td></td><td></td><td></td><td></td><td>Bc-siRNA<br><br>Target</td><td>3'GGCAGAAGCTTAAGGTAACGT 5'<br>|| |||| |||||||||||::<br>5'CCATCTTGGAATTCCATTGTG 3'</td><td>255<br><br>257</td><td>4.25</td><td>Solyc08g067800.1.1 261~282(cDNA)</td><td>Acetyltransferase (AHRD V1 **-* B4RG69_PHEZH); contains</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th>Normalized read counts A</th><th>S</th><th>B</th><th colspan="2">Target gene alignment and aligned score</th><th>SEQ ID NO:</th><th>AS*</th><th>Target gene ID/target site</th><th>Putative function of target gene</th></tr>
<tr><td></td><td></td><td></td><td></td><td></td><td></td><td></td><td></td><td></td><td>Interpro domain(s) IPR016181 Acyl-CoA N-acyltransferase</td></tr>
<tr><td>siR61 SIR3 LTR transposon TAGAAT AGAATC GTATACG TG (SEQ ID NO: 258)</td><td>230.9</td><td>515.12</td><td>10.3</td><td>Bc-siRNA<br><br>Target</td><td>3'GTGCATATGCTAAGATAAGAT 5'<br>|: ||| |||||||||||||<br>5'AATTTATTCGATTCTATTCTA 3'</td><td>258<br><br>259</td><td>4.25</td><td>AT2G17510.2 1543~1564(CDS)</td><td>ribonuclease II family protein</td></tr>
<tr><td></td><td></td><td></td><td></td><td>Bc-siRNA<br><br>Target</td><td>3'GTGCATATGCTAAGATAAGAT 5'<br>|| ||:||:||||:|:|||||<br>5'CAAGTGTATGATTTTGTTCTA 3'</td><td>258<br><br>260</td><td>4</td><td>Solyc03g078160.2.1 896~917(cDNA)</td><td>POT family domain containing protein expressed (AHRD V1 ***-D8L9H8_WHEAT); contains Interpro domain(s) IPR007493 Protein of unknown function DUF538</td></tr>
<tr><td></td><td></td><td></td><td></td><td>Bc-siRNA<br><br>Target</td><td>3'GTGCATATGCTAAGATAAGAT 5'<br>:|:|||||:|||||||||| |<br>5'TATGTATATGATTCTATTCAA 3'</td><td>258<br><br>261</td><td>3.5</td><td>Solyc03g121810.2.1 2888~2909(cDNA)</td><td>Phospholipid-transporting ATPase 1 (AHRD V1 **** C5FPS3_NANOT); contains Interpro domain(s) IPR006539 ATPase, P-</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'GTGCATATGCTAAGATAAGAT 5'<br>||:|| |||||||| |||:||<br>5'CATGTTTACGATTCAATTTTA 3'</td><td>258<br><br>262</td><td>4.5</td><td>Solyc04g082430.2.1<br>8~29(cDNA)</td><td>type, phospholipid-translocating, flippase B-like cyclin (AHRD V1 **** Q40337_MEDSA); contains Interpro domain(s) IPR014400 Cyclin, A/B/D/E</td></tr>
<tr><td>siR62 SIR2 LTR transposon TACGAC GGATTCG CAAGTA AA (SEQ ID NO: 263)</td><td>149.7</td><td>547.24</td><td>8.6</td><td>Bc-siRNA<br><br>Target</td><td>3'AAATGAACGCTTAGGCAGCAT 5'<br>|||: ||||||||||||:||<br>5'TTTGGTTGCGAATCCGTTGTT 3'</td><td>263<br><br>264</td><td>4.25</td><td>AT1G11620.1<br>353~374(CDS)</td><td>F-box and associated interaction domains-containing protein</td></tr>
<tr><td></td><td></td><td></td><td></td><td>Bc-siRNA<br><br>Target</td><td>3'AAATGAACGCTTAGGCAGCAT 5'<br>| || ||||||||:||||||<br>5'TGTAATTGCGAATTCGTCGTT 3'</td><td>263<br><br>265</td><td>4</td><td>AT4G10030.1<br>100~121(5'UTR)</td><td>alpha/beta-Hydrolases superfamily protein</td></tr>
<tr><td></td><td></td><td></td><td></td><td>Bc-siRNA<br><br>Target</td><td>3'AAATGAACGCTTAGGCAGCAT 5'<br>|||||||| |||||||| ||<br>5'TTTACTTGGGAATCCGTAGTC 3'</td><td>263<br><br>266</td><td>4</td><td>Solyc01g009570.2.1<br>236~257(cDNA)</td><td>Unknown Protein (AHRD V1)</td></tr>
<tr><td>siR65 SIR1 LTR transposon TAGCAA GAGGGA TTCTGTA GT (SEQ ID NO: 267)</td><td>14.4</td><td>583.44</td><td>22.2</td><td>Bc-siRNA<br><br>Target</td><td>3'TGATGTCTTAGGGAGAACGAT 5'<br>|| ||:||:|||||||| |||<br>5 'ACAACGGAGTCCCTCTTCCTA 3'</td><td>267<br><br>268</td><td>4</td><td>AT1G75950.1<br>282~303(CDS)</td><td>S phase kinase-associated protein 1</td></tr>
<tr><td></td><td></td><td></td><td></td><td>Bc-siRNA<br><br>Target</td><td>3'TGATGTCTTAGGGAGAACGAT 5'<br>:| |||||||||||| ||||:<br>5'GCAACAGAATCCCTCCTGCTG 3'</td><td>267<br><br>269</td><td>4</td><td>AT2G21330.1<br>974~995(CDS)</td><td>fructose-bisphosphate aldolase 1</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence<br>(5'-3')</td><td colspan="3">Normalized read counts</td><td colspan="2">Target gene alignment<br>and aligned score</td><td>SEQ ID<br>NO:</td><td>AS*</td><td>Target gene<br>ID/target site</td><td>Putative function of<br>target gene</td></tr>
<tr><td></td><td>A</td><td>S</td><td>B</td><td></td><td></td><td></td><td></td><td></td><td></td></tr>
<tr><td></td><td></td><td></td><td></td><td>Bc-siRNA<br><br>Target</td><td>3'TGATGTCTTAGGGAGAACGAT 5'<br>::| || |:|||:||||||||:<br>5'GCAACTGGATCTCTCTTGCTG 3'</td><td>267<br><br>270</td><td>4.5</td><td>AT3G23670.1<br>3292~3313(CDS)</td><td>phragmoplast-associated kinesin-related protein, putative</td></tr>
<tr><td></td><td></td><td></td><td></td><td>Bc-siRNA<br><br>Target</td><td>3'TGATGTCTTAGGGAGAACGAT 5'<br>|| |:| |||:||||||||<br>5'TCTTCGGCATCTCTCTTGCTA 3'</td><td>267<br><br>271</td><td>4.5</td><td>AT4G25980.1<br>187~208(CDS)</td><td>Peroxidase superfamily protein</td></tr>
<tr><td></td><td></td><td></td><td></td><td>Bc-siRNA<br><br>Target</td><td>3'TGATGTCTTAGGGAGAACGAT 5'<br>|:||| |||||:||||||:|<br>5'ATTACTGAATCTCTCTTGTTC 3'</td><td>267<br><br>272</td><td>4.5</td><td>A14G27680.1<br>1507~1528(3'UTR)</td><td>P-loop containing nucleoside triphosphate hydrolases superfamily protein</td></tr>
<tr><td></td><td></td><td></td><td></td><td>Bc-siRNA<br><br>Target</td><td>3'TGATGTCTTAGGGAGAACGAT 5'<br>::||:||||||:||:||||||<br>5'GTTATAGAATCTCTTTTGCTA 3'</td><td>267<br><br>273</td><td>4</td><td>Solyc07g007790.2.1<br>3439~3460(cDNA)</td><td>Sucrose phosphate synthase (AHRD V1 **** Q2HYI0_CUCME); contains Interpro domain(s) IPR012819 Sucrose phosphate synthase, plant</td></tr>
<tr><td></td><td></td><td></td><td></td><td>Bc-siRNA<br><br>Target</td><td>3'TGATGTCTTAGGGAGAACGAT 5'<br>::|||| |||||||||| ||<br>5'GTTACACAATCCCTCTTGATA 3'</td><td>267<br><br>274</td><td>4.5</td><td>Solyc12g008370.1.1<br>496~517(cDNA)</td><td>Pre-mRNA-processing protein 45 (AHRD V1 **-- D6RKF6_COPC7); contains Interpro domain(s) IPR017862 SKI-interacting protein, SKIP</td></tr>
<tr><td>siR67<br>SIR2 LTR</td><td>687.5</td><td>297.88</td><td>25.7</td><td>Bc-siRNA</td><td>3'TTTTTTAAGAGGCTAGCTAAAT 5'<br>| ||||||||||||| |||||</td><td>275</td><td>4</td><td>AT1G27880.1<br>3~25(CDS)</td><td>DEAD/DEAH (SEQ ID</td></tr>
</table>

TABLE 1-continued

<table>
<tr><th colspan="10">Bc-sRNAs that have predicted targets in both *Arabidopsis* and *S. lycopersicum*.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>transposon TAAATCG ATCGGA GAATTTT TT (SEQ ID NO: 275)</td><td></td><td></td><td></td><td>Target</td><td>5'ATAAAATTCTCCGATGGATTTC 3'</td><td>276</td><td></td><td></td><td>NOS: 277 and 278) box RNA helicase family protein</td></tr>
<tr><td></td><td></td><td></td><td></td><td>Bc-siRNA<br><br>Target</td><td>3'TTTTTTAAGAGGCTAGCTAAAT 5'<br>||:||||:||||||||||||<br>5'CAAGAATTTTCCGATCGATTTC 3'</td><td>275<br><br>279</td><td>3</td><td>Solyc05g055050.1.1 568~590(cDNA)</td><td>Calcium-dependent protein kinase 2 (AHRD V1 **** B4FZS4_MAIZE); contains Interpro domain(s) IPR002290 Serine/threonine protein kinase</td></tr>
<tr><td></td><td></td><td></td><td></td><td>Bc-siRNA<br><br>Target</td><td>3'TTTTTTAAGAGGCTAGCTAAAT 5'<br>|:|:|| ||||||||||| |||<br>5'AGAGAAATCTCCGATCGACTTA 3'</td><td>275<br><br>280</td><td>4</td><td>Solyc07g053900.2.1 421~443(cDNA)</td><td>Plant-specific domain TIGR01615 family protein (AHRD V1 *-*- B6UDN7_MAIZE); contains Interpro domain(s) IPR006502 Protein of unknown function DUF506, plant</td></tr>
<tr><td>siR68 SIR1 LTR transposon TGGATGC AGTGATC GGAATT G (SEQ ID NO: 281)</td><td>20.5</td><td>534.88</td><td>6.4</td><td>Bc-siRNA<br><br>Target</td><td>3'GTTAAGGCTAGTGACGTAGGT 5'<br>: ||||||||||||||| |||<br>5'TTATTCCGATCACTGCAACCA 3'</td><td>281<br><br>282</td><td>4.25</td><td>AT4G21700.1 167~188(CDS)</td><td>Protein of unknown function (DUF2921)</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'GTTAAGGCTAGTGACGTAGGT 5'<br>|||| |:|:||||||:|||:|<br>5'CAATACTGGTCACTGTATCTA 3'</td><td>281<br><br>283</td><td>4</td><td>Solyc04g009560.2.1<br>2811~2832(cDNA)</td><td>TBC1 domain family member 8B (AHRD V1 *--- B9A6K5_HUMAN); contains Interpro domain(s) IPR000195 RabGAP/TBC</td></tr>
<tr><td></td><td></td><td></td><td></td><td>Bc-siRNA<br><br>Target</td><td>3'GTTAAGGCTAGTGACGTAGGT 5'<br>|:| ||||:|||||| ||||:<br>5'CGAATCCGGTCACTGAATCCG 3'</td><td>281<br><br>284</td><td>4.5</td><td>Solyc10g007340.2.1<br>453~474(cDNA)</td><td>Unknown Protein (AHRD V1)</td></tr>
<tr><td>siR73 SIR3 LTR transposon TGTGCCC AATCTAT TTTCGGA (SEQ ID NO: 285)</td><td>478.6</td><td>305.28</td><td>141.6</td><td>Bc-siRNA<br><br>Target</td><td>3'AGGCTTTTATCTAACCCGTGT 5'<br>|| |||| |||||||||| |<br>5'TCAGAAACTAGATTGGGCAGA 3'</td><td>285<br><br>286</td><td>4</td><td>AT1G17020.1<br>459~480(CDS)</td><td>senescence-related gene 1</td></tr>
<tr><td></td><td></td><td></td><td></td><td>Bc-siRNA<br><br>Target</td><td>3'AGGCTTTTATCTAACCCGTGT 5'<br>|||||| | || ||||||||:<br>5'TCCGAACAGAGTTTGGGCACG 3'</td><td>285<br><br>287</td><td>4.5</td><td>Solyc01g111250.2.1<br>533~554(cDNA)</td><td>Phosphatidylinositol-specific phospholipase c (AHRD V1 *-*- B9UXN2_LISMO); contains Interpro domain(s) IPR017946 PLC-like phosphodiesterase, TIM beta/alpha-barrel domain</td></tr>
<tr><td></td><td></td><td></td><td></td><td>Bc-siRNA<br><br>Target</td><td>3'AGGCTTTTATCTAACCCGTGT 5'<br>|||||| | || ||||||||:<br>5'TCCGAACAGAGTTTGGGCACG 3'</td><td>285<br><br>288</td><td>4.5</td><td>Solyc01g111260.2.1<br>543~564(cDNA)</td><td>Phosphatidylinositol-specific phospholipase c (AHRD V1 *-*- B9UY71_LISMO); contains</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td></td><td></td><td></td><td></td><td>Bc-siRNA<br><br>Target</td><td>3'AGGCTTTTATCTAACCCGTGT 5'<br>|| ||:|| |||| |||||||<br>5'TCAGAGAAGAGATGGGGCACA 3'</td><td>285<br><br>289</td><td>4.5</td><td>Solyc06g069280.2.1<br>1359~1380(cDNA)</td><td>Interpro domain(s) IPR017946 PLC-like phosphodiesterase, TIM beta/alpha-barrel domain Protein LSM14 homolog A (AHRD V1 *---LS14A_PONAB); contains Interpro domain(s) IPR019053 FFD and TFG box motifs</td></tr>
<tr><td>siR81 SIR1 LTR transposon TGTCTCT AATCAA GCGTTGG G (SEQ ID NO: 290)</td><td>28.1</td><td>438.6</td><td>3.6</td><td>Bc-siRNA<br><br>Target</td><td>3'GGGTTGCGAACTAATCTCTGT 5'<br>||||:|:||||||:|| |||<br>5'TCCAATGTTTGATTGGAAACA 3'</td><td>290<br><br>291</td><td>4.5</td><td>AT5G48670.1<br>403~424(CDS)</td><td>AGAMOUS-like 80</td></tr>
<tr><td></td><td></td><td></td><td></td><td>Bc-siRNA<br><br>Target</td><td>3'GGGTTGCGAACTAATCTCTGT 5'<br>::||| || |||||:||||||<br>5'TTCAAAGCCTGATTGGAGACA 3'</td><td>290<br><br>292</td><td>4.5</td><td>Solyc03g082940.2.1<br>1376~1397(cDNA)</td><td>Importin subunit beta (AHRD V1 ***-B0WBR4_CULQU); contains Interpro domain(s) IPR011989 Armadillo-like helical</td></tr>
<tr><td></td><td></td><td></td><td></td><td>Bc-siRNA<br><br>Target</td><td>3'GGGTTGCGAACTAATCTCTGT 5'<br>:|||| ||||| ||||||||<br>5'TCCAAAGCTTGCTTAGAGACT 3'</td><td>290<br><br>293</td><td>4.5</td><td>Solyc08g062940.2.1<br>810~831(cDNA)</td><td>Calmodulin binding protein (AHRD V1 **-*</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td></td><td></td><td></td><td></td><td></td><td></td><td></td><td></td><td></td><td>B6T951_MAIZE); contains Interpro domain(s) IPR000048 IQ calmodulin-binding region</td></tr>
<tr><td>siR82 SIR1 LTR transposon TGATACG GATTTCT TAACTGA T (SEQ ID NO: 294)</td><td>275</td><td>335.76</td><td>26.9</td><td>Bc-siRNA<br><br>Target</td><td>3'TAGTCAATTCTTTAGGCATAGT 5'<br>||::||||| |||||:|||||<br>5'ATTGGTTAAAAAATCTGTATCC 3'</td><td>294<br><br>295</td><td>4.5</td><td>AT2G45540.1 4598~4620(CDS)</td><td>WD-40 repeat family protein/ beige-related</td></tr>
<tr><td></td><td></td><td></td><td></td><td>Bc-siRNA<br><br>Target</td><td>3'TAGTCAATTCTTTAGGCATAGT 5'<br>||| ||||| :|||||||||||<br>5'ATCTGTTAACGAATCCGTATCA 3'</td><td>294<br><br>296</td><td>4</td><td>Solyc11g006560.1.1 922~944(cDNA)</td><td>Glycosyl transferase group 1 (AHRD V1 ***- B6T775_MAIZE); contains Interpro domain(s) IPR001296 Glycosyl transferase, group 1</td></tr>
<tr><td>siR86 SIR2 LTR transposon TGTTGAT AGCTGAT TTGATGG T (SEQ ID NO: 297)</td><td>695.9</td><td>147.28</td><td>89.9</td><td>Bc-siRNA<br><br>Target</td><td>3'TGGTAGTTTAGTCGATAGTTGT 5'<br>:||: |||:|||||||||||||<br>5'GCCGCCAAGTCAGCTATCAACA 3'</td><td>297<br><br>298</td><td>3.25</td><td>AT1G10180.1 2187~2209(CDS)</td><td>uncharacterized protein. hypothetical protein</td></tr>
<tr><td></td><td></td><td></td><td></td><td>Bc-siRNA<br><br>Target</td><td>3'TGGTAGTTTAGTCGATAGTTGT 5'<br>|:||| ||||||| ||||:|||<br>5'ATCATAAAATCAGATATCGACA 3'</td><td>297<br><br>299</td><td>4.5</td><td>AT5G66650.1 734~756(CDS)</td><td>Protein of unknown function (DUF607)</td></tr>
</table>

TABLE 1-continued

Bc-sRNAs that have predicted targets in both *Arabidopsis* and *S. lycopersicum*.

<table>
<tr><th rowspan="2">Bc-siRNA ID, locus, and siRNA sequence (5'-3')</th><th colspan="3">Normalized read counts</th><th rowspan="2"></th><th rowspan="2">Target gene alignment and aligned score</th><th rowspan="2">SEQ ID NO:</th><th rowspan="2">AS*</th><th rowspan="2">Target gene ID/target site</th><th rowspan="2">Putative function of target gene</th></tr>
<tr><th>A</th><th>S</th><th>B</th></tr>
<tr><td></td><td></td><td></td><td></td><td>Bc-siRNA<br><br>Target</td><td>3'TGGTAGTTTAGTCGATAGTTGT 5'<br>||:||:|:|||| ||||||||<br>5'ACTATTAGATCATCTATCAACC 3'</td><td>297<br><br>300</td><td>4.5</td><td>Solyc01g058190.2.1<br>1101~1123(cDNA)</td><td>30S ribosomal protein S6 (AHRD V1 *-*- B4WMV0_9 GAMM); contains Interpro domain(s) IPR000529 Ribosomal protein S6</td></tr>
<tr><td></td><td></td><td></td><td></td><td>Bc-siRNA<br><br>Target</td><td>3'TGGTAGTTTAGTCGATAGTTGT 5'<br>|| :|: ||||||||||||||<br>5'ACAGTTCAATCAGCTATCAACA 3'</td><td>297<br><br>307</td><td>4.5</td><td>Solyc05g052280.2.1<br>211~233(cDNA)</td><td>Peroxidase (AHRD V1 ***- B9VRK9_CAPAN); contains Interpro domain(s) IPR002016 Haem peroxidase, plant/fungal/bacterial</td></tr>
<tr><td>siR91 SIR2 LTR transposon TGGTGCT GTTGATA GCTGATT T (SEQ ID NO: 302)</td><td>533.3</td><td>187.64</td><td>32.5</td><td>Bc-siRNA<br><br>Target</td><td>3'TTTAGTCGATAGTTGTCGTGGT 5'<br>:|:| ||||||||:|||||:||<br>5'GAGTAAGCTATCAGCAGCATCA 3'</td><td>302<br><br>303</td><td>4</td><td>AT1G70620.1<br>654~676(CDS)</td><td>cyclin-related</td></tr>
<tr><td></td><td></td><td></td><td></td><td>Bc-siRNA<br><br>Target</td><td>3'TTTAGTCGATAGTTGTCGTGGT 5'<br>:|| ||| |||||||||||| |<br>5'GAAGCAGGTATCAACAGCACAA 3'</td><td>302<br><br>304</td><td>4.5</td><td>Solyc01g006030.2.1<br>449~471(cDNA)</td><td>E3 ubiquitin-protein ligase bre1 (AHRD V1 *-*- B6K254_SCHJY); contains Interpro domain(s) IPR018957 Zinc finger, C3HC4 RING-type</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th></th><th>Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'TTTAGTCGATAGTTGTCGTGGT 5'<br>:|  || |||||||||||||||<br>5'GATACAACTATCAACAGCACCA 3'</td><td>302<br><br>305</td><td>4.5</td><td>Solyc01g060270.1.1 975~997(cDNA)</td><td>Os06g0207500 protein (Fragment) (AHRD V1 ***- Q0DDQ9_ORYSJ); contains Interpro domain(s) IPR004253 Protein of unknown function DUF231, plant</td></tr>
<tr><td></td><td></td><td></td><td></td><td>Bc-siRNA<br><br>Target</td><td>3'TTTAGTCGATAGTTGTCGTGGT 5'<br>||:|:|||||||| ||:||||<br>5'AAGTTAGCTATCAAAAGTACCA 3'</td><td>302<br><br>306</td><td>4</td><td>Solyc05g026330.1.1 322~344(cDNA)</td><td>Caffeoyl-CoA O- methyltransferase (AHRD V1 **** A2PZD5_IPONI); contains Interpro domain(s) IPR002935 O- methyltransferase, family 3</td></tr>
<tr><td></td><td></td><td></td><td></td><td>Bc-siRNA<br><br>Target</td><td>3'TTTAGTCGATAGTTGTCGTGGT 5'<br>||:|:|||||||| ||:||||<br>5'AAGTTAGCTATCAAAAGTACCA 3'</td><td>302<br><br>307</td><td>4</td><td>Solyc05g026350.1.1 444~466(cDNA)</td><td>Caffeoyl-CoA O- methyltransferase (AHRD V1 **** A2PZD5_IPONI); contains Interpro domain(s) IPR002935 O- methyltransferase, family 3</td></tr>
<tr><td></td><td></td><td></td><td></td><td>Bc-siRNA<br><br>Target</td><td>3'TTTAGTCGATAGTTGTCGTGGT 5'<br>||:|:|||||||| ||:||||<br>5'AAGTTAGCTATCAAAAGTACCA 3'</td><td>302<br><br>308</td><td>4</td><td>Solyc05g041300.1.1 183~205(cDNA)</td><td>Caffeoyl-CoA O- methyltransferase</td></tr>
</table>

TABLE 1-continued

<table>
<tr><th colspan="11">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>(AHRD V1 ***- A2PZD5_IPONI); contains Interpro domain(s) IPR002935 O-methyltransferase, family 3</td></tr>
<tr><td></td><td></td><td></td><td></td><td>Bc-siRNA<br><br>Target</td><td>3'TTTAGTCGATAGTTGTCGTGGT 5'<br>:|:|:||||||||| ||:||||<br>5'GAGTTAGCTATCAAAAGTACCA 3'</td><td>302<br><br>309</td><td>4.5</td><td>Solyc05g041320.1.1 322~344(cDNA)</td><td>Caffeoyl-CoA O-methyltransferase (AHRD V1 **** A2PZD5_IPONI); contains Interpro domain(s) IPR02935 O-methyltransferase, family 3</td></tr>
<tr><td></td><td></td><td></td><td></td><td>Bc-siRNA<br><br>Target</td><td>3'TTTAGTCGATAGTTGTCGTGGT 5'<br>:|:|:||||||||| ||:||||<br>5'GAGTTAGCTATCAAAAGTACCA 3'</td><td>302<br><br>310</td><td>4.5</td><td>Solyc05g041610.1.1 415~437(cDNA)</td><td>Caffeoyl-CoA O-methyltransferase (AHRD V1 **** A2PZD5_IPONI); contains Interpro domain(s) IPR002935 O-methyltransferase, family 3</td></tr>
<tr><td></td><td></td><td></td><td></td><td>Bc-siRNA<br><br>Target</td><td>3'TTTAGTCGATAGTTGTCGTGGT 5'<br>:|:|:||||||||| ||:||||<br>5'GAGTTAGCTATCAAAAGTACCA 3'</td><td>302<br><br>311</td><td>4.5</td><td>Solyc05g041620.1.1 322~344(cDNA)</td><td>Caffeoyl-CoA O-methyltransferase (AHRD V1 **** A2PZD5_IPONI); contains Interpro</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>domain(s) IPR002935 O-methyltransferase, family 3</td></tr>
<tr><td></td><td></td><td></td><td></td><td>Bc-siRNA<br><br>Target</td><td>3'TTTAGTCGATAGTTGTCGTGGT 5'<br>||:|:|||||||| ||:||||<br>5'AAGTTAGCTATCAAAAGTACCA 3'</td><td>302<br><br>312</td><td>4</td><td>Solyc05g041690.1.1<br>475~497(cDNA)</td><td>Caffeoyl-CoA O-methyltransferase (AHRD V1 **** A2PZD5_IPONI); contains Interpro domain(s) IPR002935 O-methyltransferase, family 3</td></tr>
<tr><td>siR92<br>SIR3 LTR transposon<br>TGTACTG TTCTGGT ATCGTAG G (SEQ ID NO: 313)</td><td>29.6</td><td>374.44</td><td>22.5</td><td>Bc-siRNA<br><br>Target</td><td>3'GGATGCTATGGTCTTGTCATGT 5'<br>:|||||||||:|||| ||||||<br>5'TCTACGATACTAGAAGAGTACA 3'</td><td>313<br><br>314</td><td>3.5</td><td>AT3G45620.1<br>701~723(CDS)</td><td>Transducin/WD40 repeat-like superfamily protein</td></tr>
<tr><td></td><td></td><td></td><td></td><td>Bc-siRNA<br><br>Target</td><td>3'GGATGCTATGGTCTTGTCATGT 5'<br>||| || ||:||||||||||<br>5'GCTAAGAAACTAGAACAGTACA 3'</td><td>313<br><br>315</td><td>4</td><td>Solyc02g085760.2.1<br>491~513(cDNA)</td><td>Rhomboid family protein (AHRD V1 ***-D7MJX8_ARALY); contains Interpro domain(s) IPR002610 Peptidase S54, rhomboid</td></tr>
<tr><td>siR95<br>SIR1 LTR transposon<br>TGCGAA GTTATGT</td><td>20.5</td><td>373.6</td><td>3.2</td><td>Bc-siRNA<br><br>Target</td><td>3'AGATGATATGTATTGAAGCGT 5'<br>|:| ||||||||||:||| ||<br>5'TTTTCTATACATAATTTCTCA 3'</td><td>316<br><br>317</td><td>4.5</td><td>AT2G03060.1<br>1405~1426(3'UTR)</td><td>AGAMOUS-like 30</td></tr>
</table>

TABLE 1-continued

<table>
<tr><td colspan="10">Bc-sRNAs that have predicted targets in both *Arabidopsis* and *S. lycopersicum*.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td>ATAGTA GA (SEQ ID NO: 316)</td><td></td><td></td><td></td><td>Bc-siRNA<br><br>Target</td><td>3'AGATGATATGTATTGAAGCGT 5'<br>||||| ||:||||||||||<br>5'ACTACTTTATATAACTTCGCT 3'</td><td>316<br><br>318</td><td>4</td><td>Solyc08g016050.2.1 1697~1718(cDNA)</td><td>Dedicator of cytokinesis family protein (AHRD V1 ***- A8P5S7_BRUMA); contains Interpro domain(s) IPR010703 Dedicator of cytokinesis</td></tr>
<tr><td>siR1017 SIR1017 Intergenic region AGGGTG GAGAGA GTTCGGA CATTC (SEQ ID NO: 319)</td><td>711.8</td><td>95.44</td><td>113.1</td><td>Bc-siRNA<br><br>Target</td><td>3'CTTACAGGCTTGAGAGAGGTGGGA 5'<br>||:|||||| | ||||| ||||||<br>5'GAGTGTCCGCAATCTCTACACCCT 3'</td><td>319<br><br>320</td><td>4.5</td><td>AT3G11910.1 1418~1442(CDS)</td><td>ubiquitin-specific protease 13</td></tr>
<tr><td></td><td></td><td></td><td></td><td>Bc-siRNA<br><br>Target</td><td>3'CTTACAGGCTTGAGAGAGGTGGGA 5'<br>||||||||||:||||:|:||| ||<br>5'GAATGTCCGAGCTCTTTTCACACT 3'</td><td>319<br><br>321</td><td>4.5</td><td>Solyc03g007760.2.1 1996~2020(cDNA)</td><td>Cell division protease ftsH (AHRD V1 *--- FTSH_SHIFL); contains Interpro domain(s) IPR003959 ATPase, AAA-type, core</td></tr>
<tr><td>siR97 SIR3 LTR transposon TATCGGG TCCATCC</td><td>114</td><td>331.64</td><td>40.2</td><td>Bc-siRNA<br><br>Target</td><td>3'GGGTTCTTCCTACCTGGGCTAT 5'<br>:||:|||:|||||| ||||||<br>5'TCCGAGAGGGATGGTCCCGATC 3'</td><td>322<br><br>323</td><td>4.5</td><td>AT4G17505.1 185~207(CDS)</td><td>Protein of Unknown Function (DUF239)</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence</th><th colspan="3">Normalized read counts</th><th colspan="2">Target gene alignment</th><th>SEQ ID</th><th></th><th>Target gene</th><th>Putative function of</th></tr>
<tr><th>(5'-3')</th><th>A</th><th>S</th><th>B</th><th colspan="2">and aligned score</th><th>NO:</th><th>AS*</th><th>ID/target site</th><th>target gene</th></tr>
<tr><td>TTCTTGG G (SEQ ID NO: 322)</td><td></td><td></td><td></td><td>Bc-siRNA<br><br>Target</td><td>3'GGGTTCTTCCTACCTGGGCTAT 5'<br>||:|:|||| ||||:||:|||:<br>5'CCTAGGAAGTATGGGCCTGATG 3'</td><td>322<br><br>324</td><td>4.5</td><td>Solyc01g091370.2.1<br>1179~1201(cDNA)</td><td>AT-hook motif nuclear localized protein 1 (AHRD V1 ***- Q8VYJ2_ARATH); contains Interpro domain(s) IPR005175 Protein of unknown function DUF296</td></tr>
<tr><td></td><td></td><td></td><td></td><td>Bc-siRNA<br><br>Target</td><td>3'GGGTTCTTCCTACCTGGGCTAT 5'<br>:|||| |:|||||||||:||||<br>5'TCCAAAAGGGATGGACCTGATA 3'</td><td>322<br><br>325</td><td>3</td><td>Solyc01g094640.2.1<br>2690~2712(cDNA)</td><td>uncharacterized protein LOC101249582 (related) (AHRD V1 ***- Q2HTJ8_MEDTR)</td></tr>
<tr><td>siR99 SIR2 LTR transposon TAGTGTC AGCTAAT TCAGGA G (SEQ ID NO: 326)</td><td>366.9</td><td>216.44</td><td>13.1</td><td>Bc-siRNA<br><br>Target</td><td>3'GAGGACTTAATCGACTGTGAT 5'<br>:|| ||||||||||| ||||<br>5'TTCATGAATTAGCTGCCACTT 3'</td><td>326<br><br>327</td><td>4.5</td><td>AT2G07360.1<br>412~433(CDS)</td><td>SH3 domain-containing protein</td></tr>
<tr><td></td><td></td><td></td><td></td><td>Bc-siRNA<br><br>Target</td><td>3'GAGGACTTAATCGACTGTGAT 5'<br>|:|| || |||||||||||<br>5'ATTCTCAAATAGCTGACACTT 3'</td><td>326<br><br>328</td><td>4.5</td><td>AT2G39100.1<br>1127~1148(3'UTR)</td><td>RING/U-box superfamily protein</td></tr>
<tr><td></td><td></td><td></td><td></td><td>Bc-siRNA<br><br>Target</td><td>3'GAGGACTTAATCGACTGTGAT 5'<br>|||||||||||| |||||||<br>5'GTCCTGAATTAGCAGACACTA 3'</td><td>326<br><br>329</td><td>3</td><td>AT5G13320.1<br>889~910(CDS)</td><td>Auxin-responsive GH3 family protein</td></tr>
<tr><td></td><td></td><td></td><td></td><td>Bc-siRNA<br><br>Target</td><td>3'GAGGACTTAATCGACTGTGAT 5'<br>| || ||||||||||| |||:<br>5'CACCAGAATTAGCTGAAACTG 3'</td><td>326<br><br>330</td><td>4.5</td><td>Solyc02g067320.1.1<br>52~73(cDNA)</td><td>Zinc finger-homeodomain protein 1</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th>Normalized read counts A</th><th>Normalized read counts S</th><th>Normalized read counts B</th><th colspan="2">Target gene alignment and aligned score</th><th>SEQ ID NO:</th><th>AS*</th><th>Target gene ID/target site</th><th>Putative function of target gene</th></tr>
<tr><td></td><td></td><td></td><td></td><td></td><td></td><td></td><td></td><td></td><td>(Fragment) (AHRD V1 **-- B0LK19_CUCSA); contains Interpro domain(s) IPR006456 ZF-HD homeobox protein Cys/His-rich dimerisation region</td></tr>
<tr><td></td><td></td><td></td><td></td><td>Bc-siRNA<br><br>Target</td><td>3'GAGGACTTAATCGACTGTGAT 5'<br>:||:||:| ||||||||:||<br>5'TTCTTGGACTAGCTGACGCTT 3'</td><td>326<br><br>331</td><td>4.5</td><td>Solyc08g066940.2.1 1557~1578(cDNA)</td><td>Peptide transporter 1 (AHRD V1 **-* Q7XAC3_VICFA); contains Interpro domain(s) IPR000109 TGF-beta receptor, type I/II extracellular region</td></tr>
<tr><td>siR1013 SIR1013 CDS TTATATG ATGAAC AAACTTT AAA (SEQ ID NO: 332)</td><td>521.1</td><td>149.76</td><td>24.4</td><td>Bc-siRNA<br><br>Target</td><td>3'AAATTTCAAACAAGTAGTATATT 5'<br>|||:|| |||| ||||||||||<br>5'TTTGAATTTTGCTCATCATATAT 3'</td><td>332<br><br>333</td><td>4.5</td><td>AT1G79840.2 77~100(5'UTR)</td><td>HD-ZIP IV family of homeobox-leucine zipper protein with lipid-binding START domain</td></tr>
<tr><td></td><td></td><td></td><td></td><td>Bc-siRNA<br><br>Target</td><td>3'AAATTTCAAACAAGTAGTATATT 5'<br>||| | ||||||||||:||||:|<br>5'TTTTATGTTTGTTCATTATATGA 3'</td><td>332<br><br>334</td><td>4</td><td>Solyc03g098070.2.1 1258~1281(cDNA)</td><td>C2H2L domain class transcription factor (AHRD V1 *--* D9ZIU3_MALDO);</td></tr>
</table>

TABLE 1-continued

<table>
<tr><th colspan="9">Bc-sRNAs that have predicted targets in both *Arabidopsis* and *S. lycopersicum*.</th></tr>
<tr><th>Bc-siRNA ID, locus, and siRNA sequence<br>(5'-3')</th><th colspan="3">Normalized read counts</th><th colspan="2">Target gene alignment<br>and aligned score</th><th>SEQ ID<br>NO:</th><th>AS*</th><th>Target gene<br>ID/target site</th><th>Putative function of<br>target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>contains Interpro domain(s) IPR007087 Zinc finger, C2H2-type</td></tr>
<tr><td>siR102 SIR13 Intergenic region TGGAGG GGAGAT TGATACA TTG (SEQ ID NO: 335)</td><td>827.3</td><td>20.56</td><td>101.5</td><td>Bc-siRNA<br><br>Target</td><td>3'GTTACATAGTTAGAGGGGAGGT 5'<br>||||||:| |||| |||||||||<br>5'CAATGTGTGAATCACCCCTCCA 3'</td><td>335<br><br>336</td><td>3.5</td><td>AT3G13750.1<br>3258~3280(3'UTR)</td><td>beta galactosidase 1</td></tr>
<tr><td></td><td></td><td></td><td></td><td>Bc-siRNA<br><br>Target</td><td>3'GTTACATAGTTAGAGGGGAGGT 5'<br>| ||| |||:||||:||||||<br>5'CCATGGATCGATCTTCCCTCCT 3'</td><td>335<br><br>337</td><td>4.5</td><td>AT5G43100.1<br>139~161(CDS)</td><td>Eukaryotic aspartyl protease family protein</td></tr>
<tr><td></td><td></td><td></td><td></td><td>Bc-siRNA<br><br>Target</td><td>3'GTTACATAGTTAGAGGGGAGGT 5'<br>|||| ||| ||||||:||||:|<br>5'CAATCTATGAATCTCTCCTCTA 3'</td><td>335<br><br>338</td><td>4</td><td>Solyc11g067000.1.1<br>2884~2906(cDNA)</td><td>ATP-binding cassette transporter (AHRD V1 ***- D8T797_SELML); contains Interpro domain(s) IPR013525 ABC-2 type transporter</td></tr>
<tr><td>siR1011 SIR1011 CDS TAATATG ATGAGC AAGATT GGT (SEQ</td><td>413.3</td><td>172.8</td><td>117.2</td><td>Bc-siRNA<br><br>Target</td><td>3'TGGTTAGAACGAGTAGTATAAT 5'<br>|:||||||||:| ||||||||<br>5'ATCAATCTTGTTAATCATATTC 3'</td><td>339<br><br>340</td><td>4.5</td><td>AT4G21215.1<br>724~746(CDS)</td><td></td></tr>
</table>

TABLE 1-continued

<table>
<tr><th colspan="10">Bc-sRNAs that have predicted targets in both *Arabidopsis* and *S. lycopersicum*.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td>ID NO: 339)</td><td></td><td></td><td></td><td>Bc-siRNA<br><br>Target</td><td>3'TGGTTAGAACGAGTAGTATAAT 5'<br>|| ||| |||:||||||||||<br>5'ACAAATATTGTTCATCATATTA 3'</td><td>339<br><br>341</td><td>3</td><td>AT5G51530.1<br>3078~3100(CDS)</td><td>Ubiquitin carboxyl-terminal hydrolase-related protein</td></tr>
<tr><td></td><td></td><td></td><td></td><td>Bc-siRNA<br><br>Target</td><td>3'TGGTTAGAACGAGTAGTATAAT 5'<br>|:|:| |||||||||||||<br>5'TCTAGTGTTGCTCATCATATTT 3'</td><td>339<br><br>342</td><td>4</td><td>AT5G67140.1<br>772~794(CDS)</td><td>F-box/RNI-like superfamily protein</td></tr>
<tr><td></td><td></td><td></td><td></td><td>Bc-siRNA<br><br>Target</td><td>3'TGGTTAGAACGAGTAGTATAAT 5'<br>| ||||:| |||||||| ||||<br>5'AGCAATTTGGCTCATCAAATTA 3'</td><td>339<br><br>343</td><td>4.5</td><td>Solyc02g093150.2.1<br>1404~1426(cDNA)</td><td>AP2-like ethylene-responsive transcription factor At1g16060 (AHRD V1 *-*-AP2L1_ARATH); contains Interpro domain(s) IPR001471 Pathogenesis-related transcriptional factor and ERF, DNA-binding</td></tr>
<tr><td>siR109 SIR3 LTR transposon TGCTGGT GTGATTT TCGTGGT (SEQ ID NO: 344)</td><td>437.6</td><td>160.48</td><td>150</td><td>Bc-siRNA<br><br>Target</td><td>3'TGGTGCTTTTAGTGTGGTCGT 5'<br>|:||||| ||||:||| ||||<br>5'ATCACGATAATCGCACAAGCA 3'</td><td>344<br><br>345</td><td>4.5</td><td>AT5G64390.1<br>377~398(CDS)</td><td>RNA-binding KH domain-containing protein</td></tr>
<tr><td></td><td></td><td></td><td></td><td>Bc-siRNA<br><br>Target</td><td>3'TGGTGCTTTTAGTGTGGTCGT 5'<br>|:|||||||||:|| |||||<br>5'TCTACGAAAATCGCAGCAGCA 3'</td><td>344<br><br>346</td><td>4.5</td><td>Solyc01g103350.2.1<br>2540~2561(cDNA)</td><td>Cell division protein kinase 13 (AHRD V1 *-*-CDK13_MOUSE); contains</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th>Normalized read counts<br>A</th><th>S</th><th>B</th><th></th><th>Target gene alignment and aligned score</th><th>SEQ ID NO:</th><th>AS*</th><th>Target gene ID/target site</th><th>Putative function of target gene</th></tr>
<tr><td></td><td></td><td></td><td></td><td></td><td></td><td></td><td></td><td></td><td>Interpro domain(s) IPR002290 Serine/threonine protein kinase</td></tr>
<tr><td></td><td></td><td></td><td></td><td>Bc-siRNA<br><br>Target</td><td>3'TGGTGCTTTTAGTGTGGTCGT 5'<br>|:|:|||::|||||||||||<br>5'TCTATGAAGGTCACACCAGCA 3'</td><td>344<br><br>347</td><td>4.25</td><td>Solyc02g069630.2.1<br>2706~2727(cDNA)</td><td>Subtilisin-like serine protease (AHRD V1 **-* Q948Q4_ARATH); contains Interpro domain(s) IPR015500 Peptidase S8, subtilisin-related</td></tr>
<tr><td></td><td></td><td></td><td></td><td>Bc-siRNA<br><br>Target</td><td>3'TGGTGCTTTTAGTGTGGTCGT 5'<br>||||:| |||||| |||||||<br>5'ACCATGCAAATCAGACCAGCA 3'</td><td>344<br><br>348</td><td>3.5</td><td>Solyc05g015510.2.1<br>3013~3034(cDNA)</td><td>Squamosa promoter-binding-like protein 11 (AHRD_V1 ***- B6TF72_MAIZE); contains Interpro domain(s) IPR004333 Transcription factor, SBP-box</td></tr>
<tr><td></td><td></td><td></td><td></td><td>Bc-siRNA<br><br>Target</td><td>3'TGGTGCTTTTAGTGTGGTCGT 5'<br>|||:| |||||||:|||||<br>5'TCCATGTAAATCACGCCAGCT 3'</td><td>344<br><br>349</td><td>4.5</td><td>Solyc09g007710.2.1<br>3351~3372(cDNA)</td><td>Tir-nbs-lrr, resistance protein</td></tr>
<tr><td></td><td></td><td></td><td></td><td>Bc-siRNA<br><br>Target</td><td>3'TGGTGCTTTTAGTGTGGTCGT 5'<br>||||:|||:|||:|||:|||<br>5'ACCATGAAGATCGCACTAGCT 3'</td><td>344<br><br>350</td><td>4</td><td>Solyc10g081020.1.1<br>3688~3709(cDNA)</td><td>Transcription elongation factor SPT6 (AHRD V1 ***- A8NF94_COPC7); contains Interpro domain(s)</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>IPR017072 Transcription elongation factor Spt6</td></tr>
<tr><td>siR1018 SIR8 Intergenic region TGATGTT GCATACC CGGCTCG G (SEQ ID NO: 351)</td><td>618.4</td><td>51</td><td>288.2</td><td>Bc-siRNA<br><br>Target</td><td>3'GGCTCGGCCCATACGTTGTAGT 5'<br>|:||||||| || ||||:||||<br>5'CTGAGCCGGCTAGGCAATATCA 3'</td><td>351<br><br>352</td><td>4.5</td><td>AT1G62970.1 1017~1039(CDS)</td><td>Chaperone DnaJ-domain superfamily protein</td></tr>
<tr><td></td><td></td><td></td><td></td><td>Bc-siRNA<br><br>Target</td><td>3'GGCTCGGCCCATACGTTGTAGT 5'<br>:||||| || ||||||||| ||<br>5'TCGAGCAGGATATGCAACACCA 3'</td><td>351<br><br>353</td><td>4.5</td><td>Solyc04g007510.2.1 3230~3252(cDNA)</td><td>ATP-dependent RNA helicase A-like protein (AHRD V1 ***-Q9FF84_ARATH); contains Interpro domain(s) IPR007502 Helicase-associated region</td></tr>
<tr><td>siR114 SIR2 LTR transposon TCCAGG GTCCTTT TGGAAT AGG (SEQ ID NO: 354)</td><td>395.8</td><td>138.24</td><td>14.3</td><td>Bc-siRNA<br><br>Target</td><td>3'GGATAAGGTTTTCCTGGGACCT 5'<br>| ||||:| |||||| ||||||<br>5'CATATTTCCAAAGGAGCCTGGA 3'</td><td>354<br><br>355</td><td>4.5</td><td>AT1G78960.1 1445~1467(CDS)</td><td>lupeol synthase 2</td></tr>
<tr><td></td><td></td><td></td><td></td><td>Bc-siRNA<br><br>Target</td><td>3'GGATAAGGTTTTCCTGGGACCT 5'<br>| ||||:||||||||:| ||||<br>5'CATATTTCAAAAGGATCGTGGA 3'</td><td>354<br><br>356</td><td>4.5</td><td>Solyc12g006510.1.1 1377~1399(cDNA)</td><td>Cycloartenol Synthase (AHRD V1 ***-O82139_PANGI); contains</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>Interpro domain(s) IPR018333 Squalene cyclase</td></tr>
<tr><td>siR1020 SIR1020 Intergenic region TTGCCACGACGAACCAGGACA (SEQ ID NO: 357)</td><td>138.3</td><td>209</td><td>10.1</td><td>Bc-siRNA<br><br>Target</td><td>3'ACAGGACCAAGCAGCACCGTT 5'<br>| ||||||||||||||| ||<br>5'TCTCCTGGTTCGTCGTGCCAT 3'</td><td>357<br><br>358</td><td>4</td><td>AT2G22810.1 1176~1197(CDS)</td><td>1-aminocyclopropane-1-carboxylate synthase 4</td></tr>
<tr><td></td><td></td><td></td><td></td><td>Bc-siRNA<br><br>Target</td><td>3'ACAGGACCAAGCAGCACCGTT 5'<br>| ||:||| ||||:||||||:<br>5'TTTCTTGGCTCGTTGTGGCAG 3'</td><td>357<br><br>359</td><td>4</td><td>Solyc04g005650.1.1 337~358(cDNA)</td><td>Mitochondrial carrier family (AHRD V1 ***-C1MWU5_MICPS); contains Interpro domain(s) IPR001993 Mitochondrial substrate carrier</td></tr>
<tr><td></td><td></td><td></td><td></td><td>Bc-siRNA<br><br>Target</td><td>3'ACAGGACCAAGCAGCACCGTT 5'<br>||||:|| ||| |:|||||||<br>5'TGTCTTGTTTCATTGTGGCAA 3'</td><td>357<br><br>360</td><td>4.5</td><td>Solyc09g091210.2.1 861~882(cDNA)</td><td>Disease resistance response/dirigent-like protein (AHRD V1 ***-Q0WPQ6_ARATH); contains Interpro domain(s) IPR004265 Plant disease resistance response protein</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence</td><td colspan="3">Normalized read counts</td><td></td><td>Target gene alignment</td><td>SEQ ID</td><td></td><td>Target gene</td><td>Putative function of</td></tr>
<tr><td>(5'-3')</td><td>A</td><td>S</td><td>B</td><td></td><td>and aligned score</td><td>NO:</td><td>AS*</td><td>ID/target site</td><td>target gene</td></tr>
<tr><td>siR1016 SIR1 LTR transposon TTGAGA GCTAAGT CAAACG GA (SEQ ID NO: 361)</td><td>22.8</td><td>255.08</td><td>5</td><td>Bc-siRNA<br><br>Target</td><td>3'AGGCAAACTGAATCGAGAGTT 5'<br>||:| ||||||||||||| ||<br>5'TCTGGTTGACTTAGCTCTAAA 3'</td><td>361<br><br>362</td><td>3.5</td><td>AT1G23190.1<br>1753~1774(CDS)</td><td>Phosphoglucomutase/ phosphomannomutase family protein</td></tr>
<tr><td></td><td></td><td></td><td></td><td>Bc-siRNA<br><br>Target</td><td>3'AGGCAAACTGAATCGAGAGTT 5'<br>|| ||||::|||||||||||<br>5'ACCATTTGGTTTAGCTCTCAA 3'</td><td>361<br><br>363</td><td>4.25</td><td>AT5G19260.1<br>184~205(CDS)</td><td>Protein of unknown function (DUF3049)</td></tr>
<tr><td></td><td></td><td></td><td></td><td>Bc-siRNA<br><br>Target</td><td>3'AGGCAAACTGAATCGAGAGTT 5'<br>|||||| ||||:|||||||:<br>5'CCCGTTTCACTTGGCTCTCAG 3'</td><td>361<br><br>364</td><td>3.5</td><td>Solyc01g101090.2.1<br>1040~1061(cDNA)</td><td>TBC1 domain family member CG11727 (AHRD V1 **-* Y1727_DROME); contains Interpro domain(s) IPR000195 RabGAP/TBC</td></tr>
<tr><td></td><td></td><td></td><td></td><td>Bc-siRNA<br><br>Target</td><td>3'AGGCAAACTGAATCGAGAGTT 5'<br>|||| ||||:|| ||||||||<br>5'TCCGGTTGATTTTGCTCTCAA 3'</td><td>361<br><br>365</td><td>4</td><td>Solyc02g082060.1.1<br>497~518(cDNA)</td><td>PPPDE peptidase domain-containing protein 1 (AHRD V1 *--- PPDE1_XENLA); contains Interpro domain(s) IPR008580 Protein of unknown function DUF862, eukaryotic</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence<br>(5'-3')</th><th colspan="3">Normalized read counts</th><th colspan="2">Target gene alignment<br>and aligned score</th><th>SEQ ID<br>NO:</th><th>AS*</th><th>Target gene<br>ID/target site</th><th>Putative function of<br>target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'AGGCAAACTGAATCGAGAGTT 5'<br>|::||||| |||||||:||||<br>5'TTTGTTTGTCTTAGCTTTCAA 3'</td><td>361<br><br>366</td><td>3.5</td><td>Solyc04g076690.2.1<br>623~644(cDNA)</td><td>Unknown Protein (AHRD V1)</td></tr>
<tr><td>siR1003 SIR1003 LTR transposon GGTAAC CAGAAC TGGCGAT GC (SEQ ID NO: 367)</td><td>615.3</td><td>2.48</td><td>0.5</td><td>Bc-siRNA<br><br>Target</td><td>3'CGTAGCGGTCAAGACCAATGG 5'<br>|| ||| ||||||||||:||<br>5'CCACCGCAAGTTCTGGTTGCC 3'</td><td>367<br><br>368</td><td>4</td><td>AT2G31220.1<br>223~244(CDS)</td><td>basic helix-loop-helix (bHLH) DNA-binding superfamily protein</td></tr>
<tr><td></td><td></td><td></td><td></td><td>Bc-siRNA<br><br>Target</td><td>3'CGTAGCGGTCAAGACCAATGG 5'<br>||||:|:| ||| ||||||||<br>5'GCATTGTCCGTTATGGTTACC 3'</td><td>367<br><br>369</td><td>4</td><td>Solyc06g050170.2.1<br>1771~1792(cDNA)</td><td>Potassium transporter (AHRD V1 **** Q1T761_PHRAU); contains Interpro domain(s) IPR018519 Potassium uptake protein, kup IPR003855 K+ potassium transporter</td></tr>
<tr><td>siR124 SIR1 LTR transposon TGACCA GAGCTCC GGGGAG GT (SEQ ID NO: 370)</td><td>17.5</td><td>232.88</td><td>3.6</td><td>Bc-siRNA<br><br>Target</td><td>3'TGGAGGGGCCTCGAGACCAGT 5'<br>:|:|:|:|||||||| |||||<br>5'GCTTTCTCGGAGCTCCGGTCA 3'</td><td>370<br><br>371</td><td>4</td><td>AT1G13270.1<br>140~161(CDS)</td><td>methionine aminopeptidase 1B</td></tr>
<tr><td></td><td></td><td></td><td></td><td>Bc-siRNA<br><br>Target</td><td>3'TGGAGGGGCCTCGAGACCAGT 5'<br>|::|:|||||| ||||||||:<br>5'ATTTTCCCGGACCTCTGGTCG 3'</td><td>370<br><br>372</td><td>4.5</td><td>AT3G59040.1<br>1252~1273(CDS)</td><td>Tetratricopeptide repeat (TPR)-like superfamily protein</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th>Normalized read counts<br>A</th><th>S</th><th>B</th><th></th><th>Target gene alignment and aligned score</th><th>SEQ ID NO:</th><th>AS*</th><th>Target gene ID/target site</th><th>Putative function of target gene</th></tr>
<tr><td></td><td></td><td></td><td></td><td>Bc-siRNA<br><br>Target</td><td>3'TGGAGGGGCCTCGAGACCAGT 5'<br>|||||:||||| ||| |||||<br>5'ACCTCTCCGGATCTCCGGTCA 3'</td><td>370<br><br>373</td><td>4.5</td><td>Solyc02g065550.2.1<br>280~301(cDNA)</td><td>Coiled-coil domain-containing protein 109A (AHRD V1 *---C109A_MOUSE); contains Interpro domain(s) IPR006769 Protein of unknown function DUF607</td></tr>
<tr><td></td><td></td><td></td><td></td><td>Bc-siRNA<br><br>Target</td><td>3'TGGAGGGGCCTCGAGACCAGT 5'<br>|||:|:| ||||||||||:|<br>5'TCCTTCTCCGAGCTCTGGTTA 3'</td><td>370<br><br>374</td><td>4</td><td>Solyc04g045540.1.1<br>127~148(cDNA)</td><td>Ycf1 (Fragment) (AHRD V1 ***-A6YA36_9MAGN); contains Interpro domain(s) IPR008896 Ycf1</td></tr>
<tr><td></td><td></td><td></td><td></td><td>Bc-siRNA<br><br>Target</td><td>3'TGGAGGGGCCTCGAGACCAGT 5'<br>|||:|:| ||||||||||:|<br>5'TCCTTCTCCGAGCTCTGGTTA 3'</td><td>370<br><br>375</td><td>4</td><td>Solyc05g047440.1.1<br>127~148(cDNA)</td><td>Ycf1 (Fragment) (AHRD V1 ***-A6Y9X6_HAMJA); contains Interpro domain(s) IPR008896 Ycf1</td></tr>
<tr><td></td><td></td><td></td><td></td><td>Bc-siRNA<br><br>Target</td><td>3'TGGAGGGGCCTCGAGACCAGT 5'<br>||||||: |||||:||||||<br>5'TCCTCCCTCGAGCTTTGGTCA 3'</td><td>370<br><br>376</td><td>4.25</td><td>Solyc05g055360.2.1<br>1577~1598(cDNA)</td><td>Unknown Protein (AHRD V1)</td></tr>
<tr><td></td><td></td><td></td><td></td><td>Bc-siRNA<br><br>Target</td><td>3'TGGAGGGGCCTCGAGACCAGT 5'<br>|||:|:| ||||||||||:|<br>5'TCCTTCTCCGAGCTCTGGTTA 3'</td><td>370<br><br>377</td><td>4</td><td>Solyc10g062330.1.1<br>82~103(cDNA)</td><td>Hypothetical chloroplast RF1 (AHRD V1 **--C3UP30_9MAGN); contains Interpro</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td></td><td></td><td></td><td></td><td></td><td></td><td></td><td></td><td></td><td>domain(s)<br>IPR008896<br>Ycf1</td></tr>
<tr><td></td><td></td><td></td><td></td><td>Bc-siRNA<br><br>Target</td><td>3'TGGAGGGGCCTCGAGACCAGT 5'<br>|||:|:| ||||||||||:|<br>5'TCCTTCTCCGAGCTCTGGTTA 3'</td><td>370<br><br>378</td><td>4</td><td>Solyc11g021310.1.1<br>127~148(cDNA)</td><td>Hypothetical chloroplast RF1 (AHRD V1 ***-C3UP30_9MAGN); contains Interpro domain(s) IPR008896 Ycf1</td></tr>
<tr><td>siR127<br>SIR2 LTR transposon<br>TGTTTTG<br>ACATGTT<br>GTTTGAC<br>G (SEQ ID NO: 379)</td><td>451.3</td><td>54.32</td><td>19.2</td><td>Bc-siRNA<br><br>Target</td><td>3'GCAGTTTGTTGTACAGTTTTGT 5'<br>| ||||| |||||||:|||||<br>5'CATCAAAGAACATGTTAAAACT 3'</td><td>379<br><br>380</td><td>4</td><td>AT5G10450.3<br>932~954(3'UTR)</td><td>G-box regulating factor 6</td></tr>
<tr><td></td><td></td><td></td><td></td><td>Bc-siRNA<br><br>Target</td><td>3'GCAGTTTGTTGTACAGTTTTGT 5'<br>||:| | |||||||||||:||<br>5'AGTTACAAAACATGTCAAAGCA 3'</td><td>379<br><br>381</td><td>4.5</td><td>Solyc01g068430.1.1<br>871~893(cDNA)</td><td>Os06g0207500 protein (Fragment) (AHRD V1 **--Q0DDQ9_ORYSJ); contains Interpro domain(s) IPR004253 Protein of unknown function DUF231, plant</td></tr>
<tr><td>siR128<br>SIR15<br>Intergenic region<br>TACAGA<br>ATACAG</td><td>574.3</td><td>3.28</td><td>7.7</td><td>Bc-siRNA<br><br>Target</td><td>3'TAGAACTAAGACATAAGACAT 5'<br>||:|||:||||||||| ||||<br>5'ATTTTGGTTCTGTATTGTGTA 3'</td><td>382<br><br>383</td><td>3</td><td>AT1G48210.1<br>1343~1364(3'UTR)</td><td>Protein kinase superfamily protein</td></tr>
</table>

TABLE 1-continued

<table>
<tr><td colspan="10">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td colspan="2">Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td><td></td></tr>
<tr><td>AATCAA GAT (SEQ ID NO: 382)</td><td></td><td></td><td></td><td></td><td></td><td></td><td></td><td></td><td></td></tr>
<tr><td></td><td></td><td></td><td></td><td>Bc-siRNA<br><br>Target</td><td>3'TAGAACTAAGACATAAGACAT 5'<br>|||| | |||| |||||||||<br>5'ATCTAGTTTCTTTATTCTGTA 3'</td><td>382<br><br>384</td><td>4</td><td>AT2G23348.1<br>402~423(3'UTR)</td><td>unknown protein, hypothetical protein, uncharacterized protein</td></tr>
<tr><td></td><td></td><td></td><td></td><td>Bc-siRNA<br><br>Target</td><td>3'TAGAACTAAGACATAAGACAT 5'<br>:|||||:||||| ||||||||<br>5'GTCTTGGTTCTGGATTCTGTA 3'</td><td>382<br><br>385</td><td>3</td><td>AT4G08990.1<br>2536~2557(CDS)</td><td>DNA (cytosine-5-)-methyltransferase family protein</td></tr>
<tr><td></td><td></td><td></td><td></td><td>Bc-siRNA<br><br>Target</td><td>3'TAGAACTAAGACATAAGACAT 5'<br>:||| |:||||| ||||||||<br>5'GTCTAGGTTCTGGATTCTGTA 3'</td><td>382<br><br>386</td><td>4</td><td>AT4G14140.1<br>2560~2581(CDS)</td><td>DNA methyltransferase 2</td></tr>
<tr><td></td><td></td><td></td><td></td><td>Bc-siRNA<br><br>Target</td><td>3'TAGAACTAAGACATAAGACAT 5'<br>:|||| | |:||||||:||||<br>5'GTCTTTACTTTGTATTTTGTA 3'</td><td>382<br><br>387</td><td>4.5</td><td>Solyc04g005530.2.1<br>1196~1217(cDNA)</td><td>Unknown Protein (AHRD V1)</td></tr>
<tr><td></td><td></td><td></td><td></td><td>Bc-siRNA<br><br>Target</td><td>3'TAGAACTAAGACATAAGACAT 5'<br>|| ||||| |||||||| ||:<br>5'ATATTGATCCTGTATTCCGTG 3'</td><td>382<br><br>388</td><td>4.5</td><td>Solyc11g012550.1.1<br>49~70(cDNA)</td><td>F-box family protein (AHRD V1 ***-D7L4T6_ARALY); contains Interpro domain(s) IPR001810 Cyclin-like F-box</td></tr>
<tr><td>siR130 SIR2 LTR transposon TGTTCAA CAAGTCT ATATTGG T (SEQ ID NO: 389)</td><td>400.4</td><td>65</td><td>6.5</td><td>Bc-siRNA<br><br>Target</td><td>3'TGGTTATATCTGAACAACTTGT 5'<br>||:| |||:|||||||||| |<br>5'ACTACTATGGACTTGTTGAAAA 3'</td><td>389<br><br>390</td><td>4</td><td>AT2G42340.1<br>486~508(CDS)</td><td>unknown protein, hypothetical protein, uncharacterized protein</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th>Normalized read counts A</th><th>S</th><th>B</th><th></th><th>Target gene alignment and aligned score</th><th>SEQ ID NO:</th><th>AS*</th><th>Target gene ID/target site</th><th>Putative function of target gene</th></tr>
<tr><td></td><td></td><td></td><td></td><td>Bc-siRNA<br><br>Target</td><td>3'TGGTTATATCTGAACAACTTGT 5'<br>| |:||:| ||||||||||||<br>5'AACGATGTCGACTTGTTGAACC 3'</td><td>389<br><br>391</td><td>4</td><td>Solyc01g008080.2.1<br>2214~2236(cDNA)</td><td>Ribosomal protein S27 (AHRD V1 ***- Q3HVK9_SOLTU); contains Interpro domain(s) IPR000592 Ribosomal protein S27e</td></tr>
<tr><td></td><td></td><td></td><td></td><td>Bc-siRNA<br><br>Target</td><td>3'TGGTTATATCTGAACAACTTGT 5'<br>|| |:|| ||||||||||||<br>5'ACAAGTACAGACTTGTTGAACT 3'</td><td>389<br><br>392</td><td>3.5</td><td>Solyc01g095740.2.1<br>2485~2507(cDNA)</td><td>ATP-dependent RNA helicase DBP4 (AHRD V1 *-** C1GZM0_PARBA); contains Interpro domain(s) IPR011545 DNA/RNA helicase, DEAD/DEAH box type, N-terminal</td></tr>
<tr><td>siR1004<br>SIR15<br>Intergenic region<br>AATGATT GGAAGG AAGGAG TTC (SEQ ID NO: 393)</td><td>485.4</td><td>14</td><td>32.8</td><td>Bc-siRNA<br><br>Target</td><td>3'CTTGAGGAAGGAAGGTTAGTAA 5'<br>||||:|||||||:|||||||<br>5'TTACTCTTTCCTTCTAATCATT 3'</td><td>393<br><br>394</td><td>4.5</td><td>AT3G07990.1<br>72~94(CDS)</td><td>serine carboxypeptidase-like 27</td></tr>
<tr><td></td><td></td><td></td><td></td><td>Bc-siRNA<br><br>Target</td><td>3'CTTGAGGAAGGAAGGTTAGTAA 5'<br>|||:| | |||||||:|||||<br>5'GAATTACGTCCTTCCGATCATG 3'</td><td>393<br><br>395</td><td>4.5</td><td>AT4G21740.1<br>99~121(CDS)</td><td>unknown protein, hypothetical protein, uncharacterized protein</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td>Bc-siRNA<br><br>Target</td><td>3'CTTGAGGAAGGAAGGTTAGTAA 5'<br>||||| :|| |||:||||||||<br>5'GAACTATTTGCTTTCAATCATT 3'</td><td>393<br><br>396</td><td>4.25</td><td>Solyc07g042910.2.1<br>1930~1952(cDNA)</td><td>Genomic DNA chromosome 5 TAC clone K21L19 (AHRD V1 **-- Q9FGT4_ARATH)</td></tr>
<tr><td>siR144 SIR6 CDS (spurious gene) TAACATG ATGATTA ATTTATC (SEQ ID NO: 397)</td><td>471</td><td>9.88</td><td>46.1</td><td>Bc-siRNA<br><br>Target</td><td>3'CTATTTAATTAGTAGTACAAT 5'<br>| ||| || ||||||||||<br>5'GTTAATTTCATCATCATGTTC 3'</td><td>397<br><br>398</td><td>4</td><td>AT2G46330.1<br>471~492(3'UTR)</td><td>arabinogalactan protein 16</td></tr>
<tr><td></td><td></td><td></td><td></td><td>Bc-siRNA<br><br>Target</td><td>3'CTATTTAATTAGTAGTACAAT 5'<br>|:| | ||:||:||||||||<br>5'GGTTATTTGATTATCATGTTA 3'</td><td>397<br><br>399</td><td>4</td><td>AT4G12040.2<br>513~534(5'UTR)</td><td>A20/AN1-like zinc finger family protein</td></tr>
<tr><td></td><td></td><td></td><td></td><td>Bc-siRNA<br><br>Target</td><td>3'CTATTTAATTAGTAGTACAAT 5'<br>|| :||| |||||||||||<br>5'GAAGAATCAATCATCATGTTC 3'</td><td>397<br><br>400</td><td>4.25</td><td>Solyc01g080260.2.1<br>2174~2195(cDNA)</td><td>At4g14280-like protein (Fragment) (AHRD V1 *-*- C7FD87_ARALP); contains Interpro domain(s) IPR011989 Armadillo-like helical</td></tr>
<tr><td></td><td></td><td></td><td></td><td>Bc-siRNA<br><br>Target</td><td>3'CTATTTAATTAGTAGTACAAT 5'<br>| |||||:||| ||||||||<br>5'CAGAAATTGATCTTCATGTTA 3'</td><td>397<br><br>401</td><td>4.5</td><td>Solyc01g098240.1.1<br>3823~3844(cDNA)</td><td>RNA polymerase Rpb1 C-terminal repeat domain-containing protein (AHRD V1 *--- C5GU31_AJEDR); contains Interpro</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th>Normalized read counts A</th><th>Normalized read counts S</th><th>Normalized read counts B</th><th></th><th>Target gene alignment and aligned score</th><th>SEQ ID NO:</th><th>AS*</th><th>Target gene ID/target site</th><th>Putative function of target gene</th></tr>
<tr><td></td><td></td><td></td><td></td><td></td><td></td><td></td><td></td><td></td><td>domain(s) IPR012474 Frigida-like</td></tr>
<tr><td></td><td></td><td></td><td></td><td>Bc-siRNA<br><br>Target</td><td>3'CTATTTAATTAGTAGTACAAT 5'<br> | |||||:|| |||||||||<br>5'TAGAAATTGATAATCATGTTA 3'</td><td>397<br><br>402</td><td>4.5</td><td>Solyc10g005650.2.1 814~835(cDNA)</td><td>Peroxisomal targeting signal 1 receptor (AHRD V1 **** Q9ZTK6_TOBAC); contains Interpro domain(s) IPR011990 Tetratricopeptide-like helical</td></tr>
<tr><td></td><td></td><td></td><td></td><td>Bc-siRNA<br><br>Target</td><td>3'CTATTTAATTAGTAGTACAAT 5'<br>|| | | | |||||||||||:<br>5'GACATACTCATCATCATGTTG 3'</td><td>397<br><br>403</td><td>4.5</td><td>Solyc12g007150.1.1 73~94(cDNA)</td><td>Pollen-specific kinase partner protein-like protein (Fragment) (AHRD V1 *--- Q5DK68_SOLLC); contains Interpro domain(s) IPR005512 Rop nucleotide exchanger, PRONE</td></tr>
<tr><td>siR137 SIR2 LTR transposon TACGATT CTATTCT AGTAGT A (SEQ ID NO: 404)</td><td>376.8</td><td>46.08</td><td>3</td><td>Bc-siRNA<br><br>Target</td><td>3'ATGATGATCTTATCTTAGCAT 5'<br>||||| || ||| ||||||||<br>5'TACTAATAAAATCGAATCGTA 3'</td><td>404<br><br>405</td><td>4</td><td>AT1G22110.1 1283~1304(3'UTR)</td><td>structural constituent of ribosome</td></tr>
<tr><td></td><td></td><td></td><td></td><td>Bc-siRNA<br><br>Target</td><td>3'ATGATGATCTTATCTTAGCAT 5'<br> |:|||||||||:|:|||||<br>5'GATTACTAGAATGGGATCGTT 3'</td><td>404<br><br>406</td><td>4.5</td><td>AT3G25510.1 5473~5494(CDS)</td><td>disease resistance protein (TIR-</td></tr>
</table>

TABLE 1-continued

<table>
<tr><td colspan="10">Bc-sRNAs that have predicted targets in both *Arabidopsis* and *S. lycopersicum*.</td></tr>
<tr><td>Bc-siRNA ID, locus, and siRNA sequence (5'-3')</td><td>Normalized read counts A</td><td>S</td><td>B</td><td></td><td>Target gene alignment and aligned score</td><td>SEQ ID NO:</td><td>AS*</td><td>Target gene ID/target site</td><td>Putative function of target gene</td></tr>
<tr><td></td><td></td><td></td><td></td><td>Bc-siRNA<br><br>Target</td><td>3'ATGATGATCTTATCTTAGCAT 5'<br>| || ||||||| |||||||:<br>5'TTCTCCTAGAATTGAATCGTG 3'</td><td>404<br><br>407</td><td>4.5</td><td>Solyc04g063230.2.1<br>1354~1375(cDNA)</td><td>NBS-LRR class), putative Dehydration-responsive family protein (AHRD V1 **-- D7LF23_ARALY); contains Interpro domain(s) IPR004159 Protein of unknown function DUF248, methyltransferase putative</td></tr>
<tr><td>siR140<br>SIR8<br>Intergenic region<br>TTGATTT TGCCGTT TCGTATG T (SEQ ID NO: 408)</td><td>417.1</td><td>27.16</td><td>49.1</td><td>Bc-siRNA<br><br>Target</td><td>3'TGTATGCTTTGCCGTTTTAGTT 5'<br>|| | | ||||||||||||:<br>5'TCACAAGCAACGGCAAAATCAG 3'</td><td>408<br><br>409</td><td>4.5</td><td>AT2G07360.1<br>3291~3313(CDS)</td><td>SH3 domain-containing protein</td></tr>
<tr><td></td><td></td><td></td><td></td><td>Bc-siRNA<br><br>Target</td><td>3'TGTATGCTTTGCCGTTTTAGTT 5'<br>||: |||| ||||:|||||||<br>5'ACGAACGATACGGTAAAATCAA 3'</td><td>408<br><br>410</td><td>4.25</td><td>Solyc04g080720.2.1<br>1084~1106(cDNA)</td><td>Transferase family protein (AHRD V1 **-* D7KBT0_ARALY); contains Interpro domain(s) IPR003480 Transferase</td></tr>
<tr><td></td><td></td><td></td><td></td><td>Bc-siRNA<br><br>Target</td><td>3'TGTATGCTTTGCCGTTTTAGTT 5'<br>|||| || ||:|||||||:||<br>5'ACATTCGCAATGGCAAAATTAA 3'</td><td>408<br><br>411</td><td>4</td><td>Solyc07g017860.2.1<br>436~458(cDNA)</td><td>Acetyl-coenzyme A synthetase (AHRD V1 ***-</td></tr>
</table>

TABLE 1-continued

Bc-sRNAs that have predicted targets in both *Arabidopsis* and *S. lycopersicum*.

<table>
<tr><th>Bc-siRNA ID, locus, and siRNA sequence (5'-3')</th><th>Normalized read counts<br>A</th><th><br>S</th><th><br>B</th><th colspan="2">Target gene alignment and aligned score</th><th>SEQ ID NO:</th><th>AS*</th><th>Target gene ID/target site</th><th>Putative function of target gene</th></tr>
<tr><td></td><td></td><td></td><td></td><td></td><td></td><td></td><td></td><td></td><td>Q2J3D0_RHOP2); contains Interpro domain(s) IPR011904 Acetate--CoA ligase</td></tr>
<tr><td></td><td></td><td></td><td></td><td>Bc-siRNA<br><br>Target</td><td>3'TGTATGCTTTGCCGTTTTAGTT 5'<br>|| ||:| |||:|||||||||||<br>5'AGATGCAAAATGGCAAAATCAA 3'</td><td>408<br><br>412</td><td>3.5</td><td>Solyc12g098610.1.1<br>641~663 (cDNA)</td><td>Xyloglucan endotransglucosylase/ hydrolase 8 (AHRD V1 ***-C0IRG7_ACTDE); contains Interpro domain(s) IPR016455 Xyloglucan endotransglucosylase/ hydrolase</td></tr>
<tr><td>siR141<br>SIR1 LTR transposon<br>TAGAAA CATTCGG ACTTCTG T (SEQ ID NO: 413)</td><td>11.4</td><td>187.64</td><td>3</td><td>Bc-siRNA<br><br>Target</td><td>3'TGTCTTCAGGCTTACAAAGAT 5'<br>|::|:|||| ||||||||||<br>5'ATGGGAGTCGGAATGTTTCTA 3'</td><td>413<br><br>414</td><td>4</td><td>AT3G01350.1<br>1191~1212(CDS)</td><td>Major facilitator superfamily protein</td></tr>
<tr><td></td><td></td><td></td><td></td><td>Bc-siRNA<br><br>Target</td><td>3'TGTCTTCAGGCTTACAAAGAT 5'<br>||| || ||||||| |||||:<br>5'ACATAATTCCGAATATTTCTG 3'</td><td>413<br><br>415</td><td>4.5</td><td>Solyc03g113070.2.1<br>1358~1379(cDNA)</td><td>ATP-binding cassette (ABC) transporter 17 (AHRD V1 *-*-Q4H493_RAT)</td></tr>
<tr><td>siR156<br>SIR18<br>Intergenic region</td><td>335</td><td>9.88</td><td>251.1</td><td>Bc-siRNA<br><br>Target</td><td>3'AGGGTTAGGGTAGGGTAGGGT 5'<br>|||| |||:|||||:||| ||<br>5'TCCCTATCTCATCCTATCGCA 3'</td><td>416<br><br>417</td><td>4.5</td><td>AT5G45973.1<br>62~83(CDS)</td><td>unknown protein, hypothetical protein,</td></tr>
</table>

TABLE 1-continued

<table>
<tr><td colspan="9">Bc-sRNAs that have predicted targets in both Arabidopsis and S. lycopersicum.</td></tr>
<tr><td>Bc-siRNA ID, locus, and siRNA sequence (5'-3')</td><td colspan="3">Normalized read counts</td><td>Target gene alignment and aligned score</td><td>SEQ ID NO:</td><td>AS*</td><td>Target gene ID/target site</td><td>Putative function of target gene</td></tr>
<tr><td></td><td>A</td><td>S</td><td>B</td><td></td><td></td><td></td><td></td><td></td></tr>
<tr><td>TGGGAT GGGATG GGATTG GGA (SEQ ID NO: 416)</td><td></td><td></td><td></td><td></td><td></td><td></td><td></td><td>uncharacterized protein</td></tr>
<tr><td></td><td></td><td></td><td></td><td>Bc-siRNA 3'AGGGTTAGGGTAGGGTAGGGT 5'<br>||:|||||:|||||||||||<br>Target 5'TCTCAATCTCATCCCATCCCT 3'</td><td>416<br><br>418</td><td>2</td><td>Solyc01g112220.2.1 163~184(cDNA)</td><td>Serine/threonine protein kinase-like (AHRD V1 **** Q5XWQ1_SOLTU); contains Interpro domain(s) IPR002290 Serine/threonine protein kinase</td></tr>
<tr><td></td><td></td><td></td><td></td><td>Bc-siRNA 3'AGGGTTAGGGTAGGGTAGGGT 5'<br>|| || |::||||:|||||||<br>Target 5'TCACATTTTCATCTCATCCCA 3'</td><td>416<br><br>419</td><td>4.5</td><td>Solyc12g019040.1.1 100~121(cDNA)</td><td>Exostosin family protein (AHRD V1 *-*- D7LPB7_ARALY)</td></tr>
<tr><td></td><td></td><td></td><td></td><td>Bc-siRNA 3'AGGGTTAGGGTAGGGTAGGGT 5'<br>||:| ||| ||||||||:||<br>Target 5'TCTCCATCACATCCCATTCCT 3'</td><td>416<br><br>420</td><td>4.5</td><td>Solyc12g096410.1.1 54~75(cDNA)</td><td>Unknown Protein (AHRD V1)</td></tr>
<tr><td>siR161 SIR1 LTR transposon TAGGCAT CATTCTC TTCCTTG G (SEQ ID NO: 421)</td><td>9.9</td><td>120.16</td><td>5.7</td><td>Bc-siRNA 3'GGTTCCTTCTCTTACTACGGAT 5'<br>||||||||||||:|| ||:||:<br>Target 5'CCAAGGAAGAGAGTGTTGTCTG 3'</td><td>421<br><br>422</td><td>4.5</td><td>AT2G16270.1 295~317(CDS)</td><td></td></tr>
<tr><td></td><td></td><td></td><td></td><td>Bc-siRNA 3'GGTTCCTTCTCTTACTACGGAT 5'<br>|:|||| |||||| |||||:||<br>Target 5'CTAAGGCAGAGAAAGATGCTTA 3'</td><td>421<br><br>423</td><td>4.5</td><td>AT3G18660.1 1168~1190(CDS)</td><td>plant glycogenin-like starch initiation protein 1</td></tr>
<tr><td></td><td></td><td></td><td></td><td>Bc-siRNA 3'GGTTCCTTCTCTTACTACGGAT 5'<br>:| | |||||||||||||:||:<br>Target 5'TCCATGAAGAGAATGATGTCTG 3'</td><td>421<br><br>424</td><td>4</td><td>AT3G63380.1 1416~1438(CDS)</td><td>ATPase E1-E2 type family protein/ haloacid</td></tr>
</table>

TABLE 1-continued

<table>
<tr><th colspan="9">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th>Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th></tr>
<tr><td></td><td></td><td></td><td></td><td></td><td></td><td></td><td></td><td>dehalogenase-like hydrolase family protein</td></tr>
<tr><td></td><td></td><td></td><td></td><td>Bc-siRNA 3'GGTTCCTTCTCTTACTACGGAT 5'<br>|: ||||:|||||||||||:||<br>Target 5'CTTAGGAGGAGAATGATGCTTA 3'</td><td>421<br><br>425</td><td>3.75</td><td>AT5G17400.1<br>863~885(CDS)</td><td>endoplasmic reticulum-adenine nucleotide transporter 1</td></tr>
<tr><td></td><td></td><td></td><td></td><td>Bc-siRNA 3'GGTTCCTTCTCTTACTACGGAT 5'<br>:|||| |:|:|||||||||||<br>Target 5'TCAAGTAGGGGAATGATGCCTA 3'</td><td>421<br><br>426</td><td>2.5</td><td>Solyc03g083340.1.1<br>1152~1174(cDNA)</td><td>Response regulator 8 (AHRD V1 *-*-Q9AV93_MAIZE); contains Interpro domain(s) IPR001789 Signal transduction response regulator, receiver region</td></tr>
<tr><td></td><td></td><td></td><td></td><td>Bc-siRNA 3'GGTTCCTTCTCTTACTACGGAT 5'<br>||| ||||:|||| |||||||<br>Target 5'GCAAAGAAGGGAATCATGCCTA 3'</td><td>421<br><br>427</td><td>4.5</td><td>Solyc04g005430.2.1<br>1312~1334(cDNA)</td><td>Dehydration-responsive protein-like (AHRD V1 **--Q653G1_ORYSJ); contains Interpro domain(s) IPR004159 Protein of unknown function DUF248, methyltransferase putative</td></tr>
<tr><td></td><td></td><td></td><td></td><td>Bc-siRNA 3'GGTTCCTTCTCTTACTACGGAT 5'<br>|:|| | |||||| ||||||||<br>Target 5'CTAAAGCAGAGAAAGATGCCTA 3'</td><td>421<br><br>428</td><td>4.5</td><td>Solyc11g005760.1.1<br>892~914(cDNA)</td><td>Glycogenin-like protein (AHRD V1 ***-Q5NA53_ORYSJ); contains</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence</th><th colspan="3">Normalized read counts</th><th colspan="2">Target gene alignment</th><th>SEQ ID</th><th></th><th>Target gene</th><th>Putative function of</th></tr>
<tr><th>(5'-3')</th><th>A</th><th>S</th><th>B</th><th colspan="2">and aligned score</th><th>NO:</th><th>AS*</th><th>ID/target site</th><th>target gene</th></tr>
<tr><td></td><td></td><td></td><td></td><td></td><td></td><td></td><td></td><td></td><td>Interpro domain(s) IPR002495 Glycosyl transferase, family 8</td></tr>
<tr><td>siR163 SIR8 Intergenic region TGATCCA AAGTAC AATGTGT A (SEQ ID NO: 429)</td><td>275</td><td>8.24</td><td>74.2</td><td>Bc-siRNA<br><br>Target</td><td>3'ATGTGTAACATGAAACCTAGT 5'<br>| |:|||||||:|||||||||<br>5'TTCGCATTGTATTTTGGATCA 3'</td><td>429<br><br>430</td><td>2.5</td><td>AT3G07140.1 1754~1775(CDS)</td><td>GPI transamidase component Gpi16 subunit family protein</td></tr>
<tr><td></td><td></td><td></td><td></td><td>Bc-siRNA<br><br>Target</td><td>3'ATGTGTAACATGAAACCTAGT 5'<br>|||::||| |||||||||||<br>5'AACATGTTGAACTTTGGATCA 3'</td><td>429<br><br>431</td><td>4.5</td><td>AT5G46640.1 1159~1180(CDS)</td><td>AT hook motif DNA-binding family protein</td></tr>
<tr><td></td><td></td><td></td><td></td><td>Bc-siRNA<br><br>Target</td><td>3'ATGTGTAACATGAAACCTAGT 5'<br>||||:| ||||||| |||||<br>5'TACATAGTGTACTTGGGATCT 3'</td><td>429<br><br>432</td><td>4.5</td><td>AT5G59810.1 293~314(CDS)</td><td>Subtilase family protein</td></tr>
<tr><td></td><td></td><td></td><td></td><td>Bc-siRNA<br><br>Target</td><td>3'ATGTGTAACATGAAACCTAGT 5'<br>|:|||| | ||:||||||||<br>5'TGCACAATTTATTTTGGATCT 3'</td><td>429<br><br>433</td><td>4.5</td><td>Solyc06g084310.2.1 598~619(cDNA)</td><td>Small nuclear ribonucleoprotein Sm D1 (AHRD V1 ***- B6TXH2_MAIZE); contains Interpro domain(s) IPR006649 Like-Sm ribonucleoprotein, eukaryotic and archaea-type, core</td></tr>
<tr><td></td><td></td><td></td><td></td><td>Bc-siRNA<br><br>Target</td><td>3'ATGTGTAACATGAAACCTAGT 5'<br>||||: |||||||||||| ||<br>5'TACATTTTGTACTTTGGACCA 3'</td><td>429<br><br>434</td><td>4.25</td><td>Solyc08g079630.2.1 1618~1639(cDNA)</td><td>AT-hook motif nuclear localized protein 1 (AHRD V1 ***-</td></tr>
</table>

TABLE 1-continued

<table>
<tr><th colspan="10">Bc-sRNAs that have predicted targets in both Arabidopsis and S. lycopersicum.</th></tr>
<tr><th>Bc-siRNA ID, locus, and siRNA sequence (5'-3')</th><th colspan="3">Normalized read counts</th><th colspan="2">Target gene alignment and aligned score</th><th>SEQ ID NO:</th><th>AS*</th><th>Target gene ID/target site</th><th>Putative function of target gene</th></tr>
<tr><th></th><th>A</th><th>S</th><th>B</th><th></th><th></th><th></th><th></th><th></th><th></th></tr>
<tr><td></td><td></td><td></td><td></td><td></td><td></td><td></td><td></td><td></td><td>Q8VYJ2_ARATH); contains Interpro domain(s) IPR005175 Protein of unknown function DUF296</td></tr>
<tr><td>siR1001 SIR1001 CDS TCACATG ATTATTA AAACAT AAT (SEQ ID NO: 435)</td><td>218</td><td>7.4</td><td>8.4</td><td>Bc-siRNA<br><br>Target</td><td>3'TAATACAAAATTATTAGTACACT 5'<br>|||||||||||||:||| ||||:<br>5'ATTATGTTTTAATGATCTTGTGG 3'</td><td>435<br><br>436</td><td>3.5</td><td>AT1G77470.1 1437~1460(3'UTR)</td><td>replication factor C subunit 3</td></tr>
<tr><td></td><td></td><td></td><td></td><td>Bc-siRNA<br><br>Target</td><td>3'TAATACAAAATTATTAGTACACT 5'<br>|||:||| || |||||| |||||<br>5'ATTGTGTCTTCATAATCCTGTGA 3'</td><td>435<br><br>437</td><td>4.5</td><td>Solyc04g055110.2.1 1474~1497(cDNA)</td><td>Mitochondrial import receptor subunit TOM34 (AHRD V1 *---TOM34_RAT); contains Interpro domain(s) IPR011990 Tetratricopeptide-like helical</td></tr>
</table>

Normalized read counts are given in reads per million *B. cinerea* sRNAs. Reads were summed from individual sRNA libraries for each category: *B. cinerea*-infected *Arabidopsis* ("A"), *B. cinerea*-infected *S. lycopersicum* ("S"), and cultured *B. cinerea* ("B").
*AS (aligned score): Target gene alignment was scored as described in Materials and Methods.

TABLE 2

Primers for constructing short tandem target mimic (STTM) against selected *B. cinerea* sRNAs listed in Table 1

| sRNA | Primer* | Primer sequence |
|---|---|---|
| Bc-siR3.2 | 3.2-STTMSwa48ntlink-PF | GccATTTAAATatggtctaaagaagaagaatACCTACAAGATctaCCACAATGTAgaattcggtacgctgaaatcaccag (SEQ ID NO: 438) |
| | 3.2-STTMSwa48ntlink-PR | GccATTTAAATtagaccataacaacaacaacTACATTGTGGtagATCTTGTAGGTaagcttgggctgtcctctccaaatg (SEQ ID NO: 439) |
| Bc-siR3.1 | 3.1-STTMSwa48ntlink-PF | GccATTTAAATatggtctaaagaagaagaatGCCCACCTACActaAGATCCACAAgaattcggtacgctgaaatcaccag (SEQ ID NO: 440) |
| | 3.1-STTMSwa49ntlink-PR | GccATTTAAATtagaccataacaacaacaacTTGTGGATCTTtagTGTAGGTGGGCaagcttgggctgtcctctccaaatg (SEQ ID NO: 441) |
| Bc-siR5 | 5-STTMSwa48ntlink-PF | GccATTTAAATatggtctaaagaagaagaatAAGTATACATTctaCCGAGTCAAAgaattcggtacgctgaaatcaccag (SEQ ID NO: 442) |
| | 5-STTMSwa49ntlink-PR | GccATTTAAATtagaccataacaacaacaacTTTGACTCGGtagAATGTATACTTaagcttgggctgtcctctccaaatg (SEQ ID NO: 443) |
| 3.1-3.2-STTMSwa48ntlink-PF (=3.2-STTMSwa48ntlink-PF) | | |
| 3.1-3.2-STTMSwa48ntlink-PR (=3.1-STTMSwa48ntlink-PR) | | |
| 5-3.2-STTMSwa48ntlink-PF (=3.2-STTMSwa48ntlink-PF) | | |
| 5-3.2-STTMSwa48ntlink-PR (=5-STTMSwa48ntlink-PR) | | |
| 5-3.1-STTMSwa48ntlink-PF (=3.1-STTMSwa48ntlink-PF) | | |
| 5-3.1-STTMSwa48ntlink-PR (=5-STTMSwa48ntlink-PR) | | |
| SiR1 | SiR1-STTMSwa48ntlink-PF | GccATTTAAATatggtctaaagaagaagaatCAGAATTCTACTctaCTTGCTTCGAgaattcggtacgctgaaatcaccag (SEQ ID NO: 444) |
| | SiR1-STTMSwa49ntlink-PR | GccATTTAAATtagaccataacaacaacaacTCGAAGCAAGtagAGTAGAATTCTGaagcttgggctgtcctctccaaatg (SEQ ID NO: 445) |
| siR1010 | 1010-STTMSwa48ntlink-PF | GccATTTAAATatggtctaaagaagaagaatAGCAATCAAAActaATTCCCCCGAgaattcggtacgctgaaatcaccag (SEQ ID NO: 446) |
| | 1010-STTMSwa48ntlink-PR | GccATTTAAATtagaccataacaacaacaacTCGGGGGAATTAGTTTTGATTGCTaagcttgggctgtcctctccaaatg (SEQ ID NO: 447) |
| siR1008 | 1008-STTMSwa48ntlink-PF | GccATTTAAATatggtctaaagaagaagaatGCATAAACTGATctaCATCATCACAgaattcggtacgctgaaatcaccag (SEQ ID NO: 448) |
| | 1008-STTMSwa48ntlink-PR | GccATTTAAATtagaccataacaacaacaacTGTGATGATGTAGATCAGTTTATGCaagcttgggctgtcctctccaaatg (SEQ ID NO: 449) |
| siR9 | 9-STTMSwa48ntlink-PF | GccATTTAAATatggtctaaagaagaagaatTCTAAAAATGCTctaCATCATAAAAgaattcggtacgctgaaatcaccag (SEQ ID NO: 450) |
| | 9-STTMSwa48ntlink-PR | GccATTTAAATtagaccataacaacaacaacTTTTATGATGTAGAGCATTTTTAGAaagcttgggctgtcctctccaaatg (SEQ ID NO: 451) |
| siR10 | 10-STTMSwa48ntlink-PF | GccATTTAAATatggtctaaagaagaagaatAGCACCCTACActaACCTAGAAAAgaattcggtacgctgaaatcaccag (SEQ ID NO: 452) |
| | 10-STTMSwa48ntlink-PR | GccATTTAAATtagaccataacaacaacaacTTTTCTAGGTTAGTGTAGGGTGCTaagcttgggctgtcctctccaaatg (SEQ ID NO: 453) |
| siR18 | 18-STTMSwa48ntlink-PF | GccATTTAAATatggtctaaagaagaagaatTGATCGACTCTctaGTTTTGGCTAgaattcggtacgctgaaatcaccag (SEQ ID NO: 454) |
| | 18-STTMSwa48ntlink-PR | GccATTTAAATtagaccataacaacaacaacTAGCCAAAACTAGAGAGTCGATCAaagcttgggctgtcctctccaaatg (SEQ ID NO: 455) |
| siR15 | 15-STTMSwa48ntlink-PF | GccATTTAAATatggtctaaagaagaagaatTCAAACAACAAGctaGTTCAACACAgaattcggtacgctgaaatcaccag (SEQ ID NO: 456) |
| | 15-STTMSwa48ntlink-PR | GccATTTAAATtagaccataacaacaacaacTGTGTTGAACTAGCTTGTTGTTTGAaagcttgggctgtcctaccaaatg (SEQ ID NO: 457) |

TABLE 2-continued

Primers for constructing short tandem target mimic (STTM) against selected *B. cinerea* sRNAs listed in Table 1

| sRNA | Primer* | Primer sequence |
|---|---|---|
| siR17 | 17-STTMSwa48ntlink-PF | GccATTTAAATatggtctaaagaagaagaatCCAGTGCCATTctaCATCATTTTAgaattcggtacgctgaaatcaccag (SEQ ID NO: 458) |
| | 17-STTMSwa48ntlink-PR | GccATTTAAATtagaccataacaacaacaacTAAAATGATGTAGAATGGCACTGGaagcttgggctgtcctctccaaatg (SEQ ID NO: 459) |
| siR22 | 22-STTMSwa48ntlink-PF | GccATTTAAATatggtctaaagaagaagaatACTACACCCTTctaGACCACGTTAgaattcggtacgctgaaatcaccag (SEQ ID NO: 460) |
| | 22-STTMSwa48ntlink-PR | GccATTTAAATtagaccataacaacaacaacTAACGTGGTCTAGAAGGGTGTAGTaagcttgggctgtcctctccaaatg (SEQ ID NO: 461) |
| siR24 | 24-STTMSwa48ntlink-PF | GccATTTAAATatggtctaaagaagaagaatGTCAAACAGAGActaGGACCAATCAgaattcggtacgctgaaatcaccag (SEQ ID NO: 462) |
| | 24-STTMSwa48ntlink-PR | GccATTTAAATtagaccataacaacaacaacTGATTGGTCCTAGTCTCTGTTTGACaagcttgggctgtcctaccaaatg (SEQ ID NO: 463) |
| siR25 | 25-STTMSwa48ntlink-PF | GccATTTAAATatggtctaaagaagaagaatAAAACCAAAATTctaTGATTCACTAgaattcggtacgctgaaatcaccag (SEQ ID NO: 464) |
| | 25-STTMSwa48ntlink-PR | GccATTTAAATtagaccataacaacaacaacTAGTGAATCATAGAATTTTGGTTTTaagcttgggctgtcctctccaaatg (SEQ ID NO: 465) |
| siR1015 | 1015-STTMSwa48ntlink-PF | GccATTTAAATatggtctaaagaagaagaatACCGATCAGActaCAACCATCAAgaattcggtacgctgaaatcaccag (SEQ ID NO: 466) |
| | 1015-STTMSwa48ntlink-PR | GccATTTAAATtagaccataacaacaacaacTTGATGGTTGTAGTCTGATCGGTaagcttgggctgtcctctccaaatg (SEQ ID NO: 467) |
| siR20 | 20-STTMSwa48ntlink-PF | GccATTTAAATatggtctaaagaagaagaatAATCAGAAAAACctaAAGAACACTAgaattcggtacgctgaaatcaccag (SEQ ID NO: 468) |
| | 20-STTMSwa48ntlink-PR | GccATTTAAATtagaccataacaacaacaacTAGTGTTCTTTAGGTTTTTCTGATTaagcttgggctgtcctctccaaatg (SEQ ID NO: 469) |
| siR1021 | 1021-STTMSwa48ntlink-PF | ccATTTAAATatggtctaaagaagaagaatACATGTTTTGTTctaCATCACTGTAgaattcggtacgctgaaatcaccag (SEQ ID NO: 470) |
| | 1021-STTMSwa48ntlink-PR | GccATTTAAATtagaccataacaacaacaacTACAGTGATGTAGAACAAAACATGTaagcttgggctgtcctctccaaatg (SEQ ID NO: 471) |
| siR1002 | 1002-STTMSwa48ntlink-PF | GccATTTAAATatggtctaaagaagaagaatTGTGTTACAAAGActaTTTGAAGAATgaattcggtacgctgaaatcaccag (SEQ ID NO: 472) |
| | 1002-STTMSwa48ntlink-PR | GccATTTAAATtagaccataacaacaacaacATTCTTCAAATAGTCTTTGTAACACAaagcttgggctgtcctctccaaatg (SEQ ID NO: 473) |
| siR28 | 28-STTMSwa48ntlink-PF | GccATTTAAATatggtctaaagaagaagaatAAGAAGATCACActaGTTTCAAAAAgaattcggtacgctgaaatcaccag (SEQ ID NO: 474) |
| | 28-STTMSwa48ntlink-PR | GccATTTAAATtagaccataacaacaacaacTTTTTGAAACTAGTGTGATCTTCTTaagcttgggctgtcctctccaaatg (SEQ ID NO: 475) |
| siR31 | 31-STTMSwa48ntlink-PF | GccATTTAAATatggtctaaagaagaagaatCATTCACGACCctaACAAGACTCAgaattcggtacgctgaaatcaccag (SEQ ID NO: 476) |
| | 31-STTMSwa48ntlink-PR | GccATTTAAATtagaccataacaacaacaacTGAGTCTTGTTAGGGTCGTGAATGaagcttgggctgtcctctccaaatg (SEQ ID NO: 477) |

TABLE 2-continued

Primers for constructing short tandem target mimic (STTM) against selected *B. cinerea* sRNAs listed in Table 1

| sRNA | Primer* | Primer sequence |
|---|---|---|
| siR29 | 29-STTMSwa48ntlink-PF | GccATTTAAATatggtctaaagaagaagaatCCCAAAAAGGActaCTATCCAACAgaattcggtacgctgaaatcaccag (SEQ ID NO: 478) |
| | 29-STTMSwa48ntlink-PR | GccATTTAAATtagaccataacaacaacaacTGTTGGATAGTAGTCCTTTTTGGGaagcttgggctgtcctctccaaatg (SEQ ID NO: 479) |
| siR41 | 41-STTMSwa48ntlink-PF | GccATTTAAATatggtctaaagaagaagaatTTCTACTCCCGctaAAAACTATCAgaattcggtacgctgaaatcaccag (SEQ ID NO: 480) |
| | 41-STTMSwa48ntlink-PR | GccATTTAAATtagaccataacaacaacaacTGATAGTTTTTAGCGGGAGTAGAAaagcttgggctgtcctctccaaatg (SEQ ID NO: 481) |
| siR35 | 35-STTMSwa48ntlink-PF | GccATTTAAATatggtctaaagaagaagaatAACGCGACATGctaGCACAGTACAgaattcggtacgctgaaatcaccag (SEQ ID NO: 482) |
| | 35-STTMSwa48ntlink-PR | GccATTTAAATtagaccataacaacaacaacTGTACTGTGCTAGCATGTCGCGTTaagcttgggctgtcctaccaaatg (SEQ ID NO: 483) |
| siR57 | 57-STTMSwa48ntlink-PF | GccATTTAAATatggtctaaagaagaagaatCCAACGAACCAGctaAGATTATCTAgaattcggtacgctgaaatcaccag (SEQ ID NO: 484) |
| | 57-STTMSwa48ntlink-PR | GccATTTAAATtagaccataacaacaacaacCCAACGAACCAGctaAGATTATCTAaagcttgggctgtcctctccaaatg (SEQ ID NO: 485) |
| siR43 | 43-STTMSwa48ntlink-PF | GccATTTAAATatggtctaaagaagaagaatCCCAACAAGAGctaAAAGCTCCCAgaattcggtacgctgaaatcaccag (SEQ ID NO: 486) |
| | 43-STTMSwa48ntlink-PR | GccATTTAAATtagaccataacaacaacaacTGGGAGCTTTTAGCTCTTGTTGGGaagcttgggctgtcctctccaaatg (SEQ ID NO: 487) |
| siR40 | 40-STTMSwa48ntlink-PF | GccATTTAAATatggtctaaagaagaagaatAACCAATACAActaGCCCATTCCAgaattcggtacgctgaaatcaccag (SEQ ID NO: 488) |
| | 40-STTMSwa48ntlink-PR | GccATTTAAATtagaccataacaacaacaacTGGAATGGGCTAGTTGTATTGGTTaagcttgggctgtcctctccaaatg (SEQ ID NO: 489) |
| siR48 | 48-STTMSwa48ntlink-PF | GccATTTAAATatggtctaaagaagaagaatTTGATCGATACctaTGTCACTTCAgaattcggtacgctgaaatcaccag (SEQ ID NO: 490) |
| | 48-STTMSwa48ntlink-PR | GccATTTAAATtagaccataacaacaacaacTGAAGTGACATAGGTATCGATCAAaagcttgggctgtcctctccaaatg (SEQ ID NO: 491) |
| siR49 | 49-STTMSwa48ntlink-PF | GccATTTAAATatggtctaaagaagaagaatTATCAAAAGACctaATAAGCCACAgaattcggtacgctgaaatcaccag (SEQ ID NO: 492) |
| | 49-STTMSwa48ntlink-PR | GccATTTAAATtagaccataacaacaacaacTGTGGCTTATTAGGTCTTTTGATAaagcttgggctgtcctctccaaatg (SEQ ID NO: 493) |
| siR58 | 58-STTMSwa48ntlink-PF | GccATTTAAATatggtctaaagaagaagaatCAGACAATGAActaTCCCAATTTAgaattcggtacgctgaaatcaccag (SEQ ID NO: 494) |
| | 58-STTMSwa48ntlink-PR | GccATTTAAATtagaccataacaacaacaacTAAATTGGGATAGTTCATTGTCTGaagcttgggctgtcctctccaaatg (SEQ ID NO: 495) |
| siR1005 | 1005-STTMSwa48ntlink-PF | GccATTTAAATatggtotaaagaagaagaatTCCTATTGAAGctaAAACTCTTTAgaattcggtacgctgaaatcaccag (SEQ ID NO: 496) |
| | 1005-STTMSwa48ntlink-PR | GccATTTAAATtagaccataacaacaacaacTAAAGAGTTTTAGCTTCAATAGGAaagcttgggctgtcctaccaaatg (SEQ ID NO: 497) |

*Forward primers are denoted as "PF." Reverse primers are denoted as "PR."

TABLE 3

<table>
<tr><th colspan="6">Predicted B. cinerea sRNA targets in V. vinifera</th></tr>
<tr><th colspan="2">sRNA and target in V. vinifera</th><th>Alignment</th><th>SEQ ID NO:</th><th>Molecular function</th><th>Target site position</th></tr>
<tr><td colspan="6">Bc-siR3.2</td></tr>
<tr><td>VIT_10s0092g00240</td><td>Target<br><br>Bc-siR3.2</td><td>5' CCCUACAAGAUUAACAAUGUA<br>    ||||||||||: ||||||||<br>3' UGGAUGUUCUAGGUGUUACAU</td><td>498<br><br>24</td><td>carbohydrate binding, hydrolase activity carbohydrate metabolic process</td><td>CDS + UTR</td></tr>
<tr><td colspan="6">Bc-siR3.1</td></tr>
<tr><td>VIT_12s0028g01140</td><td>Target<br><br>Bc-siR3.1</td><td>5' ACCCAAUUACAAGAUCCACGA<br>    |||| : ||||||||||||: |<br>3' CGGGUGGAUGUUCUAGGUGUU</td><td>499<br><br>30</td><td>Pentatricopeptide repeat</td><td>INTRON</td></tr>
<tr><td>VIT_06s0009g01890</td><td>Target<br><br>Bc-siR3.1</td><td>5' ACCAAUCUACAAAAUCCACAA<br>    || |: |||||| ||||||||<br>3' CGGGUGGAUGUUCUAGGUGUU</td><td>500<br><br>30</td><td>exonuclease</td><td>intron</td></tr>
<tr><td>VIT_10s0116g00190</td><td>Target<br><br>Bc-siR3.1</td><td>5' CCCCAAGUACAAGAACCACAA<br>    ||||  ||||||| ||||||<br>3' CGGGUGGAUGUUCUAGGUGUU</td><td>501<br><br>30</td><td>KNOX1,2 domain containing protein</td><td>Intron</td></tr>
<tr><td colspan="6">Bc-siR5</td></tr>
<tr><td>VIT_05s0020g01790</td><td>target<br><br>Bc-siR5</td><td>5' UAUAUUACAUUCCGAGUCAUG<br>    |   |||||||||||||| :<br>3' UUCAUAUGUAAGGCUCAGUUU</td><td>502<br><br>36</td><td>Lipase</td><td>CDS</td></tr>
<tr><td>VIT_01s0011g01000</td><td>target<br><br>Bc-siR5</td><td>5' AAGCAUACAUACCGAGUCAAU<br>   ||| |||||| |||||||||<br>3' UUCAUAUGUAAGGCUCAGUUU</td><td>503<br><br>36</td><td>NB-ARC and LRR domain</td><td>intron</td></tr>
<tr><td>VIT_05s0077g01510</td><td>target<br><br>Bc-siR5</td><td>5' AAGTAATCATTCCAAGTCAAA<br>   |||||  |||||| |||||||<br>3' UUCAUAUGUAAGGCUCAGUUU</td><td>504<br><br>36</td><td>DUF7 domain</td><td>intron</td></tr>
</table>

Example 2: Sequences of Promoters and sRNA-Resistant Targets

*A. thaliana* (At) BIK1 Promoter:

SEQ ID NO: 1

```
attttattatattatatagcgatgagagagacagagcttgaaggttcttt
ttagcgaaagagaaaaatccaggaagataggcgaaaaggaagatgaagcg
aagatgaggttaatataatactcatgttaaatgacaaaaatgcccttata
tgattaatgatattaccatttgagcttgctgtggaagctgtaacgaaccg
aaaattaaaaacagaataacgaacatagacggagaatatgatattattcg
ttttaccaaagaaactaacaaatagttttaactttatctaacaaaggggt
aaaacgggtaatttgtttgggatgaggtggagcgtagcggacaatcgaga
aattaaaagtttggcttggggacgaagttaaaggtgggctttaacgtttt
aaattggctgactcggacgatatttcttgtatttaataccaaaaatgaat
gactttataattcatttgtagattgaaagttacgtattgattcgaaaatc
aacacattgtgttttcaagtgggcataaactataacaccttgttgattga
ttaatagattacctaaagacattatggtttattactggtctttcaatata
tttttatcgcattgtcaatgatattgtttttgtatcccaagtccactgtt
ttggtctctacattcattttgattgggatttatctttttaaaatttcttc
taatgtttttcgatatggttattacttgctttgattttcttttcagtat
```

-continued

```
gtgtattgctttgcaaattgtttttttcttaagatgaaaaacaactcatt
aaattgtttgagaaatactactaaaacaaataaacaatgaggagaattat
ggaaaacaaagtgtaataggctttaattcattgctagtgggctttttggg
cctatgggcatattacttaccactatccaacccaaaatgccaaataaccg
acatgtctcaccaatccaattttgggccatacggccgaaattatttaaac
ctgtgctcataatttactttacaaattattacttttccataaattgtgga
aaagttatctgtaacatccgattcaactggagtctagactactatagaca
ttgatacgttttgagtttttagatacttggaagatatatgcatttatgaa
tacagattacagacacatactagtactactgtatgtctgtatatggatac
aaaaaaaatcatgtatgaatactaaaattttattagaaatctatttttca
attgttgcaacaatcaagttgtcaaatttatttttgtaaccgttaaacaa
acaaatatcgatttaggtttctaatctgaattgacatctcaaacaaaaaa
ggctgaatactttctgaaaatagtgtatggaatgaaggtggcttttagag
ccattataaccggaagaaaattcaggtgacttttagaaccattataaccg
gaagaaaaggtgaattttaatttttagctgtgtggaagacacggcaagtc
caagtagtaccttcgtacgtcaatattgtccaaccggccgtgtcgaaaat
cttcttgagaaaaattggattttcatctataaaaaaaaaaaagtccaagta
```

-continued

```
ataccaaacaaagacagcgacgtgtaaaacaatacaagactcataatcac
aaacctaccacccaagtcaaacctatattccatttagtgaattcttgatt
atgacttcttgaaatcatttgtattcatatgtataattatttaagtcatt
tttctgtaagtaaaatttttatatatctagaataacgagttccctacgac
aagatacagttgaacgtaaatgtgacatctcaattttcattggtgtctag
tactctagtgattaggttttcgacatttattgtactgattaagtaaaaat
tcatggtacaaacatcgaatatatatttttctgcttacacacaccaatta
acgtggatagaccaattgaaatattttgttacgacaaagcaaaacaaaac
aaacgtcatgtttcgctgtttgtttgtcgtcccgttaatggtaatctttc
agacacatacagtacccaaacaagtaatttgactaaaattttctctctgt
ctaaatttcagaagaaaaaaaaactttaggatatattgccaaaagatctt
aaaaatgggtcatatcattttgatcatatagaatccaacgacctttatct
tttcgccgaactatactttttgtgtccatttgtttgactttctttcaca
cacacatccacaaagaaaaaaggaccattcttctccttcttctagtcacc
cctcgtgcctctctttaacaccaaacccaaaactcccttctctttcttcc
ttcctctccgatctccgttcacatctctctctcatctttatcttcttctt
tttttgccttgtgggttgaaagtttctatattttctctttctcttctgtt
tacataatccattttcagctcaagcagctgaagaataacgatcaagaacc
aaaaaagaagaaaacgaatctgttcttagctttg
```

At PDF1.2 Promoter

SEQ ID NO: 2

```
ACGACGTTGGACTGTTTCATCATATCCCATAAAAATACATGATTGGGGTG
AAAATCTTGAACATATTAAAAAAATATTAAATCAAAATGATAAAGATAGG
GATTTATAAATGTAAAACGGGCGTGTCGAGAATTTTATGGACATTGGGAC
AAGCTTTATATGCAGCATGCATCGCCGCATCGATATCCCGAGGTGCATCG
TTTCTACTTTCATGTCCAAATTTGGGGTTAACTCACAATATATATCATGT
TGCCTATGTAAATTTATAATCATAAATCTAAACCCAAATTTTAATCCTCA
TTCCAAAGCAAAAGTTCTAAGCCCTACAAAAATATGTATTTCCCAAGTTT
AAAAAGAATTAATCTATACTTTTACAAATTTAAATTCTGATCTCTTATAA
TGTTCGGTTTTTCCTTTTTTATTTATTAAGTTAGTTAAAATTTGCAGTTA
TTTTGTTGAATGTCGTTGTTTACGAATTTACGAATAATACCTTTATAGCT
AATCTACAAAATTTTGATGACTGACAACACCGTTAATGTTTTTTTTTAAA
TTACCCTGAGCCTCTCACTTGCGGTCAGACCATGCATGTCGATAGTCCAT
TACGTTTAAGGCCACAATCAACTATAGTTTGTTTATCAATAGCCAACTAA
GCTAACTTTTAGGTTCCTGCCCTCTCCGTTCCTCCGGTACCAATCGTTTC
TTTGTCCCTTCGATAGTTTGAAAACCTACCGACGGTGAGAGCAAAATATT
GATGAATCATCCAATTTTCAGTAATAGGTGTGTCCCAGGGATATATAAAT
GGCGAAACTACGCGAGAACGGTTCCTTGTTCTGCAAACTTGGCGGAACAA
TGCTGCTCTTGAGATCAACCAAACCATATGTTTAGTCCACAACGATCTAT
ATGTCTAGGGGTGATCCTCTAATCGAAAAATGTTGTATTTGTTCGACGAT
GACGAAGGTCAGACTATGAACTGCACAGTCTGCACTTGTCCTAACCGCGA
GAATCTCTGACATCAATATACTTGTGTAACTATGGCTTGGTTAAGATATT
```

-continued

```
ATTTTCTTGAGTCTTAATCCATTCAGATTAACCAGCCGCCCATGTGAACG
ATGTAGCATTAGCTAAAAGCCGAAGCAGCCGCTTAGGTTACTTTAGATAT
CGACAGAGAAATATATGTGGTGGAGAAACCAGCCATCAACAAACAAAAAG
CAAGATCTTATCTTTTGATATTGGCTACGGGAAGATGATGTCTGTTTAAT
GTGTGGGGTTACCACGTTATTGTACGATGCACAAGTAGAAGATTAACCCA
CTACCATTTCATTATAAATAGACGTTGATCTTTGGCTTATTTCTTCACAC
AACACATACATCTATACATTGAAAACAAAATAGTAATAATCATC
```

At BIK1 homologous gene in tomato (TPK1b) Promoter

SEQ ID NO: 3

```
TTGCGTTTAATTTGTATGAATGTCATTTAATTTTTAGGATCGGCTTAAAT
TTGAAATTAAAAAAGCAAAATAATAATACTAGTATTTTCTAACTTTGTAT
TTTAATGCATGACATTATTTTTAGAAAAAATTGTAACGAAGAGAATCATA
TTTATGATAGAATTATTTGTAATTACTATTTGACTGATATTACTAGTTTA
ATTATTTCGCACACAAAGTATATTTTTTTAAAAAAAAATATTTTACATTG
ATTATTTTCTCTCTATCCCAACACCCCATCCCGTCTTTATTTTTATAGTA
TTTATTATACAAATATTTTAAAAGTATCTTATTGAACATCAAAATAATCT
TTTTTAAAAATTATTTATATCCCCAAAAAAATTATATGCACGTGTGAAAA
TGAGAAAATGTTGGTTGGGTGTGAATAATTTGTTGGTTCCCAAATATGAT
TATAATCCAAGAAAATTGGAAATTTGATTATTGCTTCCTTTTGACTTAAA
ACTCTTTGCTAAATTGCTAAGCATTCTTTTTAATTTTGTTTTTCCATTAA
TAACAATTTGGGTAATTCATATCCACTAGTCGGTGGATTTAATAGAAGTG
ATACATATTTTTTTGATGTTATTGTTAATTAATAGTGAAAGGTCCTTTTT
TCTCTCTCCTAATTTATATATAATTCATTTTTTAAAATCAATTTTGAAAG
AATGATATAGTTTCTATATTTAAGTAATGATTTATTTTATTGATAATAAA
ATAAGTTATAATCATATATATATTTTTAATATATTTAAAATTATAATTTA
AATTATTTATATCACATCAATTGAAACGGATGAAATTATTTATTTTAAAA
AAAATGATGAATGGGTGGCATCCATAAAAATGTGACATTTCTCCATGTGT
TTTGCTTAAATGAGATTTTTGACTATTTTTCTTGTGTTCATATTTATGAA
GAAGATCAACAATAAATTTTTATCAATAAAGAGGAAATTAAAAGTTGATT
AATATTAAAAATCACAAATATTTATTGAAAGTGAATAAATTTATAGTTAT
TACACATATATGGAGAGAGATCAAAATCAATATGCTAATTTTTTGTAATG
GAAGGGCACAATGAAAATAAAGTTAATTTTCATGACTAATTTAATCCATA
TAGTTAAATTCTAATCATATAAATTTCAGTGAATAAGTTCATTTGATTTT
TTTTAGATCTAATATTAATTATTAAGATGTAAATGTTAACTATGTTTTTA
TTAATGTTTCAATCACTGTGTCTATATTTGAATGATTACTACTTGTAATT
AAGTGAAAAAAATTCAGTATTTTGTGTATTAAAATTTTTTATTATTGAAAG
AGATATAGATTTAAGTGGAAAGTTAATAAAGAAAATTGCAGTTCGCCCTC
AAATGAATTATCTTTAAAATTTGTTTAATAATATTTGGATCAATAAGTTA
ACGGAGTGGAGATTTTTAAAAGATGATAGTTAAAATTTGCACATAACCGA
ACAAATTGTCTATTTAGGTATGTAATTTAGAGAGTGTCTCTTTTGAGGTT
TGATGTTTAGGGTTCAAAAATTGTCCGTTTTGGTGCCAGAAACGTGCCTA
```

-continued

```
CAACCACCATCCAATCCATTCTCAATCACAATCACCATCACTGACACCCA
ATCACTACAATAAGTCGTCATTGCCGCCATCCTTATAACAAAAGTAATTT
YTTTGCAGTCATAACTATATACTTTAATAAAAAAATGTAAATTTTTATCG
ACATTACTTAAGTATCATTAAATTTACTATCGCTAAAATCTTTAGGGAAA
TTTATAAAGAGTGTTAATTGTTATTAAAAAAATTATATTTATCGATAATT
AAATTATTGTTGCTAATTACTTACCATTGACGACCATTTTCAATGTAGTA
CATCCAATATTATCGCAATAAATCATTATCACCCGTCATTACTATTAATT
ACTACTTATATATCGTCAATCACCATCATCATTAACCATTGCTCTTCATC
CACCATAGTTATTGTCTTTCAAGCATTACCATCATTCATCATCATTATTA
ACTACTTATATATCATCAATAACGATTTATCATTCATCACAATTATTATT
TATCAACATCACCTATCGCTCTTGATCATTACTATTAATCATCATTAACC
TTTAACTGCAACTTACACTATTGTTCTTAATCGATATTCACAATCACCAT
AGTTAGTCATCACCATGAGTCCTAGCCACAAATTCAAAGCAAAACACCCT
TAAAGCCTGGTAGTGTGTGTGAATTAAAGACCAGCAGTCCAAAGAGAGAG
AGAGAGAGAGAAAATGTAGACTTTAAAGATATGTAGTAGGACCAGTCTGC
CATTAATATCTCCTTCTACCAACCTTCCTCTCCTCTTTCACTACCCTACA
TTTAACATTTTCCTATAACCACTGCTTTAGATAAGTCAAATTTAGCTCTT
TGTTTTGATCTCTGTTTCAAAAGAAAACACCTATTAAGCAGCCATCATCT
TTCTTATCTTTTCCAAAACCAAAACTACTGACTTTTCTTGAAAAAAGAAG
AGGTGGGGTGCTTTCTTTTCTTCAAAAACCTTCTCTTTGTTCTTGAAAAA
ACAGGACTCATTCATTTTTTTTTGTGTGTTTCTTTCAGAAGAAATAACAA
AGACCCTTTCTCTGTTTTCTTCATATTTCAGCTTTGAGCTACTTGGATCT
GTTTTTTTTTTTTGAATATACAAGTAGTTTGTGTGTTCTGGGGTCTACAG
AAGAAGGAGAAGCTAAAAGGGGTGATTTTGTTTTTTGTTTGTTGTTGTTC
TA
```

AtML1 promoter (AT4G21750.1 promoter sequence)

SEQ ID NO: 14

```
aagcttatcaaagaaaaaacaagaacaaaacgatgcatagtttctaaaat
gtgctaaaattcagaaactgaaacatgattcattgtctgaaactttgttt
caaattactgaaaataatcattcactggaccaaaacaaataaataaaata
aaatcgaatttctgaatttggaaattggtttttggtttttaattttaaac
aaaacaaaaacgaaatttgaaggcaataaatgagttagttggtaggcaga
agtcactcgttcccactagctattattattagaagaaacgtccccacaac
tccaaggcgtttcagttcctttaatttactgaattaccctcctcatatct
ataaaaaatcacctcttgtaccaatgccccatttacacatcctgtcgttt
atttctagactaagtggactacatgtcggttatttgattcgcaccatgcg
tatttggattatcgctaacacaccccttcaaacaatacgcttaactcgta
ttacaaaatttcaagtgatgaattatctatgtataagatatagataggaa
caactaagcatcgagaaatttgtatataaatcaactagacttatatatat
ttcgatacagaatttatacgtattatatcaaattaattagtaattgtttc
ctctacgtgagtttaattaacaatgataagctacattgagtgtatcagtt
ctaaaactttatagtatgctacaatcaatttttctaagtaacaacttcaa
gcaaggaatcacacacacacagtggtacataataaacttgattttaatat
catatgatcagcatcattaacggaataagttaagtaattcgtcatccata
ctactaagtcatattaaaatcataatcaaacttaaaagccgattagaaag
agagcaaatatatctaaaaattcacgaggaagacgacaaatgcaaggaaa
cacagctagtattattaaacttaatagatattggatgaatgactgcataa
tatatatcacattaaaagtggacataaatttgcatatgtgtaatgtacct
ctccacaattaatcgcggaccatttattttactattacaagtcaagtaac
tttatattgttgatccataattcttttcgaacataaaatcatatacttag
gccattttcaactgtcaaaactcgaatccgagaaccaaatttcaccattt
tccaaaaatgatgagtgtcgaccaaatggggtactactgtctaatcagga
acttgtgaacaaattttcaaccttttccaaataagacgagtgtcaaccaa
ctttttccaaccaagagatattgggttgctacacaaatacttaatagcca
ttgcatatttatgcatatgcaaatgcagggtcgtggcgtcagaaagaaac
ataggaccctcaacatatttaatattttgggagctatatttgactatttc
atattagaaaataataataaaaaagtgttggttttatatcaaattgtaat
ttacgaaaaacttatgcttttgcgcaatgatttttgtaaagtatctacta
tgtttagtgtttacattgattagtaggctgccgtttttttttcttgtgtat
tatgtactatatatgaatatgaacatttgtaaaagtgaatcttgtcattt
tcttgttgaaaacatatatagtatgtgcaaacaaagcataggttaatcca
ataccacacaaataacacgtcaggtaaatccaataataaatcgtatgtgc
atgtatgtgtattcatgtatgttacatgaatgtctgaatcagtcagtgta
cgtatatgatgtaggtgatgtaaatcttaatgtatgagctgtttcttgga
ccatggtccacaatggatattgctccccaactacattagtcaatcgactg
gccaatttttaattaagataattaatccaaactaccattaaatataactt
tgaccttttttctattcatttttagatattattggaacttacgtagttta
catgcatctcatccctttcttttgctccttgaaagtgggtccaatcacaa
aaaatgatcttatattttgtattttgtattttaaaaactcataattatat
aggttcaaaaatttaattaacatcagtgtatactataattactactctag
ccaacaagataaattcattttgacatcagccaaaagataaaaatttggtt
aaaaactattggattagcttttagtatttaatattttatgtactgattaa
atacgaatttagaaatctaggatataagtgagggtgtataataagggagg
ggtggaccattaatagcgatgtgcaattaaaaattatgattaagaatcta
ggaaatttgtagattgcttagttattttttatggcgatcgtcgtgtcaatg
tcatggattttgaaactttaaattaatctcttaaattagcacctaccttt
gaattttatagaatctttttattttatatgtttaattttatagaatctaa
ctagcttattttgagattaaattgtttagttacttttataacagtataaa
tgtataatgaggacctaagaatgtagtcctgtaatgttcttgctattcta
cttaatctcatcaccaatcaaccatcaaaagaagctagtactaataaaac
ctgcaggtattcgaataataattaagctcaaacactatactaatttatgg
aggattatatattcaatgaattaggaacctcatgatggacattattgact
```

-continued gatataatgtgtatactaattgtgagtatttaaaaaccatacaaagcatt
tatatgtccacatatattggacacacatgcaatcaatgttcaatatgctc
cacacacagaaataaaaatactctttctgatcatatgatacatcatacat
atactaaaaaaatctaaaatgaactataaccacaagcatatataataaca
atgaaatggtaatgtttcttcatttttatttgttcaaattcttattcggt
tgtttttttcttaccctacgagaatccgtgaggtcaaagggaaacagtgat
tttttttttgtattttgtttttaaattgatgaactgtaaaactctctct
ctagaaaaatatataagtagtagtatgaattttctctcactaaaagcatt
aatggacctttcgataatcataaatgcaatgcaccctctctatgcatttc
gcaataactccttttccttctgccacatcctcttcctcacctctttctct
tcttccctttctcctaagttcctcctccaccaaattctccatttatttcg
ttaactatcctccatttgtttcttctgaagagtgatatattctaccttt
ctctggttaaagaaactccctgaatccaccggttatgtcttgaccggcta
taagcctataaactgatgccctaagacacctttttaggtttctcaataat
tctccgcatctatcttttcttctccacaagtaagagaaccagaaaaccag
agaagaagccgagctagctagggtttcattgtgtgcacaaaagtaagatc
tctctctctaaccaatacttgtgtaatttgtctttgtttctttgagcaaa
tattgcatgtttgttcatattagccggatccgttttatatttttcatga
tctacattttatctttatttgttgtaaattaatgagtttttttttttt
ttttctgtttttgtcacgatctaaaaaacaagcgttacaaagaagaagaa
aaaccttttttggagttagaagtgtaaaaggggtttcagtttgacgaattt
tccttagtagttgtgtaaaaaaaaggccattgacttaatgtcaactctata
tatctacacatttttttattaattagtttttgtttttttcccacttcatt
tacctttagtcaatgaatttttactgaaaacgtttttcaaggtcaattt
cactgagttaaaaaaaaaaagttttatttttaaccaaaaattacgtttttt
cctaggcttcggtaacctgtgaattcctctatctcactagcttttatgta
gaagagagagagaaggcaacattaaattcgatctaaaacttcaagaaaccaa
aacaacacttcaaaaaaaaaaagagatctgttctatagagttttaatctt
ttctttcgactcgagtttggctcaacaaagtttatatcgatttggcactc
taaaatgtaagtagaaccaaatgaatcttgtattttatgtacgttaataa
aaaattagggtttcctagacgacaatctcgtcatccgtttcttctttgtc
tacctctgcgttttcttgtagatccgatgatgtgctcagtcttgtgactt
tcaagattgattttatcgttattgtttgaagatatgtggtttgattattt
tctcaacacattgtgtcctttttagcgctttacttcagtttctctctaatt
ttcataatattattattgaacattatgcttaattattcatccgaatattc
gtgtcccatttttttaaattgaatttcaggataacttgtattttatatgca
acgaggttatgtcacgtagtgggtgcatttatattcataccctttttgat
aagatgaatgcatatgcttatataagcgtataggtataaataaccatcaa
aaatagagaaaaagaccaatatttttgcttttcggttacttatgaaatgtg
aaaaagaccatataaatatatctattaaagggaagtatagtttcataaaa
tcttgaggattacattccataaaccaagattaccttccgtttttgctttg -continued atcctcttcttatcaaatatataaacatgaccatttgatctttcattttg
gatagtgggatatacaggcagaagaaaatcgagataaatcaactaaatga
tttggataatcatcttgaagatttgaaggaaaatccaagagcttcaaaaa
ctccaaaaattgataggcatccatcatcatc Tomato ML1 Solyc10g005330.2.1 promoter sequence

SEQ ID NO: 15

ATTTTGACACACGAAAAAGTAGTACGAATATTGAACTCATGATAACTTTA
TCAGTTACTTCAAGACTCTCATTTTAACACAAGAAATATATTTTACAAAG
AAAAAGGGAACATATTTTACAAAGCTTTATTTTGTATTTTCATTAATAAT
TATTTTCAAGGCTTGAACTCATAATAATTTTATCAGTTTTTTCAAGATTT
TCATTTTAACACACGAAAAAGTAATATGAATATTGAACTCATGATAATTT
TATCAGTTACTTTAAGACACTTATTTTGACACACGAAAAAAGTAATACGA
ATATCAAACACCGAATACGAAAGAAAAAAAGAAATGAAAGCATTATAGTA
GTTGCCAACCGCCCCTTCCTCCTCCTCTCTCTCTTCAACAACAACATTAA
CACCTCTATAGCAAGTCATAAATGCTATTTCATCCTCTCTATACCCTTTG
CATTAACTCCTTTGCTTCCACAATCTCTTCTCCCACCTCTTCACCTTCCC
CTTTTCACACTTTCTTTCTCTTTCTTTTTTTCTTTCATCCTTAGCCTCAA
AACTATTCTTCTTAAATTCTAGTCACAAGAAAAGTGTTCAATTTCAACCT
AGCTTCACTAAAATATATACATGTTCATTCTCCAAAAAGTACTTCTTGTC
AAAACTTAGATTTAACCATTTTCTCAAAAACCCTAATAACATCAACAACA
AAAAAGAAGAAGAAGGTGTGTTCTTGCTTTTGTCACAAGGCTTCTCTACA
ACTCATGTAAGTCAAACATATACTATCATCTTCTTGAATTTGTTGAATTC
TTTTTTACTAGCTTATAAGTGTACTATATTGTTCGAATTTTCTAAAAATA
TTATCCGATCTTTTAGGAACAATATATATTTTTAAAGATCCAATACAAAT
ATAACATTAGTTTCACAGAGTCCGAGCAAAATAGATAAATAGTTGTAAAT
TCACTTGTATTTGACTTACCTTTTCATTTTTCCGTTATATTTTGCAGAAA
TAGAAATGCCAGTGAAGTTGGACTCTGCCTAGATACTCGTGGACGTTATA
TCATATACAAGTACCTAAGTTTTGAAAAAAAAAATTAACAGTGAAAAAATA
TTAGTTTTTGAGTTCACACTATGTCAACTCTATCTTTGTTTTTTGCTAAA
TTTTTCTAGTTTCAAGTCTTTTTTTTTGTTTGACTTGTAAAACTTTTTTC
TTTTACATTATTTTTATCCCCTTAGAGATTCTATAAAAACTCTATGCCCT
AACAAAATTTCTTACTAAACAAACAGATATATCAACATATATAGAAACAA
AGGAGAGAGAAATTGTTTCTATGGCTTGAAGGGCTTATGTCATATATGTT
ATATATGGTGTAAACTCCATCACTATGAAGTTTCTGGCAAGCGGTGAATT
TCATCGTAGGTAATAGGAGGTAACAGGTATTCAGTAAGTCGTAATTTTAA
CATCGAATGTTTATACGAATCATTTTTATACAATAGATGTGAGTTCAATT
CTCTCTGTTATTCTTTGTCTAGAGAGTAGTAAAAAAAAAGATAAAAAGAT
CCGTTCGTTCTCATCTCTCTCCAATTGTTGAGATCTGTTTGGATCTTGAG
TTATTAGGTACTAATAAAGACCTTTCAAGTTGAATTATTCAATTTTATTA
TTATTTTTGCACTTTTGGACATCATTTTATGTTTTTAATCATGTCATAAT
TATATATGCATGTAGATGAAATAAATCAAAAAGTAGATTTTTATTCAAGA

-continued

ATCAAATAATTTCTTTATGTTTTTTTTCTTAAATTTATCTTCTTTTGCTT

TTTTTAGGGGCAGATTAAAA

Example 3: Sequences of sRNA Targets and Mutations for Making sRNA-Resistant Targets Polynucleotide sequences for sRNA targets (MPK1, MPK2, WAK, PRXIIF, MAPKKK4, Sl F-box (Solyc03g061650.1.1), Autophagy-related protein 2 (Solyc01g108160.2.1), Sl Vacuolar protein-sorting (Solyc09g014790.2.1), Sl Pentatricopeptide (Solyc03g112190.2.1), and TOM34 (Solyc07g066530.2.1)) are provided. Underlined sequences represent target sequences for sRNAs. Alignments of sRNAs to wild-type target sequences and mutated target sequences (target site synonymous mutations) are also provided.

SEQ ID NO: 4—Bc-siR3.2 Target At-MPK1
GTCAACTGTCCGAGCGTTGGCCAAATCTCTCTCACTTCCACAGGTTTCTCTCTCCGGCCAAAT

CTAACCTCCGGGGAACGTCGTTGGTCACTTATCACCGAGGGAAAACAAAAAATGGCGACTTT

GGTTGATCCTCCTAATGGGATAAGGAATGAAGGGAAGCATTACTTCTCAATGTGGCAAACTC

TGTTCGAGATCGACACTAAGTACATGCCTATCAAGCCTATTGGTCGTGGAGCTTACGGTGTT

GTCTGCTCCTCTGTTAACAGTGACACCAACGAGAAAGTTGCTATCAAGAAGATTCACAATGT

TTATGAGAATAGGATCGATGCGTTGAGGACTCTTCGGGAGCTCAAGCTTCTACGCCATCTTC

GACATGAGAATGTCATTGCTTTGAAAGATGTCATGATGCCAATTCATAAGATGAGCTTCAAG

GATGTTTATCTTGTTTATGAGCTCATGGACACTGATCTCCACCAGATTATCAAGTCTTCTCAA

GTTCTTAGTAACGATCATTGCCAATACTTCTTGTTCCAGTTGCTTCGAGGGCTCAAGTATATT

CATTCAGCCAATATCCTGCACCGAGATTTGAAACCTGGTAACCTTCTTGTCAACGCAAACTG

CGATTTAAAGATATGCGATTTTGGACTAGCGCGTGCGAGCAACACCAAGGGTCAGTTCATGA

CTGAATATGTTGTGACTCGTTGGTACCGAGCCCCAGAGCTTCTCCTCTGTTGTGACAACTATG

GAACATCCATTGATGTTTGGTCTGTTGGTTGCATTTTCGCCGAGCTTCTTGGTAGGAAACCGA

TATTCCAAGGAACGGAATGTCTTAACCAGCTGAAGCTCATTGTCAACATTCTCGGAAGCCAA

AGAGAAGAAGATCTTGAGTTCATAGATAACCCGAAAGCTAAAAGATACATTAGATCACTTC

CGTACTCACCTGGGATGTCTTTATCCAGACTTTACCCGGGCGCTCATGTTTTGGCCATCGACC

TTCTGCAGAAAATGCTTGTTTTTGATCCGTCAAAGAGGATTAGTGTCTCTGAAGCACTCCAG

CATCCATACATGGCGCCTCTATATGACCCGAATGCAAACCCTCCTGCTCAAGTTCCTATCGAT

CTCGATGTAGATGAGGATTTGAGAGAGGAGATGATAAGAGAAATGATGTGGAATGAGATGC

TTCACTACCATCCACAAGCTTCAACCTTAAACACTGAGCTCTGAGCTCAAGTCTTGTTTGTAC

GGGTAATTTACAGAAAACTTCTTCTTCTTATGTCTGATTGTCATCATAGACTCATAGTGTATA

TAGTCTTGAAAAATAAGATGAAGACTAACTTATAGTTTAAGCGAATAGTGATGCCATGGAA

GCTCTGTTTTATTTAATTACAAGCTTGATGTGTGTCTGTAACATATGTACATAGAGAGAGCTG

TTTTTTTTTTTTAATTACAAGTTTGATGTGTGTCTGTAACATATGTACATAGAAAGAGCTGTG

TTTTTTTTTTAATTACAAGCTTGATGTGTGTCTGTAACATATGTTCATAGAGAGAGCTGTGTT

TCTGTTTCTCTGTTTGTTTGTTGCGTTCTTGCAGAACTTTTAACCCTCTCATGCAATCCAAGCC

TTTTGATG

-continued

```
Alignments of sRNA sequence Bc-siR3.2 to wild-type (WT) At-MPK1 target and mutated
(MU) At-MPK1 target
miRNA:      3'UGGAUGUUCUAGGUGUUACAU5' (SEQ ID NO: 24)
alignment:    |:| | |||||:||||||||
WT Target:  5'ATCAAGAAGATTCACAATGTT3' SEQ ID NO: 59)

miRNA:      3'UGGAUGUUCUAGGUGUUACAU5' (SEQ ID NO: 24)
alignment:    |:  | || || ||:|| ||
MU Target:  5'ATAAAGAAAATACATAACGTT3' (SEQ ID NO: 505)
```

SEQ ID NO: 5—Bc-siR3.2 Target At-MPK2

ATGGCGACTCCTGTTGATCCACCTAATGGAATTAGGAATCAAGGGAAGCATTACTTCTCAAT

GTGGCAAACACTTTTCGAGATCGATACCAAATACGTGCCTATCAAACCGATAGGCCGAGGC

GCGTACGGTGTGGTTTGCTCTTCGGTTAACAGAGAGAGTAATGAGAGAGTGGCGATCAAGA

AGATCCACAATGTGTTTGAGAATAGGATTGATGCGTTGAGGACTCTTA*GGGAGCTCAAGCTTC*

*TACGTCATC*TTCGACATGAGAATGTGGTTGCTCTTAAAGATGTAATGATGGCTAATCATAAGA

GAAGCTTTAAGGATGTTTATCTTGTTTATGAGCTTATGGATACTGATCTTCATCAGATTATTA

AGTCTTCTCAAGTTCTAAGTAATGACCATTGCCAATACTTCTTGTTCCAGTTGCTTCGAGGGC

TCAAGTATATTCATTCAGCAAACATTCTCCATCGGGATCTGAAACCCGGTAACCTCCTTGTG

AATGCAAACTGCGACTTAAAGATATGTGACTTTGGGCTAGCGAGGACGAGCAACACCAAAG

GTCAGTTCATGACTGAATATGTTGTGACTAGATGGTACCGAGCACCAGAGCTACTCCTCTGT

TGTGACAACTATGGAACCTCCATTGATGTCTGGTCAGTCGGTTGCATATTCGCCGAGCTTCTT

GGAAGAAAACCAGTATTCCCGGGAACAGAATGTCTAAACCAGATTAAACTCATCATTAACA

TTTTGGGTAGCCAGAGAGAGGAAGATCTCGAGTTTATAGATAACCCAAAAGCCAAAAGATA

CATAGAATCACTCCCTTACTCACCAGGGATATCATTCTCTCGTCTTTACCCGGGTGCAAATGT

TTTAGCCATTGATCTGCTTCAGAAAATGCTCGTTCTTGACCCTTCGAAAAGGATTAGTGTCAC

GGAAGCGCTTCAACATCCTTACATGGCGCCTTTATATGACCCGAGTGCAAATCCTCCTGCTC

AAGTTCCTATTGATCTCGATGTAGATGAAGACGAGGATTTGGGAGCAGAGATGATAAGAGA

ATTAATGTGGAAGGAAATGATTCATTATCATCCAGAAGCTGCTACCATAAACAACAATGAG

GTCTCTGAGTTTTGA

```
Alignments of sRNA sequence Bc-siR3.2 to wild-type (WT) At-MPK2 target and mutated
(MU) At-MPK2 target
miRNA:      3'UGGAUGUUCUAGGUGUUACAU5' (SEQ ID NO: 24)
alignment:    |:| | |||||||||||||:
Target:     5'ATCAAGAAGATCCACAATGTG3' (SEQ ID NO: 60)

MUTANT
miRNA:      3'UGGAUGUUCUAGGUGUUACAU5' (SEQ ID NO: 24)
alignment:    |:  | || || ||:|| ||:
MU Target:  5'ATAAAGAAAATACATAACGTT3' (SEQ ID NO: 505)
```

SEQ ID NO: 6—Bc-siR5 Target-WAK

ATGAAAATCTTGATCTTGATTCTATCCTTTGTGACACTCTTTGAGATTTGCGTTGTGGACGC

ATGTCGATCATACTGTGGAAACATAACCGTTGATTATCCGTTTGGGATCCGAAACGGATGT

GGGCATCCAGGGTATAGAGATCTATTGTTTTGTATGAACGATGTGTTGATGTTTCACATAAG

TTCAGGTTCTTATAGAGTTTTGGACATCGATTACGCATATCAGTCCATAACACTGCATGATC

CTCACATGTCGAACTGCGAAACCATCGTGCTCGGTGGCAAAGGCAATGGCTTTGAAGCTGA

GGATTGGAGAACTCCATATTTCAATCCTACCTCAGATAATGTCTTTATGTTGATCGGATGTT

CTCCTAAATCTCCTATATTTCAAGGCTTCCCGGAAAAGAAAGTGCCGTGCCGCAACATCTCT

GGAATGAGCTGCGAAGAATACATGTCATGTCCAGCTTGGGACATGGTCGGATACAGACAAC

CGGGTATACATTCCGGGTCAGGTCCACCCATGTGTTGTGGGGTCGGGTTCGAATCCGTAAA

-continued

AGCGATTAATCTAAGTAAGTTGGAGTGTGAAGGATACAGTAGTGCGTATAATCTAGCACCC

TTGAAACTTAGAGGACCCTCTGATTGGGCTTATGGGATACGTGTTAAGTATGAACTCCAAG

GAAGTGATGCGTTTTGTCGTGCGTGTGTTGCAACTTCTGGGACTTGTGGCTATGAACCTGCT

GATGGTGGAGGGCTTAGACATGTTTGCATGTGTGACAACCATAATTCCACTACAAACTGTG

ATTCAGTTATATCACCAACCGGTGCATCATCAAGTGTTCGACCAAAAGCTATCGGATCACT

GATCATCTACTTCATAGCTATGAACATAGGCTTTCAGAGAAGACAGCGATGA

Alignments of sRNA sequence Bc-siR5 to wild-type WAK target (WAK) and mutated WAK (WAK-m) target

```
WAK         5'GGGUAUACAUUCCGGGUCAGG3' (SEQ ID NO: 21)
              ::||||||||||||:||||::
Bc-siR5     3'UUCAUAUGUAAGGCUCAGUUU5' (SEQ ID NO: 22)
              :| || || || |: || ::
WAK-m       5'UGGAAUUCACUCGGGCUCUGG3' (SEQ ID NO: 23)
```

SEQ ID NO: 7—Bc-siR3.1 Target AtPRXIIF
ATGGCGATGTCAATTCTAAAGCTAAGAAATTTATCGGCACTAAGATCGGCGGCAAATAGTG

CCCGGATCGGAGTTTCATCGAGGGGTTTCTCAAAGCTCGCGGAAGGCACTGACATAACCTC

GGCGGCGCCTGGCGTTTCTCTCCAGAAAGCTCGCAGCTGGGACGAAGGTGTTTCCTCCAAA

TTCTCCACCACGCCATTGTCAGATATCTTCAAGGGGAAGAAAGTCGTCATCTTTGGTCTTCC

TGGGGCTTACACGGGAGTTTGTTCACAGCAGCATGTGCCTAGCTACAAGAGCCACATTGAT

AAGTTTAAAGCCAAAGGCATTGATTCTGTCATCTGTGTCTCTGTTAATGATCCCTTTGCTAT

CAATGGTTGGGCAGAGAAGCTTGGTGCCAAAGATGCAATTGAGTTTTATGGAGATTTTGAT

GGGAAATTTCACAAAAGCTTGGGGCTAGACAAGGATCTCTCTGCTGCATTGCTCGGGCCAC

GGTCTGAGAGATGGTCGGCTTATGTAGAAGACGGGAAGGTTAAGGCGGTGAATGTGGAAG

AAGCACCGTCTGACTTCAAGGTTACAGGGGCAGAAGTCATCTTAGGACAGATCTAA

Alignments of sRNA sequence Bc-siR3.1 to wild-type AtPRXIIF target and mutated AtPRXIIF (MU) target

```
TargetMU   5'CCCGAGUUAUAAAAGUCAUAU3' (SEQ ID NO: 506)
              || | :||:|| | :||:|
Bc-siRNA   3'CGGGUGGAUGUUCUAGGUGUU5' (SEQ ID NO: 30)
             |||:| |||||||| |||||
Target     5'GCCUAGCUACAAGAGCCACAU3' (SEQ ID NO: 33)
```

SEQ ID NO: 8—B-siR3.2 target in tomato: MAPKKK4 Solyc08g081210.2.1
ATGCGTTCATGGTGGGGGAAGTCTTCATCTAAGGATGTAAGGAGGAAATCCACTAAGGAGA

GTTTCATTGACATAATAAATCGGAAACTGAAGATTTTCACCACGGAAAAATCAAGTGGTAAA

TCTGGATCATCTCGAAGACGACGTAAAGATACAAATTCAGTGAAGGGTTCTCAATCAAGGGT

TTCAAGGTCACCATCACCATCTACTGGATCCATAATATTAGTGACCGGTGAAGTCTCCGAGC

CATCATTGACTTTGCCTCTTCCCATGCCCAGGCATCTTCCACATGGACCAACTGCTGCAGGAG

TTGACAGGGACTTACCAACTGCTTCTGTTTCTTGTGACAGCTCCAGTGACAGTGATGATCTTA

CTGACTCACGATTTCTAAGTCCCCAAACATCTGATTATGAAAACGGGAGCAGAACTGCCTTG

AATAGTCCTTCCAGTTTGAAGCAGAAGGTTCAGTCCCCTATTGCATCCAATGCAAGCTCAGG

AGAGATGCTGAAGTCAGCTACTCTTTTGTCAGACAATCAGGCGATCCCTACATCTCCTAGAC

AGAGGCTTTTAAGATCTCATGTACCACCAGGCTTACAGATTCCTCATCATGGCGCTTCCTACA

GTGCTCCTGACAGCTCGATGTCAAGTCCTTCAAGAAGTCCCATGAGGGTATTTGGGCATGAA

ACGGTCATGAACCCTGGTTTCTGGCTAGGGAAGCCACATGGAGAGATAACCTTCTTAGGATC

AGGGCACTGCTCCAGTCCAGGTTCTGGCCAAAACTCTGGGCACAATTCAATTGGAGGTGATA

TGTTAGCGCAGCCCTTTTGGCCACACAGCAGGTGTAGTCCTGAGTGTTCACCTGTACCTAGC

CCTAGAATGACTAGTCCTGGTCCTGGCTCTAGGATACATAGTGGTGCTGTAACTCCCTTGCAT

-continued

CCTCGAGCTGGAGGAACGTTGGCTGAGTCTTCCACAGCTTCACTTGATAATGGAAAACAACA

AAGTCATCGTCTGCCTCTTCCTCCCATATCAATCCCTCATTCTTCTACTTTTTCTTTGTCATGT

TCAATGACTCCTGCAATTCCACGAAGTCCTGGTAGAACAGGTAATCCTCCAAGCCCTGGGCC

ACGTTGGAAGAAAGGACGTCTGATTGGTAGTGGCACATTTGGACATGTGTACCTTGGTTTTA

ACAGTGAAAGCGGTGAAATGTGTGCAATGAAGGAAGTAACACTTTTTC*AGACGACCCAAAG*

*TCAAGAGAAAGTGCACA*GCAGCTTGGACAAGAAATATCTCTGCTAAGTCGGTTACGCCATCCA

AATATTGTGCAATATTATGGCTCTGAAACGGTAGATGACAAGCTATACATATACCTTGAGTA

TGTTTCAGGTGGTTCGATCTATAAAATTCTTCAAGAATACGGTCAGTTGGGTGAGCTAGCAA

TTCAAAGTTACACTCAACAAATTCTGTCTGGACTTGCATATTTGCATGCTAAAAACACAGTG

CACAGAGATATTAAAGGAGCAAATATACTGGTTGACCCAAATGGCCGCGTTAAATTGGCAG

ACTTTGGGATGGCAAAACATATAACTGGTCACTACTGTCCTTTGTCTTTCAAGGGAAGTCCTT

ACTGGATGGCACCTGAGGTTATTAAAAATTCAAATGGTTGCAATCTTGCGGTAGATATATGG

AGCCTTGGATGCACGGTTTTGGAGATGGCAACAACAAAACCACCTTGGAGTCAGTATGAAG

GGGTCGCTGCTATTTTTAAGATTGGAAACAGCAAGGAAGTTCCAGCAATTCCCTATCACCTG

TCAGATAAGGGCAAGGATTTTGTGCGGCAATGTCTACAACGCAATCCACTCCACCGTCCAAC

AGCTTCTCAGCTCTTGAAACATCCCTTTGTCAAAAGTACTGCTCCAATGGAAAGATTCATTG

GCATTGGACATTTAAAAGATCCACCATGTGTGGGCTCAGAAGAAGTTGCAGTGCATCATGAG

CCTAGAAGTTCAATTTTTTTTCCTGGATTTAGCGACGTACCTGTTCCAAGATCTTGCCCAGTT

TCTCCAGTTGGGATAGAGAGCCCTGTTTACCATTCACAATCACCTAAACATATGAGTGGAAG

ATTGTCCCCCTCTACCATATCAAGCCCCCGTGCTGTATCTGGTTCATCAACACCTCTTAGCGG

TGGTGGTGGTGCTGTTCCACTATCTAACCCAATTATGCCTACAACTTCTTCATCAGAAGACAT

GGGAACATCACCAAAGGCCCAAAGTTGTTTTTACCCTGATGCTTACACTAGTCACGGTCTGA

AGTCTGACATGTCTCGAGAAGCACCTCCATATGGCAATGGTTTTTTTGGAGAAAATTTTGGG

GGCCATGCTCAAAGTGGTGTTAATGGACAACCATATCAGGGACAGTCAGTATTAGCTAATAG

GGTTGCTCAGCAGCTTTTAAGGGACCAAGTAAAATTGAGCCCATCGTTTGACCTGAACCCAG

GCTCTCCAGTTTTTAGTTGGGATAATGGGGTCTAA

Alignments of sRNA sequence Bc-siR3.2 to wild-type MAPKKK4 target and mutated MAPKKK4 (MU) target

```
TargetMU   5′CAUUUGAAGGACCCUCCUUGC3′ (SEQ ID NO: 507)
             ||::|: |:|| || |  ||
Bc-siRNA   3′GUGGAUGUUCUAGGUGUUACA5′ (SEQ ID NO: 28)
             ||::|| ||||||||| ||||
Target     5′CAUUUAAAAGAUCCACCAUGU3′ (SEQ ID NO: 29)
```

SEQ ID NO: 9—Bc-siR3.2 Target in tomato: Sl F-box (Solyc03g061650.1.1)

ATGCAAGAACATCTTGAGATGGTGGACATGAATAATCGTGGTACAAAATTGGTCATTGATGA

AAATGATATAGACAAAATCTCTAATTTGCCCATGGATATCCTTGATAAAATATTCAAGGACA

TGTCATTTCTAGAATTGGTAAAAACGTGCGTCTTGTCGAAGAAATGGGTACATTTCTGGGCT

ATGCATCCAATTCTTGTTCTAGATGGAGATTTTTTTAGAAAGATAAGTGGTAATATAAAATT

GATTGAAGATGGTTTTAGTGGCCTAATTGACAAAATTCTCTTTCAACATGTTGGATCAATAGT

CAAGTTTTCCCTTGATTTGTCAACTATCTATTATAATAATAATAGGGACCTTGGTCATTGGTT

GATTTGCGTAACAAGTAAGTGTGTCAAAGAACTTACCCTAAAAAATCACAAACACAAACAC

TATAATTTACCTTTTTGCGTATTTGATTGCCCAACTCTCACATATTTAGACGTAACCAATTTC

-continued

ATAGTTAAATTACCATCTTCCAAAACATTATTCCCAAATCTCCTTGAATTAACCTTGAAGTCC

ATCAAATTTCGCCCAACCAATGCAAATTATGTCTTGAATGCCCCTTTTCTTACCTCCTTAACA

TTAATTTCTTGCAATGGTGTTCATTGGCTCACCATATTTGCTCCCAGGATTAAGTTCTTGACA

ATTAATGATAGCCATGACATTTGCGCAAATTTTTTTGTAAATTTCTCAAATGTTAGGGAGTTG

TTATTCCGTGAAGAATCTTATTATGAAGAAGGGAGGTTCATCACATGGTCACATCTTCTTTCT

TTGTGCCCTAACCTAACAAGGCTTGTTTTGAATAATTCTTGCATTCAGGTTTTCAATACCTTG

AGAGAAAGAAACATAGGTGAAGTTATTCATTATCTAGAAGATCCAAAATGTATTGACCAAC

AATTTGAGAAGCTTGAATTTGTGGAACTAAGAAAGTTTGAGGGGACACACTTTGAGCTCATT

TTCTTAAAGAAAATATTGGGATATTCTCCTTCGCTTTCAAGGATTATTGTTGAACCTTCTGAT

GATATTGATGTTGCAGAGATATTGGATTTGTATGAAGAACTAATGATGTTTTTAAAAGCATC

ACCAACGGTAAAAGTCGTTGTGGCACCTCATGGTTAA

Alignments of sRNA sequence Bc-siR3.2 to wild-type S1F-box target and mutated S1F-box (MU) target

```
TargetMU   5'AUCUUGAGGACCCUAAGUGCA3' (SEQ ID NO: 508)
             |:||  |:|| ||  |:|| |
Bc-siRNA   3'UGGAUGUUCUAGGUGUUACAU5' (SEQ ID NO: 17)
             |:||| |||||||| ||||||
Target     5'AUCUAGAAGAUCCAAAAUGUA3' (SEQ ID NO: 27)
```

SEQ ID NO: 10—Bc-sRNA 3.1 target Autophagy-related protein 2 (Solyc01g108160.2.1)
ATGTGGAACTTCGCGAGGTCTGCGGAGAAGTTGTTCTCGCGCTGGGCAATCAAGAGGTTT

TGCAAGTTCTGGTTGAAGAAGAAATTGGGGAAATTTATACTTGGTGATATTGATCTCGAT

CAACTCGATGTGCAAGCCAGGGCCGGTATCATTCAGCTCTCTGATCTTGCCCTCAATGTT

GATTATCTCAATCAAAAGTTTGGTTCCGCAGCAGCCGTATATGTTCAAGAAGGATCAATC

GGCTCTCTGCTTATGAAAATGCCTTGGCAAGGGGATGGCTTTCGGATAGAGGTGGATGAA

CTTGAGCTTGTGCTTGCTCCTGAGGCAACCTTTTCTCCTAGCACATTTGGAAATTGTCTT

TCAACTCAAGATGGTGCTGCTTCGGTGAACCAAGAATCAGGAAACCGCAAGGATGTTGCT

GTCGATGATTGTGGGGCTAAAACAACTGCTTTTGATGTTCATGAAGGGGTCAAGACCATT

GCTAAAATGGTTAAATGGTTTCTTACTAGGTTGAATGTAGAAGTTAGAAAATTGATCATA

GTATTTGATCCCTGTTTAGGTGAGGAAAAACAGAGAGGGCTTTGCAGAACCTTAGTATTA

AGAGTAAGTGAAGTAGCCTGTGGGACATGCATCTCGGAAGGGGATTCTCTGGATACTGAA

GCAGCGGATGCTAACCTTTTGGGGTTGACTCAAATGACAAATTTTATCAAATTTAGTGGA

GCAGTTCTTGAATTCCTTCAAATTGATGAGGTTGTTGATAAGACACCAAATCCATGTGCT

TCAGGAACAGCTACAGGTGAGTGGTCAAGAAACTATTCACCAAATGTCACAACTCCTATA

ATAACCGGGGAAAGAGGCGGACTTTCTGGGAACCTAAAATTGACTATACCTTGGAGAAAT

GGTTCCTTAGATATCCGCGAAGTGGAGGTAGATGCTTCTATTGATCCTCTGGTAATCAAA

CTTCAACCTAGTAGCATCAGATGCCTAATACATTTGTGGGGAATTTTGAAAGATACGGGT

CAGAAGAAGGATACAGAATTTCCATTCTGTAATTCAGTAATGACTTGTGATTCAACAAAG

GCAGATACTTCTCTGCTCAGTATGGATGAGGTGCTTCCAGATTCTAAAGCAAATTCTGCT

GAATGTGCATTTGAGAGTGAACCTGTGAGGGAAGCTTTGCTGTCTGAGTCCCGTCTTATA

TCGAACTGGGTGAGTAGAAGCCGGAAAGTCAATGACGAAGAGGAACCAGACTTTGGGGAA

AGCGTGCACCAGTTTTTTGAGTGCTTTGATGGTCTGAGAAACTCGCAGTCAGCTCTAGGA

AACAGTGGGATGTGGAATTGGACTTGTTCTGTTTTTAGTGCGATAACTGCTGCTTCTAAT

CTTGCTTCTGGGTCGTTGCTTGTTCCTTCTGATCAGCAGCATCTTGAAACCAATATTAGG

-continued

GCTACAGTTGCCAAAGTATCTCTTCTTTTTTCTTTTATTGACGAGGAAGAGAGACATTGC

TGCACTGTGGATGCTGATAAAGGGAATGCTGGTTTTTATGTTCATTATATAAGTGCAAGT

TTTCAAGATTTGCTTCTGGTATTGCAGGTACAGCGCCAGGAAGTGAATTTTGAAGCAACA

GTTCAACATGTGGCACTTACTGATCACTTCTCAAGAGAAGATGACACTGTTGATTTCAAA

TGGTGTACATATAATAACATCAAAAAAATTCAAGACGCAATTCAAACTGCCATCCCACCT

CTTGATTGGTCCACCAAGAATGTTGATCTGGATAATCAGAGTGCATCTGCTGCTCCTTAT

CCATTAAGGATGAATTTTACTGATGGGTTCCCTCATCCAAGGAAGAAAATAAGTCTTTTT

GCTGACGATGGAGTGCAGGTAGAATTGCTTAAGACTTTTGGTGCTAGCCTCTGTCAAGCA

ACCATAAGTTCTTCAGGAAACTCATTTGTTGGGCCAACATCTTTTTCATTGAAGTTTCCA

CCATTTGTTTTCTGGGTGAACTTTAATTTGTTAACTAAAATCTCAGAATTTTTCAAGAAA

ATTGAGGATCCTATTGGAACATCTAGCACTCTGGCTCATGAGGATAAGTGTGTAGCTTCA

TCCAAAGGGAATGGAAGGACTAGCCCTTGCTCTGATACTAGAAGAAGTTCAGAACAAGAA

AGTTTCAGGGGCACTGTATCTCTTCCAACTGCCAGGATTATATTGGCTTTTCCTTGTGGA

AAAGGTGAAGATTTTAGGAGCTATTACTGTTGGCAACAGTTTATTTCTCTTGATGTTTCT

TCACCATCAGCTCCTGTGGACAAAGCAAGTCATGCAACTAAAAAATGTTCTGCTACTAGT

TCTAAAAGTTGGAATTCCGTGGCTAAATTGTGCTCTTTGTCCTTGAATTTTGGGAAGCTT

GATGTCAACTTAATCACACCATTGTCTGGAGAGAATGTTGAAATTACCTATGATAGTGTT

CTAAAGTATAGACTTTCAGCTCAGAAATTAATGACCACATCAAATGGAAGAGGGCCTTCT

GTTGTTACCTTTTCTTGGCAGGACTGTGCCAGTACTGGTCCTTGGATAATGAAGAGAGCC

AGACAGCTTGCTTGTTCAGAGAATGCAAGGTGCTTAGAGAAGTTCAGAGGAAAAGGATAT

GACTTTTCGTCTGTAACCACTGTCAAGGATTCTGGGGACATTGATAACATTCGACAAGAA

ATGATTATAAGCTCTGAGTTCTGCATTCATGCACATTTATCTCCCGTTATAATTTCTTTA

AGCAAATCAGAATTTCTTAAATTAAATGATATTGTGAGTCAGGTGATTGATAGGTTATCA

GGACTGGACTTAAATCTTGTTGATACTGAAAAAGTGACTGCTGCCTCTCAGTCATCAGTT

CTTGTTGAATGTGATTCTGTAACCATATCAATTAATGAGGAAGCCATGGAGAAGAATAAT

AAGGGTTCACTACAGAATGAAATTACTGGTTCTTGGCATAGCTTTACTCTGGAACTTCAG

AACTTTGGCCTATTATCTGTTTCAGATCTTGGAGGAACAAATGGTTCTAGCTTTCTCTGG

GTAACCCATGGTGAGGGCAACTTGTGGGGTTCAGTTACAGGGGTCCCGAGTGAAAAGTTT

CTCCTCATCTCCATCAATGACTCTTCCAGTAGCCGTGGTGACGGAGAAGGTTCAAATGTA

TTATCTTCTAAGCTGTCAGGTTTAGATATTATCCACTTTCAAGATCCACAGAGCAGTGCC

GTGTCCATCACTGTCCGGTGCGGCACTGTTGTTGCAGTTGGTGGACGCTTGGATTGGTTT

GACACAATTTTCTCATTTTTCGCTTCACCCTCCCCTGAAGCTACACAAGAATGTGATAGT

AATGTGCAGAAAGAGGGTGAAACTAGTGTTCCTTTTGAATCTTCTTTTATCCTTAGCTTG

ATAGACATTGCCTTGAGTTACGAGCCATACTTAAATAAATTGACGATGCATGGATGCGCT

GATTCTCAGTCAAGTTCTCCCAATTGTGAGGAAGCAATAGATGAGCAACATGTAGCATGT

CTGTTGGCTGCATCTTCCTTGAGGTTTTCCAGTACAACCTTTGCTGATTCTGTTATCAAG

GATTACAAAATTACTGCGCAGGATCTGGGTCTGCTTCTTTCTGCAGTGCGTGCACCGAAC

TGTGCTGGCAGTGTCTACAGTGTGGAGCATCTTCGCAAGACGGGATATGTTAAAGTTGCT

CAAGGGTCAGATGTTGAAGCTCTTTTAAGAATCAGTTCTGGAAGTGGTGCTCTTTGGGAA

ATTGATTGTTCAGAGTCACAGATTGTTCTGAACACTTGCCATGATACAGCTAGTGGATTG

-continued

ACACGTTTAGCTGCTCAAATGCAACAGCTTTTTGCCCCTGACCTGGAAGAATCTGTGGTT
CACTTGCAGACAAGGTGGAATAATGTTCAGCATGCACGTGAGGGCAAAGAATTCTGCACT
TTTGACGTGGCTGTAGCATCAACTTCAGATATGCAGCCTATGACTGGTGATGTAAGTAGC
AAATGCGGTAATATCAACTTGATGGATGAAATCTGTGAAGATGCATTTCAATTGAACCAC
GAGGAGGATGACCAAGCTGATCATCTTGAATCACCCATTTACCTGTCACCTAATAATAGT
TTCATTGGCGAGACATTTTACTACAGTAATGAAGACTCTCCAAGGTTTTTGAATAGCTCG
CCTCTCACTTGCTCAGTCCCAGTAGGTGGACAAGAAACTAGTGAGACTCCATTATCACCT
GAACAGCCACCTCAGTTTATCGAAGAATATTTCTTGTCTGACCTATGTCCTCTGTCTGAA
CTAGCATTGACAGATCAGTCATCGAAGGATATTATTAGATACGCGCCCAGTCCTCTAAGG
AGTGGTGATGATTTTAGGGGAAGTACTGGATGGTATGGGGGCAACTGTTTAAGAATTTTA
GAGAATCATGTTTCAGAAGTCGACAGAAAAGCTGGTTCGGAGGAGTTGACAGAGTCTGAG
GCTTCTAGCATTCTCAGTGAACCTGATGAAAATAAAAATGTTAAGGGTCGCATAGTTCTT
AATAACATGAATATCATCTGGAGATTGTATGCGGGATCTGATTGGCAAAATGTTGAGAGT
AATACCCAGCAATCTACAGGAACTTGTGGGCGGGATACAACTGTTTGTTTAGAACTGACA
CTGTCTGGAATGCGATTTCTGTATGACATCTTTCCTGATGGTGGAACTCGGGTATCTAGG
CAGTCCATAACAGTTCATGATTTCTTTGTTAAAGACAACAGTAATGCTGCCCCTTGGAAA
CTGGTGCTGGGGTACTATCAATCAAAAGGCTGTTTAAGGAAGTCTTCTTCCAAAGCATTT
AAGCTGGATCTGGAAGCAGTAAGACCTGATCCTGCTATCCCTCTTGAGGAGTACCGGTTA
CGAATTGCATTCCTCCCGATGCGCTTACATCTTCATCAAAACCAGTTAGATTTTCTCATC
AGCTTTTTTGGAGGAACAAAGTCAGCAGTTACCCCCTCCCAAAGTTCTTCACAAAATTTG
AGTAAATCGGAAATAGTAGCAAAGAGAACTAAATTTGGGGGTAAAGCAGTCATTGAAGAG
GCACTGCTTCCTTATTTTCAGAAATTTGATATCTGGCCTGTTCATCTTCGGGTTGACTAT
AGCCCTTGCCGTGTTGATTTAGCTGCATTAAGGGGTGGCAAGTATGTTGAGCTTGTTAAC
CTTGTGCCTTGGAAGGGGGTTGACCTGCATCTCAAACATGTTCAAGCTCTAGGTGTCTAT
GGCTGGAGTGGCATAGGTGAAATAATAGTAGGTGAATGGTTGGAAGATATATCCCAAAAT
CAGATTCATAAACTATTGAAAGGCCTTCCTCCTATTCGGTCATTGGTAGCTGTTGGTTCT
AGTGCAGCAAAGTTGGTTTCTCTGCCTGTGAAGAGTTACAAGAAGGATCAAAAGTTGCTA
AAAGGAATGCAAAGAGGTACAATAGCGTTCCTTAGAAGTATTTCGCTTGAAGCAATTGGG
CTTGGAGTGCACTTGGCTGCTGGCGCTCATGAAATCCTTCTGCAAGCAGAATATATCCTT
ACAAGTGTTCCACCATCAGTAACATGGCCTGTGCAAAGTGGAGGAAACACTAGTGTGAGA
TTTAATCAACCTAGAGATTCCCGACAAGGGATCCAACAGGCTTATGAAAGTATGAGTGAT
GGCTTCAGTAAATCTGCTTCTGCTCTAATACGCACTCCCATCAAACGGTATCAGCGTGGT
GCTGGAATGGGATCTGCTTTTGCAACTGCTGTCCAAGCAGCTCCAGCAGCAGCCATTGCC
CCAGCTTCTGCCACAGCACGAGCTGTTCATTGTGCTCTTCTAGGTGTAAGGAACAGCCTC
AATCCGGAGCGTAAGAAAGAGTCTTTGGAGAAATATTTGGGGACAAATCCATCTCAGCAG
TACATGTATTTCTCCATGAAGAGCTCCAACAAAATTTGCAAGCCAGCATTAGTTTTGTAT
AGGTGTACAGATCGTAGGACAATTAGACAAATTCTTTTATCTGAGGAGACAGGTAATCAT
GTAAATTATGTAATATCAGAGTGGTAAACTTATTTTTATGTAATATCAGAGTGGTAAACT
TATTTTTTTTGCTCGTATGGCCGGGCCTGCCACTAGTTTCAATTTTTCGGTTATGTCAGC
TGTGTTATGTGCAAATTGTGAATATATTGATTCCCTTGGTTTTGCTGGCAGAATTGTCAT
CTGTACAACATTGTTTCTTGTAATTATCTTCTGTTTGAACTT

-continued

Alignments of sRNA sequence Bc-siR3.1 to wild-type Autophagy-related protein 2 target and mutated Autophagy-related protein 2 (MU) target

```
TargetMU   5'AUACAUUUUCAGGACCCUCAG3' (SEQ ID NO: 509)
              : ||::| ||:|| || ||:
Bc-siRNA   3'CGGGUGGAUGUUCUAGGUGUU5' (SEQ ID NO: 30)
              :||||:| |||||||||||:
Target     5'AUCCACUUUCAAGAUCCACAG3' (SEQ ID NO: 34)
```

SEQ ID NO: 11—Bc-siR3.1 Target Sl Vacuolar protein-sorting (Solyc09g014790.2.1)
ATGATTTCATCATTGGGTGCAACTTCTTCTTCGTCTTCATCATCATCATCATCAGCTGCTGTTC

GTGTTGAGAAGGCAACGAGCGAGTTCTTGATAGGTCCTGATTGGACGATGAATATTGATATT

TGTGATACAATCAATTCTAACCAATGGTTGGCAAAAGATGTCGTCAAAGCTGTGAAAAAGA

GGTTGCAGCACAAGAACCCCAAAGTTCAGCTACTCGCTTTAACACTTATGGAGACAATGGTG

AAGAACTGTGGTGATAATGTGCATTTTCAAATTACTGAAAGAACTATACTGCAAGACATGGT

CAAAATTGTAAAGAAGAAGACTGATATGCATGTGAGAGATAAAGTGCTAGTACTACTGGAC

TCTTGGCAAGAAGCATTTGGTGGCCCTGGAGGAAAGTATCCCCAGTATTATTGGGCTTATGA

AGAATTGAGGCGCGCTGGTGTTGAATTTCCCAAGCGTTCATTTGATACAGCTCCTATCTTTAC

TCCTCCTGTTACTCATCCTGCACCAAGACAAGCGCAACCTGGTTATGGAATGCCAAACAATT

CCTCAACAAGACTTGACGAGGCAATGGCAGCAGACGTGGGAAACTTAAGCTTGTCCAGCAT

AAATTCTATGAGGGATGTTGCTGATCTGTTGGCTGATATGCTACAAGCTGTGACCCCAGGCG

ATCGTTTGGCTGTAAAGGATGAAGTTATAGCCGATCTTGTTGATCGGTGTCGCTCTAACCAG

AAGAAGTTGATGCAAATGTTAACAACAACAGGGGATGAAGAACTTCTTGCCCAGGGTCTTG

AATTGAATGACAACCTCCAAACTGTACTGGCTAAACATGATGCAATAGCTTCTGGTTCTCCA

CTCCCAACTCAAGTCCCAAATGACAACTTCTCTGCAAGAGAAATGCATGATCCAAGCCTCAA

ACCTGTTGAAGTTAAGCCACCCAGTCCAATAGCAGATGTCAAACCTTCTGCGCCAGTTCTTG

TAGCAACCGCAGGTCAAATTGATGAAGAGGAAGATGAGGAAGATGACTTTGCTCAACTAGC

TCGAAGACATTCAAAAACAAGTCCAGCAGCACAAACAAGTGAAGGAATGGTCTCTGCCAAT

GCTAGCAATTCTATGGGAGAACCATTGGATCCTGTTGCAAGCAATGCATTAATTCTTCGTGA

CCCACCTGCAACATCCACGAAAGAACAAGACATAATTGACCTCTTGAGCCTCACCTTGTCAT

CAAGTGTTTATCCCGAAACATCACAAAATTCTGCTTCAGCTACTCAAAACACGCATCAGGAG

CCTCTTGCCTCAACCACACATGGAAATCCATATGCATCTCAAGCTTATATTGGGTATCAGGA

TCAGAGCTTTAACAGTTATGTAGCTCCTTGGGCTCAGCCCCAACCCCAGCATCAGTCACCAC

CCCAGTTTCATCCTCAATATCAACACCAAGGCCAACCTCAGTTTCATCCTCAATTTCAACACC

CAACCCAAGCCCAGGTCCAGTCCCAACCTCAACCTCATCCACAGCAACAACCTCAATCACAA

CTTCATCATCAATCCCGACCCCAACCATCCACTCAGCCTCAACGGCAGCAACCCCAAGAATC

TTCATTACAGTCTCAGCATACATCACAACAGCTTCCACAATCTCCTGTGCAACCTGAACTGA

ACCAACCTAGAACTCAGCAAGAACTTCATCCTCAGTCTCAACCGTTATCACCACGTACTCAG

ACTCAGTTCCCACAGTACTCTGCTTATCCACCTCCACCTTGGGCAGCAACTCCCGGATATCTG

AGCAATACAACATCTAGACCAACCTACATGTACCCAACTCCACAAGCAGCCACAAATACAC

CCATGTCTTTGCAAGCCACTAGACCCATACAGAATGTTAACTCGTTCCCTAATATGGGAAGC

AATGGTATAGCTATTAATGGTGACACTCAAGTTCATCCCCACCCCAAGACAACTCCTGCTTC

TGGTCAAAAAACCTTCATTCCATCTTATAGGCTGTTTGAAGATCTTAATGTTTTTGGCAACAG

CGATCAAAGACACAACTCATCTTCTGGTTTATCAGGAACTAACAGCCAAAGTATGGTTGGTG

GACGAAAATGA

-continued

Alignments of sRNA sequence Bc-siR3.1 to wild-type Sl Vacuolar protein-sorting target and mutated Sl Vacuolar protein-sorting (MU) target

```
TargetMU   5'AUCCUCCAGCUACUUCGACUA3' (SEQ ID NO: 510)
             :|| || :| |  || || |
Bc-siRNA   3'CGGGUGGAUGUUCUAGGUGUU5' (SEQ ID NO: 30)
             |||||||:||| ||||||:|
Target     5'ACCCACCUGCAACAUCCACGA3' (SEQ ID NO: 35)
```

SEQ ID NO: 12—Bc-siR5 target: Sl Pentatricopeptide (Solyc03g112190.2.1)

ATGAATCACGGCAAGAGAATACTGAGTTCGCTTCGATTGAGGAATTCTCTTTTTTTCACTCAG

CTTTCACGAGCCACTTCTTCCAATCATCAGGTGACTCAACACTTATATCTTTCTCCTTCACTTC

TCACGCAAATTTACACTTCTACTAGTATTCTCGGTTCAAGTCAAAATGTCTTCTTTTCATCAA

AAACTGAATCTTTTGTTGACATTATACTATCCAACGACTGGTCGAAACAATTAGAAAAGGAT

TTAGGAAAAAATGACTTTCCTGTGACCCATGAAGCTGTTATGTATTTGTTGAAGAAACTTGA

TAAAGAACCGCGAAAGGCAGGGGATTTCTTGAAATGGGTTGTTAAGCAAAAGGGGTTTAAA

CCTAGTTCTTCTATGTACAGTCTGATGCTTAGAATTTATGCTAACAGGGATTCAATGAAGGA

CTTTTGGACTACTATTAAGGAAATGAAAGAGAACGGGTTTTATATTGATGAGGAAACGTATA

AATCAATTTATTCTATTTTTCGGAATTTGAAAATGGAAACTGATGCCACTGCTTTGAAGCATT

TTTATGGGAGGATGATTAAAGATAATGCTATGGGTGATGTGGCGAAAGATGTGTCTGAATTG

ATTACAAAACAAGAATGGGGAGTTGAGGTGGAGAGACAATTAGGGGAGATGAAACTCTCGG

TGTCGGATAATTTTGTGCTTAGGGTGTTGAAGGAACTTAGAGAAGTAGGAAATCCACTGAAA

GCTTTCAGCTTTTTCAAATGGGTTGCGAGGAATTTAGATTTTCAGCACAGCACTGTTACTTAT

AATGGGATTCTTAGGGTTCTTTGCCGAGAAGAGTCGATTGAGGAGTTCTGGGGTGTAGTAAA

AGAGATGATGAGCCTTGGGTTTGAAATAGATCTTGATACATATATAAAGATCTCGAGGCATT

TTCAGAAGATTAAGATGTTGAAAGATGCAGTAGAACTATATGAACTGATGATGGATGGTCA

GTTTAAACCATCACTTGGGCATTCACGCTCAAAGATTATTTATGATGTCATTCATAGGTGTTT

GACTAACTTGGGGCGATTTGAGGAAGCAGAGAAGATAACAGAAGCTATGAGAGATGCAGG

ATTTGAACCTGACAATATTACCTATAGCCAATTAATATATGGACTTTGCAAAGTGAGGAGGC

TGGAGGAGGCATCAAAGGTGATAGATGTGATGGAAGAATGTGGATGCATTCCGGATATCAA

GACTTGGACTGTTCTAATACAAGGGCATTGTTTTGCTGGTGAAGTTGATAAGGCGCTGTTTTG

TTTTGCTAAGATGATGGAGAAAAATGTTGATACAGATGCTGATCTGTTGGATGTACTACTTA

ATGGTTTTTTGAGTCAAAGAAGAGTTTTTGGTGCATATCAGTTATTGACCGAGTTGGTGAAT

AAGTTTCAAATGCGCCCATGGCAAGCAACATACAAACTTGTCATCCAAAAGCTCTTGGGGGA

AAGGAAATTCGAAGAAGCGCTTGATCTACTCCGTCGGATGAAGAAACACAATTATCCACCTT

TTCCAGAACCCTTTCTTCAATATATTTCAAAGTCAGGAACAGTGGAAGATGCAGTGGAGTTT

TTAAAGGCGTTGAGCGTCAAGGACTATCCATCTGTTTCAGCCTATCAACATGTTTTCCAGTCC

TTCTTTGCAGAAGGTAGACATTCTGAGGCAAAAGATCTGCTCTACAAGTGCCCATATCATAT

TCGGCAACACCCAGCAATTTGTGGCCTCTTTGGTTCGTCAAATTCTAACAGTGGAAAAATGA

AGAAAAAGCAGGAGCCTCATCAAGATGAAGAACATGATGTTGAAATCCTCAAGGCTGTGGC

ACAAGCCTGGCATGGACACTCGAGCAGCCGTGGAACTACTGCTGAATTCGACGCCCACCGC

CACAATTTCAAGAATAAGCCATCAAGATTCAAGCTTGAAGCTATGAACAAGGCAACCTCCA

GAGAATATGATGGAACAATTAGTAGATGGGATTTCAGCCAGTCTCTTTGGGATTCTTATGAG

ATACTCAATGTGTCCAAAAAGTTAGAAACTGGGCTAATGCTGGACCATCCATTGGATGGGTC

-continued

```
TATCCGAATTGGACAGAAGAGGAAAGAGAGTAAGAATAGCTTAAGAAATTTGCTCAATAGG

GTGTCTTCAAGAAGATATAATGATGCTGATTCAACACTAGACAAGGATGGTTAA
```

Alignments of sRNA sequence Bc-siR5 to wild-type Sl Pentatricopeptide target and mutated Sl Pentatricopeptide (MU) target

```
TargetMU   5'GGGAAGGCACUCGGAAGCUAA3' (SEQ ID NO: 511)
             ::| | :|| || ||  | ||
Bc-siRNA   3'UUCAUAUGUAAGGCUCAGUUU5' (SEQ ID NO: 22)
             |:||| ||||||:||| ||||
Target     5'AGGUAGACAUUCUGAGGCAAA3' (SEQ ID NO: 42)
```

SEQ ID NO: 13—siR5 Target TOM34 (Solyc07g066530.2.1)

```
ATGGCCTCATCAGCTGCCATCAACAACATCGAAAGAGCTCACCAGATGTACAGGGAAGGTA

GATATGCCCAAGCTCTGGGTTTTTATACCGATGCTCTTTCTTTGGCTAAAACAAACTCCCAAA

AGATCGCTCTTCACAGTAATCGTGCTGCTTGTTTCCTCAAACTTCACGATTTCAAAAAGGTTC

TTGGTTTTCCTTGTTGGTTGAGGCGTAGCCAGGATTTTAGTGAAGGGTGTTCGAACTTCGAAG

AGGCAGCAGATGAATGCACATTGGTGCTTGAACTTGATCAAAAACACACAGGCGCGCTGAT

GTTGCGCGCTCAAACCTTAGTCACCCTCAAGGAGTACCATTCAGCACTTTTTGATGTCAACA

GGTTAATTGAATTGAATCCATCATCAGAAGTGTATCAAAACCTCCATGCCCGTCTGAAGACA

CAATTGTCCCTTGCTCGAATACCTGAAGATGAAGCAGAGCTTGAAGAAGATGATGATGATTG

GGAAGAACAATGTACAAATAGAGAAACCACTGAAGTTGATGTAGGAGAAGACAAAAGAGA

TGTTGTGGAAGTAACCACAATAAAAGCTGAGTCTGGAAGTGTCAAACAGACAACTGAAGTC

AGTGATGTTCCAAAAATGGAATCGTCTGAACAACCGTCGTCTAGCTGGGAAGCAATCCCACA

GCCAAAAGGACATTCACGGCTTGACTATTCAAGATGGGATAGGGTTGAAGATGAGTCTAGT

GAAGATGACGATGACGATGATGATGACAATGATTCTCAACCTCAGTATAGATTCCGTGTCAA

AACTATTGGTGTACGAGCTGTTAAGTAA
```

Alignments of sRNA sequence siR5 to wild-type TOM34 target and mutated TOM34 (MU) target

```
TargetMU   5'CAAUACAGGUUUCGUGUGAAG3' (SEQ ID NO: 512)
              | || | :||:|| || ||:
Bc-siRNA   3'UUCAUAUGUAAGGCUCAGUUU5' (SEQ ID NO: 22)
             |||||| |||||| ||||||
Target     5'CAGUAUAGAUUCCGUGUCAAA3' (SEQ ID NO: 41)
```

Example 4: STTM Primers for Blocking the Function of Pathogen sRNAs

STTM primer sequences were designed against 30 *Botyritis* sRNAs ("Bc-sRNAs") from Table 1 that were identified as having targets in both *Arabidopsis* and tomato. The designed STTM sequences can be used in other species which are also targeted by the Bc-sRNAs. The STTM primer sequences (forward primers and reverse primers) for generating STTM constructs, and the Bc-sRNAs targeted by each set of primers, are shown in Table 2.

STTM sequences can be expressed in plants according to the methods described in Yan et al., *Plant Cell* 24:415-427 (2012). Briefly, the STTM modules are inserted in a vector (e.g., the pOT2 vector) between the promoter and terminator. Insertion of the STTM modules is accomplished by PCR amplification of the vector with a proofreading Taq polymerase and a pair of long primers covering the entire STTM sequences (to minimize errors in STTM regions during the PCR reaction). The PCR product is and transformed into cells, e.g., XL1-blue. Single colonies are propagated for plasmid isolation and the recombinant constructs are verified, e.g., by linearization of the plasmids by a restriction enzyme. The recombinant plasmids are further amplified, and the PCR products containing the STTM and a selection marker (e.g., chloramphenicol) are introduced into a binary vector. Recombinant binary plasmids are selected on Luria-Bertani plates containing the appropriate selection antibiotics (e.g., chloramphenicol and kanamycin). The final constructs are verified by DNA sequencing before being used for plant transformation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pathogen-resistant plant comprising a heterologous expression cassette, the expression cassette comprising a promoter operably linked to a polynucleotide that is complementary to a plant immunity suppressing small RNA (sRNA) of a *Botrytis* pathogen or a polynucleotide that encodes a short tandem target mimic (STTM) of the sRNA, wherein the sRNA comprises the sequence set forth in SEQ ID NO:52, and wherein the plant is less susceptible to the pathogen compared to a control plant lacking the expression cassette.

2. The pathogen-resistant plant of claim 1, wherein the pathogen is *Botrytis cinerea.*

3. The pathogen-resistant plant of claim 1, wherein the polynucleotide encodes a STTM of the sRNA.

4. The pathogen-resistant plant of claim 3, wherein the STTM is generated using the primer pair SEQ ID NO:440 and SEQ ID NO:441.

5. The pathogen-resistant plant of claim 1, wherein the polynucleotide encodes an antisense nucleic acid that is complementary to the sRNA.

6. The pathogen-resistant plant of claim 1, wherein the promoter is an inducible promoter.

7. The pathogen-resistant plant of claim 6, wherein the promoter is a pathogen inducible promoter.

8. The pathogen-resistant plant of claim 7, wherein the promoter is induced upon infection by *Botrytis.*

9. The pathogen-resistant plant of claim 1, wherein the promoter is a tissue-specific promoter.

10. A method of making the pathogen-resistant plant of claim 1, the method comprising: introducing a nucleic acid comprising the expression cassette into a plurality of plants; and selecting a plant comprising the expression cassette.

11. An isolated nucleic acid comprising an expression cassette comprising a promoter operably linked to a polynucleotide that is complementary to a plant immunity suppressing small RNA (sRNA) of a *Botrytis* pathogen or a polynucleotide that encodes a short tandem target mimic (STTM) of the sRNA, wherein the sRNA comprises the sequence set forth in SEQ ID NO:52.

12. The isolated nucleic acid of claim 11, wherein the polynucleotide encodes a STTM of the sRNA.

13. The isolated nucleic acid of claim 12, wherein the STTM is generated using the primer pair SEQ ID NO:440 and SEQ ID NO:441.

14. The isolated nucleic acid of claim 11, wherein the polynucleotide encodes an antisense nucleic acid that is complementary to the sRNA.

15. The isolated nucleic acid of claim 11, wherein the promoter is an inducible promoter.

16. The isolated nucleic acid of claim 15, wherein the promoter is a pathogen inducible promoter.

17. The isolated nucleic acid of claim 16, wherein the promoter is induced upon infection by *Botrytis.*

18. The isolated nucleic acid of claim 11, wherein the promoter is a tissue-specific promoter.

19. A host cell comprising the nucleic acid of claim 11.

* * * * *

SEQUENCE LISTING

<160> NUMBER OF SEQ ID NOS: 512

<210> SEQ ID NO 1
<211> LENGTH: 2534
<212> TYPE: DNA
<213> ORGANISM: Arabidopsis thaliana
<220> FEATURE:
<221> NAME/KEY: promoter
<222> LOCATION: (1)...(2534)
<223> OTHER INFORMATION: Arabidopsis thaliana (At) Botrytis-Induced
      Kinase 1 (BIK1) pathogen inducible promoter

<400> SEQUENCE: 1
attttattat attatatagc gatgagagag acagagcttg aaggttcttt ttagcgaaag 60
agaaaaatcc aggaagatag gcgaaaagga agatgaagcg aagatgaggt taatataata 120
ctcatgttaa atgacaaaaa tgcccttata tgattaatga tattaccatt tgagcttgct 180
gtggaagctg taacgaaccg aaaattaaaa acagaataac gaacatagac ggagaatatg 240
atattattcg ttttaccaaa gaaactaaca aatagtttta actttatcta acaaaggggt 300
aaaacgggta atttgtttgg gatgaggtgg agcgtagcgg acaatcgaga aattaaaagt 360
ttggcttggg gacgaagtta aaggtgggct ttaacgtttt aaattggctg actcggacga 420
tatttcttgt atttaatacc aaaaatgaat gactttataa ttcatttgta gattgaaagt 480
tacgtattga ttcgaaaatc aacacattgt gttttcaagt gggcataaac tataacacct 540
tgttgattga ttaatagatt acctaaagac attatggttt attactggtc tttcaatata 600
tttttatcgc attgtcaatg atattgtttt tgtatcccaa gtccactgtt ttggtctcta 660
cattcatttt gattgggatt tatcttttta aaatttcttc taatgttttt tcgatatggt 720
tattacttgc tttgattttc ttttcagtat gtgtattgct ttgcaaattg tttttttctt 780
aagatgaaaa acaactcatt aaattgtttg agaaatacta ctaaaacaaa taaacaatga 840
ggagaattat ggaaaacaaa gtgtaatagg ctttaattca ttgctagtgg gctttttggg 900
cctatgggca tattacttac cactatccaa cccaaaatgc caaataaccg acatgtctca 960
ccaatccaat tttgggccat acggccgaaa ttatttaaac ctgtgctcat aatttacttt 1020
acaaattatt acttttccat aaattgtgga aaagttatct gtaacatccg attcaactgg 1080
agtctagact actatagaca ttgatacgtt ttgagttttt agatacttgg aagatatatg 1140
catttatgaa tacagattac agacacatac tagtactact gtatgtctgt atatggatac 1200
aaaaaaaatc atgtatgaat actaaaattt tattagaaat ctatttttca attgttgcaa 1260
caatcaagtt gtcaaattta tttttgtaac cgttaaacaa acaaatatcg atttaggttt 1320
ctaatctgaa ttgacatctc aaacaaaaaa ggctgaatac tttctgaaaa tagtgtatgg 1380
aatgaaggtg gcttttagag ccattataac cggaagaaaa ttcaggtgac ttttagaacc 1440
attataaccg gaagaaaagg tgaattttaa tttttagctg tgtggaagac acggcaagtc 1500
caagtagtac cttcgtacgt caatattgtc caaccggccg tgtcgaaaat cttcttgaga 1560
aaaattggat tttcatctat aaaaaaaaaa agtccaagta ataccaaaca aagacagcga 1620
cgtgtaaaac aatacaagac tcataatcac aaacctacca cccaagtcaa acctatattc 1680
catttagtga attcttgatt atgacttctt gaaatcattt gtattcatat gtataattat 1740
ttaagtcatt tttctgtaag taaaattttt atatatctag aataacgagt tccctacgac 1800
aagatacagt tgaacgtaaa tgtgacatct caattttcat tggtgtctag tactctagtg 1860
attaggtttt cgacatttat tgtactgatt aagtaaaaat tcatggtaca aacatcgaat 1920
atatattttt ctgcttacac acaccaatta acgtggatag accaattgaa atattttgtt 1980
acgacaaagc aaaacaaaac aaacgtcatg tttcgctgtt tgtttgtcgt cccgttaatg 2040
gtaatctttc agacacatac agtacccaaa caagtaattt gactaaaatt ttctctctgt 2100
ctaaatttca gaagaaaaaa aaactttagg atatattgcc aaaagatctt aaaaatgggt 2160
catatcattt tgatcatata gaatccaacg acctttatct tttcgccgaa ctatactttt 2220
ttgtgtccat ttgtttgact ttctttcaca cacacatcca caaagaaaaa aggaccattc 2280
ttctccttct tctagtcacc cctcgtgcct ctctttaaca ccaaacccaa aactcccttc 2340
tctttcttcc ttcctctccg atctccgttc acatctctct ctcatcttta tcttcttctt 2400
tttttgcctt gtgggttgaa agtttctata ttttctcttt ctcttctgtt tacataatcc 2460
attttcagct caagcagctg aagaataacg atcaagaacc aaaaaagaag aaaacgaatc 2520
tgttcttagc tttg 2534

<210> SEQ ID NO 2
<211> LENGTH: 1394
<212> TYPE: DNA
<213> ORGANISM: Arabidopsis thaliana
<220> FEATURE:
<221> NAME/KEY: promoter
<222> LOCATION: (1)...(1394)
<223> OTHER INFORMATION: Arabidopsis thaliana (At) plant defensing gene PDF1.2 pathogen inducible promoter

<400> SEQUENCE: 2
acgacgttgg actgtttcat catatcccat aaaaatacat gattggggtg aaaatcttga 60
acatattaaa aaaatattaa atcaaaatga taaagatagg gatttataaa tgtaaaacgg 120
gcgtgtcgag aattttatgg acattgggac aagctttata tgcagcatgc atcgccgcat 180
cgatatcccg aggtgcatcg tttctacttt catgtccaaa tttggggtta actcacaata 240
tatatcatgt tgcctatgta aatttataat cataaatcta aacccaaatt ttaatcctca 300
ttccaaagca aaagttctaa gccctacaaa aatatgtatt tcccaagttt aaaaagaatt 360
aatctatact tttacaaatt taaattctga tctcttataa tgttcggttt ttcctttttt 420
atttattaag ttagttaaaa tttgcagtta ttttgttgaa tgtcgttgtt tacgaattta 480
cgaataatac ctttatagct aatctacaaa attttgatga ctgacaacac cgttaatgtt 540 ttttttttaaa ttaccctgag cctctcactt gcggtcagac catgcatgtc gatagtccat 600
tacgtttaag gccacaatca actatagttt gtttatcaat agccaactaa gctaactttt 660
aggttcctgc cctctccgtt cctccggtac caatcgtttc tttgtccctt cgatagtttg 720
aaaacctacc gacggtgaga gcaaaatatt gatgaatcat ccaattttca gtaataggtg 780
tgtcccaggg atatataaat ggcgaaacta cgcgagaacg gttccttgtt ctgcaaactt 840
ggcggaacaa tgctgctctt gagatcaacc aaaccatatg tttagtccac aacgatctat 900
atgtctaggg gtgatcctct aatcgaaaaa tgttgtattt gttcgacgat gacgaaggtc 960
agactatgaa ctgcacagtc tgcacttgtc ctaaccgcga gaatctctga catcaatata 1020
cttgtgtaac tatggcttgg ttaagatatt attttcttga gtcttaatcc attcagatta 1080
accagccgcc catgtgaacg atgtagcatt agctaaaagc cgaagcagcc gcttaggtta 1140
ctttagatat cgacagagaa atatatgtgg tggagaaacc agccatcaac aaacaaaaag 1200

```
caagatctta tcttttgata ttggctacgg gaagatgatg tctgtttaat gtgtggggtt   1260

accacgttat tgtacgatgc acaagtagaa gattaaccca ctaccatttc attataaata   1320

gacgttgatc tttggcttat ttcttcacac aacacataca tctatacatt gaaaacaaaa   1380

tagtaataat catc                                                     1394


<210> SEQ ID NO 3
<211> LENGTH: 2802
<212> TYPE: DNA
<213> ORGANISM: Solanum lycopersicum
<220> FEATURE:
<221> NAME/KEY: promoter
<222> LOCATION: (1)...(2802)
<223> OTHER INFORMATION: Solanum lycopersicum (tomato) TPK1b pathogen
      inducible promoter, Arabidopsis thaliana (At) BIK1
      homologous gene

<400> SEQUENCE: 3

ttgcgtttaa tttgtatgaa tgtcatttaa tttttaggat cggcttaaat ttgaaattaa     60

aaaagcaaaa taataatact agtattttct aactttgtat tttaatgcat gacattattt    120

ttagaaaaaa ttgtaacgaa gagaatcata tttatgatag aattatttgt aattactatt    180

tgactgatat tactagttta attatttcgc acacaaagta tattttttta aaaaaaaata    240

ttttacattg attattttct ctctatccca acaccccatc ccgtctttat ttttatagta    300

tttattatac aaatatttta aaagtatctt attgaacatc aaaataatct tttttaaaaa    360

ttatttatat ccccaaaaaa attatatgca cgtgtgaaaa tgagaaaatg ttggttgggt    420

gtgaataatt tgttggttcc caaatatgat tataatccaa gaaaattgga aatttgatta    480

ttgcttcctt ttgacttaaa actctttgct aaattgctaa gcattctttt taattttgtt    540

tttccattaa taacaatttg ggtaattcat atccactagt cggtggattt aatagaagtg    600

atacatattt ttttgatgtt attgttaatt aatagtgaaa ggtccttttt tctctctcct    660

aatttatata taattcattt tttaaaatca attttgaaag aatgatatag tttctatatt    720

taagtaatga tttattttat tgataataaa ataagttata atcatatata tatttttaat    780

atatttaaaa ttataattta aattatttat atcacatcaa ttgaaacgga tgaaattatt    840

tattttaaaa aaaatgatga atgggtggca tccataaaaa tgtgacattt ctccatgtgt    900

tttgcttaaa tgagattttt gactattttt cttgtgttca tatttatgaa gaagatcaac    960

aataaatttt tatcaataaa gaggaaatta aaagttgatt aatattaaaa atcacaaata   1020

tttattgaaa gtgaataaat ttatagttat tacacatata tggagagaga tcaaaatcaa   1080

tatgctaatt ttttgtaatg gaagggcaca atgaaaataa agttaatttt catgactaat   1140

ttaatccata tagttaaatt ctaatcatat aaatttcagt gaataagttc atttgatttt   1200

ttttagatct aatattaatt attaagatgt aaatgttaac tatgttttta ttaatgtttc   1260

aatcactgtg tctatatttg aatgattact acttgtaatt aagtgaaaaa attcagtatt   1320

ttgtgtatta aaatttttta ttattgaaag agatatagat ttaagtggaa agttaataaa   1380

gaaaattgca gttcgccctc aaatgaatta tctttaaaat ttgtttaata atatttggat   1440

caataagtta acggagtgga gatttttaaa agatgatagt taaaatttgc acataaccga   1500

acaaattgtc tatttaggta tgtaatttag agagtgtctc ttttgaggtt tgatgtttag   1560

ggttcaaaaa ttgtccgttt tggtgccaga aacgtgccta caaccaccat ccaatccatt   1620

ctcaatcaca atcaccatca ctgacaccca atcactacaa taagtcgtca ttgccgccat   1680

ccttataaca aaagtaattt ttttgcagtc ataactatat actttaataa aaaaatgtaa   1740
```

-continued

```
atttttatcg acattactta agtatcatta aatttactat cgctaaaatc tttagggaaa   1800
tttataaaga gtgttaattg ttattaaaaa aattatattt atcgataatt aaattattgt   1860
tgctaattac ttaccattga cgaccatttt caatgtagta catccaatat tatcgcaata   1920
aatcattatc acccgtcatt actattaatt actacttata tatcgtcaat caccatcatc   1980
attaaccatt gctcttcatc caccatagtt attgtctttc aagcattacc atcattcatc   2040
atcattatta actacttata tatcatcaat aacgatttat cattcatcac aattattatt   2100
tatcaacatc acctatcgct cttgatcatt actattaatc atcattaacc tttaactgca   2160
acttacacta ttgttcttaa tcgatattca caatcaccat agttagtcat caccatgagt   2220
cctagccaca aattcaaagc aaaacaccct taaagcctgg tagtgtgtgt gaattaaaga   2280
ccagcagtcc aaagagagag agagagagag aaaatgtaga ctttaaagat atgtagtagg   2340
accagtctgc cattaatatc tccttctacc aaccttcctc tcctctttca ctaccctaca   2400
tttaacattt tcctataacc actgctttag ataagtcaaa tttagctctt tgttttgatc   2460
tctgtttcaa aagaaaacac ctattaagca gccatcatct ttcttatctt ttccaaaacc   2520
aaaactactg acttttcttg aaaaaagaag aggtggggtg ctttcttttc ttcaaaaacc   2580
ttctctttgt tcttgaaaaa acaggactca ttcatttttt tttgtgtgtt tctttcagaa   2640
gaaataacaa agaccctttc tctgttttct tcatatttca gctttgagct acttggatct   2700
gttttttttt tttgaatata caagtagttt gtgtgttctg gggtctacag aagaaggaga   2760
agctaaaagg ggtgattttg ttttttgttt gttgttgttc ta                      2802
```

<210> SEQ ID NO 4
<211> LENGTH: 1631
<212> TYPE: DNA
<213> ORGANISM: Arabidopsis thaliana
<220> FEATURE:
<223> OTHER INFORMATION: Bc-siR3.2 target Arabidopsis thaliana (At) mitogen activated protein kinase 1 (MPK1)

<400> SEQUENCE: 4

```
gtcaactgtc cgagcgttgg ccaaatctct ctcacttcca caggtttctc tctccggcca     60
aatctaacct ccggggaacg tcgttggtca cttatcaccg agggaaaaca aaaaatggcg    120
actttggttg atcctcctaa tgggataagg aatgaaggga agcattactt ctcaatgtgg    180
caaactctgt tcgagatcga cactaagtac atgcctatca agcctattgg tcgtggagct    240
tacggtgttg tctgctcctc tgttaacagt gacaccaacg agaaagttgc tatcaagaag    300
attcacaatg tttatgagaa taggatcgat gcgttgagga ctcttcggga gctcaagctt    360
ctacgccatc ttcgacatga gaatgtcatt gctttgaaag atgtcatgat gccaattcat    420
aagatgagct tcaaggatgt ttatcttgtt tatgagctca tggacactga tctccaccag    480
attatcaagt cttctcaagt tcttagtaac gatcattgcc aatacttctt gttccagttg    540
cttcgagggc tcaagtatat tcattcagcc aatatcctgc accgagattt gaaacctggt    600
aaccttcttg tcaacgcaaa ctgcgattta aagatatgcg attttggact agcgcgtgcg    660
agcaacacca agggtcagtt catgactgaa tatgttgtga ctcgttggta ccgagcccca    720
gagcttctcc tctgttgtga caactatgga acatccattg atgtttggtc tgttggttgc    780
attttcgccg agcttcttgg taggaaaccg atattccaag gaacggaatg tcttaaccag    840
ctgaagctca ttgtcaacat tctcggaagc caaagagaag aagatcttga gttcatagat    900
aacccgaaag ctaaaagata cattagatca cttccgtact cacctgggat gtctttatcc    960
```

```
agactttacc cgggcgctca tgttttggcc atcgaccttc tgcagaaaat gcttgttttt   1020

gatccgtcaa agaggattag tgtctctgaa gcactccagc atccatacat ggcgcctcta   1080

tatgacccga atgcaaaccc tcctgctcaa gttcctatcg atctcgatgt agatgaggat   1140

ttgagagagg agatgataag agaaatgatg tggaatgaga tgcttcacta ccatccacaa   1200

gcttcaacct taaacactga gctctgagct caagtcttgt ttgtacgggt aatttacaga   1260

aaacttcttc ttcttatgtc tgattgtcat catagactca tagtgtatat agtcttgaaa   1320

aataagatga agactaactt atagtttaag cgaatagtga tgccatggaa gctctgtttt   1380

atttaattac aagcttgatg tgtgtctgta acatatgtac atagagagag ctgttttttt   1440

tttttaatta caagtttgat gtgtgtctgt aacatatgta catagaaaga gctgtgtttt   1500

ttttttaatt acaagcttga tgtgtgtctg taacatatgt tcatagagag agctgtgttt   1560

ctgtttctct gtttgtttgt tgcgttcttg cagaactttt aaccctctca tgcaatccaa   1620

gccttttgat g                                                         1631
```

```
<210> SEQ ID NO 5
<211> LENGTH: 1131
<212> TYPE: DNA
<213> ORGANISM: Arabidopsis thaliana
<220> FEATURE:
<223> OTHER INFORMATION: Bc-siR3.2 target Arabidopsis thaliana (At)
      mitogen activated protein kinase 2 (MPK2)

<400> SEQUENCE: 5

atggcgactc ctgttgatcc acctaatgga attaggaatc aagggaagca ttacttctca     60

atgtggcaaa cacttttcga gatcgatacc aaatacgtgc ctatcaaacc gataggccga    120

ggcgcgtacg gtgtggtttg ctcttcggtt aacagagaga gtaatgagag agtggcgatc    180

aagaagatcc acaatgtgtt tgagaatagg attgatgcgt tgaggactct tagggagctc    240

aagcttctac gtcatcttcg acatgagaat gtggttgctc ttaaagatgt aatgatggct    300

aatcataaga gaagctttaa ggatgtttat cttgtttatg agcttatgga tactgatctt    360

catcagatta ttaagtcttc tcaagttcta agtaatgacc attgccaata cttcttgttc    420

cagttgcttc gagggctcaa gtatattcat tcagcaaaca ttctccatcg ggatctgaaa    480

cccggtaacc tccttgtgaa tgcaaactgc gacttaaaga tatgtgactt tgggctagcg    540

aggacgagca acaccaaagg tcagttcatg actgaatatg ttgtgactag atggtaccga    600

gcaccagagc tactcctctg ttgtgacaac tatggaacct ccattgatgt ctggtcagtc    660

ggttgcatat tcgccgagct tcttggaaga aaaccagtat tcccgggaac agaatgtcta    720

aaccagatta aactcatcat taacattttg ggtagccaga gagaggaaga tctcgagttt    780

atagataacc caaaagccaa aagatacata gaatcactcc cttactcacc agggatatca    840

ttctctcgtc tttacccggg tgcaaatgtt ttagccattg atctgcttca gaaaatgctc    900

gttcttgacc cttcgaaaag gattagtgtc acggaagcgc ttcaacatcc ttacatggcg    960

cctttatatg acccgagtgc aaatcctcct gctcaagttc ctattgatct cgatgtagat   1020

gaagacgagg atttgggagc agagatgata agagaattaa tgtggaagga aatgattcat   1080

tatcatccag aagctgctac cataaacaac aatgaggtct ctgagttttg a            1131
```

```
<210> SEQ ID NO 6
<211> LENGTH: 912
<212> TYPE: DNA
<213> ORGANISM: Arabidopsis thaliana
```

-continued

<220> FEATURE:
<223> OTHER INFORMATION: Bc-siR5 target cell-wall associated kinase
(WAK)

<400> SEQUENCE: 6
atgaaaatct tgatcttgat tctatccttt gtgacactct ttgagatttg cgttgtggac 60
gcatgtcgat catactgtgg aaacataacc gttgattatc cgtttgggat ccgaaacgga 120
tgtgggcatc cagggtatag agatctattg ttttgtatga acgatgtgtt gatgtttcac 180
ataagttcag gttcttatag agttttggac atcgattacg catatcagtc cataacactg 240
catgatcctc acatgtcgaa ctgcgaaacc atcgtgctcg gtggcaaagg caatggcttt 300
gaagctgagg attggagaac tccatatttc aatcctacct cagataatgt ctttatgttg 360
atcggatgtt ctcctaaatc tcctatattt caaggcttcc cggaaaagaa agtgccgtgc 420
cgcaacatct ctggaatgag ctgcgaagaa tacatgtcat gtccagcttg ggacatggtc 480
ggatacagac aaccgggtat acattccggg tcaggtccac ccatgtgttg tggggtcggg 540
ttcgaatccg taaaagcgat taatctaagt aagttggagt gtgaaggata cagtagtgcg 600
tataatctag cacccttgaa acttagagga ccctctgatt gggcttatgg gatacgtgtt 660
aagtatgaac tccaaggaag tgatgcgttt tgtcgtgcgt gtgttgcaac ttctgggact 720
tgtggctatg aacctgctga tggtggaggg cttagacatg tttgcatgtg tgacaaccat 780
aattccacta caaactgtga ttcagttata tcaccaaccg gtgcatcatc aagtgttcga 840
ccaaaagcta tcggatcact gatcatctac ttcatagcta tgaacatagg ctttcagaga 900
agacagcgat ga 912

<210> SEQ ID NO 7
<211> LENGTH: 606
<212> TYPE: DNA
<213> ORGANISM: Arabidopsis thaliana
<220> FEATURE:
<223> OTHER INFORMATION: Bc-siR3.1 target Arabidopsis thaliana (At)
peroxiredoxin (PRXIIF)

<400> SEQUENCE: 7
atggcgatgt caattctaaa gctaagaaat ttatcggcac taagatcggc ggcaaatagt 60
gcccggatcg gagtttcatc gaggggtttc tcaaagctcg cggaaggcac tgacataacc 120
tcggcggcgc ctggcgtttc tctccagaaa gctcgcagct gggacgaagg tgtttcctcc 180
aaattctcca ccacgccatt gtcagatatc ttcaagggga agaaagtcgt catctttggt 240
cttcctgggg cttacacggg agtttgttca cagcagcatg tgcctagcta caagagccac 300
attgataagt ttaaagccaa aggcattgat tctgtcatct gtgtctctgt taatgatccc 360
tttgctatca atggttgggc agagaagctt ggtgccaaag atgcaattga gttttatgga 420
gattttgatg ggaaatttca caaaagcttg gggctagaca aggatctctc tgctgcattg 480
ctcgggccac ggtctgagag atggtcggct tatgtagaag acgggaaggt taaggcggtg 540
aatgtggaag aagcaccgtc tgacttcaag gttacagggg cagaagtcat cttaggacag 600
atctaa 606

<210> SEQ ID NO 8
<211> LENGTH: 2523
<212> TYPE: DNA
<213> ORGANISM: Solanum lycopersicum
<220> FEATURE:
<223> OTHER INFORMATION: Bc-siR3.2 target Solanum lycopersicum (tomato)
mitogen activated protein kinase kinase kinase 4

-continued (MAPKKK4) (Solyc08g081210.2.1)

<400> SEQUENCE: 8

```
atgcgttcat ggtgggggaa gtcttcatct aaggatgtaa ggaggaaatc cactaaggag     60
agtttcattg acataataaa tcggaaactg aagattttca ccacggaaaa atcaagtggt    120
aaatctggat catctcgaag acgacgtaaa gatacaaatt cagtgaaggg ttctcaatca    180
agggtttcaa ggtcaccatc accatctact ggatccataa tattagtgac cggtgaagtc    240
tccgagccat cattgacttt gcctcttccc atgcccaggc atcttccaca tggaccaact    300
gctgcaggag ttgacaggga cttaccaact gcttctgttt cttgtgacag ctccagtgac    360
agtgatgatc ttactgactc acgatttcta agtccccaaa catctgatta tgaaaacggg    420
agcagaactg ccttgaatag tccttccagt ttgaagcaga aggttcagtc ccctattgca    480
tccaatgcaa gctcaggaga gatgctgaag tcagctactc ttttgtcaga caatcaggcg    540
atccctacat ctcctagaca gaggctttta agatctcatg taccaccagg cttacagatt    600
cctcatcatg gcgcttccta cagtgctcct gacagctcga tgtcaagtcc ttcaagaagt    660
cccatgaggg tatttgggca tgaaacggtc atgaaccctg gtttctggct agggaagcca    720
catggagaga taaccttctt aggatcaggg cactgctcca gtccaggttc tggccaaaac    780
tctgggcaca attcaattgg aggtgatatg ttagcgcagc ccttttggcc acacagcagg    840
tgtagtcctg agtgttcacc tgtacctagc cctagaatga ctagtcctgg tcctggctct    900
aggatacata gtggtgctgt aactcccttg catcctcgag ctggaggaac gttggctgag    960
tcttccacag cttcacttga taatggaaaa caacaaagtc atcgtctgcc tcttcctccc   1020
atatcaatcc ctcattcttc tacttttttct ttgtcatgtt caatgactcc tgcaattcca   1080
cgaagtcctg gtagaacagg taatcctcca agccctgggc cacgttggaa gaaaggacgt   1140
ctgattggta gtggcacatt tggacatgtg taccttggtt ttaacagtga aagcggtgaa   1200
atgtgtgcaa tgaaggaagt aacacttttt tcagacgacc caaagtcaag agaaagtgca   1260
cagcagcttg gacaagaaat atctctgcta agtcggttac gccatccaaa tattgtgcaa   1320
tattatggct ctgaaacggt agatgacaag ctatacatat accttgagta tgtttcaggt   1380
ggttcgatct ataaaattct tcaagaatac ggtcagttgg gtgagctagc aattcaaagt   1440
tacactcaac aaattctgtc tggacttgca tatttgcatg ctaaaaacac agtgcacaga   1500
gatattaaag gagcaaatat actggttgac ccaaatggcc gcgttaaatt ggcagacttt   1560
gggatggcaa aacatataac tggtcactac tgtcctttgt ctttcaaggg aagtccttac   1620
tggatggcac ctgaggttat taaaaattca aatggttgca atcttgcggt agatatatgg   1680
agccttggat gcacggtttt ggagatggca acaacaaaac caccttggag tcagtatgaa   1740
ggggtcgctg ctatttttaa gattggaaac agcaaggaag ttccagcaat tccctatcac   1800
ctgtcagata agggcaagga ttttgtgcgg caatgtctac aacgcaatcc actccaccgt   1860
ccaacagctt ctcagctctt gaaacatccc tttgtcaaaa gtactgctcc aatggaaaga   1920
ttcattggca ttggacattt aaaagatcca ccatgtgtgg gctcagaaga agttgcagtg   1980
catcatgagc ctagaagttc aattttttttt cctggattta gcgacgtacc tgttccaaga  2040
tcttgcccag tttctccagt tgggatagag agccctgttt accattcaca atcacctaaa   2100
catatgagtg gaagattgtc cccctctacc atatcaagcc cccgtgctgt atctggttca   2160
tcaacacctc ttagcggtgg tggtggtgct gttccactat ctaacccaat tatgcctaca   2220
acttcttcat cagaagacat gggaacatca ccaaaggccc aaagttgttt ttaccctgat   2280
```

```
gcttacacta gtcacggtct gaagtctgac atgtctcgag aagcacctcc atatggcaat   2340

ggttttttg gagaaaattt tgggggccat gctcaaagtg gtgttaatgg acaaccatat   2400

cagggacagt cagtattagc taatagggtt gctcagcagc ttttaaggga ccaagtaaaa   2460

ttgagcccat cgtttgacct gaacccaggc tctccagttt ttagttggga taatggggtc   2520

taa                                                                 2523


<210> SEQ ID NO 9
<211> LENGTH: 1161
<212> TYPE: DNA
<213> ORGANISM: Solanum lycopersicum
<220> FEATURE:
<223> OTHER INFORMATION: Bc-siR3.2 target Solanum lycopersicum (tomato)
      Sl F-box (Solyc03g061650.1.1)

<400> SEQUENCE: 9

atgcaagaac atcttgagat ggtggacatg aataatcgtg gtacaaaatt ggtcattgat     60

gaaaatgata tagacaaaat ctctaatttg cccatggata tccttgataa aatattcaag    120

gacatgtcat ttctagaatt ggtaaaaacg tgcgtcttgt cgaagaaatg ggtacatttc    180

tgggctatgc atccaattct tgttctagat ggagattttt ttagaaagat aagtggtaat    240

ataaaattga ttgaagatgg ttttagtggc ctaattgaca aaattctctt tcaacatgtt    300

ggatcaatag tcaagttttc ccttgatttg tcaactatct attataataa taatagggac    360

cttggtcatt ggttgatttg cgtaacaagt aagtgtgtca aagaacttac cctaaaaaat    420

cacaaacaca aacactataa tttacctttt tgcgtatttg attgcccaac tctcacatat    480

ttagacgtaa ccaatttcat agttaaatta ccatcttcca aaacattatt cccaaatctc    540

cttgaattaa ccttgaagtc catcaaattt cgcccaacca atgcaaatta tgtcttgaat    600

gccccttttc ttacctcctt aacattaatt tcttgcaatg gtgttcattg gctcaccata    660

tttgctccca ggattaagtt cttgacaatt aatgatagcc atgacatttg cgcaaatttt    720

tttgtaaatt tctcaaatgt tagggagttg ttattccgtg aagaatctta ttatgaagaa    780

gggaggttca tcacatggtc acatcttctt tctttgtgcc ctaacctaac aaggcttgtt    840

ttgaataatt cttgcattca ggttttcaat accttgagag aaagaaacat aggtgaagtt    900

attcattatc tagaagatcc aaaatgtatt gaccaacaat ttgagaagct tgaatttgtg    960

gaactaagaa agtttgaggg gacacacttt gagctcattt tcttaaagaa aatattggga   1020

tattctcctt cgctttcaag gattattgtt gaaccttctg atgatattga tgttgcagag   1080

atattggatt tgtatgaaga actaatgatg tttttaaaag catcaccaac ggtaaaagtc   1140

gttgtggcac ctcatggtta a                                             1161


<210> SEQ ID NO 10
<211> LENGTH: 6282
<212> TYPE: DNA
<213> ORGANISM: Solanum lycopersicum
<220> FEATURE:
<223> OTHER INFORMATION: Bc-sRNA3.1 target Autophagy-related protein 2
      (Solyc01g108160.2.1)

<400> SEQUENCE: 10

atgtggaact tcgcgaggtc tgcggagaag ttgttctcgc gctgggcaat caagaggttt     60

tgcaagttct ggttgaagaa gaaattgggg aaatttatac ttggtgatat tgatctcgat    120

caactcgatg tgcaagccag ggccggtatc attcagctct ctgatcttgc cctcaatgtt    180
```

-continued

```
gattatctca atcaaaagtt tggttccgca gcagccgtat atgttcaaga aggatcaatc    240
ggctctctgc ttatgaaaat gccttggcaa ggggatggct ttcggataga ggtggatgaa    300
cttgagcttg tgcttgctcc tgaggcaacc ttttctccta gcacatttgg aaattgtctt    360
tcaactcaag atggtgctgc ttcggtgaac caagaatcag gaaaccgcaa ggatgttgct    420
gtcgatgatt gtggggctaa aacaactgct tttgatgttc atgaaggggt caagaccatt    480
gctaaaatgg ttaaatggtt tcttactagg ttgaatgtag aagttagaaa attgatcata    540
gtatttgatc cctgtttagg tgaggaaaaa cagagagggc tttgcagaac cttagtatta    600
agagtaagtg aagtagcctg tgggacatgc atctcggaag ggattctct ggatactgaa    660
gcagcggatg ctaacctttt ggggttgact caaatgacaa attttatcaa atttagtgga    720
gcagttcttg aattccttca aattgatgag gttgttgata agacaccaaa tccatgtgct    780
tcaggaacag ctacaggtga gtggtcaaga aactattcac caaatgtcac aactcctata    840
ataaccgggg aaagaggcgg actttctggg aacctaaaat tgactatacc ttggagaaat    900
ggttccttag atatccgcga agtggaggta gatgcttcta ttgatcctct ggtaatcaaa    960
cttcaaccta gtagcatcag atgcctaata catttgtggg gaattttgaa agatacgggt   1020
cagaagaagg atacagaatt tccattctgt aattcagtaa tgacttgtga ttcaacaaag   1080
gcagatactt ctctgctcag tatggatgag gtgcttccag attctaaagc aaattctgct   1140
gaatgtgcat ttgagagtga acctgtgagg gaagctttgc tgtctgagtc ccgtcttata   1200
tcgaactggg tgagtagaag ccggaaagtc aatgacgaag aggaaccaga ctttggggaa   1260
agcgtgcacc agtttttga gtgctttgat ggtctgagaa actcgcagtc agctctagga   1320
aacagtggga tgtggaattg gacttgttct gtttttagtg cgataactgc tgcttctaat   1380
cttgcttctg ggtcgttgct tgttccttct gatcagcagc atcttgaaac caatattagg   1440
gctacagttg ccaaagtatc tcttcttttt tcttttattg acgaggaaga gagacattgc   1500
tgcactgtgg atgctgataa agggaatgct ggtttttatg ttcattatat aagtgcaagt   1560
tttcaagatt tgcttctggt attgcaggta cagcgccagg aagtgaattt tgaagcaaca   1620
gttcaacatg tggcacttac tgatcacttc tcaagagaag atgacactgt tgatttcaaa   1680
tggtgtacat ataataacat caaaaaaatt caagacgcaa ttcaaactgc catcccacct   1740
cttgattggt ccaccaagaa tgttgatctg gataatcaga gtgcatctgc tgctccttat   1800
ccattaagga tgaattttac tgatgggttc cctcatccaa ggaagaaaat aagtcttttt   1860
gctgacgatg gagtgcaggt agaattgctt aagacttttg gtgctagcct ctgtcaagca   1920
accataagtt cttcaggaaa ctcatttgtt gggccaacat ctttttcatt gaagtttcca   1980
ccatttgttt tctgggtgaa ctttaatttg ttaactaaaa tctcagaatt tttcaagaaa   2040
attgaggatc ctattggaac atctagcact ctggctcatg aggataagtg tgtagcttca   2100
tccaaaggga atggaaggac tagcccttgc tctgatacta gaagaagttc agaacaagaa   2160
agtttcaggg gcactgtatc tcttccaact gccaggatta tattggcttt tccttgtgga   2220
aaaggtgaag attttaggag ctattactgt tggcaacagt ttatttctct tgatgtttct   2280
tcaccatcag ctcctgtgga caaagcaagt catgcaacta aaaaatgttc tgctactagt   2340
tctaaaagtt ggaattccgt ggctaaattg tgctctttgt ccttgaattt tgggaagctt   2400
gatgtcaact taatcacacc attgtctgga gagaatgttg aaattaccta tgatagtgtt   2460
ctaaagtata gactttcagc tcagaaatta atgaccacat caaatggaag agggccttct   2520
gttgttacct tttcttggca ggactgtgcc agtactggtc cttggataat gaagagagcc   2580
```

-continued

```
agacagcttg cttgttcaga gaatgcaagg tgcttagaga agttcagagg aaaaggatat   2640
gacttttcgt ctgtaaccac tgtcaaggat tctggggaca ttgataacat tcgacaagaa   2700
atgattataa gctctgagtt ctgcattcat gcacatttat ctcccgttat aatttcttta   2760
agcaaatcag aatttcttaa attaaatgat attgtgagtc aggtgattga taggttatca   2820
ggactggact taaatcttgt tgatactgaa aaagtgactg ctgcctctca gtcatcagtt   2880
cttgttgaat gtgattctgt aaccatatca attaatgagg aagccatgga gaagaataat   2940
aagggttcac tacagaatga aattactggt tcttggcata gctttactct ggaacttcag   3000
aactttggcc tattatctgt ttcagatctt ggaggaacaa atggttctag ctttctctgg   3060
gtaacccatg gtgagggcaa cttgtggggt tcagttacag ggtcccgag tgaaaagttt    3120
ctcctcatct ccatcaatga ctcttccagt agccgtggtg acggagaagg ttcaaatgta   3180
ttatcttcta agctgtcagg tttagatatt atccactttc aagatccaca gagcagtgcc   3240
gtgtccatca ctgtccggtg cggcactgtt gttgcagttg gtggacgctt ggattggttt   3300
gacacaattt tctcattttt cgcttcaccc tcccctgaag ctacacaaga atgtgatagt   3360
aatgtgcaga aagagggtga aactagtgtt ccttttgaat cttcttttat ccttagcttg   3420
atagacattg ccttgagtta cgagccatac ttaaataaat tgacgatgca tggatgcgct   3480
gattctcagt caagttctcc caattgtgag gaagcaatag atgagcaaca tgtagcatgt   3540
ctgttggctg catcttcctt gaggttttcc agtacaacct ttgctgattc tgttatcaag   3600
gattacaaaa ttactgcgca ggatctgggt ctgcttcttt ctgcagtgcg tgcaccgaac   3660
tgtgctggca gtgtctacag tgtggagcat cttcgcaaga cgggatatgt taaagttgct   3720
caagggtcag atgttgaagc tcttttaaga atcagttctg gaagtggtgc tctttgggaa   3780
attgattgtt cagagtcaca gattgttctg aacacttgcc atgatacagc tagtggattg   3840
acacgtttag ctgctcaaat gcaacagctt tttgcccctg acctggaaga atctgtggtt   3900
cacttgcaga caaggtggaa taatgttcag catgcacgtg agggcaaaga attctgcact   3960
tttgacgtgg ctgtagcatc aacttcagat atgcagccta tgactggtga tgtaagtagc   4020
aaatgcggta atatcaactt gatggatgaa atctgtgaag atgcatttca attgaaccac   4080
gaggaggatg accaagctga tcatcttgaa tcacccattt acctgtcacc taataatagt   4140
ttcattggcg agacatttta ctacagtaat gaagactctc caaggttttt gaatagctcg   4200
cctctcactt gctcagtccc agtaggtgga caagaaacta gtgagactcc attatcacct   4260
gaacagccac ctcagtttat cgaagaatat ttcttgtctg acctatgtcc tctgtctgaa   4320
ctagcattga cagatcagtc atcgaaggat attattagat acgcgcccag tcctctaagg   4380
agtggtgatg attttagggg aagtactgga tggtatgggg gcaactgttt aagaatttta   4440
gagaatcatg tttcagaagt cgacagaaaa gctggttcgg aggagttgac agagtctgag   4500
gcttctagca ttctcagtga acctgatgaa aataaaaatg ttaagggtcg catagttctt   4560
aataacatga atatcatctg gagattgtat gcgggatctg attggcaaaa tgttgagagt   4620
aatacccagc aatctacagg aacttgtggg cgggatacaa ctgtttgttt agaactgaca   4680
ctgtctggaa tgcgatttct gtatgacatc tttcctgatg gtggaactcg ggtatctagg   4740
cagtccataa cagttcatga tttctttgtt aaagacaaca gtaatgctgc cccttggaaa   4800
ctggtgctgg ggtactatca atcaaaaggc tgtttaagga agtcttcttc caaagcattt   4860
aagctggatc tggaagcagt aagacctgat cctgctatcc ctcttgagga gtaccggtta   4920
```

```
cgaattgcat tcctcccgat gcgcttacat cttcatcaaa accagttaga ttttctcatc   4980

agctttttg gaggaacaaa gtcagcagtt accccctccc aaagttcttc acaaaatttg   5040

agtaaatcgg aaatagtagc aaagagaact aaatttgggg gtaaagcagt cattgaagag   5100

gcactgcttc cttattttca gaaatttgat atctggcctg ttcatcttcg ggttgactat   5160

agcccttgcc gtgttgattt agctgcatta aggggtggca agtatgttga gcttgttaac   5220

cttgtgcctt ggaagggggt tgacctgcat ctcaaacatg ttcaagctct aggtgtctat   5280

ggctggagtg gcataggtga aataatagta ggtgaatggt tggaagatat atcccaaaat   5340

cagattcata aactattgaa aggccttcct cctattcggt cattggtagc tgttggttct   5400

agtgcagcaa agttggtttc tctgcctgtg aagagttaca agaaggatca aaagttgcta   5460

aaaggaatgc aaagaggtac aatagcgttc cttagaagta tttcgcttga agcaattggg   5520

cttggagtgc acttggctgc tggcgctcat gaaatccttc tgcaagcaga atatatcctt   5580

acaagtgttc caccatcagt aacatggcct gtgcaaagtg gaggaaacac tagtgtgaga   5640

tttaatcaac ctagagattc ccgacaaggg atccaacagg cttatgaaag tatgagtgat   5700

ggcttcagta aatctgcttc tgctctaata cgcactccca tcaaacggta tcagcgtggt   5760

gctggaatgg gatctgcttt tgcaactgct gtccaagcag ctccagcagc agccattgcc   5820

ccagcttctg ccacagcacg agctgttcat tgtgctcttc taggtgtaag gaacagcctc   5880

aatccggagc gtaagaaaga gtctttggag aaatatttgg ggacaaatcc atctcagcag   5940

tacatgtatt tctccatgaa gagctccaac aaaatttgca agccagcatt agttttgtat   6000

aggtgtacag atcgtaggac aattagacaa attcttttat ctgaggagac aggtaatcat   6060

gtaaattatg taatatcaga gtggtaaact tatttttatg taatatcaga gtggtaaact   6120

tatttttttt gctcgtatgg ccgggcctgc cactagtttc aatttttcgg ttatgtcagc   6180

tgtgttatgt gcaaattgtg aatatattga ttcccttggt tttgctggca gaattgtcat   6240

ctgtacaaca ttgtttcttg taattatctt ctgtttgaac tt                      6282
```

<210> SEQ ID NO 11
<211> LENGTH: 2118
<212> TYPE: DNA
<213> ORGANISM: Solanum lycopersicum
<220> FEATURE:
<223> OTHER INFORMATION: Bc-siR3.1 target Solanum lycopersicum (tomato)
Sl Vacuolar protein-sorting (Solyc09g014790.2.1)

<400> SEQUENCE: 11

```
atgatttcat cattgggtgc aacttcttct tcgtcttcat catcatcatc atcagctgct     60

gttcgtgttg agaaggcaac gagcgagttc ttgataggtc ctgattggac gatgaatatt    120

gatatttgtg atacaatcaa ttctaaccaa tggttggcaa aagatgtcgt caaagctgtg    180

aaaaagaggt tgcagcacaa gaaccccaaa gttcagctac tcgctttaac acttatggag    240

acaatggtga agaactgtgg tgataatgtg cattttcaaa ttactgaaag aactatactg    300

caagacatgg tcaaaattgt aaagaagaag actgatatgc atgtgagaga taaagtgcta    360

gtactactgg actcttggca agaagcattt ggtggccctg gaggaaagta tccccagtat    420

tattgggctt atgaagaatt gaggcgcgct ggtgttgaat ttcccaagcg ttcatttgat    480

acagctccta tctttactcc tcctgttact catcctgcac caagacaagc gcaacctggt    540

tatggaatgc caaacaattc ctcaacaaga cttgacgagg caatggcagc agacgtggga    600

aacttaagct tgtccagcat aaattctatg agggatgttg ctgatctgtt ggctgatatg    660
```

-continued

```
ctacaagctg tgaccccagg cgatcgtttg gctgtaaagg atgaagttat agccgatctt    720

gttgatcggt gtcgctctaa ccagaagaag ttgatgcaaa tgttaacaac aacaggggat    780

gaagaacttc ttgcccaggg tcttgaattg aatgacaacc tccaaactgt actggctaaa    840

catgatgcaa tagcttctgg ttctccactc ccaactcaag tcccaaatga caacttctct    900

gcaagagaaa tgcatgatcc aagcctcaaa cctgttgaag ttaagccacc cagtccaata    960

gcagatgtca aaccttctgc gccagttctt gtagcaaccg caggtcaaat tgatgaagag   1020

gaagatgagg aagatgactt tgctcaacta gctcgaagac attcaaaaac aagtccagca   1080

gcacaaacaa gtgaaggaat ggtctctgcc aatgctagca attctatggg agaaccattg   1140

gatcctgttg caagcaatgc attaattctt cgtgacccac ctgcaacatc cacgaaagaa   1200

caagacataa ttgacctctt gagcctcacc ttgtcatcaa gtgtttatcc cgaaacatca   1260

caaaattctg cttcagctac tcaaaacacg catcaggagc ctcttgcctc aaccacacat   1320

ggaaatccat atgcatctca agcttatatt gggtatcagg atcagagctt taacagttat   1380

gtagctcctt gggctcagcc ccaaccccag catcagtcac caccccagtt tcatcctcaa   1440

tatcaacacc aaggccaacc tcagtttcat cctcaatttc aacacccaac ccaagcccag   1500

gtccagtccc aacctcaacc tcatccacag caacaacctc aatcacaact tcatcatcaa   1560

tcccgacccc aaccatccac tcagcctcaa cggcagcaac cccaagaatc ttcattacag   1620

tctcagcata catcacaaca gcttccacaa tctcctgtgc aacctgaact gaaccaacct   1680

agaactcagc aagaacttca tcctcagtct caaccgttat caccacgtac tcagactcag   1740

ttcccacagt actctgctta tccacctcca ccttgggcag caactcccgg atatctgagc   1800

aatacaacat ctagaccaac ctacatgtac ccaactccac aagcagccac aaatacaccc   1860

atgtctttgc aagccactag acccatacag aatgttaact cgttccctaa tatgggaagc   1920

aatggtatag ctattaatgg tgacactcaa gttcatcccc accccaagac aactcctgct   1980

tctggtcaaa aaaccttcat tccatcttat aggctgtttg aagatcttaa tgtttttggc   2040

aacagcgatc aaagacacaa ctcatcttct ggtttatcag gaactaacag ccaaagtatg   2100

gttggtggac gaaaatga                                                 2118
```

<210> SEQ ID NO 12
<211> LENGTH: 2223
<212> TYPE: DNA
<213> ORGANISM: Solanum lycopersicum
<220> FEATURE:
<223> OTHER INFORMATION: Bc-siR5 target Solanum lycopersicum (tomato) Sl pentatricopeptide (Solyc03g112190.2.1)

<400> SEQUENCE: 12

```
atgaatcacg gcaagagaat actgagttcg cttcgattga ggaattctct ttttttcact     60

cagctttcac gagccacttc ttccaatcat caggtgactc aacacttata tctttctcct    120

tcacttctca cgcaaattta cacttctact agtattctcg gttcaagtca aaatgtcttc    180

ttttcatcaa aaactgaatc ttttgttgac attatactat ccaacgactg gtcgaaacaa    240

ttagaaaagg atttaggaaa aaatgacttt cctgtgaccc atgaagctgt tatgtatttg    300

ttgaagaaac ttgataaaga accgcgaaag gcaggggatt tcttgaaatg ggttgttaag    360

caaaaggggt ttaaacctag ttcttctatg tacagtctga tgcttagaat ttatgctaac    420

agggattcaa tgaaggactt ttggactact attaaggaaa tgaaagagaa cgggttttat    480

attgatgagg aaacgtataa atcaatttat tctatttttc ggaatttgaa aatggaaact    540
```

-continued

```
gatgccactg ctttgaagca tttttatggg aggatgatta aagataatgc tatgggtgat    600

gtggcgaaag atgtgtctga attgattaca aaacaagaat ggggagttga ggtggagaga    660

caattagggg agatgaaact ctcggtgtcg gataattttg tgcttagggt gttgaaggaa    720

cttagagaag taggaaatcc actgaaagct ttcagctttt tcaaatgggt tgcgaggaat    780

ttagattttc agcacagcac tgttacttat aatgggattc ttagggttct ttgccgagaa    840

gagtcgattg aggagttctg ggtgtagta aaagagatga tgagccttgg gtttgaaata    900

gatcttgata catatataaa gatctcgagg cattttcaga agattaagat gttgaaagat    960

gcagtagaac tatatgaact gatgatggat ggtcagttta aaccatcact tgggcattca   1020

cgctcaaaga ttatttatga tgtcattcat aggtgtttga ctaacttggg gcgatttgag   1080

gaagcagaga agataacaga agctatgaga gatgcaggat ttgaacctga caatattacc   1140

tatagccaat taatatatgg actttgcaaa gtgaggaggc tggaggaggc atcaaaggtg   1200

atagatgtga tggaagaatg tggatgcatt ccggatatca agacttggac tgttctaata   1260

caagggcatt gttttgctgg tgaagttgat aaggcgctgt tttgttttgc taagatgatg   1320

gagaaaaatg ttgatacaga tgctgatctg ttggatgtac tacttaatgg ttttttgagt   1380

caaagaagag tttttggtgc atatcagtta ttgaccgagt tggtgaataa gtttcaaatg   1440

cgcccatggc aagcaacata caaacttgtc atccaaaagc tcttggggga aaggaaattc   1500

gaagaagcgc ttgatctact ccgtcggatg aagaaacaca attatccacc ttttccagaa   1560

ccctttcttc aatatatttc aaagtcagga acagtggaag atgcagtgga gtttttaaag   1620

gcgttgagcg tcaaggacta tccatctgtt tcagcctatc aacatgtttt ccagtccttc   1680

tttgcagaag gtagacattc tgaggcaaaa gatctgctct acaagtgccc atatcatatt   1740

cggcaacacc cagcaatttg tggcctcttt ggttcgtcaa attctaacag tggaaaaatg   1800

aagaaaaagc aggagcctca tcaagatgaa gaacatgatg ttgaaatcct caaggctgtg   1860

gcacaagcct ggcatggaca ctcgagcagc cgtggaacta ctgctgaatt cgacgcccac   1920

cgccacaatt tcaagaataa gccatcaaga ttcaagcttg aagctatgaa caaggcaacc   1980

tccagagaat atgatggaac aattagtaga tgggatttca gccagtctct ttgggattct   2040

tatgagatac tcaatgtgtc caaaaagtta gaaactgggc taatgctgga ccatccattg   2100

gatgggtcta tccgaattgg acagaagagg aaagagagta agaatagctt aagaaatttg   2160

ctcaataggg tgtcttcaag aagatataat gatgctgatt caacactaga caaggatggt   2220

taa                                                                 2223


<210> SEQ ID NO 13
<211> LENGTH: 831
<212> TYPE: DNA
<213> ORGANISM: Solanum lycopersicum
<220> FEATURE:
<223> OTHER INFORMATION: siR5 target mitochondrial import receptor
      subunit TOM34 (Solyc07g066530.2.1)

<400> SEQUENCE: 13

atggcctcat cagctgccat caacaacatc gaaagagctc accagatgta cagggaaggt     60

agatatgccc aagctctggg tttttatacc gatgctcttt ctttggctaa aacaaactcc    120

caaaagatcg ctcttcacag taatcgtgct gcttgtttcc tcaaacttca cgatttcaaa    180

aaggttcttg gttttccttg ttggttgagg cgtagccagg attttagtga agggtgttcg    240

aacttcgaag aggcagcaga tgaatgcaca ttggtgcttg aacttgatca aaaacacaca    300
```

```
ggcgcgctga tgttgcgcgc tcaaacctta gtcaccctca aggagtacca ttcagcactt    360

tttgatgtca acaggttaat tgaattgaat ccatcatcag aagtgtatca aaacctccat    420

gcccgtctga agacacaatt gtcccttgct cgaatacctg aagatgaagc agagcttgaa    480

gaagatgatg atgattggga agaacaatgt acaaatagag aaaccactga agttgatgta    540

ggagaagaca aaagagatgt tgtggaagta accacaataa aagctgagtc tggaagtgtc    600

aaacagacaa ctgaagtcag tgatgttcca aaaatggaat cgtctgaaca accgtcgtct    660

agctgggaag caatcccaca gccaaaagga cattcacggc ttgactattc aagatgggat    720

agggttgaag atgagtctag tgaagatgac gatgacgatg atgatgacaa tgattctcaa    780

cctcagtata gattccgtgt caaaactatt ggtgtacgag ctgttaagta a             831
```

```
<210> SEQ ID NO 14
<211> LENGTH: 4981
<212> TYPE: DNA
<213> ORGANISM: Arabidopsis thaliana
<220> FEATURE:
<221> NAME/KEY: promoter
<222> LOCATION: (1)...(4981)
<223> OTHER INFORMATION: Arabidopsis thaliana (At) Meristem Layer 1
      (ML1) promoter (AT4G21750.1 promoter)

<400> SEQUENCE: 14

aagcttatca aagaaaaaac aagaacaaaa cgatgcatag tttctaaaat gtgctaaaat     60

tcagaaactg aaacatgatt cattgtctga aactttgttt caaattactg aaaataatca    120

ttcactggac caaaacaaat aaataaaata aaatcgaatt tctgaatttg gaaattggtt    180

tttggttttt aattttaaac aaaacaaaaa cgaaatttga aggcaataaa tgagttagtt    240

ggtaggcaga agtcactcgt tcccactagc tattattatt agaagaaacg tccccacaac    300

tccaaggcgt ttcagttcct ttaatttact gaattaccct cctcatatct ataaaaaatc    360

acctcttgta ccaatgcccc atttacacat cctgtcgttt atttctagac taagtggact    420

acatgtcggt tatttgattc gcaccatgcg tatttggatt atcgctaaca caccccttca    480

aacaatacgc ttaactcgta ttacaaaatt tcaagtgatg aattatctat gtataagata    540

tagataggaa caactaagca tcgagaaatt tgtatataaa tcaactagac ttatatatat    600

ttcgatacag aatttatacg tattatatca aattaattag taattgtttc ctctacgtga    660

gtttaattaa caatgataag ctacattgag tgtatcagtt ctaaaacttt atagtatgct    720

acaatcaatt tttctaagta acaacttcaa gcaaggaatc acacacacac agtggtacat    780

aataaacttg attttaatat catatgatca gcatcattaa cggaataagt taagtaattc    840

gtcatccata ctactaagtc atattaaaat cataatcaaa cttaaaagcc gattagaaag    900

agagcaaata tatctaaaaa ttcacgagga agacgacaaa tgcaaggaaa cacagctagt    960

attattaaac ttaatagata ttggatgaat gactgcataa tatatatcac attaaaagtg   1020

gacataaatt tgcatatgtg taatgtacct ctccacaatt aatcgcggac catttatttt   1080

actattacaa gtcaagtaac tttatattgt tgatccataa ttcttttcga acataaaatc   1140

atatacttag gccattttca actgtcaaaa ctcgaatccg agaaccaaat ttcaccattt   1200

tccaaaaatg atgagtgtcg accaaatggg gtactactgt ctaatcagga acttgtgaac   1260

aaattttcaa ccttttccaa ataagacgag tgtcaaccaa ctttttccaa ccaagagata   1320

ttgggttgct acacaaatac ttaatagcca ttgcatattt atgcatatgc aaatgcaggg   1380

tcgtggcgtc agaaagaaac ataggaccct caacatattt aatattttgg gagctatatt   1440
```

-continued

```
tgactatttc atattagaaa ataataataa aaaagtgttg gttttatatc aaattgtaat   1500
ttacgaaaaa cttatgcttt tgcgcaatga tttttgtaaa gtatctacta tgtttagtgt   1560
ttacattgat tagtaggctg ccgttttttt tcttgtgtat tatgtactat atatgaatat   1620
gaacatttgt aaaagtgaat cttgtcattt tcttgttgaa aacatatata gtatgtgcaa   1680
acaaagcata ggttaatcca ataccacaca aataacacgt caggtaaatc caataataaa   1740
tcgtatgtgc atgtatgtgt attcatgtat gttacatgaa tgtctgaatc agtcagtgta   1800
cgtatatgat gtaggtgatg taaatcttaa tgtatgagct gtttcttgga ccatggtcca   1860
caatggatat tgctccccaa ctacattagt caatcgactg gccaattttt aattaagata   1920
attaatccaa actaccatta aatataactt tgaccttttt tctattcatt tttagatatt   1980
attggaactt acgtagttta catgcatctc atccctttct tttgctcctt gaaagtgggt   2040
ccaatcacaa aaaatgatct tatattttgt attttgtatt ttaaaaactc ataattatat   2100
aggttcaaaa atttaattaa catcagtgta tactataatt actactctag ccaacaagat   2160
aaattcattt tgacatcagc caaaagataa aaatttggtt aaaaactatt ggattagctt   2220
ttagtattta atattttatg tactgattaa atacgaattt agaaatctag gatataagtg   2280
agggtgtata ataagggagg ggtggaccat taatagcgat gtgcaattaa aaattatgat   2340
taagaatcta ggaaatttgt agattgctta gttattttta tggcgatcgt cgtgtcaatg   2400
tcatggattt tgaaacttta aattaatctc ttaaattagc acctaccttt gaattttata   2460
gaatcttttt attttatatg tttaatttta tagaatctaa ctagcttatt ttgagattaa   2520
attgtttagt tacttttata acagtataaa tgtataatga ggacctaaga atgtagtcct   2580
gtaatgttct tgctattcta cttaatctca tcaccaatca accatcaaaa gaagctagta   2640
ctaataaaac ctgcaggtat tcgaataata attaagctca aacactatac taatttatgg   2700
aggattatat attcaatgaa ttaggaacct catgatggac attattgact gatataatgt   2760
gtatactaat tgtgagtatt taaaaaccat acaaagcatt tatatgtcca catatattgg   2820
acacacatgc aatcaatgtt caatatgctc cacacacaga aataaaaata ctctttctga   2880
tcatatgata catcatacat atactaaaaa aatctaaaat gaactataac cacaagcata   2940
tataataaca atgaaatggt aatgtttctt catttttatt tgttcaaatt cttattcggt   3000
tgttttttct taccctacga gaatccgtga ggtcaaaggg aaacagtgat ttttttttg    3060
tattttgttt tttaaattga tgaactgtaa aactctctct ctagaaaaat atataagtag   3120
tagtatgaat tttctctcac taaaagcatt aatggacctt tcgataatca taaatgcaat   3180
gcaccctctc tatgcatttc gcaataactc cttttccttc tgccacatcc tcttcctcac   3240
ctctttctct tcttcccttt ctcctaagtt cctcctccac caaattctcc atttatttcg   3300
ttaactatcc tccatttgtt ttcttctgaa gagtgatata ttctaccttt ctctggttaa   3360
agaaactccc tgaatccacc ggttatgtct tgaccggcta taagcctata aactgatgcc   3420
ctaagacacc tttttaggtt tctcaataat tctccgcatc tatcttttct tctccacaag   3480
taagagaacc agaaaaccag agaagaagcc gagctagcta gggtttcatt gtgtgcacaa   3540
aagtaagatc tctctctcta accaatactt gtgtaatttg tctttgtttc tttgagcaaa   3600
tattgcatgt ttgttcatat tagccggatc cgttttatat tttttcatga tctacatttt   3660
atctttattt tgtttgtaaa ttaatgagtt tttttttttt ttttctgttt ttgtcacgat   3720
ctaaaaaaca agcgttacaa agaagaagaa aaaccttttt ggagttagaa gtgtaaaagg   3780
ggtttcagtt tgacgaattt tccttagtag ttgtgtaaaa aaaggccatt gacttaatgt   3840
```

caactctata tatctacaca ttttttttatt aattagtttt tgttttttttc ccacttcatt 3900 tacctttagt caatgaattt ttactgaaaa cgttttttca aggtcaattt cactgagtta 3960
aaaaaaaaag ttttattttt aaccaaaaat tacgtttttt cctaggcttc ggtaacctgt 4020
gaattcctct atctcactag cttttatgta gaagagagag aaggcaacat taaattcgat 4080
ctaaaacttc aagaaaccaa aacaacactt caaaaaaaaa aagagatctg ttctatagag 4140
ttttaatctt ttctttcgac tcgagtttgg ctcaacaaag tttatatcga tttggcactc 4200
taaaatgtaa gtagaaccaa atgaatcttg tattttatgt acgttaataa aaaattaggg 4260
tttcctagac gacaatctcg tcatccgttt cttctttgtc tacctctgcg ttttcttgta 4320
gatccgatga tgtgctcagt cttgtgactt tcaagattga ttttatcgtt attgtttgaa 4380
gatatgtggt ttgattattt tctcaacaca ttgtgtcctt ttagcgcttt acttcagttt 4440
ctctctaatt ttcataatat tattattgaa cattatgctt aattattcat ccgaatattc 4500
gtgtcccatt ttttaaattg aatttcagga taacttgtat tttatatgca acgaggttat 4560
gtcacgtagt gggtgcattt atattcatac cctttttgat aagatgaatg catatgctta 4620
tataagcgta taggtataaa taaccatcaa aaatagagaa aaagaccaat attttgcttt 4680
tcggttactt atgaaatgtg aaaaagacca tataaatata tctattaaag ggaagtatag 4740
tttcataaaa tcttgaggat tacattccat aaaccaagat taccttccgt ttttgctttg 4800
atcctcttct tatcaaatat ataaacatga ccatttgatc tttcattttg gatagtggga 4860
tatacaggca gaagaaaatc gagataaatc aactaaatga tttggataat catcttgaag 4920
atttgaagga aaatccaaga gcttcaaaaa ctccaaaaat tgataggcat ccatcatcat 4980
c 4981

<210> SEQ ID NO 15
<211> LENGTH: 1820
<212> TYPE: DNA
<213> ORGANISM: Solanum lycopersicum
<220> FEATURE:
<221> NAME/KEY: promoter
<222> LOCATION: (1)...(1820)
<223> OTHER INFORMATION: Solanum lycopersicum (tomato) Meristem Layer 1
(ML1) promoter (Solyc10g005330.2.1 promoter)

<400> SEQUENCE: 15
attttgacac acgaaaaagt agtacgaata ttgaactcat gataacttta tcagttactt 60
caagactctc attttaacac aagaaatata ttttacaaag aaaaagggaa catattttac 120
aaagctttat tttgtatttt cattaataat tattttcaag gcttgaactc ataataattt 180
tatcagtttt ttcaagattt tcattttaac acacgaaaaa gtaatatgaa tattgaactc 240
atgataattt tatcagttac tttaagacac ttattttgac acacgaaaaa agtaatacga 300
atatcaaaca ccgaatacga aagaaaaaaa gaaatgaaag cattatagta gttgccaacc 360
gccccttcct cctcctctct ctcttcaaca acaacattaa cacctctata gcaagtcata 420
aatgctattt catcctctct ataccctttg cattaactcc tttgcttcca caatctcttc 480
tcccacctct tcaccttccc cttttcacac tttctttctc tttctttttt tctttcatcc 540
ttagcctcaa aactattctt cttaaattct agtcacaaga aaagtgttca atttcaacct 600
agcttcacta aaatatatac atgttcattc tccaaaaagt acttcttgtc aaaacttaga 660
tttaaccatt ttctcaaaaa ccctaataac atcaacaaca aaaaagaaga agaaggtgtg 720
ttcttgcttt tgtcacaagg cttctctaca actcatgtaa gtcaaacata tactatcatc 780

-continued ttcttgaatt tgttgaattc ttttttacta gcttataagt gtactatatt gttcgaattt 840
tctaaaaata ttatccgatc ttttaggaac aatatatatt tttaaagatc caatacaaat 900
ataacattag tttcacagag tccgagcaaa atagataaat agttgtaaat tcacttgtat 960
ttgacttacc ttttcatttt tccgttatat tttgcagaaa tagaaatgcc agtgaagttg 1020
gactctgcct agatactcgt ggacgttata tcatatacaa gtacctaagt tttgaaaaaa 1080
aaattaacag tgaaaaaata ttagtttttg agttcacact atgtcaactc tatctttgtt 1140
ttttgctaaa tttttctagt ttcaagtctt tttttttgtt tgacttgtaa aactttttttc 1200 ttttacatta tttttatccc cttagagatt ctataaaaac tctatgccct aacaaaattt 1260
cttactaaac aaacagatat atcaacatat atagaaacaa aggagagaga aattgtttct 1320
atggcttgaa gggcttatgt catatatgtt atatatggtg taaactccat cactatgaag 1380
tttctggcaa gcggtgaatt tcatcgtagg taataggagg taacaggtat tcagtaagtc 1440
gtaattttaa catcgaatgt ttatacgaat catttttata caatagatgt gagttcaatt 1500
ctctctgtta ttctttgtct agagagtagt aaaaaaaaag ataaaaagat ccgttcgttc 1560
tcatctctct ccaattgttg agatctgttt ggatcttgag ttattaggta ctaataaaga 1620
cctttcaagt tgaattattc aattttatta ttatttttgc acttttggac atcattttat 1680
gtttttaatc atgtcataat tatatatgca tgtagatgaa ataaatcaaa aagtagattt 1740
ttattcaaga atcaaataat ttctttatgt tttttttctt aaatttatct tcttttgctt 1800
tttttagggg cagattaaaa 1820

<210> SEQ ID NO 16
<211> LENGTH: 21
<212> TYPE: RNA
<213> ORGANISM: Artificial Sequence
<220> FEATURE:
<223> OTHER INFORMATION: synthetic Bc-siRNA target site Arabidopsis thaliana (At) mitogen activated protein kinase 2 (MPK2)

<400> SEQUENCE: 16
aucaagaaga uccacaaugu g 21

<210> SEQ ID NO 17
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA) Bc-siR3.2

<400> SEQUENCE: 17
uacauugugg aucuuguagg u 21

<210> SEQ ID NO 18
<211> LENGTH: 21
<212> TYPE: RNA
<213> ORGANISM: Artificial Sequence
<220> FEATURE:
<223> OTHER INFORMATION: synthetic Bc-siRNA target site mutated version Arabidopsis thaliana (At) mitogen activated protein kinase 2 (MPK2-m)

<400> SEQUENCE: 18
auaaagaaaa uacauaacgu u 21

<210> SEQ ID NO 19
<211> LENGTH: 21
<212> TYPE: RNA
<213> ORGANISM: Artificial Sequence
<220> FEATURE:
<223> OTHER INFORMATION: synthetic Bc-siRNA target site Arabidopsis
thaliana (At) mitogen activated protein kinase 1
(MPK1)

<400> SEQUENCE: 19
aucaagaaga uucacaaugu u 21

<210> SEQ ID NO 20
<211> LENGTH: 21
<212> TYPE: RNA
<213> ORGANISM: Artificial Sequence
<220> FEATURE:
<223> OTHER INFORMATION: synthetic Bc-siRNA target site mutated version
Arabidopsis thaliana (At) mitogen activated
protein kinase 1 (MPK1-m)

<400> SEQUENCE: 20
auaaagaaaa uacauaacgu u 21

<210> SEQ ID NO 21
<211> LENGTH: 21
<212> TYPE: RNA
<213> ORGANISM: Artificial Sequence
<220> FEATURE:
<223> OTHER INFORMATION: synthetic Bc-siRNA target site cell-wall
associated kinase (WAK)

<400> SEQUENCE: 21
ggguauacau uccgggucag g 21

<210> SEQ ID NO 22
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR5

<400> SEQUENCE: 22
uuugacucgg aauguauacu u 21

<210> SEQ ID NO 23
<211> LENGTH: 21
<212> TYPE: RNA
<213> ORGANISM: Artificial Sequence
<220> FEATURE:
<223> OTHER INFORMATION: synthetic Bc-siRNA target site mutated version
cell-wall associated kinase (WAK-m)

<400> SEQUENCE: 23
uggaauucac ucgggcucug g 21

<210> SEQ ID NO 24
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2

<400> SEQUENCE: 24
uacauugugg aucuuguagg u 21

<210> SEQ ID NO 25
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2 host target Arabidopsis thaliana (At)
mitogen activated protein kinase 2 (MPK2)

<400> SEQUENCE: 25
aucaagaaga uccacaaugu g 21

<210> SEQ ID NO 26
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2 host target Arabidopsis thaliana (At)
mitogen activated protein kinase 1 (MPK1)

<400> SEQUENCE: 26
aucaagaaga uucacaaugu u 21

<210> SEQ ID NO 27
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2 host target Solanum lycopersicum
(tomato) Sl F-box

<400> SEQUENCE: 27
aucuagaaga uccaaaaugu a 21

<210> SEQ ID NO 28
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2

<400> SEQUENCE: 28
acauugugga ucuuguaggu g 21

<210> SEQ ID NO 29
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2 host target Solanum lycopersicum
(tomato) mitogen activated protein kinase kinase
kinase 4 (MAPKKK4)

<400> SEQUENCE: 29
cauuuaaaag auccaccaug u 21

<210> SEQ ID NO 30
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1

<400> SEQUENCE: 30
uuguggaucu uguagguggg c 21

<210> SEQ ID NO 31
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 host target Arabidopsis thaliana (At)
Aminotransferase-like

<400> SEQUENCE: 31
auccacauac aagauccaca a 21

<210> SEQ ID NO 32
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 host target Arabidopsis thaliana (At)
Microspore-specific

<400> SEQUENCE: 32
guccccuuac aacauccaca a 21

<210> SEQ ID NO 33
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 host target Arabidopsis thaliana (At)
peroxiredoxin (PRXIIF)

<400> SEQUENCE: 33
gccuagcuac aagagccaca u 21

<210> SEQ ID NO 34
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 host target Solanum lycopersicum
(tomato) Sl Autophagy ATG2-like

<400> SEQUENCE: 34
auccacuuuc aagauccaca g 21

<210> SEQ ID NO 35
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 host target Solanum lycopersicum
(tomato) Sl Vacuolar protein-sorting

<400> SEQUENCE: 35
acccaccugc aacauccacg a 21

<210> SEQ ID NO 36
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5

<400> SEQUENCE: 36
uuugacucgg aauguauacu u 21

<210> SEQ ID NO 37
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 host target Arabidopsis thaliana (At)
      unknown

<400> SEQUENCE: 37
uaggaaacuu uccgagucaa a 21

<210> SEQ ID NO 38
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 host target Arabidopsis thaliana (At)
      clathrin, heavy-chain

<400> SEQUENCE: 38
gaguuugcau uccgggucga a 21

<210> SEQ ID NO 39
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 host target Arabidopsis thaliana (At)
      cell-wall associated kinase (WAK)

<400> SEQUENCE: 39
ggguauacau uccgggucag g 21

<210> SEQ ID NO 40
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 host target Arabidopsis thaliana (At) MADS
      transcription factor

<400> SEQUENCE: 40
gaauuuacaa uccgagucaa a 21

<210> SEQ ID NO 41
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 host target Solanum lycopersicum (tomato)
      mitochondrial import receptor subunit TOM34

<400> SEQUENCE: 41
caguauagau uccgugucaa a 21

```
<210> SEQ ID NO 42
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 host target Solanum lycopersicum (tomato)
      Sl pentatricopeptide

<400> SEQUENCE: 42

agguagacau ucugaggcaa a                                               21


<210> SEQ ID NO 43
<211> LENGTH: 21
<212> TYPE: DNA
<213> ORGANISM: Artificial Sequence
<220> FEATURE:
<223> OTHER INFORMATION: synthetic sRNA-resistant target resistant to
      gene silencing by Bc-siR3.1

<400> SEQUENCE: 43

ttgtggatct tgtaggtggg c                                               21


<210> SEQ ID NO 44
<211> LENGTH: 21
<212> TYPE: DNA
<213> ORGANISM: Artificial Sequence
<220> FEATURE:
<223> OTHER INFORMATION: synthetic sRNA-resistant target resistant to
      gene silencing by Bc-siR3.2

<400> SEQUENCE: 44

tacattgtgg atcttgtagg t                                               21


<210> SEQ ID NO 45
<211> LENGTH: 21
<212> TYPE: DNA
<213> ORGANISM: Artificial Sequence
<220> FEATURE:
<223> OTHER INFORMATION: synthetic sRNA-resistant target resistant to
      gene silencing by Bc-siR5

<400> SEQUENCE: 45

tttgactcgg aatgtatact t                                               21


<210> SEQ ID NO 46
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR1, SIR1 LTR transposon locus, 2-cysteine
      peroxiredoxin B, AT5G06290.1 target gene, target
      site 686~708 (CDS)

<400> SEQUENCE: 46

tcgaagcaag agtagaattc tg                                              22


<210> SEQ ID NO 47
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR1 target, SIR1 LTR transposon locus,
      2-cysteine peroxiredoxin B, AT5G06290.1 target
      gene, target site 686~708 (CDS)

<400> SEQUENCE: 47
```

ctgaattatc ctcttgtttc gg 22

<210> SEQ ID NO 48
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1 target, SIR1 LTR transposon locus, Wd-repeat protein (AHRD V1 C1FDE0_9CHLO), contains Interpro domain IPR017986 WD40 repeat region, Solyc01g068070.2.1 target gene, target site 1754~1776 (cDNA)

<400> SEQUENCE: 48
cggaattccg ctcttgcttt gg 22

<210> SEQ ID NO 49
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1010, SIR1010 intergenic region locus, RING/U-box superfamily protein, AT1G69330.1 target gene, target site 566~587 (CDS)

<400> SEQUENCE: 49
tcgggggaat ttttgattgc t 21

<210> SEQ ID NO 50
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1010 target, SIR1010 intergenic region locus, RING/U-box superfamily protein, AT1G69330.1 target gene, target site 566~587 (CDS)

<400> SEQUENCE: 50
ggtaatctaa agttccctcg g 21

<210> SEQ ID NO 51
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1010 target, SIR1010 intergenic region locus, DNA mismatch repair protein muts (AHRD V1 Q16P35_AEDAE), Solyc07g018350.2.1 target gene, target site 581~602 (cDNA)

<400> SEQUENCE: 51
agaagtgaaa aatttcctcg a 21

<210> SEQ ID NO 52
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.1, SIR2 LTR transposon locus, aminotransferase-like, plant mobile domain family protein, AT1G50760.1 target gene, target site 86~107 (CDS)

<400> SEQUENCE: 52
ttgtggatct tgtaggtggg c 21

<210> SEQ ID NO 53
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.1 target, SIR2 LTR transposon locus, aminotransferase-like, plant mobile domain family protein, AT1G50760.1 target gene, target site 86~107 (CDS)

<400> SEQUENCE: 53
atccacatac aagatccaca a 21

<210> SEQ ID NO 54
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.1 target, SIR2 LTR transposon locus, peroxiredoxin IIF, AT3G06050.1 target gene, target site 333~354 (CDS)

<400> SEQUENCE: 54
gcctagctac aagagccaca t 21

<210> SEQ ID NO 55
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.1 target, SIR2 LTR transposon locus, microspore-specific promoter 2, AT3G06050.1 target gene, target site 333~354 (CDS)

<400> SEQUENCE: 55
gtccccttac aacatccaca a 21

<210> SEQ ID NO 56
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.1 target, SIR2 LTR transposon locus, autophagy-related protein 2 (AHRD V1 C1GCV2_PARBD), Solyc01g108160.2.1 target gene, target site 3210~3231 (cDNA)

<400> SEQUENCE: 56
atccactttc aagatccaca g 21

<210> SEQ ID NO 57
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.1 target, SIR2 LTR transposon locus, Class E vacuolar protein-sorting machinery protein hse1 (AHRD V1 HSE1_EMENI), Solyc09g014790.2.1 target gene, target site 1194~1215 (cDNA)

<400> SEQUENCE: 57
acccacctgc aacatccacg a 21

<210> SEQ ID NO 58
<211> LENGTH: 21
<212> TYPE: DNA

<213> ORGANISM: Artificial Sequence
<220> FEATURE:
<223> OTHER INFORMATION: synthetic Botrytis cinerea small RNA (sRNA)
Bc-siR3.2, SIR2 LTR transposon locus,
mitogen-activated protein kinase 1, AT1G10210.1
target gene, target site 291~312 (CDS)

<400> SEQUENCE: 58
tacattgtgg atcttgtagg t 21

<210> SEQ ID NO 59
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR3.2 target, SIR2 LTR transposon locus,
mitogen-activated protein kinase 1 (MPK1),
AT1G10210.1 target gene, target site 291~312 (CDS)

<400> SEQUENCE: 59
atcaagaaga ttcacaatgt t 21

<210> SEQ ID NO 60
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR3.2 target, SIR2 LTR transposon locus,
mitogen-activated protein kinase homolog 2,
AT1G59580.1 target gene, target site 353~374 (CDS)

<400> SEQUENCE: 60
atcaagaaga tccacaatgt g 21

<210> SEQ ID NO 61
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR3.2 target, SIR2 LTR transposon locus,
TOPLESS-related 2, AT3G16830.1 target gene, target
site 585~606 (CDS)

<400> SEQUENCE: 61
atctgcaagg tctataatgt a 21

<210> SEQ ID NO 62
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR3.2 target, SIR2 LTR transposon locus,
protein of unknown function (DUF1421), AT4G28300.1
target gene, target site 1444~1465 (CDS)

<400> SEQUENCE: 62
acttgcaagg tccacaaggt g 21

<210> SEQ ID NO 63
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR3.2 target, SIR2 LTR transposon locus, F-box/LRR-repeat protein At3g26922 (AHRD V1 FBL47_ARATH), Solyc03g061650.1.1 target gene, target site 907~928 (cDNA)

<400> SEQUENCE: 63
atctagaaga tccaaaatgt a 21

<210> SEQ ID NO 64
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR3.2 target, SIR2 LTR transposon locus, beta-amylase (AHRD V1 E0AE02_SOLLC), Solyc09g091030.2.1 target gene, target site 1510~1531 (cDNA)

<400> SEQUENCE: 64
agccacaaga tgcacaatgt g 21

<210> SEQ ID NO 65
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA) Bc-siR3.2, SIR2 LTR transposon locus, mitogen activated protein kinase kinase kinase 4 (MPKKK4), Solyc08g081210.2.1 target gene, target site 1936~1956 (cDNA)

<400> SEQUENCE: 65
acauugugga ucuuguaggu g 21

<210> SEQ ID NO 66
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA) Bc-siR3.2 target, SIR2 LTR transposon locus, mitogen activated protein kinase kinase kinase 4 (MPKKK4), Solyc08g081210.2.1 target gene, target site 1936~1956 (cDNA)

<400> SEQUENCE: 66
cauuuaaaag auccaccaug u 21

<210> SEQ ID NO 67
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1008, SIR6 CDS (spurious gene) locus, unknown protein, hypothetical protein, AT1G04650.1 target gene, target site 2418~2440 (CDS)

<400> SEQUENCE: 67
tgtgatgatg atcagtttat gc 22

<210> SEQ ID NO 68
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1008 target, SIR6 CDS (spurious gene) locus, unknown protein, hypothetical protein, AT1G04650.1 target gene, target site 2418~2440 (CDS)

<400> SEQUENCE: 68
tcagaaacta atcatcatca ta 22

<210> SEQ ID NO 69
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR1008 target, SIR6 CDS (spurious gene) locus, Sec14p-like
phosphatidylinositol transfer family protein, AT4G39180.2 target
gene, target site 1911~1933 (3'UTR)

<400> SEQUENCE: 69
tcataaacta atcattatca ta 22

<210> SEQ ID NO 70
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR1008 target, SIR6 CDS (spurious gene) locus,
cationic amino acid transporter 3, AT5G36940.1
target gene, target site 221~243 (CDS)

<400> SEQUENCE: 70
gcagagactc atcatcatca cc 22

<210> SEQ ID NO 71
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR1008 target, SIR6 CDS (spurious gene) locus,
At1g69160/F4N2_9 (AHRD V1 Q93Z37_ARATH), Solyc05g012030.1.1 target
gene, target site 603~625 (cDNA)

<400> SEQUENCE: 71
gcatatgctg atcatcataa ca 22

<210> SEQ ID NO 72
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR1008 target, SIR6 CDS (spurious gene) locus,
unknown Protein (AHRD V1), Solyc06g076130.2.1
target gene, target site 1605~1627 (cDNA)

<400> SEQUENCE: 72
gcaaaagcag atcatcatga ca 22

<210> SEQ ID NO 73
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR5, SIR3 LTR transposon locus, MADS-box
transcription factor family protein, AT3G05860.1
target gene, target site 655~676 (CDS)

<400> SEQUENCE: 73
tttgactcgg aatgtatact t 21

```
<210> SEQ ID NO 74
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR5 target, SIR3 LTR transposon locus,
      MADS-box transcription factor family protein,
      AT3G05860.1 target gene, target site 655~676 (CDS)

<400> SEQUENCE: 74

gaatttacaa tccgagtcaa a                                              21


<210> SEQ ID NO 75
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR5 target, SIR3 LTR transposon locus, unknown protein,
      hypothetical protein, uncharacterized protein, AT3G07730.1 target
      gene, target site 491~512 (CDS)

<400> SEQUENCE: 75

taggaaactt tccgagtcaa a                                              21


<210> SEQ ID NO 76
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR5 target, SIR3 LTR transposon locus,
      clathrin, heavy chain, AT3G08530.1 target gene,
      target site 3491~3512 (CDS)

<400> SEQUENCE: 76

gagtttgcat tccgggtcga a                                              21


<210> SEQ ID NO 77
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR5 target, SIR3 LTR transposon locus, pentatricopeptide
      repeat-containing protein (AHRD V1 pD7LRK9_ARALY),
      Solyc03g112190.2.1 target gene, target site 1764~1785 (cDNA)

<400> SEQUENCE: 77

aggtagacat tctgaggcaa a                                              21


<210> SEQ ID NO 78
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR5 target, SIR3 LTR transposon locus, mitochondrial import
      receptor subunit TOM34 (AHRD V1 B5X380_SALSA), Solyc07g066530.2.1
      target gene, target site 910~931 (cDNA)

<400> SEQUENCE: 78

cagtatagat tccgtgtcaa a                                              21


<210> SEQ ID NO 79
<211> LENGTH: 21
<212> TYPE: RNA
<213> ORGANISM: Artificial Sequence
```

<220> FEATURE:
<223> OTHER INFORMATION: synthetic Botrytis cinerea small RNA (sRNA) Bc-siR5, SIR3 LTR transposon locus, wall associated kinase (WAK), AT5G50290 target gene, target site 495~515 (CDS)

<400> SEQUENCE: 79
uuugacucgg aauguauacu u 21

<210> SEQ ID NO 80
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA) Bc-siR5 target, SIR3 LTR transposon locus, wall associated kinase (WAK), AT5G50290 target gene, target site 495~515 (CDS)

<400> SEQUENCE: 80
ggguauacau uccgggucag g 21

<210> SEQ ID NO 81
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9, SIR6 CDS (spurious gene) locus, UDP-glucosyl transferase 89B1, AT1G73880.1 target gene, target site 146~168 (CDS)

<400> SEQUENCE: 81
ttttatgatg agcattttta ga 22

<210> SEQ ID NO 82
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9 target, SIR6 CDS (spurious gene) locus, UDP-glucosyl transferase 89B1, AT1G73880.1 target gene, target site 146~168 (CDS)

<400> SEQUENCE: 82
actagaaaag ctcattatga aa 22

<210> SEQ ID NO 83
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9 target, SIR6 CDS (spurious gene) locus, Cc-nbs-lrr, resistance protein, Solyc04g005540.2.1 target gene, target site 1920~1942 (cDNA)

<400> SEQUENCE: 83
tttagaaatt ctcagcataa aa 22

<210> SEQ ID NO 84
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9 target, SIR6 CDS (spurious gene) locus, Cc-nbs-lrr, resistance protein with an R1 specific domain, Solyc05g007170.2.1 target gene, target site 7265~7287 (cDNA)

<400> SEQUENCE: 84
tcttgaaacg ttcatcataa aa 22

<210> SEQ ID NO 85
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9 target, SIR6 CDS (spurious gene) locus, peroxidase (AHRD V1 D4NYQ9_9ROSI), Solyc07g017880.2.1 target gene, target site 780~802 (cDNA)

<400> SEQUENCE: 85
tttgataatg cttattataa aa 22

<210> SEQ ID NO 86
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9 target, SIR6 CDS (spurious gene) locus, protein binding protein (AHRD V1 D7M3B0_ARALY), Solyc10g050580.1.1 target gene, target site 306~328 (cDNA)

<400> SEQUENCE: 86
gctgaaaatg ttcatcatga aa 22

<210> SEQ ID NO 87
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR9 target, SIR6 CDS (spurious gene) locus, beta-1, 3-galactosyltransferase 6 (AHRD V1 B6UBH3_MAIZE), Solyc11g013490.1.1 target gene, target site 561~583 (cDNA)

<400> SEQUENCE: 87
tctgaagaag ctcaacataa ag 22

<210> SEQ ID NO 88
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR10, SIR2 LTR transposon locus, disease resistance protein (TIR-NBS-LRR class) family, AT1G63860.1 target gene, target site 1124~1145 (CDS)

<400> SEQUENCE: 88
ttttctaggt tgtagggtgc t 21

<210> SEQ ID NO 89
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR10 target, SIR2 LTR transposon locus, disease resistance protein (TIR-NBS-LRR class) family, AT1G63860.1 target gene, target site 1124~1145 (CDS)

<400> SEQUENCE: 89
agtaatctgc agcctagaaa a 21

<210> SEQ ID NO 90
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR10 target, SIR2 LTR transposon locus, vacuolar protein sorting-associated protein 20.2, AT5G09260.1 target gene, target site 511~532 (CDS)

<400> SEQUENCE: 90
agaattcgac aacctagaaa g 21

<210> SEQ ID NO 91
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR10 target, SIR2 LTR transposon locus, receptor protein kinase-like protein (AHRD V1 Q9LRY1_ARATH), Solyc04g050970.2.1 target gene, target site 19~40 (cDNA)

<400> SEQUENCE: 91
tgcaactttc aacctggaaa a 21

<210> SEQ ID NO 92
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR10 target, SIR2 LTR transposon locus, Iojap-like protein (AHRD V1 B5ZUF1_RHILW), Solyc05g014650.2.1 target gene, target site 541~562 (cDNA)

<400> SEQUENCE: 92
agcatactac aacttagaga a 21

<210> SEQ ID NO 93
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR18, SIR1 LTR transposon locus, Sec-independent periplasmic protein translocase, AT2G01110.1 target gene, target site 511~532 (CDS)

<400> SEQUENCE: 93
tagccaaaac agagtcgatc a 21

<210> SEQ ID NO 94
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR18 target, SIR1 LTR transposon locus, Sec-independent periplasmic protein translocase, AT2G01110.1 target gene, target site 511~532 (CDS)

<400> SEQUENCE: 94
tattcgtctc tgttttggct g 21

<210> SEQ ID NO 95

<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR18 target, SIR1 LTR transposon locus,
PHYTOCYSTATIN 2, AT2G31980.1 target gene, target
site 490~511 (CDS)

<400> SEQUENCE: 95
tgtttgactc tgttgtggtt a 21

<210> SEQ ID NO 96
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR18 target, SIR1 LTR transposon locus, cytochrome P450,
family 71, subfamily B, polypeptide 34, AT3G26300.1 target gene,
target site 1345~1366 (CDS)

<400> SEQUENCE: 96
tggtcgagtt tggtttggct a 21

<210> SEQ ID NO 97
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR18 target, SIR1 LTR transposon locus,
tonoplast intrinsic protein 5;1, AT3G47440.1
target gene, target site 366~387 (CDS)

<400> SEQUENCE: 97
tgattgcctc tgttatggct t 21

<210> SEQ ID NO 98
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR18 target, SIR1 LTR transposon locus, SKU5
similar 15, AT4G37160.1 target gene, target site
52~73 (CDS)

<400> SEQUENCE: 98
ggttaggctc tgttttggtt a 21

<210> SEQ ID NO 99
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR18 target, SIR1 LTR transposon locus, DUF1264 domain protein
(AHRD V1 A1CBM4_ASPCL), Solyc02g071770.2.1 target gene, target
site 1000~1021 (cDNA)

<400> SEQUENCE: 99
tgagcaactc tgttttgtct a 21

<210> SEQ ID NO 100
<211> LENGTH: 21
<212> TYPE: DNA
<213> ORGANISM: Artificial Sequence
<220> FEATURE:

<223> OTHER INFORMATION: synthetic Botrytis cinerea small RNA (sRNA)
      Bc-siR18 target, SIR1 LTR transposon locus, sister chromatid
      cohesion 2 (AHRD V1 D7M7D7_ARALY), Solyc03g059420.2.1 target gene,
      target site 2896~2917 (cDNA)

<400> SEQUENCE: 100
tgattgattc tgttttgcct t                                              21

<210> SEQ ID NO 101
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR18 target, SIR1 LTR transposon locus,
      unknown protein (AHRD V1), Solyc07g017240.1.1
      target gene, target site 1~22 (cDNA)

<400> SEQUENCE: 101
tgatagtctc tgttttggtt g                                              21

<210> SEQ ID NO 102
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR15, SIR3 LTR transposon locus, protein
      kinase superfamily protein, AT2G23080.1 target
      gene, target site 1250~1272 (3'UTR)

<400> SEQUENCE: 102
tgtgttgaac cttgttgttt ga                                             22

<210> SEQ ID NO 103
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR15 target, SIR3 LTR transposon locus,
      protein kinase superfamily protein, AT2G23080.1
      target gene, target site 1250~1272 (3'UTR)

<400> SEQUENCE: 103
ttaaaaaaaa aggttccaca ca                                             22

<210> SEQ ID NO 104
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR15 target, SIR3 LTR transposon locus, protein kinase
      superfamily protein with octicosapeptide/Phox/Bem1p domain,
      AT3G46920.1 target gene, target site 3478~3500 (CDS)

<400> SEQUENCE: 104
ccaaagaaca aggctcaaca ca                                             22

<210> SEQ ID NO 105
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR15 target, SIR3 LTR transposon locus, unknown protein,
      hypothetical protein, uncharacterized protein, AT5G48860.1 target
      gene, target site 291~313 (CDS)

<400> SEQUENCE: 105
tcgaaaaaca aggtgcaaca ca 22

<210> SEQ ID NO 106
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR15 target, SIR3 LTR transposon locus, protein transport protein sec31 (AHRD V1 C8V1I6_EMENI), Solyc01g088020.2.1 target gene, target site 786~808 (cDNA)

<400> SEQUENCE: 106
tggaacaaca aggttcagca ta 22

<210> SEQ ID NO 107
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR17, SIR6 CDS (spurious gene) locus, phosphoglycerate kinase family protein, AT1G56190.1 target gene, target site 1738~1759 (3'UTR)

<400> SEQUENCE: 107
taaaatgatg aatggcactg g 21

<210> SEQ ID NO 108
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR17 target, SIR6 CDS (spurious gene) locus, phosphoglycerate kinase family protein, AT1G56190.1 target gene, target site 1738~1759 (3'UTR)

<400> SEQUENCE: 108
acagtgacat tcgttatttt g 21

<210> SEQ ID NO 109
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR17 target, SIR6 CDS (spurious gene) locus, homeodomain-like/ winged-helix DNA-binding family protein, AT1G72740.1 target gene, target site 661~682 (CDS)

<400> SEQUENCE: 109
tcagttccat ttatcatttc a 21

<210> SEQ ID NO 110
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR17 target, SIR6 CDS (spurious gene) locus, solute carrier family 15 member 4 (AHRD V1 S15A4_XENLA), Solyc05g005950.2.1 target gene, target site 262~283 (cDNA)

<400> SEQUENCE: 110
accatgccat tcatcatttt g 21

<210> SEQ ID NO 111
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR17 target, SIR6 CDS (spurious gene) locus, peptide
transporter 1 (AHRD V1 Q7XAC3_VICFA), Solyc05g005960.2.1 target
gene, target site 69~90 (cDNA)

<400> SEQUENCE: 111
accatgccat tcatcatttt g 21

<210> SEQ ID NO 112
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR17 target, SIR6 CDS (spurious gene) locus, nodulin-like
protein (AHRD V1 Q9FHJ9_ARATH), Solyc08g075450.2.1 target gene,
target site 222~243 (cDNA)

<400> SEQUENCE: 112
ctactgtcat tcttcatttt a 21

<210> SEQ ID NO 113
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR17 target, SIR6 CDS (spurious gene) locus, nodulin-like
protein (AHRD V1 Q9FHJ9_ARATH), Solyc08g075460.2.1 target gene,
target site 424~445 (cDNA)

<400> SEQUENCE: 113
ctactgtcat tcttcatttt a 21

<210> SEQ ID NO 114
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR22, SIR3 LTR transposon locus, phragmoplast
orienting kinesin 1, AT3G17360.1 target gene,
target site 625~646 (CDS)

<400> SEQUENCE: 114
taacgtggtc aagggtgtag t 21

<210> SEQ ID NO 115
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR22 target, SIR3 LTR transposon locus,
phragmoplast orienting kinesin 1, AT3G17360.1
target gene, target site 625~646 (CDS)

<400> SEQUENCE: 115
gattcacctt tgaccacgtt g 21

<210> SEQ ID NO 116
<211> LENGTH: 21

<212> TYPE: DNA
<213> ORGANISM: Artificial Sequence
<220> FEATURE:
<223> OTHER INFORMATION: synthetic Botrytis cinerea small RNA (sRNA)
Bc-siR22 target, SIR3 LTR transposon locus, gamma
carbonic anhydrase 3, AT5G66510.1 target gene,
target site 438~459 (CDS)

<400> SEQUENCE: 116
acaacgctct tgtccacgtt g 21

<210> SEQ ID NO 117
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR22 target, SIR3 LTR transposon locus, aspartokinase (AHRD V1
B9RGY9_RICCO), Solyc01g005240.2.1 target gene, target site
1912~1933 (cDNA)

<400> SEQUENCE: 117
actactccct tgcccacgtt g 21

<210> SEQ ID NO 118
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR24, SIR3 LTR transposon locus, SAD1/UNC-84
domain protein 1, AT5G04990.1 target gene, target
site 1226~1248 (CDS)

<400> SEQUENCE: 118
tgattggtcc tctctgtttg ac 22

<210> SEQ ID NO 119
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR24 target, SIR3 LTR transposon locus,
SAD1/UNC-84 domain protein 1, AT5G04990.1 target
gene, target site 1226~1248 (CDS)

<400> SEQUENCE: 119
atcaggctga gaggaccaat ca 22

<210> SEQ ID NO 120
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR24 target, SIR3 LTR transposon locus, cathepsin B (AHRD V1
Q1HER6_NICBE), Solyc02g069090.2.1 target gene, target site
2009~2031 (cDNA)

<400> SEQUENCE: 120
gtcaaacaaa gagggccaat aa 22

<210> SEQ ID NO 121
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)

Bc-siR24 target, SIR3 LTR transposon locus, pentatricopeptide repeat-containing protein (AHRD V1 D7ML46_ARALY), Solyc03g007390.2.1 target gene, target site 2085~2107 (cDNA)

<400> SEQUENCE: 121
ttcagaaata gaggatcaat ca 22

<210> SEQ ID NO 122
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR24 target, SIR3 LTR transposon locus, SWI/SNF complex subunit SMARCC1 (AHRD V1 SMRC1_HUMAN), Solyc03g097450.2.1 target gene, target site 1351~1373 (cDNA)

<400> SEQUENCE: 122
gtgagacaga gaggacaagt ca 22

<210> SEQ ID NO 123
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR24 target, SIR3 LTR transposon locus, unknown protein (AHRD V1), Solyc09g089970.1.1 target gene, target site 287~309 (cDNA)

<400> SEQUENCE: 123
atctaccgga gaggatcaat ca 22

<210> SEQ ID NO 124
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR25, SIR2 LTR transposon locus, exostosin family protein, AT5G41250.1 target gene, target site 1349~1371 (CDS)

<400> SEQUENCE: 124
tagtgaatca aattttggtt tt 22

<210> SEQ ID NO 125
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR25 target, SIR2 LTR transposon locus, exostosin family protein, AT5G41250.1 target gene, target site 1349~1371 (CDS)

<400> SEQUENCE: 125
gagatcagta tttgattcac ta 22

<210> SEQ ID NO 126
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR25 target, SIR2 LTR transposon locus, cellulose synthase A4, AT5G44030.1 target gene, target site 3330~3352 (3'UTR)

<400> SEQUENCE: 126
aatacaaaac tttgattcac tt 22

<210> SEQ ID NO 127
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR25 target, SIR2 LTR transposon locus,
unknown protein (AHRD V1), Solyc01g044240.2.1
target gene, target site 1312~1334 (cDNA)

<400> SEQUENCE: 127
taaattaaaa tttgatttat ta 22

<210> SEQ ID NO 128
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR25 target, SIR2 LTR transposon locus, peroxidase 27 (AHRD V1
D7LAI1_ARALY), Solyc12g005790.1.1 target gene, target site 512~534
(cDNA)

<400> SEQUENCE: 128
aaaaacaaga tttggttcat ta 22

<210> SEQ ID NO 129
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015, SIR1015 intergenic region locus,
translation elongation factor EFG/EF2 protein,
AT2G45030.1 target gene, target site 2328~2348 (3'UTR)

<400> SEQUENCE: 129
ttgatggttg tctgatcggt 20

<210> SEQ ID NO 130
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region
locus, translation elongation factor EFG/EF2
protein, AT2G45030.1 target gene, target site 2328~2348 (3'UTR)

<400> SEQUENCE: 130
acggttcaca caaccatcaa 20

<210> SEQ ID NO 131
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region
locus, heat shock cognate protein 70-1,
AT5G02500.1 target gene, target site 954~974 (CDS)

<400> SEQUENCE: 131
actgctcaga ccaccatcga 20

<210> SEQ ID NO 132
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region locus, naphthoate
synthase (AHRD V1 A8I2W2_CHLRE), Solyc05g005180.2.1 target gene,
target site 437~457 (cDNA)

<400> SEQUENCE: 132
attgctaaga taaccatcaa 20

<210> SEQ ID NO 133
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region
locus, unknown protein (AHRD V1), Solyc06g036150.1.1
target gene, target site 564~584 (cDNA)

<400> SEQUENCE: 133
actgttctga cagccattaa 20

<210> SEQ ID NO 134
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region locus, unknown
protein (AHRD V1), contains Interpro domain IPR008889 VQ,
Solyc07g043250.1.1 target gene, target site 116~136 (cDNA)

<400> SEQUENCE: 134
gcccatcaga cgacgatcaa 20

<210> SEQ ID NO 135
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region locus, Ulp1 protease
family C-terminal catalytic domain containing protein (AHRD V1
Q60D46_SOLDE), Solyc08g063100.1.1 target gene, target site 438~458
(cDNA)

<400> SEQUENCE: 135
actgttctga caaccattaa 20

<210> SEQ ID NO 136
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region locus, genomic DNA
chromosome 5 P1 clone MTE17 (AHRD V1 Q9FJ71_ARATH),
Solyc10g006090.2.1 target gene, target site 2583~2603 (cDNA)

<400> SEQUENCE: 136
actgattgga caaccatcca 20

<210> SEQ ID NO 137
<211> LENGTH: 20

<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region locus, F-box family
protein (AHRD V1 D7LXD8_ARALY), Solyc12g044780.1.1 target gene,
target site 816~836 (cDNA)

<400> SEQUENCE: 137
actggttgga caaccatcac 20

<210> SEQ ID NO 138
<211> LENGTH: 20
<212> TYPE: DNA
<213> ORGANISM: Artificial Sequence
<220> FEATURE:
<223> OTHER INFORMATION: synthetic Botrytis cinerea small RNA (sRNA)
Bc-siR1015 target, SIR1015 intergenic region locus, F-box family
protein (AHRD V1 D7LXD8_ARALY), Solyc12g044790.1.1 target gene,
target site 816~836 (cDNA)

<400> SEQUENCE: 138
actggttgga caaccatcac 20

<210> SEQ ID NO 139
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR20, SIR2 LTR transposon locus, WUSCHEL
related homeobox 1, AT3G18010.1 target gene,
target site 1076~1098 (CDS)

<400> SEQUENCE: 139
tagtgttctt gtttttctga tt 22

<210> SEQ ID NO 140
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR20 target, SIR2 LTR transposon locus,
WUSCHEL related homeobox 1, AT3G18010.1 target
gene, target site 1076~1098 (CDS)

<400> SEQUENCE: 140
ggtgagaaag acaagaacat ta 22

<210> SEQ ID NO 141
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR20 target, SIR2 LTR transposon locus,
organic cation/carnitine transporter 4,
AT3G20660.1 target gene, target site 43~65 (5'UTR)

<400> SEQUENCE: 141
aaacacaaaa acaaaaacac tg 22

<210> SEQ ID NO 142
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)

Bc-siR20 target, SIR2 LTR transposon locus, heavy metal transport/ detoxification superfamily protein, AT4G23882.1 target gene, target site 549~571 (CDS)

<400> SEQUENCE: 142
aataagagaa gcaagaacac aa 22

<210> SEQ ID NO 143
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR20 target, SIR2 LTR transposon locus, disease resistance protein (TIR-NBS-LRR class), putative, AT5G17680.1 target gene, target site 3220~3242 (CDS)

<400> SEQUENCE: 143
agtcagcaaa accagaacac tc 22

<210> SEQ ID NO 144
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR20 target, SIR2 LTR transposon locus, cathepsin B-like cysteine proteinase (AHRD V1 CYSP_SCHMA), Solyc02g076690.2.1 target gene, target site 598~620 (cDNA)

<400> SEQUENCE: 144
aaacagcaga acaagaccac ta 22

<210> SEQ ID NO 145
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR20 target, SIR2 LTR transposon locus, DCN1-like protein 4 (AHRD V1 B6TI85_MAIZE), Solyc03g117110.2.1 target gene, target site 462~484 (cDNA)

<400> SEQUENCE: 145
agtctgaaaa acaaggatac tt 22

<210> SEQ ID NO 146
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR20 target, SIR2 LTR transposon locus, BHLH transcription factor-like protein (AHRD V1 Q5ZAK6_ORYSJ), Solyc03g120530.2.1 target gene, target site 462~484 (cDNA)

<400> SEQUENCE: 146
agtaagaaaa acaataatac ta 22

<210> SEQ ID NO 147
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR20 target, SIR2 LTR transposon locus, nucleoporin NUP188 homolog (AHRD V1 NU188_HUMAN), Solyc11g039880.1.1 target gene, target site 1821~1843 (cDNA)

<400> SEQUENCE: 147
aattataaaa acaagcacac tc 22

<210> SEQ ID NO 148
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1021, SIR1021 CDS locus, nucleotidyltransferase family protein, AT2G40520.1 target gene, target site 815~837 (CDS)

<400> SEQUENCE: 148
tacagtgatg aacaaaacat gt 22

<210> SEQ ID NO 149
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1021 target, SIR1021 CDS locus, nucleotidyltransferase family protein, AT2G40520.1 target gene, target site 815~837 (CDS)

<400> SEQUENCE: 149
acatgtctta ttcatcactg tc 22

<210> SEQ ID NO 150
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1021 target, SIR1021 CDS locus, vacuolar protein sorting 55 (VPS55) family protein, AT3G11530.1 target gene, target site 682~704 (3'UTR)

<400> SEQUENCE: 150
aaaagtttta ttcatcactg tg 22

<210> SEQ ID NO 151
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1021 target, SIR1021 CDS locus, fatty acid elongase 3-ketoacyl-CoA synthase (AHRD V1 Q6DUV5_BRANA), Solyc05g009280.2.1 target gene, target site 1339~1361 (cDNA)

<400> SEQUENCE: 151
acacgtcttc ttcatcattg tg 22

<210> SEQ ID NO 152
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA) Bc-siR1002, SIR1002 intergenic region locus, acyl-CoA synthetase 5, AT1G62940.1 target gene, target site 111~134 (CDS)

<400> SEQUENCE: 152
attcttcaaa tctttgtaac aca 23

<210> SEQ ID NO 153
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1002 target, SIR1002 intergenic region
      locus, acyl-CoA synthetase 5, AT1G62940.1 target
      gene, target site 111~134 (CDS)

<400> SEQUENCE: 153
tgtgctccaa ggagttgaag aat 23

<210> SEQ ID NO 154
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1002 target, SIR1002 intergenic region locus, nodulin MtN21/
      EamA-like transporter family protein, AT4G30420.1 target gene,
      target site 1039~1062 (CDS)

<400> SEQUENCE: 154
tctgtaataa agatctgaag aat 23

<210> SEQ ID NO 155
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1002 target, SIR1002 intergenic region locus, transducin/
      WD40 repeat-like superfamily protein, AT4G34380.1 target gene,
      target site 285~308 (5'UTR)

<400> SEQUENCE: 155
tttgtgataa agatttgaag aaa 23

<210> SEQ ID NO 156
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1002 target, SIR1002 intergenic region locus, xenotropic and
      polytropic retrovirus receptor (AHRD V1 B2GU54_XENTR),
      Solyc08g060920.2.1 target gene, target site 98~121 (cDNA)

<400> SEQUENCE: 156
tgagttacaa agatctgaag aaa 23

<210> SEQ ID NO 157
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1002 target, SIR1002 intergenic region locus, At5g63850-like
      protein (fragment) (AHRD V1 Q3YI76_ARALY), Solyc08g081380.2.1
      target gene, target site 989~1012 (cDNA)

<400> SEQUENCE: 157
tgtattgcaa ggatttgagg aaa 23

<210> SEQ ID NO 158
<211> LENGTH: 23
<212> TYPE: DNA

<213> ORGANISM: Artificial Sequence
<220> FEATURE:
<223> OTHER INFORMATION: synthetic Botrytis cinerea small RNA (sRNA)
      Bc-siR1002 target, SIR1002 intergenic region locus, xenotropic and
      polytropic retrovirus receptor (AHRD V1 B2GU54_XENTR),
      Solyc12g009480.1.1 target gene, target site 67~90 (cDNA)

<400> SEQUENCE: 158
tgtcatacaa ggatttgaag aaa 23

<210> SEQ ID NO 159
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR28, SIR1 LTR transposon locus, protein kinase protein with
      adenine nucleotide alpha hydrolases-like domain, AT1G16760.1
      target gene, target site 1454~1476 (CDS)

<400> SEQUENCE: 159
tttttgaaac tgtgatcttc tt 22

<210> SEQ ID NO 160
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR28 target, SIR1 LTR transposon locus, protein kinase protein
      with adenine nucleotide alpha hydrolases-like domain, AT1G16760.1
      target gene, target site 1454~1476 (CDS)

<400> SEQUENCE: 160
aggaagatca cagtttcaca aa 22

<210> SEQ ID NO 161
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR28 target, SIR1 LTR transposon locus, protein kinase protein
      with adenine nucleotide alpha hydrolases-like domain, AT1G78940.1
      target gene, target site 1425~1447 (CDS)

<400> SEQUENCE: 161
agggagatca cagtttcaga aa 22

<210> SEQ ID NO 162
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR28 target, SIR1 LTR transposon locus, PLANT
      U-BOX 12, AT2G28830.1 target gene, target site
      2571~2593 (CDS)

<400> SEQUENCE: 162
aagaagaaca aagtttcaga aa 22

<210> SEQ ID NO 163
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR28 target, SIR1 LTR transposon locus, tetratricopeptide repeat (TPR)-like superfamily protein, AT2G40720.1 target gene, target site 2191~2213 (CDS)

<400> SEQUENCE: 163
aagaagctta cagttttata aa 22

<210> SEQ ID NO 164
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, protein kinase protein with adenine nucleotide alpha hydrolases-like domain, AT3G20200.1 target gene, target site 1777~1799 (CDS)

<400> SEQUENCE: 164
aggaagatct caatttcaaa ga 22

<210> SEQ ID NO 165
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, protein kinase protein with adenine nucleotide alpha hydrolases-like domain, AT4G31230.1 target gene, target site 1505~1527 (CDS)

<400> SEQUENCE: 165
aggcaggtca cagtttcaga aa 22

<210> SEQ ID NO 166
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, unknown protein (AHRD V1), Solyc01g080610.2.1 target gene, target site 852~874 (cDNA)

<400> SEQUENCE: 166
aagaggttct cagtttcaaa ta 22

<210> SEQ ID NO 167
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, pentatricopeptide repeat-containing protein (AHRD V1 D7L610_ARALY), Solyc01g080720.2.1 target gene, target site 319~341 (cDNA)

<400> SEQUENCE: 167
aagaggttct cagtttcaaa ta 22

<210> SEQ ID NO 168
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, NAC domain protein IPR003441 (AHRD V1 B9I557_POPTR), Solyc03g115850.2.1 target gene, target site 934~956 (cDNA)

<400> SEQUENCE: 168
acggacatca gagtttcaaa aa 22

<210> SEQ ID NO 169
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, unknown protein (AHRD V1), Solyc05g024450.1.1 target gene, target site 196~218 (cDNA)

<400> SEQUENCE: 169
aagaagttca tagtttcaag aa 22

<210> SEQ ID NO 170
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, polygalacturonase (AHRD V1 Q2M4X6_LILLO), Solyc06g009200.2.1 target gene, target site 664~686 (cDNA)

<400> SEQUENCE: 170
aatgacatta cagtttcaaa aa 22

<210> SEQ ID NO 171
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, ankyrin repeat family protein (AHRD V1 D7LCV0_ARALY), Solyc06g031690.2.1 target gene, target site 345~367 (cDNA)

<400> SEQUENCE: 171
aaggatatta cagtttcaga ga 22

<210> SEQ ID NO 172
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR28 target, SIR1 LTR transposon locus, OBP3-responsive gene 4 (AHRD V1 D7L9C5_ARALY), Solyc07g041780.2.1 target gene, target site 450~472 (cDNA)

<400> SEQUENCE: 172
aagaagatcc cagttacaaa at 22

<210> SEQ ID NO 173
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR31, SIR1 LTR transposon locus, xanthine/uracil permease family protein, AT1G65550.1 target gene, target site 761~782 (CDS)

<400> SEQUENCE: 173
tgagtcttgt ggtcgtgaat g 21

<210> SEQ ID NO 174
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR31 target, SIR1 LTR transposon locus,
xanthine/uracil permease family protein,
AT1G65550.1 target gene, target site 761~782 (CDS)

<400> SEQUENCE: 174
tgtttatgac cacaagtctc a 21

<210> SEQ ID NO 175
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR31 target, SIR1 LTR transposon locus, F-box
family protein with a domain of unknown function
(DUF295), AT2G05970.1 target gene, target site 569~590 (CDS)

<400> SEQUENCE: 175
tgtttacgaa cacaagactc a 21

<210> SEQ ID NO 176
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR31 target, SIR1 LTR transposon locus,
xanthine/uracil/vitamin C permease, AT5G25420.1
target gene, target site 716~737 (CDS)

<400> SEQUENCE: 176
tgtttatgac cacaagcctc a 21

<210> SEQ ID NO 177
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR31 target, SIR1 LTR transposon locus, phospholipid-
transporting ATPase (AHRD V1 C5G6U4_AJEDR), Solyc01g011090.2.1
target gene, target site 3435~3456 (cDNA)

<400> SEQUENCE: 177
aatttaagac cacaagattc a 21

<210> SEQ ID NO 178
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR31 target, SIR1 LTR transposon locus,
unknown protein (AHRD V1), Solyc01g110700.2.1
target gene, target site 36445~36466 (cDNA)

<400> SEQUENCE: 178
aatttaagat cacaagattc a 21

<210> SEQ ID NO 179
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR31 target, SIR1 LTR transposon locus,
      unknown protein (AHRD V1), Solyc01g111180.2.1
      target gene, target site 6734~6755 (cDNA)

<400> SEQUENCE: 179
aatttaagat cacaagattc a 21

<210> SEQ ID NO 180
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR29, SIR2 LTR transposon locus, expansin B4,
      AT2G45110.1 target gene, target site 729~750 (CDS)

<400> SEQUENCE: 180
tgttggatag tcctttttgg g 21

<210> SEQ ID NO 181
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR29 target, SIR2 LTR transposon locus,
      expansin B4, AT2G45110.1 target gene, target site
      729~750 (CDS)

<400> SEQUENCE: 181
ccctaagagg accattcaac a 21

<210> SEQ ID NO 182
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR29 target, SIR2 LTR transposon locus,
      malectin/receptor-like protein kinase family
      protein, AT5G38990.1 target gene, target site 1156~1177 (CDS)

<400> SEQUENCE: 182
tacaaagagg actatccaac c 21

<210> SEQ ID NO 183
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR29 target, SIR2 LTR transposon locus,
      unknown protein (AHRD V1), Solyc00g025660.1.1
      target gene, target site 576~597 (cDNA)

<400> SEQUENCE: 183
tccaagaagg acaatccagc a 21

<210> SEQ ID NO 184
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR29 target, SIR2 LTR transposon locus, formamidopyrimidine-
      DNA glycosylase (AHRD V1 C5JTH8_AJEDS), Solyc03g117510.2.1 target
      gene, target site 745~766 (cDNA)

<400> SEQUENCE: 184
tccaaagagg actgtgcaac a 21

<210> SEQ ID NO 185
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR41, SIR3 LTR transposon locus, exocyst subunit exo70 family protein H3, AT3G09530.1 target gene, target site 826~847 (CDS)

<400> SEQUENCE: 185
tgatagtttt cgggagtaga a 21

<210> SEQ ID NO 186
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR41 target, SIR3 LTR transposon locus, exocyst subunit exo70 family protein H3, AT3G09530.1 target gene, target site 826~847 (CDS)

<400> SEQUENCE: 186
ttggattccc ggaaactatc a 21

<210> SEQ ID NO 187
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR41 target, SIR3 LTR transposon locus, protein of unknown function, AT3G19780.1 target gene, target site 1248~1269 (CDS)

<400> SEQUENCE: 187
tgccacttcc gaaaactgtc c 21

<210> SEQ ID NO 188
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR41 target, SIR3 LTR transposon locus, inner membrane protein oxaA (AHRD V1 B9L0L4_THERP), OxaA/YidC, Solyc05g014050.2.1 target gene, target site 1422~1443 (cDNA)

<400> SEQUENCE: 188
ttccacttct gaaaattatc g 21

<210> SEQ ID NO 189
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR35, SIR3 LTR transposon locus, purple acid phosphatase 21, AT3G52810.1 target gene, target site 978~999 (CDS)

<400> SEQUENCE: 189
tgtactgtgc catgtcgcgt t 21

<210> SEQ ID NO 190
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR35 target, SIR3 LTR transposon locus, purple acid phosphatase 21, AT3G52810.1 target gene, target site 978~999 (CDS)

<400> SEQUENCE: 190
cacacgccat ggtacagtac a 21

<210> SEQ ID NO 191
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR35 target, SIR3 LTR transposon locus, DNA polymerase I (AHRD V1 B6U7X8_MAIZE), Solyc11g017230.1.1 target gene, target site 721~742 (cDNA)

<400> SEQUENCE: 191
aacactatgt ggcacagtac a 21

<210> SEQ ID NO 192
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR57, SIR1 LTR transposon locus, P-glycoprotein 18, AT3G28390.1 target gene, target site 3253~3275 (CDS)

<400> SEQUENCE: 192
tagataatct ctggttcgtt gg 22

<210> SEQ ID NO 193
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR57 target, SIR1 LTR transposon locus, P-glycoprotein 18, AT3G28390.1 target gene, target site 3253~3275 (CDS)

<400> SEQUENCE: 193
tcgacgaatc ggagattatc ga 22

<210> SEQ ID NO 194
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR57 target, SIR1 LTR transposon locus, ABI five binding protein 3, AT3G29575.1 target gene, target site 350~372 (CDS)

<400> SEQUENCE: 194
tcgaagaaac agagattgtc tg 22

<210> SEQ ID NO 195
<211> LENGTH: 22

```
<212> TYPE: DNA
<213> ORGANISM: Artificial Sequence
<220> FEATURE:
<223> OTHER INFORMATION: synthetic Botrytis cinerea small RNA (sRNA)
      Bc-siR57 target, SIR1 LTR transposon locus, receptor-like protein
      kinase (AHRD V1 Q9FLV4_ARATH), Solyc03g007790.2.1 target gene,
      target site 2084~2106 (cDNA)

<400> SEQUENCE: 195

ccgaggaacc agaggttatc ta                                            22


<210> SEQ ID NO 196
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR43, SIR1 LTR transposon locus, response
      regulator 7, AT1G19050.1 target gene, target site
      592~613 (CDS)

<400> SEQUENCE: 196

tgggagcttt ctcttgttgg g                                             21


<210> SEQ ID NO 197
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR43 target, SIR1 LTR transposon locus,
      response regulator 7, AT1G19050.1 target gene,
      target site 592~613 (CDS)

<400> SEQUENCE: 197

tctaacaaga gaaagcttca a                                             21


<210> SEQ ID NO 198
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR43 target, SIR1 LTR transposon locus,
      carbohydrate-binding X8 domain superfamily
      protein, AT1G26450.1 target gene, target site 401~422 (CDS)

<400> SEQUENCE: 198

actatcaaaa gaaagcttcc a                                             21


<210> SEQ ID NO 199
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR43 target, SIR1 LTR transposon locus,
      ZIM-LIKE 2, AT1G51600.1 target gene, target site
      1398~1419 (3'UTR)

<400> SEQUENCE: 199

acaagcaaga gaaagatccc a                                             21


<210> SEQ ID NO 200
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
```

Bc-siR43 target, SIR1 LTR transposon locus, ribosomal protein L7/L12, oligomerisation, C-terminal/adaptor protein ClpS-like, AT1G70190.1 target gene, target site 202~223 (CDS)

<400> SEQUENCE: 200
ttcgatcaga gaaagctccc a 21

<210> SEQ ID NO 201
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR43 target, SIR1 LTR transposon locus, basic helix-loop-helix (bHLH) DNA-binding superfamily protein, AT3G19860.1 target gene, target site 979~1000 (CDS)

<400> SEQUENCE: 201
ctcaatagaa gaaagctctc a 21

<210> SEQ ID NO 202
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR43 target, SIR1 LTR transposon locus, trypsin family protein, AT5G45030.1 target gene, target site 65~86 (5'UTR)

<400> SEQUENCE: 202
cacgacatga gaaagatccc a 21

<210> SEQ ID NO 203
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR43 target, SIR1 LTR transposon locus, glycosyltransferase (AHRD V1 B9IC41_POPTR), Solyc01g093970.2.1 target gene, target site 809~830 (cDNA)

<400> SEQUENCE: 203
cctgaaaaaa gaaagttccc a 21

<210> SEQ ID NO 204
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR43 target, SIR1 LTR transposon locus, mediator of RNA polymerase II transcription subunit 13 (AHRD V1 MED13_DICDI), Solyc04g039950.2.1 target gene, target site 2037~2058 (cDNA)

<400> SEQUENCE: 204
ccctacaggg gagagctccc a 21

<210> SEQ ID NO 205
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR40, SIR2 LTR transposon locus, TRF-like 7, AT1G06910.1 target gene, target site 756~777 (CDS)

<400> SEQUENCE: 205

```
tggaatgggc ttgtattggt t                                              21


<210> SEQ ID NO 206
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR40 target, SIR2 LTR transposon locus,
      TRF-like 7, AT1G06910.1 target gene, target site
      756~777 (CDS)

<400> SEQUENCE: 206

agtcaattca atcccattcc a                                              21


<210> SEQ ID NO 207
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR40 target, SIR2 LTR transposon locus,
      galactinol synthase 3, AT1G09350.1 target gene,
      target site 723~744 (CDS)

<400> SEQUENCE: 207

gacatataca agcctattcc a                                              21


<210> SEQ ID NO 208
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR40 target, SIR2 LTR transposon locus, Arabidopsis
      phospholipase-like protein (PEARLI 4) family, AT4G38550.1 target
      gene, target site 604~625 (CDS)

<400> SEQUENCE: 208

aagcaatgcg agcccatttc a                                              21


<210> SEQ ID NO 209
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR40 target, SIR2 LTR transposon locus, Ulp1 protease family
      C-terminal catalytic domain containing protein (AHRD V1
      Q60D46_SOLDE), Solyc02g037560.1.1 target gene, target site 542~563
      (cDNA)

<400> SEQUENCE: 209

agctaataca agcacatttc a                                              21


<210> SEQ ID NO 210
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR40 target, SIR2 LTR transposon locus,
      unknown protein (AHRD V1), Solyc08g074820.1.1
      target gene, target site 86~107 (cDNA)

<400> SEQUENCE: 210

gactaataca agcacatttc a                                              21
```

<210> SEQ ID NO 211
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR38, SIR2 LTR transposon locus, C2H2 and C2HC
zinc fingers superfamily protein, AT3G23130.1
target gene, target site 1039~1060 (3'UTR)

<400> SEQUENCE: 211
taattcagga gacgatatcg t 21

<210> SEQ ID NO 212
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR38 target, SIR2 LTR transposon locus, C2H2
and C2HC zinc fingers superfamily protein,
AT3G23130.1 target gene, target site 1039~1060 (3'UTR)

<400> SEQUENCE: 212
acaattttgt ctccttaatt a 21

<210> SEQ ID NO 213
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR38 target, SIR2 LTR transposon locus, BRCA1-A complex
subunit BRE (AHRD V1 BRE_XENTR), Solyc04g081500.2.1 target gene,
target site 836~857 (cDNA)

<400> SEQUENCE: 213
ttggtatctt ctcctgaatt g 21

<210> SEQ ID NO 214
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR46, SIR9 intergenic region locus, chaperone
DnaJ-domain superfamily protein, AT5G21430.1
target gene, target site 703~725 (CDS)

<400> SEQUENCE: 214
ctaacgattg aaggccacca ac 22

<210> SEQ ID NO 215
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR46 target, SIR9 intergenic region locus,
chaperone DnaJ-domain superfamily protein,
AT5G21430.1 target gene, target site 703~725 (CDS)

<400> SEQUENCE: 215
ttcggttgcg ttcaatcgtt ag 22

<210> SEQ ID NO 216
<211> LENGTH: 22
<212> TYPE: DNA

<213> ORGANISM: Artificial Sequence
<220> FEATURE:
<223> OTHER INFORMATION: synthetic Botrytis cinerea small RNA (sRNA)
      Bc-siR46 target, SIR9 intergenic region locus, PWWP domain-
      containing protein (AHRD V1 D7L8B3_ARALY), contains Interpro
      domain IPR000313 PWWP, Solyc09g007340.2.1 target gene, target site
      938~960 (cDNA)

<400> SEQUENCE: 216
gttggtggcc ttcaatcgct gg 22

<210> SEQ ID NO 217
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR48, SIR1 LTR transposon locus,
      emp24/gp25L/p24 family/GOLD family protein,
      AT2G03040.1 target gene, target site 444~465 (CDS)

<400> SEQUENCE: 217
tgaagtgaca gtatcgatca a 21

<210> SEQ ID NO 218
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR48 target, SIR1 LTR transposon locus,
      emp24/gp25L/p24 family/GOLD family protein,
      AT2G03040.1 target gene, target site 444~465 (CDS)

<400> SEQUENCE: 218
ttgatggata ctgttatttc c 21

<210> SEQ ID NO 219
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR48 target, SIR1 LTR transposon locus,
      emp24/gp25L/p24 family/GOLD family protein,
      AT2G03290.1 target gene, target site 444~465 (CDS)

<400> SEQUENCE: 219
ttgatggata ctgttatttc c 21

<210> SEQ ID NO 220
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR48 target, SIR1 LTR transposon locus,
      DNA-binding bromodomain-containing protein,
      AT2G44430.1 target gene, target site 511~532 (CDS)

<400> SEQUENCE: 220
ttgttcgata ctatcgcttc a 21

<210> SEQ ID NO 221
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)

Bc-siR48 target, SIR1 LTR transposon locus, actin binding, AT5G58160.1 target gene, target site 1894~1915 (CDS)

<400> SEQUENCE: 221
ttcattgtta ctgtcacctc a 21

<210> SEQ ID NO 222
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR48 target, SIR1 LTR transposon locus, pyrophosphate-energized proton pump (AHRD V1 B0SRX3_LEPBP), Solyc06g068240.2.1 target gene, target site 441~462 (cDNA)

<400> SEQUENCE: 222
ttgcttggtg ctgtcacttc a 21

<210> SEQ ID NO 223
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR48 target, SIR1 LTR transposon locus, kinase family protein (AHRD V1 D7KVQ9_ARALY), Solyc12g099250.1.1 target gene, target site 1641~1662 (cDNA)

<400> SEQUENCE: 223
ttcatgggtg ctgttacttc a 21

<210> SEQ ID NO 224
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1007, SIR1007 LTR transposon locus, myb domain protein 3r-3, AT3G09370.1 target gene, target site 334~356 (CDS)

<400> SEQUENCE: 224
gtaggtgatc ctgcggaagg at 22

<210> SEQ ID NO 225
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1007 target, SIR1007 LTR transposon locus, myb domain protein 3r-3, AT3G09370.1 target gene, target site 334~356 (CDS)

<400> SEQUENCE: 225
gtcctgccac agtatcacct ac 22

<210> SEQ ID NO 226
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1007 target, SIR1007 LTR transposon locus, genomic DNA chromosome 5 TAC clone K20J1 (AHRD V1 Q9FH24_ARATH), Solyc12g099450.1.1 target gene, target site 514~536 (cDNA)

<400> SEQUENCE: 226
attcttccac aggatcatct at 22

<210> SEQ ID NO 227
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR56, SIR1 LTR transposon locus, unknown protein, hypothetical
protein, uncharacterized protein, AT5G37010.1 target gene, target
site 1380~1401 (CDS)

<400> SEQUENCE: 227
tcgttcatcc tgtagttgcg t 21

<210> SEQ ID NO 228
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR56 target, SIR1 LTR transposon locus, unknown protein,
hypothetical protein, uncharacterized protein, AT5G37010.1 target
gene, target site 1380~1401 (CDS)

<400> SEQUENCE: 228
atgcaactgc aggatcaacg t 21

<210> SEQ ID NO 229
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR56 target, SIR1 LTR transposon locus,
cytochrome P450, Solyc03g019870.2.1 target gene,
target site 915~936 (cDNA)

<400> SEQUENCE: 229
aagcaactac aggatgagca a 21

<210> SEQ ID NO 230
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR49, SIR2 LTR transposon locus, major
facilitator superfamily protein, AT3G45700.1
target gene, target site 1535~1556 (CDS)

<400> SEQUENCE: 230
tgtggcttat gtcttttgat a 21

<210> SEQ ID NO 231
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR49 target, SIR2 LTR transposon locus, major
facilitator superfamily protein, AT3G45700.1
target gene, target site 1535~1556 (CDS)

<400> SEQUENCE: 231
taccaaatga cataaaccac g 21

<210> SEQ ID NO 232
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR49 target, SIR2 LTR transposon locus, late embryogenesis
      abundant (LEA) hydroxyproline-rich glycoprotein family,
      AT4G01410.1 target gene, target site 940~961 (3'UTR)

<400> SEQUENCE: 232
aattaaaagg cataagccaa a 21

<210> SEQ ID NO 233
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR49 target, SIR2 LTR transposon locus,
      beta-1,4-xylosidase (AHRD V1 D7LA14_ARALY),
      Solyc01g107100.2.1 target gene, target site 82~103 (cDNA)

<400> SEQUENCE: 233
tatgaagaaa cacaagccac a 21

<210> SEQ ID NO 234
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR49 target, SIR2 LTR transposon locus, polygalacturonase
      (AHRD V1 B6SZN5_MAIZE), Solyc07g042160.2.1 target gene, target
      site 1440~1461 (cDNA)

<400> SEQUENCE: 234
tactagagga cataagctac a 21

<210> SEQ ID NO 235
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR58, SIR1 LTR transposon locus, phosphotransferases, alcohol
      group as acceptor, inositol or phosphatidylinositol kinases,
      AT4G36080.1 target gene, target site 4572~4593 (CDS)

<400> SEQUENCE: 235
taaattggga ttcattgtct g 21

<210> SEQ ID NO 236
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR58 target, SIR1 LTR transposon locus, phosphotransferases,
      alcohol group as acceptor, inositol or phosphatidylinositol
      kinases, AT4G36080.1 target gene, target site 4572~4593 (CDS)

<400> SEQUENCE: 236
cagacaaaga atctcaatat g 21

<210> SEQ ID NO 237
<211> LENGTH: 21
<212> TYPE: DNA

<213> ORGANISM: Artificial Sequence
<220> FEATURE:
<223> OTHER INFORMATION: synthetic Botrytis cinerea small RNA (sRNA)
Bc-siR58 target, SIR1 LTR transposon locus, WRKY transcription
factor 31 (AHRD V1 C9DI20_9ROSI), Solyc01g058540.2.1 target gene,
target site 1023~1044 (cDNA)

<400> SEQUENCE: 237
ctgataatga atcttaattt a 21

<210> SEQ ID NO 238
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR58 target, SIR1 LTR transposon locus, BEL1-like homeodomain
protein 6 (AHRD V1 BLH6_ARATH), Solyc01g109980.2.1 target gene,
target site 2186~2207 (cDNA)

<400> SEQUENCE: 238
tatatagtca atcccaattt g 21

<210> SEQ ID NO 239
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR63, SIR1 LTR transposon locus, binding to
TOMV RNA 1L (long form), AT5G04430.1 target gene,
target site 1461~1482 (3'UTR)

<400> SEQUENCE: 239
taatagttga tgagagaatg t 21

<210> SEQ ID NO 240
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR63 target, SIR1 LTR transposon locus,
binding to TOMV RNA 1L (long form), AT5G04430.1
target gene, target site 1461~1482 (3'UTR)

<400> SEQUENCE: 240
tctttctttt atcaactatt t 21

<210> SEQ ID NO 241
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR63 target, SIR1 LTR transposon locus,
FRIGIDA-like protein, AT5G48385.1 target gene,
target site 2124~2145 (3'UTR)

<400> SEQUENCE: 241
agattttctt attaattatt a 21

<210> SEQ ID NO 242
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR63 target, SIR1 LTR transposon locus, vacuolar protein sorting 36 family protein (AHRD V1 D7LY74_ARALY),
Solyc01g096910.2.1 target gene, target site 975~996 (cDNA)

<400> SEQUENCE: 242
gcattgtatc atcaacaatt a 21

<210> SEQ ID NO 243
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005, SIR1005 LTR transposon locus, PAM
domain (PCI/PINT associated module) protein,
AT1G20200.1 target gene, target site 1224~1245 (CDS)

<400> SEQUENCE: 243
taaagagttt cttcaatagg a 21

<210> SEQ ID NO 244
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus,
PAM domain (PCI/PINT associated module) protein,
AT1G20200.1 target gene, target site 1224~1245 (CDS)

<400> SEQUENCE: 244
tcctactcaa gaatctcttt a 21

<210> SEQ ID NO 245
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus,
protein kinase superfamily protein, AT1G20650.1
target gene, target site 1502~1523 (CDS)

<400> SEQUENCE: 245
tcttaatgaa gaagctcatt a 21

<210> SEQ ID NO 246
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus, unknown protein,
hypothetical protein, uncharacterized protein, AT1G67540.1 target
gene, target site 352~373 (CDS)

<400> SEQUENCE: 246
ggctattgag gaaactcttt g 21

<210> SEQ ID NO 247
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus,
protein of unknown function (DUF607), AT2G23790.1
target gene, target site 82~103 (CDS)

<400> SEQUENCE: 247
ttttatcgaa gaaactcttc a 21

<210> SEQ ID NO 248
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus,
HOPZ-ACTIVATED RESISTANCE 1, AT3G50950.1 target
gene, target site 2116~2137 (CDS)

<400> SEQUENCE: 248
tcttgttcaa gaaactcctt g 21

<210> SEQ ID NO 249
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus,
CRM family member 3B, AT4G14510.1 target gene,
target site 1862~1883 (CDS)

<400> SEQUENCE: 249
tactcttgga gaaactcttg a 21

<210> SEQ ID NO 250
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus,
flavin-binding monooxygenase family protein,
AT5G61290.1 target gene, target site 1366~1387 (CDS)

<400> SEQUENCE: 250
tcttcttcaa gaaactcttc a 21

<210> SEQ ID NO 251
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus, NAD dependent
epimerase dehydratase family protein expressed (AHRD V1
Q2MJA7_ORYSJ), Solyc01g091200.2.1 target gene, target site 824~845
(cDNA)

<400> SEQUENCE: 251
ccctcttgaa gaaacttttt g 21

<210> SEQ ID NO 252
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus, zinc finger
transcription factor (AHRD V1 Q7K9G4_DROME), Solyc04g028560.2.1
target gene, target site 2604~2625 (cDNA)

<400> SEQUENCE: 252
ttcaattgaa gaaactctgt t 21

<210> SEQ ID NO 253
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus, UDP-D-glucuronate
4-epimerase 2 (AHRD V1 D7M5S7_ARALY), Solyc05g050990.1.1 target
gene, target site 478~499 (cDNA)

<400> SEQUENCE: 253
ccctcttgaa gaaacttttt g 21

<210> SEQ ID NO 254
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1005 target, SIR1005 LTR transposon locus, CT099 (fragment)
(AHRD V1 Q4KR02_SOLCI), Solyc10g005940.1.1 target gene, target
site 191~212 (cDNA)

<400> SEQUENCE: 254
tcatatcgga gatactcttt a 21

<210> SEQ ID NO 255
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR60, SIR1 LTR transposon locus, BRI1 like,
AT1G55610.1 target gene, target site 817~838 (CDS)

<400> SEQUENCE: 255
tgcaatggaa ttcgaagacg g 21

<210> SEQ ID NO 256
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR60 target, SIR1 LTR transposon locus, BRI1
like, AT1G55610.1 target gene, target site 817~838
(CDS)

<400> SEQUENCE: 256
ttgtcttcga attctatttc a 21

<210> SEQ ID NO 257
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR60 target, SIR1 LTR transposon locus, acetyltransferase
(AHRD V1 B4RG69_PHEZH), Solyc08g067800.1.1 target gene,
target site 261~282 (cDNA)

<400> SEQUENCE: 257
ccatcttgga attccattgt g 21

<210> SEQ ID NO 258
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR61, SIR3 LTR transposon locus, ribonuclease
      II family protein, AT2G17510.2 target gene, target
      site 1543~1564 (CDS)

<400> SEQUENCE: 258
tagaatagaa tcgtatacgt g                                              21

<210> SEQ ID NO 259
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR61 target, SIR3 LTR transposon locus,
      ribonuclease II family protein, AT2G17510.2 target
      gene, target site 1543~1564 (CDS)

<400> SEQUENCE: 259
aatttattcg attctattct a                                              21

<210> SEQ ID NO 260
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR61 target, SIR3 LTR transposon locus, POT family domain
      containing protein expressed (AHRD V1 D8L9H8_WHEAT),
      Solyc03g078160.2.1 target gene, target site 896~917 (cDNA)

<400> SEQUENCE: 260
caagtgtatg attttgttct a                                              21

<210> SEQ ID NO 261
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR61 target, SIR3 LTR transposon locus, phospholipid-
      transporting ATPase 1 (AHRD V1 C5FPS3_NANOT), Solyc03g121810.2.1
      target gene, target site 2888~2909 (cDNA)

<400> SEQUENCE: 261
tatgtatatg attctattca a                                              21

<210> SEQ ID NO 262
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR61 target, SIR3 LTR transposon locus, B-like cyclin (AHRD V1
      Q40337_MEDSA), Solyc04g082430.2.1 target gene, target site 8~29
      (cDNA)

<400> SEQUENCE: 262
catgtttacg attcaatttt a                                              21

<210> SEQ ID NO 263
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR62, SIR2 LTR transposon locus, F-box and
      associated interaction domains-containing protein, AT1G11620.1 target gene, target site 353~374 (CDS)

<400> SEQUENCE: 263
tacgacggat tcgcaagtaa a 21

<210> SEQ ID NO 264
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR62 target, SIR2 LTR transposon locus, F-box
and associated interaction domains-containing
protein, AT1G11620.1 target gene, target site 353~374 (CDS)

<400> SEQUENCE: 264
tttggttgcg aatccgttgt t 21

<210> SEQ ID NO 265
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR62 target, SIR2 LTR transposon locus,
alpha/beta-hydrolases superfamily protein,
AT4G10030.1 target gene, target site 100~121 (5'UTR)

<400> SEQUENCE: 265
tgtaattgcg aattcgtcgt t 21

<210> SEQ ID NO 266
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR62 target, SIR2 LTR transposon locus,
unknown protein (AHRD V1), Solyc01g009570.2.1
target gene, target site 236~257 (cDNA)

<400> SEQUENCE: 266
tttacttggg aatccgtagt c 21

<210> SEQ ID NO 267
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR65, SIR1 LTR transposon locus, S phase
kinase-associated protein 1, AT1G75950.1 target
gene, target site 282~303 (CDS)

<400> SEQUENCE: 267
tagcaagagg gattctgtag t 21

<210> SEQ ID NO 268
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR65 target, SIR1 LTR transposon locus, S
phase kinase-associated protein 1, AT1G75950.1
target gene, target site 282~303 (CDS)

<400> SEQUENCE: 268
acaacggagt ccctcttcct a 21

<210> SEQ ID NO 269
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR65 target, SIR1 LTR transposon locus, fructose-bisphosphate aldolase 1, AT2G21330.1 target gene, target site 974~995 (CDS)

<400> SEQUENCE: 269
gcaacagaat ccctcctgct g 21

<210> SEQ ID NO 270
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR65 target, SIR1 LTR transposon locus, phragmoplast-associated kinesin-related protein, putative, AT3G23670.1 target gene, target site 3292~3313 (CDS)

<400> SEQUENCE: 270
gcaactggat ctctcttgct g 21

<210> SEQ ID NO 271
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR65 target, SIR1 LTR transposon locus, peroxidase superfamily protein, AT4G25980.1 target gene, target site 187~208 (CDS)

<400> SEQUENCE: 271
tcttcggcat ctctcttgct a 21

<210> SEQ ID NO 272
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR65 target, SIR1 LTR transposon locus, P-loop containing nucleoside triphosphate hydrolases superfamily protein, AT4G27680.1 target gene, target site 1507~1528 (3'UTR)

<400> SEQUENCE: 272
attactgaat ctctcttgtt c 21

<210> SEQ ID NO 273
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR65 target, SIR1 LTR transposon locus, sucrose phosphate synthase (AHRD V1 Q2HYI0_CUCME), Solyc07g007790.2.1 target gene, target site 3439~3460 (cDNA)

<400> SEQUENCE: 273
gttatagaat ctcttttgct a 21

<210> SEQ ID NO 274

<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR65 target, SIR1 LTR transposon locus, pre-mRNA-processing
protein 45 (AHRD V1 D6RKF6_COPC7), Solyc12g008370.1.1
target gene, target site 496~517 (cDNA)

<400> SEQUENCE: 274
gttacacaat ccctcttgat a 21

<210> SEQ ID NO 275
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR67, SIR2 LTR transposon locus, DEAD/DEAH box
RNA helicase family protein, AT1G27880.1 target
gene, target site 3~25 (CDS)

<400> SEQUENCE: 275
taaatcgatc ggagaatttt tt 22

<210> SEQ ID NO 276
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR67 target, SIR2 LTR transposon locus,
DEAD/DEAH box RNA helicase family protein,
AT1G27880.1 target gene, target site 3~25 (CDS)

<400> SEQUENCE: 276
ataaaattct ccgatggatt tc 22

<210> SEQ ID NO 277
<211> LENGTH: 4
<212> TYPE: PRT
<213> ORGANISM: Artificial Sequence
<220> FEATURE:
<223> OTHER INFORMATION: synthetic DEAD box

<400> SEQUENCE: 277

Asp Glu Ala Asp
1

<210> SEQ ID NO 278
<211> LENGTH: 4
<212> TYPE: PRT
<213> ORGANISM: Artificial Sequence
<220> FEATURE:
<223> OTHER INFORMATION: synthetic DEAH box

<400> SEQUENCE: 278

Asp Glu Ala His
1

<210> SEQ ID NO 279
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR67 target, SIR2 LTR transposon locus, calcium-dependent
protein kinase 2 (AHRD V1 B4FZS4_MAIZE), Solyc05g055050.1.1 target
gene, target site 568~590 (cDNA)

<400> SEQUENCE: 279
caagaatttt ccgatcgatt tc 22

<210> SEQ ID NO 280
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR67 target, SIR2 LTR transposon locus, plant-specific domain
TIGR01615 family protein (AHRD V1 B6UDN7_MAIZE),
Solyc07g053900.2.1 target gene, target site 421~443 (cDNA)

<400> SEQUENCE: 280
agagaaatct ccgatcgact ta 22

<210> SEQ ID NO 281
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR68, SIR1 LTR transposon locus, protein of
unknown function (DUF2921), AT4G21700.1 target
gene, target site 167~188 (CDS)

<400> SEQUENCE: 281
tggatgcagt gatcggaatt g 21

<210> SEQ ID NO 282
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR68 target, SIR1 LTR transposon locus,
protein of unknown function (DUF2921), AT4G21700.1
target gene, target site 167~188 (CDS)

<400> SEQUENCE: 282
ttattccgat cactgcaacc a 21

<210> SEQ ID NO 283
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR68 target, SIR1 LTR transposon locus, TBC1 domain family
member 8B (AHRD V1 B9A6K5_HUMAN), Solyc04g009560.2.1 target gene,
target site 2811~2832 (cDNA)

<400> SEQUENCE: 283
caatactggt cactgtatct a 21

<210> SEQ ID NO 284
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR68 target, SIR1 LTR transposon locus,
unknown protein (AHRD V1), Solyc10g007340.2.1
target gene, target site 453~474 (cDNA)

<400> SEQUENCE: 284
cgaatccggt cactgaatcc g 21

<210> SEQ ID NO 285
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR73, SIR3 LTR transposon locus,
senescence-related gene 1, AT1G17020.1 target
gene, target site 459~480 (CDS)

<400> SEQUENCE: 285
tgtgcccaat ctattttcgg a 21

<210> SEQ ID NO 286
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR73 target, SIR3 LTR transposon locus,
senescence-related gene 1, AT1G17020.1 target
gene, target site 459~480 (CDS)

<400> SEQUENCE: 286
tcagaaacta gattgggcag a 21

<210> SEQ ID NO 287
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR73 target, SIR3 LTR transposon locus, phosphatidylinositol-
specific phospholipase c (AHRD V1 B9UXN2_LISMO), Solyc01g111250.2.1
target gene, target site 533~554 (cDNA)

<400> SEQUENCE: 287
tccgaacaga gtttgggcac g 21

<210> SEQ ID NO 288
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR73 target, SIR3 LTR transposon locus, phosphatidylinositol-
specific phospholipase c (AHRD V1 B9UY71_LISMO),
Solyc01g111260.2.1 target gene, target site 543~564 (cDNA)

<400> SEQUENCE: 288
tccgaacaga gtttgggcac g 21

<210> SEQ ID NO 289
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR73 target, SIR3 LTR transposon locus, protein LSM14 homolog
A (AHRD V1 LS14A_PONAB), Solyc06g069280.2.1 target gene, target
site 1359~1380 (cDNA)

<400> SEQUENCE: 289
tcagagaaga gatggggcac a 21

<210> SEQ ID NO 290
<211> LENGTH: 21

<212> TYPE: DNA
<213> ORGANISM: Artificial Sequence
<220> FEATURE:
<223> OTHER INFORMATION: synthetic Botrytis cinerea small RNA (sRNA)
Bc-siR81, SIR1 LTR transposon locus, AGAMOUS-like
80, AT5G48670.1 target gene, target site 403~424
(CDS)

<400> SEQUENCE: 290
tgtctctaat caagcgttgg g 21

<210> SEQ ID NO 291
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR81 target, SIR1 LTR transposon locus,
AGAMOUS-like 80, AT5G48670.1 target gene, target
site 403~424 (CDS)

<400> SEQUENCE: 291
tccaatgttt gattggaaac a 21

<210> SEQ ID NO 292
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR81 target, SIR1 LTR transposon locus, importin subunit beta
(AHRD V1 B0WBR4_CULQU), Solyc03g082940.2.1 target gene, target
site 1376~1397 (cDNA)

<400> SEQUENCE: 292
ttcaaagcct gattggagac a 21

<210> SEQ ID NO 293
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR81 target, SIR1 LTR transposon locus, calmodulin binding
protein (AHRD V1 B6T951_MAIZE), Solyc08g062940.2.1
target gene, target site 810~831 (cDNA)

<400> SEQUENCE: 293
tccaaagctt gcttagagac t 21

<210> SEQ ID NO 294
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR82, SIR1 LTR transposon locus, WD-40 repeat
family protein/beige-related, AT2G45540.1 target
gene, target site 4598~4620 (CDS)

<400> SEQUENCE: 294
tgatacggat ttcttaactg at 22

<210> SEQ ID NO 295
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)

Bc-siR82 target, SIR1 LTR transposon locus, WD-40
repeat family protein/beige-related, AT2G45540.1
target gene, target site 4598~4620 (CDS)

<400> SEQUENCE: 295
attggttaaa aaatctgtat cc 22

<210> SEQ ID NO 296
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR82 target, SIR1 LTR transposon locus, glycosyl transferase
group 1 (AHRD V1 B6T775_MAIZE), Solyc11g006560.1.1
target gene, target site 922~944 (cDNA)

<400> SEQUENCE: 296
atctgttaac gaatccgtat ca 22

<210> SEQ ID NO 297
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR86, SIR2 LTR transposon locus, hypothetical
protein, uncharacterized protein, AT1G10180.1
target gene, target site 2187~2209 (CDS)

<400> SEQUENCE: 297
tgttgatagc tgatttgatg gt 22

<210> SEQ ID NO 298
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR86 target, SIR2 LTR transposon locus,
hypothetical protein, uncharacterized protein,
AT1G10180.1 target gene, target site 2187~2209 (CDS)

<400> SEQUENCE: 298
gccgccaagt cagctatcaa ca 22

<210> SEQ ID NO 299
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR86 target, SIR2 LTR transposon locus,
protein of unknown function (DUF607), AT5G66650.1
target gene, target site 734~756 (CDS)

<400> SEQUENCE: 299
atcataaaat cagatatcga ca 22

<210> SEQ ID NO 300
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR86 target, SIR2 LTR transposon locus, 30S ribosomal protein
S6 (AHRD V1 B4WXW0_9GAMM), Solyc01g058190.2.1 target gene, target
site 1101~1123 (cDNA)

<400> SEQUENCE: 300
actattagat catctatcaa cc 22

<210> SEQ ID NO 301
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR86 target, SIR2 LTR transposon locus, peroxidase (AHRD V1 B9VRK9_CAPAN), Solyc05g052280.2.1 target gene, target site 211~233 (cDNA)

<400> SEQUENCE: 301
acagttcaat cagctatcaa ca 22

<210> SEQ ID NO 302
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91, SIR2 LTR transposon locus, cyclin-related, AT1G70620.1 target gene, target site 654~676 (CDS)

<400> SEQUENCE: 302
tggtgctgtt gatagctgat tt 22

<210> SEQ ID NO 303
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, cyclin-related, AT1G70620.1 target gene, target site 654~676 (CDS)

<400> SEQUENCE: 303
gagtaagcta tcagcagcat ca 22

<210> SEQ ID NO 304
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, E3 ubiquitin-protein ligase bre1 (AHRD V1 B6K254_SCHJY), Solyc01g006030.2.1 target gene, target site 449~471 (cDNA)

<400> SEQUENCE: 304
gaagcaggta tcaacagcac aa 22

<210> SEQ ID NO 305
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, Os06g0207500 protein (fragment) (AHRD V1 Q0DDQ9_ORYSJ), Solyc01g060270.1.1 target gene, target site 975~997 (cDNA)

<400> SEQUENCE: 305
gatacaacta tcaacagcac ca 22

<210> SEQ ID NO 306
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g026330.1.1 target gene, target site 322~344 (cDNA)

<400> SEQUENCE: 306
aagttagcta tcaaaagtac ca 22

<210> SEQ ID NO 307
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g026350.1.1 target gene, target site 444~466 (cDNA)

<400> SEQUENCE: 307
aagttagcta tcaaaagtac ca 22

<210> SEQ ID NO 308
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g041300.1.1 target gene, target site 183~205 (cDNA)

<400> SEQUENCE: 308
aagttagcta tcaaaagtac ca 22

<210> SEQ ID NO 309
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g041320.1.1 target gene, target site 322~344 (cDNA)

<400> SEQUENCE: 309
gagttagcta tcaaaagtac ca 22

<210> SEQ ID NO 310
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g041610.1.1 target gene, target site 415~437 (cDNA)

<400> SEQUENCE: 310
gagttagcta tcaaaagtac ca 22

<210> SEQ ID NO 311
<211> LENGTH: 22
<212> TYPE: DNA

<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g041620.1.1 target gene, target site 322~344 (cDNA)

<400> SEQUENCE: 311
gagttagcta tcaaaagtac ca 22

<210> SEQ ID NO 312
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR91 target, SIR2 LTR transposon locus, caffeoyl-CoA O-methyltransferase (AHRD V1 A2PZD5_IPONI), Solyc05g041690.1.1 target gene, target site 475~497 (cDNA)

<400> SEQUENCE: 312
aagttagcta tcaaaagtac ca 22

<210> SEQ ID NO 313
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR92, SIR3 LTR transposon locus, transducin/WD40 repeat-like superfamily protein, AT3G45620.1 target gene, target site 701~723 (CDS)

<400> SEQUENCE: 313
tgtactgttc tggtatcgta gg 22

<210> SEQ ID NO 314
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR92 target, SIR3 LTR transposon locus, transducin/WD40 repeat-like superfamily protein, AT3G45620.1 target gene, target site 701~723 (CDS)

<400> SEQUENCE: 314
tctacgatac tagaagagta ca 22

<210> SEQ ID NO 315
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR92 target, SIR3 LTR transposon locus, rhomboid family protein (AHRD V1 D7MJX8_ARALY), Solyc02g085760.2.1 target gene, target site 491~513 (cDNA)

<400> SEQUENCE: 315
gctaagaaac tagaacagta ca 22

<210> SEQ ID NO 316
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR95, SIR1 LTR transposon locus, AGAMOUS-like 30, AT2G03060.1 target gene, target site 1405~1426
(3'UTR)

<400> SEQUENCE: 316
tgcgaagtta tgtatagtag a 21

<210> SEQ ID NO 317
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR95 target, SIR1 LTR transposon locus,
AGAMOUS-like 30, AT2G03060.1 target gene, target
site 1405~1426 (3'UTR)

<400> SEQUENCE: 317
ttttctatac ataatttctc a 21

<210> SEQ ID NO 318
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR95 target, SIR1 LTR transposon locus, dedicator of
cytokinesis family protein (AHRD V1 A8P5S7_BRUMA),
Solyc08g016050.2.1 target gene, target site 1697~1718 (cDNA)

<400> SEQUENCE: 318
actactttat ataacttcgc t 21

<210> SEQ ID NO 319
<211> LENGTH: 24
<212> TYPE: DNA
<213> ORGANISM: Artificial Sequence
<220> FEATURE:
<223> OTHER INFORMATION: synthetic Botrytis cinerea small RNA (sRNA)
Bc-siR1017, SIR1017 intergenic region locus,
ubiquitin-specific protease 13, AT3G11910.1 target
gene, target site 1418~1442 (CDS)

<400> SEQUENCE: 319
agggtggaga gagttcggac attc 24

<210> SEQ ID NO 320
<211> LENGTH: 24
<212> TYPE: DNA
<213> ORGANISM: Artificial Sequence
<220> FEATURE:
<223> OTHER INFORMATION: synthetic Botrytis cinerea small RNA (sRNA)
Bc-siR1017 target, SIR1017 intergenic region
locus, ubiquitin-specific protease 13, AT3G11910.1
target gene, target site 1418~1442 (CDS)

<400> SEQUENCE: 320
gagtgtccgc aatctctaca ccct 24

<210> SEQ ID NO 321
<211> LENGTH: 24
<212> TYPE: DNA
<213> ORGANISM: Artificial Sequence
<220> FEATURE:
<223> OTHER INFORMATION: synthetic Botrytis cinerea small RNA (sRNA)
Bc-siR1017 target, SIR1017 intergenic region locus, cell division
protease ftsH (AHRD V1 FTSH_SHIFL), Solyc03g007760.2.1 target
gene, target site 1996~2020 (cDNA)

<400> SEQUENCE: 321
gaatgtccga gctcttttca cact 24

<210> SEQ ID NO 322
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR97, SIR3 LTR transposon locus, protein of
unknown function (DUF239), AT4G17505.1 target
gene, target site 185~207 (CDS)

<400> SEQUENCE: 322
tatcgggtcc atccttcttg gg 22

<210> SEQ ID NO 323
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR97 target, SIR3 LTR transposon locus,
protein of unknown function (DUF239), AT4G17505.1
target gene, target site 185~207 (CDS)

<400> SEQUENCE: 323
tccgagaggg atggtcccga tc 22

<210> SEQ ID NO 324
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR97 target, SIR3 LTR transposon locus, AT-hook motif nuclear
localized protein 1 (AHRD V1 Q8VYJ2_ARATH), Solyc01g091370.2.1
target gene, target site 1179~1201 (cDNA)

<400> SEQUENCE: 324
cctaggaagt atgggcctga tg 22

<210> SEQ ID NO 325
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR97 target, SIR3 LTR transposon locus, uncharacterized
protein LOC101249582 (related) (AHRD V1 Q2HTJ8_MEDTR),
Solyc01g094640.2.1 target gene, target site 2690~2712 (cDNA)

<400> SEQUENCE: 325
tccaaaaggg atggacctga ta 22

<210> SEQ ID NO 326
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR99, SIR2 LTR transposon locus, SH3
domain-containing protein, AT2G07360.1 target
gene, target site 412~433 (CDS)

<400> SEQUENCE: 326
tagtgtcagc taattcagga g 21

<210> SEQ ID NO 327
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR99 target, SIR2 LTR transposon locus, SH3
domain-containing protein, AT2G07360.1 target
gene, target site 412~433 (CDS)

<400> SEQUENCE: 327
ttcatgaatt agctgccact t 21

<210> SEQ ID NO 328
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR99 target, SIR2 LTR transposon locus,
RING/U-box superfamily protein, AT2G39100.1 target
gene, target site 1127~1148 (3'UTR)

<400> SEQUENCE: 328
attctcaaat agctgacact t 21

<210> SEQ ID NO 329
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR99 target, SIR2 LTR transposon locus,
auxin-responsive GH3 family protein, AT5G13320.1
target gene, target site 889~910 (CDS)

<400> SEQUENCE: 329
gtcctgaatt agcagacact a 21

<210> SEQ ID NO 330
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR99 target, SIR2 LTR transposon locus, zinc finger-
homeodomain protein 1 (fragment) (AHRD V1 B0LK19_CUCSA),
Solyc02g067320.1.1 target gene, target site 52~73 (cDNA)

<400> SEQUENCE: 330
caccagaatt agctgaaact g 21

<210> SEQ ID NO 331
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR99 target, SIR2 LTR transposon locus, peptide transporter 1
(AHRD V1 Q7XAC3_VICFA), Solyc08g066940.2.1 target gene, target
site 1557~1578 (cDNA)

<400> SEQUENCE: 331
ttcttggact agctgacgct t 21

<210> SEQ ID NO 332
<211> LENGTH: 23
<212> TYPE: DNA
<213> ORGANISM: Artificial Sequence

```
<220> FEATURE:
<223> OTHER INFORMATION: synthetic Botrytis cinerea small RNA (sRNA)
      Bc-siR1013, SIR1013 CDS locus, HD-ZIP IV family of homeobox-
      leucine zipper protein with lipid-binding START domain,
      AT1G79840.2 target gene, target site 77~100 (5'UTR)

<400> SEQUENCE: 332

ttatatgatg aacaaacttt aaa                                          23


<210> SEQ ID NO 333
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1013 target, SIR1013 CDS locus, HD-ZIP IV family of
      homeobox-leucine zipper protein with lipid-binding START domain,
      AT1G79840.2 target gene, target site 77~100 (5'UTR)

<400> SEQUENCE: 333

tttgaatttt gctcatcata tat                                          23


<210> SEQ ID NO 334
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
      Bc-siR1013 target, SIR1013 CDS locus, C2H2L domain class
      transcription factor (AHRD V1 D9ZIU3_MALDO), Solyc03g098070.2.1
      target gene, target site 1258~1281 (cDNA)

<400> SEQUENCE: 334

ttttatgttt gttcattata tga                                          23


<210> SEQ ID NO 335
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR102, SIR13 intergenic region locus, beta
      galactosidase 1, AT3G13750.1 target gene, target
      site 3258~3280 (3'UTR)

<400> SEQUENCE: 335

tggaggggag attgatacat tg                                           22


<210> SEQ ID NO 336
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR102 target, SIR13 intergenic region locus,
      beta galactosidase 1, AT3G13750.1 target gene,
      target site 3258~3280 (3'UTR)

<400> SEQUENCE: 336

caatgtgtga atcacccctc ca                                           22


<210> SEQ ID NO 337
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR102 target, SIR13 intergenic region locus,
      eukaryotic aspartyl protease family protein,
```

AT5G43100.1 target gene, target site 139~161 (CDS)

<400> SEQUENCE: 337
ccatggatcg atcttccctc ct 22

<210> SEQ ID NO 338
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR102 target, SIR13 intergenic region locus, ATP-binding cassette transporter (AHRD V1 D8T797_SELML), Solyc11g067000.1.1 target gene, target site 2884~2906 (cDNA)

<400> SEQUENCE: 338
caatctatga atctctcctc ta 22

<210> SEQ ID NO 339
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1011, SIR1011 CDS locus, unknown protein, hypothetical protein, uncharacterized protein, AT4G21215.1 target gene, target site 724~746 (CDS)

<400> SEQUENCE: 339
taatatgatg agcaagattg gt 22

<210> SEQ ID NO 340
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1011 target, SIR1011 CDS locus, unknown protein, hypothetical protein, uncharacterized protein, AT4G21215.1 target gene, target site 724~746 (CDS)

<400> SEQUENCE: 340
atcaatcttg ttaatcatat tc 22

<210> SEQ ID NO 341
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1011 target, SIR1011 CDS locus, ubiquitin carboxyl-terminal hydrolase-related protein, AT5G51530.1 target gene, target site 3078~3100 (CDS)

<400> SEQUENCE: 341
acaaatattg ttcatcatat ta 22

<210> SEQ ID NO 342
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1011 target, SIR1011 CDS locus, F-box/RNI-like superfamily protein, AT5G67140.1 target gene, target site 772~794 (CDS)

<400> SEQUENCE: 342
tctagtgttg ctcatcatat tt 22

<210> SEQ ID NO 343
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1011 target, SIR1011 CDS locus, AP2-like ethylene-responsive transcription factor At1g16060 (AHRD V1 AP2L1_ARATH), Solyc02g093150.2.1 target gene, target site 1404~1426 (cDNA)

<400> SEQUENCE: 343
agcaatttgg ctcatcaaat ta 22

<210> SEQ ID NO 344
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR67 target, SIR2 LTR transposon locus, calcium-dependent protein kinase 2 (AHRD V1 B4FZS4_MAIZE), Solyc05g055050.1.1 target gene, target site 568~590 (cDNA)

<400> SEQUENCE: 344
tgctggtgtg attttcgtgg t 21

<210> SEQ ID NO 345
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR109 target, SIR3 LTR transposon locus, RNA-binding KH domain-containing protein, AT5G64390.1 target gene, target site 377~398 (CDS)

<400> SEQUENCE: 345
atcacgataa tcgcacaagc a 21

<210> SEQ ID NO 346
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR109 target, SIR3 LTR transposon locus, cell division protein kinase 13 (AHRD V1 CDK13_MOUSE), Solyc01g103350.2.1 target gene, target site 2540~2561 (cDNA)

<400> SEQUENCE: 346
tctacgaaaa tcgcagcagc a 21

<210> SEQ ID NO 347
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR109 target, SIR3 LTR transposon locus, subtilisin-like serine protease (AHRD V1 Q948Q4_ARATH), Solyc02g069630.2.1 target gene, target site 2706~2727 (cDNA)

<400> SEQUENCE: 347
tctatgaagg tcacaccagc a 21

<210> SEQ ID NO 348

<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR109 target, SIR3 LTR transposon locus, squamosa promoter-binding-like protein 11 (AHRD V1 B6TF72_MAIZE), Solyc05g015510.2.1 target gene, target site 3013~3034 (cDNA)

<400> SEQUENCE: 348
accatgcaaa tcagaccagc a 21

<210> SEQ ID NO 349
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR109 target, SIR3 LTR transposon locus, Tir-nbs-lrr, resistance protein, Solyc09g007710.2.1 target gene, target site 3351~3372 (cDNA)

<400> SEQUENCE: 349
tccatgtaaa tcacgccagc t 21

<210> SEQ ID NO 350
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR109 target, SIR3 LTR transposon locus, transcription elongation factor SPT6 (AHRD V1 A8NF94_COPC7), Solyc10g081020.1.1 target gene, target site 3688~3709 (cDNA)

<400> SEQUENCE: 350
accatgaaga tcgcactagc t 21

<210> SEQ ID NO 351
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1018, SIR8 intergenic region locus, chaperone DnaJ-domain superfamily protein, AT1G62970.1 target gene, target site 1017~1039 (CDS)

<400> SEQUENCE: 351
tgatgttgca tacccggctc gg 22

<210> SEQ ID NO 352
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1018 target, SIR8 intergenic region locus, chaperone DnaJ-domain superfamily protein, AT1G62970.1 target gene, target site 1017~1039 (CDS)

<400> SEQUENCE: 352
ctgagccggc taggcaatat ca 22

<210> SEQ ID NO 353
<211> LENGTH: 22
<212> TYPE: DNA
<213> ORGANISM: Artificial Sequence
<220> FEATURE:

<223> OTHER INFORMATION: synthetic Botrytis cinerea small RNA (sRNA)
Bc-siR1018 target, SIR8 intergenic region locus, ATP-dependent RNA
helicase A-like protein (AHRD V1 Q9FF84_ARATH), Solyc04g007510.2.1
target gene, target site 3230~3252 (cDNA)

<400> SEQUENCE: 353
tcgagcagga tatgcaacac ca 22

<210> SEQ ID NO 354
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR114, SIR2 LTR transposon locus, lupeol
synthase 2, AT1G78960.1 target gene, target site
1445~1467 (CDS)

<400> SEQUENCE: 354
tccagggtcc ttttggaata gg 22

<210> SEQ ID NO 355
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR114 target, SIR2 LTR transposon locus,
lupeol synthase 2, AT1G78960.1 target gene, target
site 1445~1467 (CDS)

<400> SEQUENCE: 355
catatttcca aaggagcctg ga 22

<210> SEQ ID NO 356
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR114 target, SIR2 LTR transposon locus, cycloartenol synthase
(AHRD V1 O82139_PANGI), Solyc12g006510.1.1 target gene, target
site 1377~1399 (cDNA)

<400> SEQUENCE: 356
catatttcaa aaggatcgtg ga 22

<210> SEQ ID NO 357
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1020, SIR1020 intergenic region locus,
1-aminocyclopropane-1-carboxylate synthase 4,
AT2G22810.1 target gene, target site 1176~1197 (CDS)

<400> SEQUENCE: 357
ttgccacgac gaaccaggac a 21

<210> SEQ ID NO 358
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR1020 target, SIR1020 intergenic region
locus, 1-aminocyclopropane-1-carboxylate synthase
4, AT2G22810.1 target gene, target site 1176~1197 (CDS)

<400> SEQUENCE: 358
tctcctggtt cgtcgtgcca t 21

<210> SEQ ID NO 359
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1020 target, SIR1020 intergenic region locus, mitochondrial carrier family (AHRD V1 C1MWU5_MICPS), Solyc04g005650.1.1 target gene, target site 337~358 (cDNA)

<400> SEQUENCE: 359
tttcttggct cgttgtggca g 21

<210> SEQ ID NO 360
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1020 target, SIR1020 intergenic region locus, disease resistance response/dirigent-like protein (AHRD V1 Q0WPQ6_ARATH), Solyc09g091210.2.1 target gene, target site 861~882 (cDNA)

<400> SEQUENCE: 360
tgtcttgttt cattgtggca a 21

<210> SEQ ID NO 361
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1016, SIR1 LTR transposon locus, phosphoglucomutase/phosphomannomutase family protein, AT1G23190.1 target gene, target site 1753~1774 (CDS)

<400> SEQUENCE: 361
ttgagagcta agtcaaacgg a 21

<210> SEQ ID NO 362
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1016 target, SIR1 LTR transposon locus, phosphoglucomutase/phosphomannomutase family protein, AT1G23190.1 target gene, target site 1753~1774 (CDS)

<400> SEQUENCE: 362
tctggttgac ttagctctaa a 21

<210> SEQ ID NO 363
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1016 target, SIR1 LTR transposon locus, protein of unknown function (DUF3049), AT5G19260.1 target gene, target site 184~205 (CDS)

<400> SEQUENCE: 363
accatttggt ttagctctca a 21

<210> SEQ ID NO 364
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1016 target, SIR1 LTR transposon locus, TBC1 domain family member CG11727 (AHRD V1 Y1727_DROME), Solyc01g101090.2.1 target gene, target site 1040~1061 (cDNA)

<400> SEQUENCE: 364
cccgtttcac ttggctctca g 21

<210> SEQ ID NO 365
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1016 target, SIR1 LTR transposon locus, PPPDE peptidase domain-containing protein 1 (AHRD V1 PPDE1_XENLA), Solyc02g082060.1.1 target gene, target site 497~518 (cDNA)

<400> SEQUENCE: 365
tccggttgat tttgctctca a 21

<210> SEQ ID NO 366
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1016 target, SIR1 LTR transposon locus, unknown protein (AHRD V1), Solyc04g076690.2.1 target gene, target site 623~644 (cDNA)

<400> SEQUENCE: 366
tttgtttgtc ttagctttca a 21

<210> SEQ ID NO 367
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1003, SIR1003 LTR transposon locus, basic helix-loop-helix (bHLH) DNA-binding superfamily protein, AT2G31220.1 target gene, target site 223~244 (CDS)

<400> SEQUENCE: 367
ggtaaccaga actggcgatg c 21

<210> SEQ ID NO 368
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR1003 target, SIR1003 LTR transposon locus, basic helix-loop-helix (bHLH) DNA-binding superfamily protein, AT2G31220.1 target gene, target site 223~244 (CDS)

<400> SEQUENCE: 368
ccaccgcaag ttctggttgc c 21

<210> SEQ ID NO 369
<211> LENGTH: 21

<212> TYPE: DNA
<213> ORGANISM: Artificial Sequence
<220> FEATURE:
<223> OTHER INFORMATION: synthetic Botrytis cinerea small RNA (sRNA) Bc-siR1003 target, SIR1003 LTR transposon locus, potassium transporter (AHRD V1 Q1T761_PHRAU), Solyc06g050170.2.1 target gene, target site 1771~1792 (cDNA)

<400> SEQUENCE: 369
gcattgtccg ttatggttac c 21

<210> SEQ ID NO 370
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR124, SIR1 LTR transposon locus, methionine aminopeptidase 1B, AT1G13270.1 target gene, target site 140~161 (CDS)

<400> SEQUENCE: 370
tgaccagagc tccggggagg t 21

<210> SEQ ID NO 371
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR124 target, SIR1 LTR transposon locus, methionine aminopeptidase 1B, AT1G13270.1 target gene, target site 140~161 (CDS)

<400> SEQUENCE: 371
gctttctcgg agctccggtc a 21

<210> SEQ ID NO 372
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR124 target, SIR1 LTR transposon locus, tetratricopeptide repeat (TPR)-like superfamily protein, AT3G59040.1 target gene, target site 1252~1273 (CDS)

<400> SEQUENCE: 372
attttcccgg acctctggtc g 21

<210> SEQ ID NO 373
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR124 target, SIR1 LTR transposon locus, coiled-coil domain-containing protein 109A (AHRD V1 C109A_MOUSE), Solyc02g065550.2.1 target gene, target site 280~301 (cDNA)

<400> SEQUENCE: 373
acctctccgg atctccggtc a 21

<210> SEQ ID NO 374
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)

Bc-siR124 target, SIR1 LTR transposon locus, Ycf1 (fragment)
(AHRD V1 A6YA36_9MAGN), Solyc04g045540.1.1
target gene, target site 127~148 (cDNA)

<400> SEQUENCE: 374
tccttctccg agctctggtt a 21

<210> SEQ ID NO 375
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR124 target, SIR1 LTR transposon locus, Ycf1 (fragment)
(AHRD V1 A6Y9X6_HAMJA), Solyc05g047440.1.1
target gene, target site 127~148 (cDNA)

<400> SEQUENCE: 375
tccttctccg agctctggtt a 21

<210> SEQ ID NO 376
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR124 target, SIR1 LTR transposon locus,
unknown protein (AHRD V1), Solyc05g055360.2.1
target gene, target site 1577~1598 (cDNA)

<400> SEQUENCE: 376
tcctccctcg agctttggtc a 21

<210> SEQ ID NO 377
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR124 target, SIR1 LTR transposon locus, hypothetical
chloroplast RF1 (AHRD V1 C3UP30_9MAGN), contains Interpro domain
IPR008896 Ycf1, Solyc10g062330.1.1 target gene, target site 82~103
(cDNA)

<400> SEQUENCE: 377
tccttctccg agctctggtt a 21

<210> SEQ ID NO 378
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR124 target, SIR1 LTR transposon locus, hypothetical
chloroplast RF1 (AHRD V1 C3UP30_9MAGN), contains Interpro domain
IPR008896 Ycf1, Solyc11g021310.1.1 target gene, target site
127~148 (cDNA)

<400> SEQUENCE: 378
tccttctccg agctctggtt a 21

<210> SEQ ID NO 379
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR127, SIR2 LTR transposon locus, G-box
regulating factor 6, AT5G10450.3 target gene, target site 932~954 (3'UTR)

<400> SEQUENCE: 379
tgttttgaca tgttgtttga cg 22

<210> SEQ ID NO 380
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR127 target, SIR2 LTR transposon locus, G-box regulating factor 6, AT5G10450.3 target gene, target site 932~954 (3'UTR)

<400> SEQUENCE: 380
catcaaagaa catgttaaaa ct 22

<210> SEQ ID NO 381
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR127 target, SIR2 LTR transposon locus, Os06g0207500 protein (fragment) (AHRD V1 Q0DDQ9_ORYSJ), Solyc01g068430.1.1 target gene, target site 871~893 (cDNA)

<400> SEQUENCE: 381
agttacaaaa catgtcaaag ca 22

<210> SEQ ID NO 382
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR128, SIR15 intergenic region locus, protein kinase superfamily protein, AT1G48210.1 target gene, target site 1343~1364 (3'UTR)

<400> SEQUENCE: 382
tacagaatac agaatcaaga t 21

<210> SEQ ID NO 383
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR128 target, SIR15 intergenic region locus, protein kinase superfamily protein, AT1G48210.1 target gene, target site 1343~1364 (3'UTR)

<400> SEQUENCE: 383
attttggttc tgtattgtgt a 21

<210> SEQ ID NO 384
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR128 target, SIR15 intergenic region locus, unknown protein, hypothetical protein, uncharacterized protein, AT2G23348.1 target gene, target site 402~423 (3'UTR)

<400> SEQUENCE: 384

-continued

```
atctagtttc tttattctgt a                                              21


<210> SEQ ID NO 385
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR128 target, SIR15 intergenic region locus,
      DNA (cytosine-5-)-methyltransferase family
      protein, AT4G08990.1 target gene, target site 2536~2557 (CDS)

<400> SEQUENCE: 385

gtcttggttc tggattctgt a                                              21


<210> SEQ ID NO 386
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR128 target, SIR15 intergenic region locus,
      DNA methyltransferase 2, AT4G14140.1 target gene,
      target site 2560~2581 (CDS)

<400> SEQUENCE: 386

gtctaggttc tggattctgt a                                              21


<210> SEQ ID NO 387
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR128 target, SIR15 intergenic region locus,
      unknown protein (AHRD V1), Solyc04g005530.2.1
      target gene, target site 1196~1217 (cDNA)

<400> SEQUENCE: 387

gtctttactt tgtattttgt a                                              21


<210> SEQ ID NO 388
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR128 target, SIR15 intergenic region locus, F-box family
      protein (AHRD V1 D7L4T6_ARALY), Solyc11g012550.1.1 target gene,
      target site 49~70 (cDNA)

<400> SEQUENCE: 388

atattgatcc tgtattccgt g                                              21


<210> SEQ ID NO 389
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR130, SIR2 LTR transposon locus, unknown
      protein, hypothetical protein, uncharacterized
      protein, AT2G42340.1 target gene, target site 486~508 (CDS)

<400> SEQUENCE: 389

tgttcaacaa gtctatattg gt                                             22


<210> SEQ ID NO 390
```

<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR130 target, SIR2 LTR transposon locus, unknown protein, hypothetical protein, uncharacterized protein, AT2G42340.1 target gene, target site 486~508 (CDS)

<400> SEQUENCE: 390
actactatgg acttgttgaa aa 22

<210> SEQ ID NO 391
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR130 target, SIR2 LTR transposon locus, ribosomal protein S27 (AHRD V1 Q3HVK9_SOLTU), Solyc01g008080.2.1 target gene, target site 2214~2236 (cDNA)

<400> SEQUENCE: 391
aacgatgtcg acttgttgaa cc 22

<210> SEQ ID NO 392
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR130 target, SIR2 LTR transposon locus, ATP-dependent RNA helicase DBP4 (AHRD V1 C1GZM0_PARBA), Solyc01g095740.2.1 target gene, target site 2485~2507 (cDNA)

<400> SEQUENCE: 392
acaagtacag acttgttgaa ct 22

<210> SEQ ID NO 393
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1004, SIR15 intergenic region locus, serine carboxypeptidase-like 27, AT3G07990.1 target gene, target site 72~94 (CDS)

<400> SEQUENCE: 393
aatgattgga aggaaggagt tc 22

<210> SEQ ID NO 394
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1004 target, SIR15 intergenic region locus, serine carboxypeptidase-like 27, AT3G07990.1 target gene, target site 72~94 (CDS)

<400> SEQUENCE: 394
ttactctttc cttctaatca tt 22

<210> SEQ ID NO 395
<211> LENGTH: 22
<212> TYPE: DNA
<213> ORGANISM: Artificial Sequence
<220> FEATURE:

<223> OTHER INFORMATION: synthetic Botrytis cinerea small RNA (sRNA) Bc-siR1004 target, SIR15 intergenic region locus, unknown protein, hypothetical protein, uncharacterized protein, AT4G21740.1 target gene, target site 99~121 (CDS)

<400> SEQUENCE: 395
gaattacgtc cttccgatca tg 22

<210> SEQ ID NO 396
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR1004 target, SIR15 intergenic region locus, genomic DNA chromosome 5 TAC clone K21L19 (AHRD V1 Q9FGT4_ARATH), Solyc07g042910.2.1 target gene, target site 1930~1952 (cDNA)

<400> SEQUENCE: 396
gaactatttg ctttcaatca tt 22

<210> SEQ ID NO 397
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144, SIR6 CDS (spurious gene) locus, arabinogalactan protein 16, AT2G46330.1 target gene, target site 471~492 (3'UTR)

<400> SEQUENCE: 397
taacatgatg attaatttat c 21

<210> SEQ ID NO 398
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144 target, SIR6 CDS (spurious gene) locus, arabinogalactan protein 16, AT2G46330.1 target gene, target site 471~492 (3'UTR)

<400> SEQUENCE: 398
gttaatttca tcatcatgtt c 21

<210> SEQ ID NO 399
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144 target, SIR6 CDS (spurious gene) locus, A20/AN1-like zinc finger family protein, AT4G12040.2 target gene, target site 513~534 (5'UTR)

<400> SEQUENCE: 399
ggttatttga ttatcatgtt a 21

<210> SEQ ID NO 400
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144 target, SIR6 CDS (spurious gene) locus, At4g14280-like protein (fragment) (AHRD V1 C7FD87_ARALP), Solyc01g080260.2.1 target gene, target site 2174~2195 (cDNA)

<400> SEQUENCE: 400
gaagaatcaa tcatcatgtt c 21

<210> SEQ ID NO 401
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144 target, SIR6 CDS (spurious gene) locus, RNA polymerase Rpb1 C-terminal repeat domain-containing protein (AHRD V1 C5GU31_AJEDR), Solyc01g098240.1.1 target gene, target site 3823~3844 (cDNA)

<400> SEQUENCE: 401
cagaaattga tcttcatgtt a 21

<210> SEQ ID NO 402
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144 target, SIR6 CDS (spurious gene) locus, peroxisomal targeting signal 1 receptor (AHRD V1 Q9ZTK6_TOBAC), Solyc10g005650.2.1 target gene, target site 814~835 (cDNA)

<400> SEQUENCE: 402
tagaaattga taatcatgtt a 21

<210> SEQ ID NO 403
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR144 target, SIR6 CDS (spurious gene) locus, pollen-specific kinase partner protein-like protein (fragment) (AHRD V1 Q5DK68_SOLLC), Solyc12g007150.1.1 target gene, target site 73~94 (cDNA)

<400> SEQUENCE: 403
gacatactca tcatcatgtt g 21

<210> SEQ ID NO 404
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR137, SIR2 LTR transposon locus, structural constituent of ribosome, AT1G22110.1 target gene, target site 1283~1304 (3'UTR)

<400> SEQUENCE: 404
tacgattcta ttctagtagt a 21

<210> SEQ ID NO 405
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR137 target, SIR2 LTR transposon locus, structural constituent of ribosome, AT1G22110.1 target gene, target site 1283~1304 (3'UTR)

<400> SEQUENCE: 405
tactaataaa atcgaatcgt a 21

<210> SEQ ID NO 406
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR137 target, SIR2 LTR transposon locus, disease resistance protein (TIR-NBS-LRR class), putative, AT3G25510.1 target gene, target site 5473~5494 (CDS)

<400> SEQUENCE: 406
gattactaga atgggatcgt t 21

<210> SEQ ID NO 407
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR137 target, SIR2 LTR transposon locus, dehydration-responsive family protein (AHRD V1 D7LF23_ARALY), Solyc04g063230.2.1 target gene, target site 1354~1375 (cDNA)

<400> SEQUENCE: 407
ttctcctaga attgaatcgt g 21

<210> SEQ ID NO 408
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR140, SIR8 intergenic region locus, SH3 domain-containing protein, AT2G07360.1 target gene, target site 3291~3313 (CDS)

<400> SEQUENCE: 408
ttgattttgc cgtttcgtat gt 22

<210> SEQ ID NO 409
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR140 target, SIR8 intergenic region locus, SH3 domain-containing protein, AT2G07360.1 target gene, target site 3291~3313 (CDS)

<400> SEQUENCE: 409
tcacaagcaa cggcaaaatc ag 22

<210> SEQ ID NO 410
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR140 target, SIR8 intergenic region locus, transferase family protein (AHRD V1 D7KBT0_ARALY), Solyc04g080720.2.1 target gene, target site 1084~1106 (cDNA)

<400> SEQUENCE: 410
acgaacgata cggtaaaatc aa 22

<210> SEQ ID NO 411
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR140 target, SIR8 intergenic region locus, acetyl-coenzyme A
synthetase (AHRD V1 Q2J3D0_RHOP2), Solyc07g017860.2.1 target
gene, target site 436~458 (cDNA)

<400> SEQUENCE: 411
acattcgcaa tggcaaaatt aa 22

<210> SEQ ID NO 412
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
Bc-siR140 target, SIR8 intergenic region locus, xyloglucan
endotransglucosylase/hydrolase 8 (AHRD V1 C0IRG7_ACTDE),
Solyc12g098610.1.1 target gene, target site 641~663 (cDNA)

<400> SEQUENCE: 412
agatgcaaaa tggcaaaatc aa 22

<210> SEQ ID NO 413
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR141, SIR1 LTR transposon locus, major
facilitator superfamily protein, AT3G01350.1
target gene, target site 1191~1212 (CDS)

<400> SEQUENCE: 413
tagaaacatt cggacttctg t 21

<210> SEQ ID NO 414
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR141 target, SIR1 LTR transposon locus, major
facilitator superfamily protein, AT3G01350.1
target gene, target site 1191~1212 (CDS)

<400> SEQUENCE: 414
atgggagtcg gaatgtttct a 21

<210> SEQ ID NO 415
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR141 target, SIR1 LTR transposon locus, ATP-binding cassette
(ABC) transporter 17 (AHRD V1 Q4H493_RAT), Solyc03g113070.2.1
target gene, target site 1358~1379 (cDNA)

<400> SEQUENCE: 415
acataattcc gaatatttct g 21

<210> SEQ ID NO 416
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR156, SIR18 intergenic region locus, unknown
      protein, hypothetical protein, uncharacterized
      protein, AT5G45973.1 target gene, target site 62~83 (CDS)

<400> SEQUENCE: 416
tgggatggga tgggattggg a                                              21

<210> SEQ ID NO 417
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR156 target, SIR18 intergenic region locus, unknown protein,
      hypothetical protein, uncharacterized protein, AT5G45973.1 target
      gene, target site 62~83 (CDS)

<400> SEQUENCE: 417
tccctatctc atcctatcgc a                                              21

<210> SEQ ID NO 418
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR156 target, SIR18 intergenic region locus, serine/threonine
      protein kinase-like (AHRD V1 Q5XWQ1_SOLTU), Solyc01g112220.2.1
      target gene, target site 163~184 (cDNA)

<400> SEQUENCE: 418
tctcaatctc atcccatccc t                                              21

<210> SEQ ID NO 419
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR156 target, SIR18 intergenic region locus,
      exostosin family protein (AHRD V1 D7LPB7_ARALY),
      Solyc12g019040.1.1 target gene, target site 100~121 (cDNA)

<400> SEQUENCE: 419
tcacattttc atctcatccc a                                              21

<210> SEQ ID NO 420
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
      Bc-siR156 target, SIR18 intergenic region locus,
      unknown protein (AHRD V1), Solyc12g096410.1.1
      target gene, target site 54~75 (cDNA)

<400> SEQUENCE: 420
tctccatcac atcccattcc t                                              21

<210> SEQ ID NO 421
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA)
      Bc-siR161, SIR1 LTR transposon locus, unknown
      protein, hypothetical protein, uncharacterized protein, AT2G16270.1 target gene, target site 295~317 (CDS)

<400> SEQUENCE: 421
taggcatcat tctcttcctt gg 22

<210> SEQ ID NO 422
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, unknown protein, hypothetical protein, uncharacterized protein, AT2G16270.1 target gene, target site 295~317 (CDS)

<400> SEQUENCE: 422
ccaaggaaga gagtgttgtc tg 22

<210> SEQ ID NO 423
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, plant glycogenin-like starch initiation protein 1, AT3G18660.1 target gene, target site 1168~1190 (CDS)

<400> SEQUENCE: 423
ctaaggcaga gaaagatgct ta 22

<210> SEQ ID NO 424
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, ATPase E1-E2 type family protein/haloacid dehalogenase-like hydrolase family protein, AT3G63380.1 target gene, target site 1416~1438 (CDS)

<400> SEQUENCE: 424
tccatgaaga gaatgatgtc tg 22

<210> SEQ ID NO 425
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, endoplasmic reticulum-adenine nucleotide transporter 1, AT5G17400.1 target gene, target site 863~885 (CDS)

<400> SEQUENCE: 425
cttaggagga gaatgatgct ta 22

<210> SEQ ID NO 426
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, response regulator 8 (AHRD V1 Q9AV93_MAIZE), Solyc03g083340.1.1 target gene, target site 1152~1174 (cDNA)

<400> SEQUENCE: 426
tcaagtaggg gaatgatgcc ta 22

<210> SEQ ID NO 427
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, dehydration-responsive protein-like (AHRD V1 Q653G1_ORYSJ), Solyc04g005430.2.1 target gene, target site 1312~1334 (cDNA)

<400> SEQUENCE: 427
gcaaagaagg gaatcatgcc ta 22

<210> SEQ ID NO 428
<211> LENGTH: 22
<212> TYPE: DNA
<213> ORGANISM: Artificial Sequence
<220> FEATURE:
<223> OTHER INFORMATION: synthetic Botrytis cinerea small RNA (sRNA) Bc-siR161 target, SIR1 LTR transposon locus, glycogenin-like protein (AHRD V1 Q5NA53_ORYSJ), target gene, target site 892~914 (cDNA)

<400> SEQUENCE: 428
ctaaagcaga gaaagatgcc ta 22

<210> SEQ ID NO 429
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR163, SIR8 intergenic region locus, GPI transamidase component Gpi16 subunit family protein, AT3G07140.1 target gene, target site 1754~1775 (CDS)

<400> SEQUENCE: 429
tgatccaaag tacaatgtgt a 21

<210> SEQ ID NO 430
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR163 target, SIR8 intergenic region locus, GPI transamidase component Gpi16 subunit family protein, AT3G07140.1 target gene, target site 1754~1775 (CDS)

<400> SEQUENCE: 430
ttcgcattgt attttggatc a 21

<210> SEQ ID NO 431
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA) Bc-siR163 target, SIR8 intergenic region locus, AT hook motif DNA-binding family protein, AT5G46640.1 target gene, target site 1159~1180 (CDS)

<400> SEQUENCE: 431
aacatgttga actttggatc a 21

<210> SEQ ID NO 432

<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR163 target, SIR8 intergenic region locus,
subtilase family protein, AT5G59810.1 target gene,
target site 293~314 (CDS)

<400> SEQUENCE: 432
tacatagtgt acttgggatc t 21

<210> SEQ ID NO 433
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR163 target, SIR8 intergenic region locus, small nuclear
ribonucleoprotein Sm D1 (AHRD V1 B6TXH2_MAIZE), Solyc06g084310.2.1
target gene, target site 598~619 (cDNA)

<400> SEQUENCE: 433
tgcacaattt attttggatc t 21

<210> SEQ ID NO 434
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR163 target, SIR8 intergenic region locus, AT-hook motif
nuclear localized protein 1 (AHRD V1 Q8VYJ2_ARATH),
Solyc08g079630.2.1 target gene, target site 1618~1639 (cDNA)

<400> SEQUENCE: 434
tacattttgt actttggacc a 21

<210> SEQ ID NO 435
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
Bc-siR1001, SIR1001 CDS locus, replication factor
C subunit 3, AT1G77470.1 target gene, target site
1437~1460 (3'UTR)

<400> SEQUENCE: 435
tcacatgatt attaaaacat aat 23

<210> SEQ ID NO 436
<211> LENGTH: 23
<212> TYPE: DNA
<213> ORGANISM: Artificial Sequence
<220> FEATURE:
<223> OTHER INFORMATION: synthetic Botrytis cinerea small RNA (sRNA)
Bc-siR1001 target, SIR1001 CDS locus, replication
factor C subunit 3, AT1G77470.1 target gene,
target site 1437~1460 (3'UTR)

<400> SEQUENCE: 436
attatgtttt aatgatcttg tgg 23

<210> SEQ ID NO 437
<211> LENGTH: 23
<212> TYPE: DNA
<213> ORGANISM: Artificial Sequence
<220> FEATURE:

<223> OTHER INFORMATION: synthetic Botrytis cinerea small RNA (sRNA)
      Bc-siR1001 target, SIR1001 CDS locus, mitochondrial import
      receptor subunit TOM34 (AHRD V1 TOM34_RAT), Solyc04g055110.2.1
      target gene, target site 1474~1497 (cDNA)

<400> SEQUENCE: 437
attgtgtctt cataatcctg tga 23

<210> SEQ ID NO 438
<211> LENGTH: 80
<212> TYPE: DNA
<213> ORGANISM: Artificial Sequence
<220> FEATURE:
<223> OTHER INFORMATION: synthetic 3.2-STTMSwa48ntlink-PF forward primer
      for constructing short tandem target mimic (STTM)
      against Botrytis cinerea small RNA (sRNA)
      Bc-siR3.2

<400> SEQUENCE: 438
gccatttaaa tatggtctaa agaagaagaa tacctacaag atctaccaca atgtagaatt 60
cggtacgctg aaatcaccag 80

<210> SEQ ID NO 439
<211> LENGTH: 80
<212> TYPE: DNA
<213> ORGANISM: Artificial Sequence
<220> FEATURE:
<223> OTHER INFORMATION: synthetic 3.2-STTMSwa48ntlink-PR reverse primer
      for constructing short tandem target mimic (STTM)
      against Botrytis cinerea small RNA (sRNA)
      Bc-siR3.2

<400> SEQUENCE: 439
gccatttaaa ttagaccata acaacaacaa ctacattgtg gtagatcttg taggtaagct 60
tgggctgtcc tctccaaatg 80

<210> SEQ ID NO 440
<211> LENGTH: 80
<212> TYPE: DNA
<213> ORGANISM: Artificial Sequence
<220> FEATURE:
<223> OTHER INFORMATION: synthetic 3.1-STTMSwa48ntlink-PF forward primer
      for constructing short tandem target mimic (STTM)
      against Botrytis cinerea small RNA (sRNA)
      Bc-siR3.1

<400> SEQUENCE: 440
gccatttaaa tatggtctaa agaagaagaa tgcccaccta cactaagatc cacaagaatt 60
cggtacgctg aaatcaccag 80

<210> SEQ ID NO 441
<211> LENGTH: 80
<212> TYPE: DNA
<213> ORGANISM: Artificial Sequence
<220> FEATURE:
<223> OTHER INFORMATION: synthetic 3.1-STTMSwa49ntlink-PR reverse primer
      for constructing short tandem target mimic (STTM)
      against Botrytis cinerea small RNA (sRNA)
      Bc-siR3.1

<400> SEQUENCE: 441
gccatttaaa ttagaccata acaacaacaa cttgtggatc ttagtgtagg tgggcaagct 60
tgggctgtcc tctccaaatg 80

<210> SEQ ID NO 442

<211> LENGTH: 80
<212> TYPE: DNA
<213> ORGANISM: Artificial Sequence
<220> FEATURE:
<223> OTHER INFORMATION: synthetic 5-STTMSwa48ntlink-PF forward primer
for constructing short tandem target mimic (STTM)
against Botrytis cinerea small RNA (sRNA) Bc-siR5

<400> SEQUENCE: 442
gccatttaaa tatggtctaa agaagaagaa taagtataca ttctaccgag tcaaagaatt 60
cggtacgctg aaatcaccag 80

<210> SEQ ID NO 443
<211> LENGTH: 80
<212> TYPE: DNA
<213> ORGANISM: Artificial Sequence
<220> FEATURE:
<223> OTHER INFORMATION: synthetic 5-STTMSwa49ntlink-PR reverse primer
for constructing short tandem target mimic (STTM)
against Botrytis cinerea small RNA (sRNA) Bc-siR5

<400> SEQUENCE: 443
gccatttaaa ttagaccata acaacaacaa ctttgactcg gtagaatgta tacttaagct 60
tgggctgtcc tctccaaatg 80

<210> SEQ ID NO 444
<211> LENGTH: 81
<212> TYPE: DNA
<213> ORGANISM: Artificial Sequence
<220> FEATURE:
<223> OTHER INFORMATION: synthetic SiR1-STTMSwa48ntlink-PF forward
primer for constructing short tandem target mimic (STTM)
against Botrytis cinerea small RNA (sRNA) SiR1

<400> SEQUENCE: 444
gccatttaaa tatggtctaa agaagaagaa tcagaattct actctacttg cttcgagaat 60
tcggtacgct gaaatcacca g 81

<210> SEQ ID NO 445
<211> LENGTH: 81
<212> TYPE: DNA
<213> ORGANISM: Artificial Sequence
<220> FEATURE:
<223> OTHER INFORMATION: synthetic SiR1-STTMSwa49ntlink-PR reverse
primer for constructing short tandem target mimic (STTM)
against Botrytis cinerea small RNA (sRNA) SiR1

<400> SEQUENCE: 445
gccatttaaa ttagaccata acaacaacaa ctcgaagcaa gtagagtaga attctgaagc 60
ttgggctgtc ctctccaaat g 81

<210> SEQ ID NO 446
<211> LENGTH: 80
<212> TYPE: DNA
<213> ORGANISM: Artificial Sequence
<220> FEATURE:
<223> OTHER INFORMATION: synthetic 1010-STTMSwa48ntlink-PF forward
primer for constructing short tandem target mimic (STTM)
against Botrytis cinerea small RNA (sRNA) siR1010

<400> SEQUENCE: 446
gccatttaaa tatggtctaa agaagaagaa tagcaatcaa aactaattcc cccgagaatt 60
cggtacgctg aaatcaccag 80

-continued

<210> SEQ ID NO 447
<211> LENGTH: 80
<212> TYPE: DNA
<213> ORGANISM: Artificial Sequence
<220> FEATURE:
<223> OTHER INFORMATION: synthetic 1010-STTMSwa48ntlink-PR reverse
primer for constructing short tandem target mimic (STTM)
against Botrytis cinerea small RNA (sRNA) siR1010

<400> SEQUENCE: 447
gccatttaaa ttagaccata acaacaacaa ctcgggggaa ttagttttga ttgctaagct 60
tgggctgtcc tctccaaatg 80

<210> SEQ ID NO 448
<211> LENGTH: 81
<212> TYPE: DNA
<213> ORGANISM: Artificial Sequence
<220> FEATURE:
<223> OTHER INFORMATION: synthetic 1008-STTMSwa48ntlink-PF forward
primer for constructing short tandem target mimic (STTM)
against Botrytis cinerea small RNA (sRNA) siR1008

<400> SEQUENCE: 448
gccatttaaa tatggtctaa agaagaagaa tgcataaact gatctacatc atcacagaat 60
tcggtacgct gaaatcacca g 81

<210> SEQ ID NO 449
<211> LENGTH: 81
<212> TYPE: DNA
<213> ORGANISM: Artificial Sequence
<220> FEATURE:
<223> OTHER INFORMATION: synthetic 1008-STTMSwa48ntlink-PR reverse
primer for constructing short tandem target mimic (STTM)
against Botrytis cinerea small RNA (sRNA) siR1008

<400> SEQUENCE: 449
gccatttaaa ttagaccata acaacaacaa ctgtgatgat gtagatcagt ttatgcaagc 60
ttgggctgtc ctctccaaat g 81

<210> SEQ ID NO 450
<211> LENGTH: 81
<212> TYPE: DNA
<213> ORGANISM: Artificial Sequence
<220> FEATURE:
<223> OTHER INFORMATION: synthetic 9-STTMSwa48ntlink-PF forward primer
for constructing short tandem target mimic (STTM)
against Botrytis cinerea small RNA (sRNA) siR9

<400> SEQUENCE: 450
gccatttaaa tatggtctaa agaagaagaa ttctaaaaat gctctacatc ataaaagaat 60
tcggtacgct gaaatcacca g 81

<210> SEQ ID NO 451
<211> LENGTH: 81
<212> TYPE: DNA
<213> ORGANISM: Artificial Sequence
<220> FEATURE:
<223> OTHER INFORMATION: synthetic 9-STTMSwa48ntlink-PR reverse primer
for constructing short tandem target mimic (STTM)
against Botrytis cinerea small RNA (sRNA) siR9

<400> SEQUENCE: 451
gccatttaaa ttagaccata acaacaacaa cttttatgat gtagagcatt tttagaaagc 60
ttgggctgtc ctctccaaat g 81

<210> SEQ ID NO 452
<211> LENGTH: 80
<212> TYPE: DNA
<213> ORGANISM: Artificial Sequence
<220> FEATURE:
<223> OTHER INFORMATION: synthetic 10-STTMSwa48ntlink-PF forward primer
      for constructing short tandem target mimic (STTM)
      against Botrytis cinerea small RNA (sRNA) siR10

<400> SEQUENCE: 452
gccatttaaa tatggtctaa agaagaagaa tagcacccta cactaaccta gaaaagaatt     60
cggtacgctg aaatcaccag                                                 80

<210> SEQ ID NO 453
<211> LENGTH: 80
<212> TYPE: DNA
<213> ORGANISM: Artificial Sequence
<220> FEATURE:
<223> OTHER INFORMATION: synthetic 10-STTMSwa48ntlink-PR reverse primer
      for constructing short tandem target mimic (STTM)
      against Botrytis cinerea small RNA (sRNA) siR10

<400> SEQUENCE: 453
gccatttaaa ttagaccata acaacaacaa cttttctagg ttagtgtagg gtgctaagct     60
tgggctgtcc tctccaaatg                                                 80

<210> SEQ ID NO 454
<211> LENGTH: 80
<212> TYPE: DNA
<213> ORGANISM: Artificial Sequence
<220> FEATURE:
<223> OTHER INFORMATION: synthetic 18-STTMSwa48ntlink-PF forward primer
      for constructing short tandem target mimic (STTM)
      against Botrytis cinerea small RNA (sRNA) siR18

<400> SEQUENCE: 454
gccatttaaa tatggtctaa agaagaagaa ttgatcgact ctctagtttt ggctagaatt     60
cggtacgctg aaatcaccag                                                 80

<210> SEQ ID NO 455
<211> LENGTH: 80
<212> TYPE: DNA
<213> ORGANISM: Artificial Sequence
<220> FEATURE:
<223> OTHER INFORMATION: synthetic 18-STTMSwa48ntlink-PR reverse primer
      for constructing short tandem target mimic (STTM)
      against Botrytis cinerea small RNA (sRNA) siR18

<400> SEQUENCE: 455
gccatttaaa ttagaccata acaacaacaa ctagccaaaa ctagagagtc gatcaaagct     60
tgggctgtcc tctccaaatg                                                 80

<210> SEQ ID NO 456
<211> LENGTH: 81
<212> TYPE: DNA
<213> ORGANISM: Artificial Sequence
<220> FEATURE:
<223> OTHER INFORMATION: synthetic 15-STTMSwa48ntlink-PF forward primer
      for constructing short tandem target mimic (STTM)
      against Botrytis cinerea small RNA (sRNA) siR15

<400> SEQUENCE: 456
gccatttaaa tatggtctaa agaagaagaa ttcaaacaac aagctagttc aacacagaat     60
tcggtacgct gaaatcacca g                                               81

<210> SEQ ID NO 457
<211> LENGTH: 81
<212> TYPE: DNA
<213> ORGANISM: Artificial Sequence
<220> FEATURE:
<223> OTHER INFORMATION: synthetic 15-STTMSwa48ntlink-PR reverse primer for constructing short tandem target mimic (STTM) against Botrytis cinerea small RNA (sRNA) siR15

<400> SEQUENCE: 457
gccatttaaa ttagaccata acaacaacaa ctgtgttgaa ctagcttgtt gtttgaaagc 60
ttgggctgtc ctctccaaat g 81

<210> SEQ ID NO 458
<211> LENGTH: 80
<212> TYPE: DNA
<213> ORGANISM: Artificial Sequence
<220> FEATURE:
<223> OTHER INFORMATION: synthetic 17-STTMSwa48ntlink-PF forward primer for constructing short tandem target mimic (STTM) against Botrytis cinerea small RNA (sRNA) siR17

<400> SEQUENCE: 458
gccatttaaa tatggtctaa agaagaagaa tccagtgcca ttctacatca ttttagaatt 60
cggtacgctg aaatcaccag 80

<210> SEQ ID NO 459
<211> LENGTH: 80
<212> TYPE: DNA
<213> ORGANISM: Artificial Sequence
<220> FEATURE:
<223> OTHER INFORMATION: synthetic 17-STTMSwa48ntlink-PR reverse primer for constructing short tandem target mimic (STTM) against Botrytis cinerea small RNA (sRNA) siR17

<400> SEQUENCE: 459
gccatttaaa ttagaccata acaacaacaa ctaaaatgat gtagaatggc actggaagct 60
tgggctgtcc tctccaaatg 80

<210> SEQ ID NO 460
<211> LENGTH: 80
<212> TYPE: DNA
<213> ORGANISM: Artificial Sequence
<220> FEATURE:
<223> OTHER INFORMATION: synthetic 22-STTMSwa48ntlink-PF forward primer for constructing short tandem target mimic (STTM) against Botrytis cinerea small RNA (sRNA) siR22

<400> SEQUENCE: 460
gccatttaaa tatggtctaa agaagaagaa tactacaccc ttctagacca cgttagaatt 60
cggtacgctg aaatcaccag 80

<210> SEQ ID NO 461
<211> LENGTH: 80
<212> TYPE: DNA
<213> ORGANISM: Artificial Sequence
<220> FEATURE:
<223> OTHER INFORMATION: synthetic 22-STTMSwa48ntlink-PR reverse primer for constructing short tandem target mimic (STTM) against Botrytis cinerea small RNA (sRNA) siR22

<400> SEQUENCE: 461
gccatttaaa ttagaccata acaacaacaa ctaacgtggt ctagaagggt gtagtaagct 60
tgggctgtcc tctccaaatg 80

<210> SEQ ID NO 462
<211> LENGTH: 81
<212> TYPE: DNA
<213> ORGANISM: Artificial Sequence
<220> FEATURE:
<223> OTHER INFORMATION: synthetic 24-STTMSwa48ntlink-PF forward primer for constructing short tandem target mimic (STTM) against Botrytis cinerea small RNA (sRNA) siR24

<400> SEQUENCE: 462
gccatttaaa tatggtctaa agaagaagaa tgtcaaacag agactaggac caatcagaat 60
tcggtacgct gaaatcacca g 81

<210> SEQ ID NO 463
<211> LENGTH: 81
<212> TYPE: DNA
<213> ORGANISM: Artificial Sequence
<220> FEATURE:
<223> OTHER INFORMATION: synthetic 24-STTMSwa48ntlink-PR reverse primer for constructing short tandem target mimic (STTM) against Botrytis cinerea small RNA (sRNA) siR24

<400> SEQUENCE: 463
gccatttaaa ttagaccata acaacaacaa ctgattggtc ctagtctctg tttgacaagc 60
ttgggctgtc ctctccaaat g 81

<210> SEQ ID NO 464
<211> LENGTH: 81
<212> TYPE: DNA
<213> ORGANISM: Artificial Sequence
<220> FEATURE:
<223> OTHER INFORMATION: synthetic 25-STTMSwa48ntlink-PF forward primer for constructing short tandem target mimic (STTM) against Botrytis cinerea small RNA (sRNA) siR25

<400> SEQUENCE: 464
gccatttaaa tatggtctaa agaagaagaa taaaaccaaa attctatgat tcactagaat 60
tcggtacgct gaaatcacca g 81

<210> SEQ ID NO 465
<211> LENGTH: 81
<212> TYPE: DNA
<213> ORGANISM: Artificial Sequence
<220> FEATURE:
<223> OTHER INFORMATION: synthetic 25-STTMSwa48ntlink-PR reverse primer for constructing short tandem target mimic (STTM) against Botrytis cinerea small RNA (sRNA) siR25

<400> SEQUENCE: 465
gccatttaaa ttagaccata acaacaacaa ctagtgaatc atagaatttt ggttttaagc 60
ttgggctgtc ctctccaaat g 81

<210> SEQ ID NO 466
<211> LENGTH: 79
<212> TYPE: DNA
<213> ORGANISM: Artificial Sequence
<220> FEATURE:
<223> OTHER INFORMATION: synthetic 1015-STTMSwa48ntlink-PF forward primer for constructing short tandem target mimic (STTM) against Botrytis cinerea small RNA (sRNA) siR1015

<400> SEQUENCE: 466
gccatttaaa tatggtctaa agaagaagaa taccgatcag actacaacca tcaagaattc 60
ggtacgctga aatcaccag 79

<210> SEQ ID NO 467
<211> LENGTH: 79
<212> TYPE: DNA
<213> ORGANISM: Artificial Sequence
<220> FEATURE:
<223> OTHER INFORMATION: synthetic 1015-STTMSwa48ntlink-PR reverse primer for constructing short tandem target mimic (STTM) against Botrytis cinerea small RNA (sRNA) siR1015

<400> SEQUENCE: 467
gccatttaaa ttagaccata acaacaacaa cttgatggtt gtagtctgat cggtaagctt 60
gggctgtcct ctccaaatg 79

<210> SEQ ID NO 468
<211> LENGTH: 81
<212> TYPE: DNA
<213> ORGANISM: Artificial Sequence
<220> FEATURE:
<223> OTHER INFORMATION: synthetic 20-STTMSwa48ntlink-PF forward primer for constructing short tandem target mimic (STTM) against Botrytis cinerea small RNA (sRNA) siR20

<400> SEQUENCE: 468
gccatttaaa tatggtctaa agaagaagaa taatcagaaa aacctaaaga acactagaat 60
tcggtacgct gaaatcacca g 81

<210> SEQ ID NO 469
<211> LENGTH: 81
<212> TYPE: DNA
<213> ORGANISM: Artificial Sequence
<220> FEATURE:
<223> OTHER INFORMATION: synthetic 20-STTMSwa48ntlink-PR reverse primer for constructing short tandem target mimic (STTM) against Botrytis cinerea small RNA (sRNA) siR20

<400> SEQUENCE: 469
gccatttaaa ttagaccata acaacaacaa ctagtgttct ttaggttttt ctgattaagc 60
ttgggctgtc ctctccaaat g 81

<210> SEQ ID NO 470
<211> LENGTH: 81
<212> TYPE: DNA
<213> ORGANISM: Artificial Sequence
<220> FEATURE:
<223> OTHER INFORMATION: synthetic 1021-STTMSwa48ntlink-PF forward primer for constructing short tandem target mimic (STTM) against Botrytis cinerea small RNA (sRNA) siR1021

<400> SEQUENCE: 470
gccatttaaa tatggtctaa agaagaagaa tacatgtttt gttctacatc actgtagaat 60
tcggtacgct gaaatcacca g 81

<210> SEQ ID NO 471
<211> LENGTH: 81
<212> TYPE: DNA
<213> ORGANISM: Artificial Sequence
<220> FEATURE:
<223> OTHER INFORMATION: synthetic 1021-STTMSwa48ntlink-PR reverse primer for constructing short tandem target mimic (STTM) against Botrytis cinerea small RNA (sRNA) siR1021

<400> SEQUENCE: 471

-continued

```
gccatttaaa ttagaccata acaacaacaa ctacagtgat gtagaacaaa acatgtaagc     60

ttgggctgtc ctctccaaat g                                               81


<210> SEQ ID NO 472
<211> LENGTH: 82
<212> TYPE: DNA
<213> ORGANISM: Artificial Sequence
<220> FEATURE:
<223> OTHER INFORMATION: synthetic 1002-STTMSwa48ntlink-PF forward
      primer for constructing short tandem target mimic (STTM)
      against Botrytis cinerea small RNA (sRNA) siR1002

<400> SEQUENCE: 472

gccatttaaa tatggtctaa agaagaagaa ttgtgttaca aagactattt gaagaatgaa     60

ttcggtacgc tgaaatcacc ag                                              82


<210> SEQ ID NO 473
<211> LENGTH: 82
<212> TYPE: DNA
<213> ORGANISM: Artificial Sequence
<220> FEATURE:
<223> OTHER INFORMATION: synthetic 1002-STTMSwa48ntlink-PR reverse
      primer for constructing short tandem target mimic (STTM)
      against Botrytis cinerea small RNA (sRNA) siR1002

<400> SEQUENCE: 473

gccatttaaa ttagaccata acaacaacaa cattcttcaa atagtctttg taacacaaag     60

cttgggctgt cctctccaaa tg                                              82


<210> SEQ ID NO 474
<211> LENGTH: 81
<212> TYPE: DNA
<213> ORGANISM: Artificial Sequence
<220> FEATURE:
<223> OTHER INFORMATION: synthetic 28-STTMSwa48ntlink-PF forward primer
      for constructing short tandem target mimic (STTM)
      against Botrytis cinerea small RNA (sRNA) siR28

<400> SEQUENCE: 474

gccatttaaa tatggtctaa agaagaagaa taagaagatc acactagttt caaaaagaat     60

tcggtacgct gaaatcacca g                                               81


<210> SEQ ID NO 475
<211> LENGTH: 81
<212> TYPE: DNA
<213> ORGANISM: Artificial Sequence
<220> FEATURE:
<223> OTHER INFORMATION: synthetic 28-STTMSwa48ntlink-PR reverse primer
      for constructing short tandem target mimic (STTM)
      against Botrytis cinerea small RNA (sRNA) siR28

<400> SEQUENCE: 475

gccatttaaa ttagaccata acaacaacaa ctttttgaaa ctagtgtgat cttcttaagc     60

ttgggctgtc ctctccaaat g                                               81


<210> SEQ ID NO 476
<211> LENGTH: 80
<212> TYPE: DNA
<213> ORGANISM: Artificial Sequence
<220> FEATURE:
<223> OTHER INFORMATION: synthetic 31-STTMSwa48ntlink-PF forward primer
      for constructing short tandem target mimic (STTM)
      against Botrytis cinerea small RNA (sRNA) siR31

<400> SEQUENCE: 476
```

gccatttaaa tatggtctaa agaagaagaa tcattcacga ccctaacaag actcagaatt 60
cggtacgctg aaatcaccag 80

<210> SEQ ID NO 477
<211> LENGTH: 80
<212> TYPE: DNA
<213> ORGANISM: Artificial Sequence
<220> FEATURE:
<223> OTHER INFORMATION: synthetic 31-STTMSwa48ntlink-PR reverse primer for constructing short tandem target mimic (STTM) against Botrytis cinerea small RNA (sRNA) siR31

<400> SEQUENCE: 477
gccatttaaa ttagaccata acaacaacaa ctgagtcttg ttagggtcgt gaatgaagct 60
tgggctgtcc tctccaaatg 80

<210> SEQ ID NO 478
<211> LENGTH: 80
<212> TYPE: DNA
<213> ORGANISM: Artificial Sequence
<220> FEATURE:
<223> OTHER INFORMATION: synthetic 29-STTMSwa48ntlink-PF forward primer for constructing short tandem target mimic (STTM) against Botrytis cinerea small RNA (sRNA) siR29

<400> SEQUENCE: 478
gccatttaaa tatggtctaa agaagaagaa tcccaaaaag gactactatc caacagaatt 60
cggtacgctg aaatcaccag 80

<210> SEQ ID NO 479
<211> LENGTH: 80
<212> TYPE: DNA
<213> ORGANISM: Artificial Sequence
<220> FEATURE:
<223> OTHER INFORMATION: synthetic 29-STTMSwa48ntlink-PR reverse primer for constructing short tandem target mimic (STTM) against Botrytis cinerea small RNA (sRNA) siR29

<400> SEQUENCE: 479
gccatttaaa ttagaccata acaacaacaa ctgttggata gtagtccttt ttgggaagct 60
tgggctgtcc tctccaaatg 80

<210> SEQ ID NO 480
<211> LENGTH: 80
<212> TYPE: DNA
<213> ORGANISM: Artificial Sequence
<220> FEATURE:
<223> OTHER INFORMATION: synthetic 41-STTMSwa48ntlink-PF forward primer for constructing short tandem target mimic (STTM) against Botrytis cinerea small RNA (sRNA) siR41

<400> SEQUENCE: 480
gccatttaaa tatggtctaa agaagaagaa tttctactcc cgctaaaaac tatcagaatt 60
cggtacgctg aaatcaccag 80

<210> SEQ ID NO 481
<211> LENGTH: 80
<212> TYPE: DNA
<213> ORGANISM: Artificial Sequence
<220> FEATURE:
<223> OTHER INFORMATION: synthetic 41-STTMSwa48ntlink-PR reverse primer for constructing short tandem target mimic (STTM) against Botrytis cinerea small RNA (sRNA) siR41

<400> SEQUENCE: 481
gccatttaaa ttagaccata acaacaacaa ctgatagttt ttagcgggag tagaaaagct 60
tgggctgtcc tctccaaatg 80

<210> SEQ ID NO 482
<211> LENGTH: 80
<212> TYPE: DNA
<213> ORGANISM: Artificial Sequence
<220> FEATURE:
<223> OTHER INFORMATION: synthetic 35-STTMSwa48ntlink-PF forward primer
for constructing short tandem target mimic (STTM)
against Botrytis cinerea small RNA (sRNA) siR35

<400> SEQUENCE: 482
gccatttaaa tatggtctaa agaagaagaa taacgcgaca tgctagcaca gtacagaatt 60
cggtacgctg aaatcaccag 80

<210> SEQ ID NO 483
<211> LENGTH: 80
<212> TYPE: DNA
<213> ORGANISM: Artificial Sequence
<220> FEATURE:
<223> OTHER INFORMATION: synthetic 35-STTMSwa48ntlink-PR reverse primer
for constructing short tandem target mimic (STTM)
against Botrytis cinerea small RNA (sRNA) siR35

<400> SEQUENCE: 483
gccatttaaa ttagaccata acaacaacaa ctgtactgtg ctagcatgtc gcgttaagct 60
tgggctgtcc tctccaaatg 80

<210> SEQ ID NO 484
<211> LENGTH: 81
<212> TYPE: DNA
<213> ORGANISM: Artificial Sequence
<220> FEATURE:
<223> OTHER INFORMATION: synthetic 57-STTMSwa48ntlink-PF forward primer
for constructing short tandem target mimic (STTM)
against Botrytis cinerea small RNA (sRNA) siR57

<400> SEQUENCE: 484
gccatttaaa tatggtctaa agaagaagaa tccaacgaac cagctaagat tatctagaat 60
tcggtacgct gaaatcacca g 81

<210> SEQ ID NO 485
<211> LENGTH: 81
<212> TYPE: DNA
<213> ORGANISM: Artificial Sequence
<220> FEATURE:
<223> OTHER INFORMATION: synthetic 57-STTMSwa48ntlink-PR reverse primer
for constructing short tandem target mimic (STTM)
against Botrytis cinerea small RNA (sRNA) siR57

<400> SEQUENCE: 485
gccatttaaa ttagaccata acaacaacaa cccaacgaac cagctaagat tatctaaagc 60
ttgggctgtc ctctccaaat g 81

<210> SEQ ID NO 486
<211> LENGTH: 80
<212> TYPE: DNA
<213> ORGANISM: Artificial Sequence
<220> FEATURE:
<223> OTHER INFORMATION: synthetic 43-STTMSwa48ntlink-PF forward primer
for constructing short tandem target mimic (STTM)
against Botrytis cinerea small RNA (sRNA) siR43

<400> SEQUENCE: 486
gccatttaaa tatggtctaa agaagaagaa tcccaacaag agctaaaagc tcccagaatt 60
cggtacgctg aaatcaccag 80

<210> SEQ ID NO 487
<211> LENGTH: 80
<212> TYPE: DNA
<213> ORGANISM: Artificial Sequence
<220> FEATURE:
<223> OTHER INFORMATION: synthetic 43-STTMSwa48ntlink-PR reverse primer for constructing short tandem target mimic (STTM) against Botrytis cinerea small RNA (sRNA) siR43

<400> SEQUENCE: 487
gccatttaaa ttagaccata acaacaacaa ctgggagctt ttagctcttg ttgggaagct 60
tgggctgtcc tctccaaatg 80

<210> SEQ ID NO 488
<211> LENGTH: 80
<212> TYPE: DNA
<213> ORGANISM: Artificial Sequence
<220> FEATURE:
<223> OTHER INFORMATION: synthetic 40-STTMSwa48ntlink-PF forward primer for constructing short tandem target mimic (STTM) against Botrytis cinerea small RNA (sRNA) siR40

<400> SEQUENCE: 488
gccatttaaa tatggtctaa agaagaagaa taaccaatac aactagccca ttccagaatt 60
cggtacgctg aaatcaccag 80

<210> SEQ ID NO 489
<211> LENGTH: 80
<212> TYPE: DNA
<213> ORGANISM: Artificial Sequence
<220> FEATURE:
<223> OTHER INFORMATION: synthetic 40-STTMSwa48ntlink-PR reverse primer for constructing short tandem target mimic (STTM) against Botrytis cinerea small RNA (sRNA) siR40

<400> SEQUENCE: 489
gccatttaaa ttagaccata acaacaacaa ctggaatggg ctagttgtat tggttaagct 60
tgggctgtcc tctccaaatg 80

<210> SEQ ID NO 490
<211> LENGTH: 80
<212> TYPE: DNA
<213> ORGANISM: Artificial Sequence
<220> FEATURE:
<223> OTHER INFORMATION: synthetic 48-STTMSwa48ntlink-PF forward primer for constructing short tandem target mimic (STTM) against Botrytis cinerea small RNA (sRNA) siR48

<400> SEQUENCE: 490
gccatttaaa tatggtctaa agaagaagaa tttgatcgat acctatgtca cttcagaatt 60
cggtacgctg aaatcaccag 80

<210> SEQ ID NO 491
<211> LENGTH: 80
<212> TYPE: DNA
<213> ORGANISM: Artificial Sequence
<220> FEATURE:
<223> OTHER INFORMATION: synthetic 48-STTMSwa48ntlink-PR reverse primer for constructing short tandem target mimic (STTM)

against Botrytis cinerea small RNA (sRNA) siR48

<400> SEQUENCE: 491
gccatttaaa ttagaccata acaacaacaa ctgaagtgac ataggtatcg atcaaaagct 60
tgggctgtcc tctccaaatg 80

<210> SEQ ID NO 492
<211> LENGTH: 80
<212> TYPE: DNA
<213> ORGANISM: Artificial Sequence
<220> FEATURE:
<223> OTHER INFORMATION: synthetic 49-STTMSwa48ntlink-PF forward primer
for constructing short tandem target mimic (STTM)
against Botrytis cinerea small RNA (sRNA) siR49

<400> SEQUENCE: 492
gccatttaaa tatggtctaa agaagaagaa ttatcaaaag acctaataag ccacagaatt 60
cggtacgctg aaatcaccag 80

<210> SEQ ID NO 493
<211> LENGTH: 80
<212> TYPE: DNA
<213> ORGANISM: Artificial Sequence
<220> FEATURE:
<223> OTHER INFORMATION: synthetic 49-STTMSwa48ntlink-PR reverse primer
for constructing short tandem target mimic (STTM)
against Botrytis cinerea small RNA (sRNA) siR49

<400> SEQUENCE: 493
gccatttaaa ttagaccata acaacaacaa ctgtggctta ttaggtcttt tgataaagct 60
tgggctgtcc tctccaaatg 80

<210> SEQ ID NO 494
<211> LENGTH: 80
<212> TYPE: DNA
<213> ORGANISM: Artificial Sequence
<220> FEATURE:
<223> OTHER INFORMATION: synthetic 58-STTMSwa48ntlink-PF forward primer
for constructing short tandem target mimic (STTM)
against Botrytis cinerea small RNA (sRNA) siR58

<400> SEQUENCE: 494
gccatttaaa tatggtctaa agaagaagaa tcagacaatg aactatccca atttagaatt 60
cggtacgctg aaatcaccag 80

<210> SEQ ID NO 495
<211> LENGTH: 80
<212> TYPE: DNA
<213> ORGANISM: Artificial Sequence
<220> FEATURE:
<223> OTHER INFORMATION: synthetic 58-STTMSwa48ntlink-PR reverse primer
for constructing short tandem target mimic (STTM)
against Botrytis cinerea small RNA (sRNA) siR58

<400> SEQUENCE: 495
gccatttaaa ttagaccata acaacaacaa ctaaattggg atagttcatt gtctgaagct 60
tgggctgtcc tctccaaatg 80

<210> SEQ ID NO 496
<211> LENGTH: 80
<212> TYPE: DNA
<213> ORGANISM: Artificial Sequence
<220> FEATURE:
<223> OTHER INFORMATION: synthetic 1005-STTMSwa48ntlink-PF forward primer for constructing short tandem target mimic (STTM)
against Botrytis cinerea small RNA (sRNA) siR1005

<400> SEQUENCE: 496
gccatttaaa tatggtctaa agaagaagaa ttcctattga agctaaaact ctttagaatt 60
cggtacgctg aaatcaccag 80

<210> SEQ ID NO 497
<211> LENGTH: 80
<212> TYPE: DNA
<213> ORGANISM: Artificial Sequence
<220> FEATURE:
<223> OTHER INFORMATION: synthetic 1005-STTMSwa48ntlink-PR reverse
primer for constructing short tandem target mimic (STTM)
against Botrytis cinerea small RNA (sRNA) siR1005

<400> SEQUENCE: 497
gccatttaaa ttagaccata acaacaacaa ctaaagagtt ttagcttcaa taggaaagct 60
tgggctgtcc tctccaaatg 80

<210> SEQ ID NO 498
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2 target Vitis vinifera VIT_10s0092g00240
carbohydrate binding, hydrolase activity, CDS+UTR
target site

<400> SEQUENCE: 498
cccuacaaga uuaacaaugu a 21

<210> SEQ ID NO 499
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.2 target Vitis vinifera VIT_10s0092g00240
carbohydrate binding, hydrolase activity, CDS+UTR
target site

<400> SEQUENCE: 499
acccaauuac aagauccacg a 21

<210> SEQ ID NO 500
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 target Vitis vinifera VIT_06s0009g01890
exonuclease, intron target site

<400> SEQUENCE: 500
accaaucuac aaaauccaca a 21

<210> SEQ ID NO 501
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 target Vitis vinifera VIT_10s0116g00190
KNOX1,2 domain containing protein, intron target
site

<400> SEQUENCE: 501
ccccaaguac aagaaccaca a 21

<210> SEQ ID NO 502
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR5 target Vitis vinifera VIT_05s0020g01790
lipase, CDS target site

<400> SEQUENCE: 502
uauauuacau uccgagucau g 21

<210> SEQ ID NO 503
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR5 target Vitis vinifera VIT_01s0011g01000
NB-ARC and LRR domain, intron target site

<400> SEQUENCE: 503
aagcauacau accgagucaa u 21

<210> SEQ ID NO 504
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR5 target Vitis vinifera VIT_05s0077g01510
DUF7 domain, intron target site

<400> SEQUENCE: 504
aagtaatcat tccaagtcaa a 21

<210> SEQ ID NO 505
<211> LENGTH: 21
<212> TYPE: DNA
<213> ORGANISM: Artificial Sequence
<220> FEATURE:
<223> OTHER INFORMATION: synthetic Botrytis cinerea small RNA (sRNA)
Bc-siR3.2 mutated (MU) At-MPK1 target, mutated
(MU) At-MPK2 target

<400> SEQUENCE: 505
ataaagaaaa tacataacgt t 21

<210> SEQ ID NO 506
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
Bc-siR3.1 mutated (MU) AtPRXIIF target

<400> SEQUENCE: 506
cccgaguuau aaaagucaua u 21

<210> SEQ ID NO 507
<211> LENGTH: 21
<212> TYPE: RNA
<213> ORGANISM: Artificial Sequence -continued
<220> FEATURE:
<223> OTHER INFORMATION: synthetic Botrytis cinerea small RNA (sRNA)
      Bc-siR3.2 mutated (MU) MAPKKK4 Solyc08g081210.2.1
      target

<400> SEQUENCE: 507
cauuugaagg acccuccuug c 21

<210> SEQ ID NO 508
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR3.2 mutated (MU) Sl F-box
      (Solyc03g061650.1.1) target

<400> SEQUENCE: 508
aucuugagga cccuaagugc a 21

<210> SEQ ID NO 509
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR3.1 mutated (MU) Autophagy-related protein 2
      (Solyc01g108160.2.1) target

<400> SEQUENCE: 509
auacauuuuc aggacccuca g 21

<210> SEQ ID NO 510
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR3.1 mutated (MU) Sl Vacuolar protein-sorting
      (Solyc09g014790.2.1) target

<400> SEQUENCE: 510
auccuccagc uacuucgacu a 21

<210> SEQ ID NO 511
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 mutated (MU) Sl Pentatricopeptide
      (Solyc03g112190.2.1) target

<400> SEQUENCE: 511
gggaaggcac ucggaagcua a 21

<210> SEQ ID NO 512
<211> LENGTH: 21
<212> TYPE: RNA
<213> ORGANISM: Artificial Sequence
<220> FEATURE:
<223> OTHER INFORMATION: synthetic Botrytis cinerea small RNA (sRNA)
      Bc-siR5 mutated (MU) TOM34 (Solyc07g066530.2.1)
      target

<400> SEQUENCE: 512
caauacaggu uucgugugaa g 21